US009878991B2

(12) United States Patent
Tafesse

(10) Patent No.: US 9,878,991 B2
(45) Date of Patent: *Jan. 30, 2018

(54) TRPV1 ANTAGONISTS INCLUDING DIHYDROXY SUBSTITUENT AND USES THEREOF

(71) Applicant: Purdue Pharma L.P., Stamford, CT (US)

(72) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,612

(22) Filed: Jun. 10, 2016

(65) Prior Publication Data

US 2016/0355499 A1    Dec. 8, 2016

Related U.S. Application Data

(60) Continuation of application No. 14/498,724, filed on Sep. 26, 2014, now Pat. No. 9,365,563, which is a continuation of application No. 13/852,913, filed on Mar. 28, 2013, now Pat. No. 8,889,690, which is a division of application No. 12/110,155, filed on Apr. 25, 2008, now Pat. No. 8,476,277.

(60) Provisional application No. 60/962,409, filed on Jul. 27, 2007, provisional application No. 60/937,003, filed on Jun. 21, 2007, provisional application No. 60/930,036, filed on May 11, 2007, provisional application No. 60/926,661, filed on Apr. 27, 2007.

(51) Int. Cl.

| | | |
|---|---|---|
| *C07D 401/04* | (2006.01) |
| *C07D 401/14* | (2006.01) |
| *C07D 417/12* | (2006.01) |
| *C07D 417/14* | (2006.01) |
| *C07D 405/14* | (2006.01) |
| *C07D 213/72* | (2006.01) |
| *C07D 213/74* | (2006.01) |
| *C07D 401/12* | (2006.01) |
| *C07D 213/61* | (2006.01) |
| *C07D 407/14* | (2006.01) |

(52) U.S. Cl.
CPC ......... *C07D 401/04* (2013.01); *C07D 213/61* (2013.01); *C07D 213/72* (2013.01); *C07D 213/74* (2013.01); *C07D 401/12* (2013.01); *C07D 401/14* (2013.01); *C07D 405/14* (2013.01); *C07D 407/14* (2013.01); *C07D 417/12* (2013.01); *C07D 417/14* (2013.01)

(58) Field of Classification Search
CPC .. C07D 401/04; C07D 401/14; C07D 417/12; C07D 417/14; C07D 405/14; C07D 213/72
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,409,229 A | 10/1983 | Ong et al. |
| 4,797,419 A | 1/1989 | Moos et al. |
| 5,059,595 A | 10/1991 | Le Grazie |
| 5,073,543 A | 12/1991 | Marshall et al. |
| 5,120,548 A | 6/1992 | McClelland et al. |
| 5,138,058 A | 8/1992 | Geisen et al. |
| 5,354,556 A | 10/1994 | Sparks et al. |
| 5,399,574 A | 3/1995 | Robertson et al. |
| 5,442,064 A | 8/1995 | Pieper et al. |
| 5,529,998 A | 6/1996 | Habich et al. |

(Continued)

FOREIGN PATENT DOCUMENTS

| | | |
|---|---|---|
| CA | 2114178 | 1/1994 |
| EP | 1388538 | 7/2003 |

(Continued)

OTHER PUBLICATIONS

Anilkumar, et al., "A Simple and Efficient Iodination of Alcohols on Polymer-Supported Triphenylphosphine," *Organic Process Res. & Devel.* 6(2):190-191 (2002).
Article 96(2) Communication dated Jul. 3, 2006 in connection with EP 1648879 B1.
Barnett, et al., "Synthesis of picenadol via Metalloenamine Alkylation Methodology," *J. Org. Chem.* 54(20):4795-4800 (1989).
Barthó, et al., "Involvement of capsaicin-sensitive neurons in hyperalgesia and enhanced opioid antinociception in inflammation," *Naunyn-Schmiedeberg's Arch. Pharmacol.* 342:666-670 (1990).

(Continued)

*Primary Examiner* — Timothy R Rozof
(74) *Attorney, Agent, or Firm* — Dechert LLP

(57) ABSTRACT

The invention relates to compounds of formula IA (IA)

Figure 2:
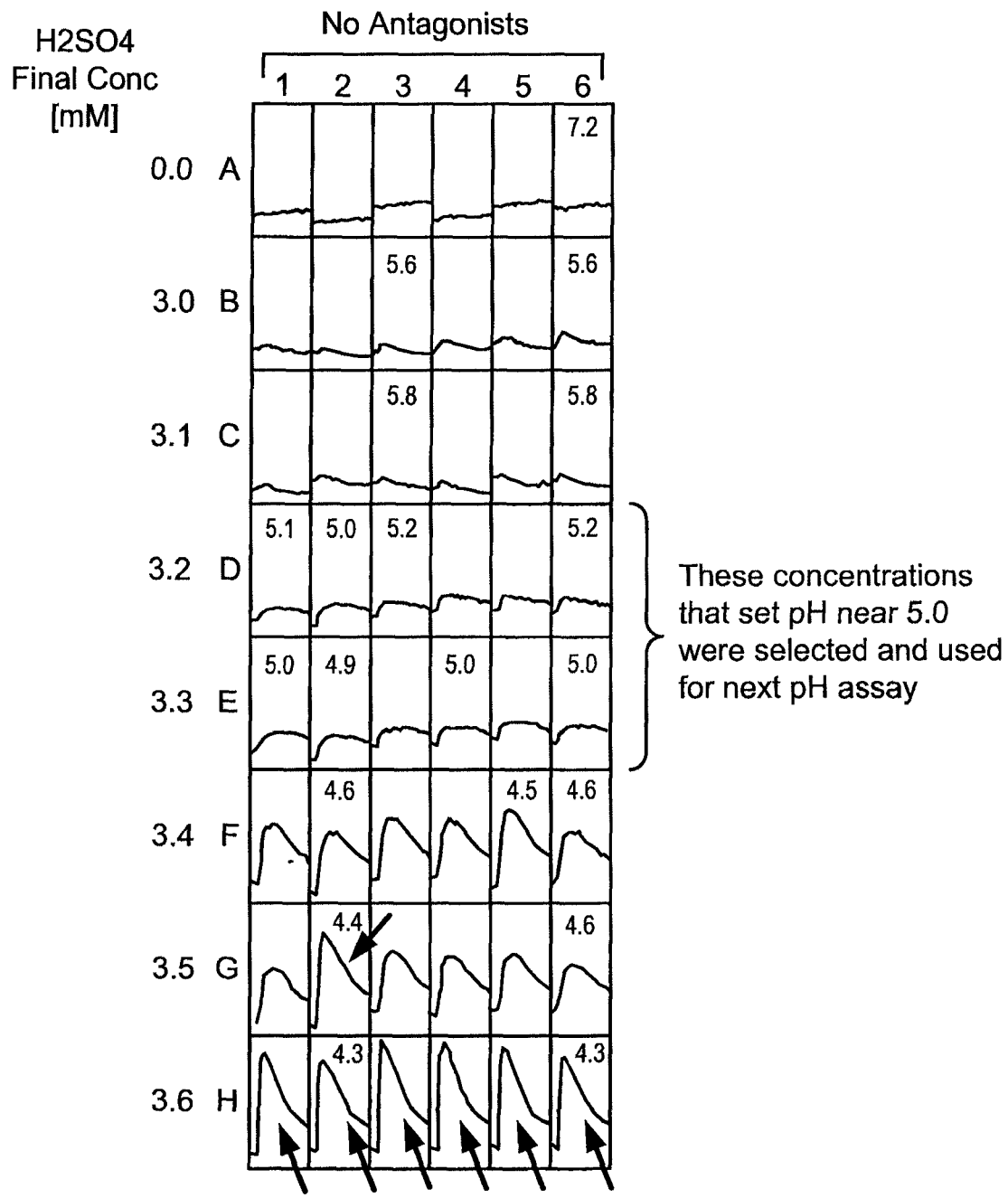

and pharmaceutically acceptable derivatives thereof, compositions comprising an effective amount of a compound of formula IA or a pharmaceutically acceptable derivative thereof, and methods for treating or preventing a condition such as pain, UI, an ulcer, IBD and IBS, comprising administering to an animal in need thereof an effective amount of a compound of formula IA or a pharmaceutically acceptable derivative thereof.

22 Claims, 3 Drawing Sheets

(56) References Cited

U.S. PATENT DOCUMENTS

| | | | |
|---|---|---|---|
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,728,704 A | 3/1998 | Mylari et al. |
| 5,733,566 A | 3/1998 | Lewis |
| 5,837,716 A | 11/1998 | Hough |
| 5,854,245 A | 12/1998 | Duggan et al. |
| 5,891,889 A | 4/1999 | Anthony et al. |
| 5,948,786 A | 9/1999 | Fujiwara et al. |
| 5,990,107 A | 11/1999 | Egbertson et al. |
| 6,051,712 A | 4/2000 | Binggeli et al. |
| 6,136,839 A | 10/2000 | Isakson et al. |
| 6,150,129 A | 11/2000 | Cook et al. |
| 6,239,267 B1 | 5/2001 | Duckworth et al. |
| 6,248,756 B1 | 6/2001 | Anthony et al. |
| 6,335,180 B1 | 1/2002 | Julius et al. |
| 6,406,908 B1 | 6/2002 | Mcintyre et al. |
| 6,414,149 B1 | 7/2002 | Chu-Moyer et al. |
| 6,482,479 B1 | 11/2002 | Dubal et al. |
| 6,544,998 B2 | 4/2003 | Mylari |
| 6,602,875 B2 | 8/2003 | Chu-Moyer et al. |
| 6,673,799 B1 | 1/2004 | Taniguchi et al. |
| 6,723,730 B2 | 4/2004 | Bakthavatchalam et al. |
| 6,812,236 B2 | 11/2004 | Gibson et al. |
| 6,852,732 B2 | 2/2005 | Nakazato et al. |
| 6,887,870 B1 | 5/2005 | Ahmad et al. |
| 6,963,000 B2 | 11/2005 | Alanine et al. |
| 6,974,818 B2 | 12/2005 | Kyle et al. |
| 7,060,331 B2 | 6/2006 | Kirsch et al. |
| 7,071,335 B2 | 7/2006 | Kyle et al. |
| 7,129,235 B2 | 10/2006 | Zheng et al. |
| 7,157,462 B2 | 1/2007 | Sun et al. |
| 7,193,113 B2 | 3/2007 | Ishihara et al. |
| 7,223,788 B2 | 5/2007 | Schwink et al. |
| 7,256,193 B2 | 8/2007 | Kyle et al. |
| 7,262,194 B2 | 8/2007 | Kyle et al. |
| 7,279,493 B2 | 10/2007 | Kyle et al. |
| 7,312,246 B2 | 12/2007 | Hamilton et al. |
| 7,332,495 B2 | 2/2008 | Li et al. |
| 7,335,658 B2 | 2/2008 | Chakka et al. |
| 7,342,017 B2 | 3/2008 | Kyle et al. |
| 7,390,813 B1 | 6/2008 | Gray-Keller et al. |
| 7,456,180 B2 | 11/2008 | Sviridov et al. |
| 7,514,436 B2 | 4/2009 | Gschwend et al. |
| 7,528,134 B2 | 5/2009 | Bhatia et al. |
| 7,538,121 B2 | 5/2009 | MacDonald et al. |
| 7,569,583 B2 | 8/2009 | Schwink et al. |
| 7,572,812 B2 | 8/2009 | Sun et al. |
| 7,572,815 B2 | 8/2009 | Nakagawa et al. |
| 7,582,635 B2 | 9/2009 | Sun et al. |
| 7,592,343 B2 | 9/2009 | Kamboj et al. |
| 7,632,950 B2 | 12/2009 | Kuwabara et al. |
| 7,683,063 B2 | 3/2010 | Kyle et al. |
| 7,696,207 B2 | 4/2010 | Kyle et al. |
| 7,737,148 B2 | 6/2010 | Sun et al. |
| 7,776,861 B2 | 8/2010 | Sun et al. |
| 7,829,713 B2 | 11/2010 | Keenan et al. |
| 7,855,210 B2 | 12/2010 | Sun et al. |
| 7,919,484 B2 | 4/2011 | Kamboj et al. |
| 8,138,168 B1 | 3/2012 | Jones et al. |
| 8,476,271 B2 | 7/2013 | Tsuno et al. |
| 8,476,277 B2 | 7/2013 | Tafesse |
| 8,575,199 B2 | 11/2013 | Tafesse |
| 8,642,634 B2 | 2/2014 | Pasteris et al. |
| 8,889,690 B2 | 11/2014 | Tafesse |
| 2003/0153568 A1 | 8/2003 | Scott et al. |
| 2003/0186994 A1 | 10/2003 | Mylari |
| 2003/0232996 A1 | 12/2003 | Brown et al. |
| 2004/0034061 A1 | 2/2004 | Nakazato et al. |
| 2004/0038982 A1 | 2/2004 | Bondinell et al. |
| 2004/0102450 A1 | 5/2004 | Ewing et al. |
| 2004/0152690 A1 | 8/2004 | Balan et al. |
| 2004/0186111 A1 | 9/2004 | Sun et al. |
| 2004/0259912 A1 | 12/2004 | Matsumoto et al. |
| 2005/0009841 A1 | 1/2005 | Zheng et al. |
| 2005/0107384 A1 | 5/2005 | Angibaud et al. |
| 2005/0119251 A1 | 6/2005 | Fu et al. |
| 2005/0222410 A1 | 10/2005 | Stokes et al. |
| 2006/0009459 A1 | 1/2006 | Chakka et al. |
| 2006/0052403 A1 | 3/2006 | Isobe et al. |
| 2006/0116368 A1 | 6/2006 | Calvo et al. |
| 2006/0128717 A1 | 6/2006 | Sun et al. |
| 2006/0128755 A1 | 6/2006 | Nakagawa et al. |
| 2006/0148844 A1 | 7/2006 | Nakade et al. |
| 2006/0199802 A1 | 9/2006 | Abreo et al. |
| 2006/0199824 A1 | 9/2006 | Sun et al. |
| 2006/0223849 A1 | 10/2006 | Mjalli et al. |
| 2006/0235004 A1 | 10/2006 | Geneste et al. |
| 2006/0293308 A1 | 12/2006 | Abreo et al. |
| 2007/0135423 A1 | 6/2007 | Bayliss et al. |
| 2007/0155707 A1 | 7/2007 | Dasse et al. |
| 2007/0208001 A1 | 9/2007 | Zhuo et al. |
| 2007/0244088 A1 | 10/2007 | Brickmann et al. |
| 2008/0015230 A1 | 1/2008 | Kamboj et al. |
| 2008/0039629 A1 | 2/2008 | Ramesh et al. |
| 2008/0076924 A1 | 3/2008 | Betschmann et al. |
| 2008/0096895 A1 | 4/2008 | Kamboj et al. |
| 2008/0153835 A1 | 6/2008 | Kyle et al. |
| 2008/0167321 A1 | 7/2008 | Kamboj et al. |
| 2008/0182851 A1 | 7/2008 | Thomas et al. |
| 2008/0200472 A1 | 8/2008 | Kyle et al. |
| 2008/0280916 A1 | 11/2008 | Bilich et al. |
| 2008/0293733 A1 | 11/2008 | Bearss et al. |
| 2009/0062345 A1 | 3/2009 | Vasudevan et al. |
| 2009/0093497 A1 | 4/2009 | Bolin et al. |
| 2009/0105271 A1 | 4/2009 | Martinborough et al. |
| 2009/0131447 A1 | 5/2009 | Kamboj et al. |
| 2009/0143302 A1 | 6/2009 | Yen et al. |
| 2009/0170867 A1 | 7/2009 | Kurose |
| 2009/0176796 A1 | 7/2009 | Tafesse |
| 2010/0022530 A1 | 1/2010 | Schiemann et al. |
| 2010/0331369 A1 | 12/2010 | Sun et al. |
| 2011/0071192 A1 | 3/2011 | Sun et al. |
| 2011/0152324 A1 | 6/2011 | Kyle et al. |
| 2013/0274265 A1 | 10/2013 | Fuchino et al. |
| 2013/0338170 A1 | 12/2013 | Tafesse |

FOREIGN PATENT DOCUMENTS

| | | |
|---|---|---|
| EP | 1631285 | 3/2006 |
| EP | 1648879 | 4/2006 |
| EP | 1862458 | 12/2007 |
| EP | 1867644 | 12/2007 |
| EP | 1939175 | 7/2008 |
| EP | 1939189 | 7/2008 |
| EP | 2060260 | 5/2009 |
| EP | 2080757 | 7/2009 |
| JP | 62-89679 | 4/1987 |
| JP | 6-80054 | 10/1994 |
| JP | 11-199573 | 7/1999 |
| JP | 2003095951 | 4/2003 |
| JP | 2003-192673 | 7/2003 |
| JP | 2009-249346 | 10/2009 |
| WO | WO 1997/28140 | 8/1997 |
| WO | WO 1998/31669 | 7/1998 |
| WO | WO 1998/31677 | 7/1998 |
| WO | WO 1999/65896 | 12/1999 |
| WO | WO 2000/01688 | 1/2000 |
| WO | WO 2000/42852 | 7/2000 |
| WO | WO 2000/69816 | 11/2000 |
| WO | WO 2001/17965 | 3/2001 |
| WO | WO 2003/053922 | 7/2003 |
| WO | WO 2004/010942 | 2/2004 |
| WO | WO 2005/004866 | 1/2005 |
| WO | WO 2005/009988 | 2/2005 |
| WO | WO 2005/037284 | 4/2005 |
| WO | WO 2006/100081 | 9/2006 |
| WO | WO 2006/108965 | 10/2006 |
| WO | WO 2007/082731 | 7/2007 |
| WO | WO 2008/132600 | 11/2008 |
| WO | WO 2008/147864 | 12/2008 |
| WO | WO 2008/156610 | 12/2008 |
| WO | WO 2009/005645 | 1/2009 |

(56) References Cited

FOREIGN PATENT DOCUMENTS

| WO | WO 2009/006437 | 1/2009 |
|---|---|---|
| WO | WO 2009/023059 | 2/2009 |
| WO | WO 2009/045382 | 4/2009 |
| WO | WO 2009/076512 | 6/2009 |

OTHER PUBLICATIONS

Bingham, et al., "Over one hundred solvates of sulfathiazole," *ChemComm* 7:603-604 (2001).
Birder, "TRPs in bladder diseases," *Biochim. Biophys Acta* 1772:879-884 (2007).
Bleicher, et al., "New phenylfluorenyl based linkers for solid phase synthesis," *Tetrahedron Let.* 41:9037-9042 (2000).
Bley, et al., "TRPV1 agonist-based therapies: mechanism of action and clinical prospects," in *Turning up the Heat on Pain: TRPV1 Receptors in Pain and Inflammation*, pp. 191-209 {Malmberg, et al., eds, Birkhauser Verlag, Basel, Switzerland, 2005).
Buchwald, et al., "Long-term, continuous intravenous heparin administration by an implantable infusion pump in ambulatory patients with recurrent venous thrombosis," *Surgery* 88:507-516 (1980).
Bundgaard, "(C) Means to Enhance Penetration (1) Prodrugs as a means to improve the delivery of peptide drugs," *Advanced Drug Delivery Revs* 8:1-38 (1992).
Bundgaard, "Design and Application of Prodrugs," Chapter 5, pp. 113-191 in *A Textbook of Drug Design and Development*, Krogsgaard-Larsen and Bundgaard eds., Harwood Academic Publishers (1991).
Bundgaard, et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).
Caira, et al., "Preparation and Crystal Characterization of a Polymorph, a Monohydrate, and an Ethyl Acetate Solvate of the Antifungal Fluconazole," *J. Pharmaceut. Sci.* 93(3):601-611 (2004).
Cammack, et al., "Synthesis of Ketobemidone Precursors via Phase-Transfer Catalysis," *J. Heterocyclic Chem.* 23:73-75 (1986).
Cheng, et al., "The Sulfone Linker in Solid-Phase Synthesis: Preparation of 3,5-Disubstituted Cyclopent-2-enones," *J. Org. Chem.* 67(13):4387-4391 (2002).
Chu-Moyer, et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem.* 45(2):511-528 (2002).
Cotarca, et al., "Bis(trichloromethyl) Carbonate in Organic Synthesis," *Synthesis* 1996:553-576 (1996).
D'Ambra, et al., "Novel synthesis of iperidinecarboxamides via aryl isocyanate acylation of a-amino carbanions," *J. Org. Chem.* 54(23):5632-5635 (1989).
D'Amour, et al., "A Method for Determining Loss of Pain Sensation," *J. Pharmacol. Exp. Ther.* 72:74-79 (1941).
Dauban, et al.,"$N^1$-Arylsulfonyl-$N^2$-(1-arypethy1-3-phenylpropane-1,2-diamines as Novel Calcimimetics Acting on the Calcium Sensing Receptor," *Bioorganic & Medicinal Chem. Let.* 10(17):2001-2004 (2000).
Dedov, et al., "Gingerols: a novel class of vanilloid receptor (VR1) agonists," *Brit. J. Pharmacol.* 137(6):793-798 (2002).
Di Marzo, et al., "End ovanilloid signaling in pain," *Current Opinion in Neurobiology* 12:372-379 (2002).
During, et al., "Controlled Release of Dopamine from a Polymeric Brain Implant: in Vivo Characterization," *Amer. Neurological Assn* 25:351-356 (1989).
Eckert, et al., "Bis(trichloromethyl) carbonate as an alternative reagent for phosgene," *General Org. Chem.* 106:4294 (1987).
Eckert, et al., "Tri phosgene, a Crystalline Phosgene Substitute," *Angew. Chem. Int. Ed Engl.* 26(9):894-895 (1987).

Extended European Search Report dated Apr. 9, 2009 in connection with EP 2060260 A1.
Extended European Search Report dated Dec. 21, 2007 in connection with EP 1862458 B1.
Extended European Search Report dated Jun. 5, 2009 in connection with EP 2080757 A1.
Extended European Search Report dated Oct. 31, 2007 in connection with EP 1867644 B1.
Feuer, et al., "Alkyl nitrate nitration of active methylene compounds, VI. Synthesis of α-nitroalkyl heterocyclics," *J. Am. Chem. Soc.* 91(7):1856-1857 (1969).
Foley, "Pain," *Cecil Textbook of Medicine*, pp. 100-107 (20$^{th}$ ed. 1996).
Gavva, et al., "AMG 9810 [(E)-3-(4-t-Butylpheny1)-N-(2,3-dihydrobenzo[b][1,4] dioxin-6-yl)acrylamide], a Novel Vanilloid Receptor 1 (TRPV1) Antagonist with Antihyperalgesic Properties," *J. Pharmacol. Exper. Therapeutics* 313, No. 1):474-484 (2005).
Geppetti, et al., "Activation and sensitisation of the vanilloid receptor: role in gastrointestinal inflammation and function," *Brit. J. Pharmacol.* 141:1313-1320 (2004).
Gharat, et al., "Medicinal chemistry of the vanilloid (Capsaicin) TRPV1 receptor: current knowledge and future perspectives," *Drug Develop. Res.* 68:477-497 (2007).
Gnecco, et al., "An Improved Preparation of 1-Methyl-4-Cyano-4-Phenylpiperidine," *OPPI Briefs* 28(4):478-480 (1996).
Goodson, "Dental Applications," in *Medical Applications of Controlled Release*, Chapter 6, vol. 11, pp. 115-138 (1984).
Grupp, et al., "Protection against Hypoxia-reoxygenation in the Absence of Poly (ADP-ribose) Synthetase in Isolated Working Hearts," *J. Mol. Cell Cardiol.* 31:297-303 (1999).
Hallot, et al., "Synthesis and activity of 6-aryl-3-(hydroxypolymethyleneamino)pyridazines in animal models of epilepsy," *J. Med. Chem.* 39(3):369-375 (1986).
Hanson, "Analgesic, Antipyretic and Anti-inflammatory Drugs," in *Remington: The Science and Practice of Pharmacy*, vol. II, pp. 1196-1221 (A.R. Gennaro ed. 19$^{th}$ ed. 1995).
Hargreaves, et al., "A new and sensitive method for measuring thermal nociception in cutaneous hyperalgesia," *Pain* 32:77-88 (1988).
Harmon, et al., "Carbonium Ion Salts. VIII. Synthesis of Iodoborates and an Improved Route to Triphenylmethyl Iodide," *J. Am. Chem. Soc.* 87(3):539-542 (1965).
Hicks, "TRP channels as therapeutic targets: hot property, or time to cool down?," *Neurogastroenterol. Motil.* 18(8):590-594 (2006).
Holmes, et al., "Approaches to the synthesis of the tetrahydropyran subunit of the polyether nigericin," *J. Org. Chem.* 54(1):98-108 (1989).
Howard, et al., "Intracerebral drug delivery in rats with lesion-induced memory deficits," *J. Neurosurg.* 71:105-112 (1989).
Insel, "Analgesic-Antipyretic and Anti-inflammatory Agents and Drugs Employed in the Treatment of Gout," in *Goodman & Gilman: The Pharmacological Basis of Therapeutics*, pp. 617-657 (Molinhoff and Ruddon, eds., 9$^{th}$ ed. 1996).
International Preliminary Report on Patentability dated Jun. 30, 2005 in connection with WO 2005/009988 A1.
International Preliminary Report on Patentability dated Mar. 16, 2005 in connection with WO 2005/004866 A1.
International Search Report and the Written Opinion of the International Searching Authority for International Application No. PCT/IB2008/001069 dated Jan. 20, 2009.
Kakeya, et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32(2):692-698 (1984).
Kanie, et al., "A Convenient Synthesis of Trifluoromethyl Esters by Oxidative Desulfurization-Fluorination of Dithiocarbonates," *Bull. Chem. Soc. Jpn.* 73(2):471-484 (2000).
Kanie, et al., "Oxidative desulfurization-fluorination of alkanol xanthates. Control of the reaction pathway to fluorination or trifluoromethoxylation," *Chem. Commun.* 3:309-310 (1997).
Khadse, et al., "Synthesis and Study of 2-($N^4$-substituted-$N^1$-piperazinyl)-pyrido-(3,2-d)-thiazoles, 5-nitro-2-($N^4$-substituted-$N^1$-

(56) References Cited

OTHER PUBLICATIONS piperazinyl)-Benzthiazoles and allied compounds as possible anthelmintic agents," *Bull. Haff. Inst.* 1(3):27-32 (1975).
Kim, et al., "An experimental model for peripheral neuropathy produced by segmental spinal nerve ligation in the rat," *Pain* 50:355-363 (1992).
Langer, et al., "Chemical and Physical Structure of Polymers as Carriers for Controlled Release of Bioactive Agents: A Review," *J. Macromol. Sci. Rev. Macromol. Chem.* C23:61-126 (1983).
Langer, "New Methods of Drug Delivery," *Science* 249:1527-1533.
Lee, et al., "N-(3-Acyloxy-2-benzylpropyl)-N'[4-(methylsulfonylamino)benzyl]thiourea Analogues: Novel Potent and High Affinity Antagonists and Partial Antagonists of the Vanilloid Receptor," *J. Med. Chem.* 46:3116-3126 (2003).
Levy, R. J., "Inhibition of Calcification of Bioprosthetic Heart Valves by Local Controlled-Release Diphosphonate," *Science* 228:190-192 (1985).
Li, et al., "An Improved Procedure for the Preparation of Isothiocyanates from Primary Amines by Using Hydrogen Peroxide as the Dehydrosulfurization Reagent," *J. Org. Chem.* 62(13):4539-4540 (1997).
Llama, et al., "Synthesis and antinociceptive activity of 9-phenyloxy or 9-acyl-oxy derivatives of xanthene, thioxanthene and acridine," *Eur. J. Med. Chem.* 24:391-396 (1989).
Lopez-Berestein, "Treatment of Systemic Fungal Infections with Liposomal-Amphotericin B," in *Liposomes in the Therapy of Infectious Disease and Cancer*, pp. 317-327 (Lopez-Bereste in, et al., eds, Alan R. Liss, Inc., New York, 1989).
Martinez, et al., "Herstellung von 1,1-Dihaloalkamen," *Synthesis* 12:1076-1078 (1986).
Martnez, et al., "Hindered Rotation in Diphenylmethane Derivatives. Electrostatic vs Charge-Transfer and Homoconjugative Aryl-Aryl Interactions," *J. Am. Chem. Soc.* 120(4):673-679 (1998).
Maya, et al., "A practical one-pot synthesis of O-unprotected glycosyl thioureas," *Tetrahedron Let.* 42:5413-5416 (2001).
Morgenstern, et al., "Studies on the Reaction of 2-Aminoacetophenone with Thiophosgene," *J. Heterocyclic Chem.* 28(4):1091-1097 (1991).
Mouysset, et al., "Contribution of the Diethyl Phosphonate Group to a First Approach of Calcium-Inhibiting Activity: Study of a Series of Various Substituted 2-Phenylbenzothiazoles," *Il. Farmaco* 45(9):945-952 (1990).
Notice of Allowance and Fees Due for U.S. Appl. No. 11/338,502 dated Nov. 21, 2007.
Notice of Allowance and Fees Due for U.S. Appl. No. 11/338,502 dated Jan. 6, 2010.
Notice of Allowance and Fees Due for U.S. Appl. No. 12/110,212 dated Nov. 15, 2011.
Notice of Allowance and Fees Due for U.S. Appl. No. 13/852,913 dated Jun. 27, 2014.
Office Communication for U.S. Appl. No. 10/867,546 dated Apr. 30, 2007.
Office Communication for U.S. Appl. No. 10/867,546 dated Dec. 8, 2008.
Office Communication for U.S. Appl. No. 11/338,502 dated Apr. 20, 2009.
Office Communication for U.S. Appl. No. 11/338,502 dated Sep. 3, 2008.
Office Communication for U.S. Appl. No. 12/110,089 dated Jul. 9, 2010.
Office Communication for U.S. Appl. No. 12/110,212 dated Dec. 10, 2010.
Office Communication for U.S. Appl. No. 12/110,212 dated May 19, 2010.
Office Communication for U.S. Appl. No. 12/110,212 dated Sep. 9, 2009.
Office Communication for U.S. Appl. No. 13/852,913 dated Jan. 2, 2014.
Ognyanov, et al., "Design of Potent, Orally Available Antagonists of the Transient Receptor Potential Vanilloid 1. Structure-Activity Relationships of 2-Piperazin-1-yl-1H-benzimidazoles," *J. Med. Chem.* 49:3719-3742 (2006).
Ohta, et al., "Molecular cloning, functional characterization of the porcine transient receptor potential V1 (pTRPV1) and pharmacological comparison with endogenous pTRPV1," *Biochem. Pharmacol.* 71:173-185 (2005).
Ong, et al., "Novel tetracyclic spiropiperidines. 1. 3-Aryl-1,3-dihydrospiro[benzo[c]thiophene-1,4'-piperidines] as potential antidepressants," *J. Med. Chem.* 24(1):74-79 (1981).
Orfanopoulos, et al., "Intermediates in the ene reactions of singlet oxygen and N-phenyl-1,2,4-triazoline-3,5-dione with olefins," *J. Am. Chem. Soc.* 112(9):3607-3614 (1990).
Orjales, et al., "New 2-Piperazinylbenzimidazole Derivatives as 5-HT Antagonists. Synthesis and Pharmacological Evaluation," *J. Med. Chem.* 40(4):586-593 (1997).
Ouadi, et al., "Synthesis of a novel bifunctional chelating agent for actinium complexation," *Tetrahedron Let.* 41:7207-7209 (2000).
PCT International Preliminary Report on Patentability and Written Opinion for International Application No. PCT/IB2008/001069 dated Oct. 27, 2009.
Prakash, et al., "A Novel Synthesis of Fluorinated Pyrido-[2,3-d]-Pyrimidine Derivatives," *J. Fluorine Chem.* 41:303-310 (1988).
Ramalingam, et al., "Syntheses of Some Isothiocyanatophenylboronic Acids," *Org. Preparations and Proc. Int.* 23(6):729-734 (1991).
Reetz, "Chemoselective and Position Specific Methylation of tert-Alkyl Halides with Methyltitanium(IV) Chlorides," *Angew. Chem. Int'l Ed. Engl.* 92(11):901-902 (1980).
Saudek, et al., "A Preliminary Trial of the Programmable Implantable Medication System for Insulin Delivery," *New England J. Medicine* 321:574-579 (1989).
Schlosser, et al., "α-Fluoro Analogues of Inflammation Inhibiting α-Arylpropionic Acids," *Tetrahedron* 52(24):8257-8262 (1996).
Sefton, M.V., "Implantable Pumps," *CRC Crit. Rev. Biomed. Eng.* 14(3):201-240 (1987).
Seltzer, et al., "A novel behavioral model of neuropathic pain disorders produced in rats by partial sciatic nerve injury," *Pain* 43:205-218 (1990).
Sharpless, et al., "The osmium-catalyzed asymmetric dihydroxylation: a new ligand class and a process improvement," *J. Org. Chem.* 57(10):2768-2771 (1992).
Singh, et al., "Concentration-Dependent Reactions of Deoxofluor with Arylglyoxal Hydrates: A New Route to Polyfluoro Ethers," *Org. Lett.* 3(17):2713-2715 (2001).
Stein, et al., "Unilateral Inflammation of the Hindpaw in Rats as a Model of Prolonged Noxious Stimulation: Alterations in Behavior and Nociceptive Thresholds," *Pharmacol. Biochem. & Behavior* 31:445-451 (1988).
Supplementary European Search Report dated Apr. 10, 2006 in connection with EP 1631285 B1.
Szallasi, et al., "TRPV1: a therapeutic target for novel analgesic drugs?," *Trends in Mol. Medicine* 12(11):545-554 (2006).
Szallasi, et al., "The vanilloid receptor TRPV1: 10 years from channel cloning to antagonist proof-of-concept," *Nature Revs. Drug Discovery* 6:357-372 & Corregendum (2007).
The Merck Manual of Medical Information, Berkow, Beers and Fletcher (eds.), New Jersey pp. 525-526 (1997).
The Merck Manual of Medical Information, Berkow, Beers and Fletcher (eds.), New Jersey pp. 528-530 (1997).
Thépot, et al., "A convenient synthesis of bromopentaarylcyclopentadienes containing methyl or fluorine substituents," *J. Organometallic Chem.* 627:179-188 (2001).
Treat, et al., "Liposome Encapsulated Doxorubicin Preliminary Results of Phase I and Phase II Trials," in *Liposomes in the Therapy of Infectious Disease and Cancer*, pp. 353-365 (Lopez-Berestein, et al., eds, Alan R. Liss, Inc., New York, 1989).
Van Der Werf, et al., "Mycolactones and *Mycobacterium ulcerans* disease," *Lancet* 362:1062-1064 (2003).
Van Tonder, et al., "Preparation and Physicochemical Characterization of 5 Niclosamide Solvates and 1 Hemisolvate,"*AAPS Pharm. Sci. Tech.* 5(1):86-95 (2004).

(56) References Cited

OTHER PUBLICATIONS

Vartanian, et al., "Synthesis of 4-Phenyl-4-formal Derivatives of Piperidine and Tetrahydropyran Series," *Arm. Khim. Zh.* (*Armenian Chem. J.*) 30(9):723-727 (1977).
West, "Solid Solutions," in *Solid State Chemistry and its Applications*, pp. 358 & 365 (John Wiley & Sons, Chichester, 1988).
Written Opinion dated Dec. 3, 2004 in connection with WO 2005/004866 A1.
Written Opinion dated Nov. 19, 2004 in connection with WO 2005/009988 A1.
Carey, et al., "Bond Energies, Lengths, and Dipoles," Tables 1.5-1.7 in *Advanced Organic Chemistry, Part A: Structure and Mechanisms*, Section 1.2. on pp. 14-15 (2007).
Duchowicz, et al., "QSPR Studies on Aqueous Solubilities of Drug-Like Compounds," *Int'l. J. Mol. Sci.* 10:2558-2577 (2009).
Extended European Search Report dated May 22, 2013 in connection with EP 2604598 A1.
Extended European Search Report dated May 22, 2013 in connection with EP 2604599 A1.
Meanwell, "Synopsis of Some Recent Tactical Application of Bioisosteres in Drug Design," *J. Med. Chem.* 54:2529-2591 (2011).
Patani, et al., "Bioisosterism: A Rational Approach in Drug Design," *Chem. Rev.* 96:3147-3176 (1996).

| Agonist Plate | 1 | 2 | 3 | 4 | 5 | 6 | 7 | 8 | 9 | 10 | 11 | 12 |
|---|---|---|---|---|---|---|---|---|---|---|---|---|
| A | Buffer | | | | | | | | | | | |
| B | $H_2SO_4$ 15.0 mM (final 3.0 mM) | | | | | | | | | | | |
| C | $H_2SO_4$ 15.5 mM (final 3.1 mM) | | | | | | | | | | | |
| D | $H_2SO_4$ 16.0 mM (final 3.2 mM) | | | | | | | | | | | |
| E | $H_2SO_4$ 16.5 mM (final 3.3 mM) | | | | | | | | | | | |
| F | $H_2SO_4$ 17.0 mM (final 3.4 mM) | | | | | | | | | | | |
| G | $H_2SO_4$ 17.5 mM (final 3.5 mM) | | | | | | | | | | | |
| H | $H_2SO_4$ 18.0 mM (final 3.6 mM) | | | | | | | | | | | |

*FIG. 1*

```
                        SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagatcttc gctggttgca cactgggcca ca                                 32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatcttc ggggacagtg acggttggat gt                                 32

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
ggatccagca aggatgaaga aatgg                                    25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtctgcgtg acgtcctcac ttct                                     24
```

TRPV1 ANTAGONISTS INCLUDING DIHYDROXY SUBSTITUENT AND USES THEREOF

This application is a continuation of application Ser. No. 14/498,724, filed Sep. 26, 2014, now U.S. Pat. No. 9,365,563, which is a continuation of application Ser. No. 13/852,913, filed Mar. 28, 2013, now U.S. Pat. No. 8,889,690, which is a divisional of application Ser. No. 12/110,155, filed Apr. 25, 2008, now U.S. Pat. No. 8,476,277, which claims the benefit under 35 U.S.C. § 119(e) of U.S. provisional application No. 60/926,661, filed Apr. 27, 2007, U.S. provisional application No. 60/930,036, filed May 11, 2007, U.S. provisional application No. 60/937,003, filed Jun. 21, 2007, and U.S. provisional application No. 60/962,409, filed Jul. 27, 2007, the contents of all of which are incorporated herein by reference.

1. FIELD OF THE INVENTION

The invention relates to compounds of formula I, and pharmaceutically acceptable derivatives thereof, compositions comprising an effective amount of a compound of formula I and methods for treating or preventing a condition such as pain, UI, an ulcer, IBD, and IBS, comprising administering to an animal in need thereof an effective amount of a compound of formula I.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (V. Di Marzo et al., *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenytoin), NMDA antagonists (e.g., ketamine, dextromethorphan), topical lidocaine (for post-herpetic neuralgia), and tricyclic antidepressants (e.g., fluoxetine, sertraline and amitriptyline).

UI is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

International publication no. WO 98/31677 describes a class of aromatic amines derived from cyclic amines that are useful as antidepressant drugs.

International publication no. WO 01/027107 describes a class of heterocyclic compounds that are sodium/proton exchange inhibitors.

International publication no. WO 99/37304 describes substituted oxoazaheterocycly compounds useful for inhibiting factor Xa.

U.S. Pat. No. 6,248,756 to Anthony et al. and international publication no. WO 97/38665 describe a class of piperidine-containing compounds that inhibit farnesyl-protein transferase (Ftase).

International publication no. WO 98/31669 describes a class of aromatic amines derived from cyclic amines useful as antidepressant drugs.

International publication no. WO 97/28140 describes a class of piperidines derived from 1-(piperazin-1-yl)aryl(oxy/amino)carbonyl-4-aryl-piperidine that are useful as 5-HT$_{1Db}$ receptor antagonists.

International publication no. WO 97/38665 describes a class of piperidine containing compounds that are useful as inhibitors of farnesyl-protein transferase.

U.S. Pat. No. 4,797,419 to Moos et al. describes a class of urea compounds for stimulating the release of acetylcholine and useful for treating symptoms of senile cognitive decline.

U.S. Pat. No. 5,891,889 describes a class of substituted piperidine compounds that are useful as inhibitors of farnesyl-protein transferase, and the farnesylation of the oncogene protein Ras.

U.S. Pat. No. 6,150,129 to Cook et al. describes a class of dinitrogen heterocycles useful as antibiotics.

U.S. Pat. No. 5,529,998 to Habich et al. describes a class of benzooxazolyl- and benzothiazolyloxazolidones useful as antibacterials.

International publication no. WO 01/57008 describes a class of 2-benzothiazolyl urea derivatives useful as inhibitors of serine/threonine and tyrosine kinases.

International publication no. WO 02/08221 describes aryl piperazine compounds useful for treating chronic and acute pain conditions, itch, and urinary incontinence.

International publication no. WO 00/59510 describes aminopyrimidines useful as sorbitol dehydrogenase inhibitors.

Japanese patent application no. 11-199573 to Kiyoshi et al. describes benzothiazole derivatives that are neuronal 5HT3 receptor agonists in the intestinal canal nervous system and useful for treating digestive disorders and pancreatic insufficiency.

German patent application no 199 34 799 to Rainer et al. describes a chiral-smectic liquid crystal mixture containing compounds with 2 linked (hetero)aromatic rings or compounds with 3 linked (hetero)aromatic rings.

M. Chu-Moyer et al., *J. Med. Chem.* 45:511-528 (2002) describes heterocycle-substituted piperazino-pyrimidines useful as sorbitol dehydrogenase inhibitors.

B. G. Khadse et al., *Bull. Haff Instt.* 1(3):27-32 (1975) describes 2-(N$^4$-substituted-N$^1$-piperazinyl) pyrido(3,2-d) thiazoles and 5-nitro-2-(N$^4$-substituted-N$^1$-piperazinyl)benzothiazoles useful as anthelmintic agents.

U.S. Patent Application Publication No. US 2004/0186111 A1 and International publication no. WO 2004/058754 A1 describe a class of compounds that are useful for treating pain.

U.S. Patent Application Publication No. US 2006/0199824-A1 and International publication no. WO 2005/009987 A1 describe a class of compounds that are useful for treating pain.

U.S. Patent Application Publication No. US 2006/0128717 A1 and International publication no. WO 2005/009988 A1 describe a class of compounds that are useful for treating pain.

There remains, however, a clear need in the art for new drugs useful for treating or preventing pain, UI, an ulcer, IBD, and IBS. Citation of any reference in Section 2 of this application is not to be construed as an admission that such reference is prior art to the present application.

3. SUMMARY OF THE INVENTION

The invention encompasses compounds of formula I:

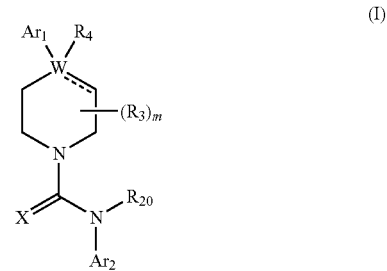

or a pharmaceutically acceptable derivative thereof, where
X is O, S, N—CN, N—OH, or N—OR$_{10}$;
W is N or C;
the dashed line denotes the presence or absence of a bond, and when the dashed line denotes the presence of a bond or W is N then R$_4$ is absent, otherwise R$_4$ is —H, —OH, —OCF$_3$, -halo, —(C$_1$-C$_6$)alkyl, —CH$_2$OH, —CH$_2$Cl, —CH₂Br, —CH₂I, —CH₂F, —CH(halo)₂, —CF₃, —OR₁₀, —SR₁₀, —COOH, —COOR₁₀, —C(O)R₁₀, —C(O)H, —OC(O)R₁₀, —OC(O)NHR₁₀, —NHC(O)R₁₃, —CON(R₁₃)₂, —S(O)₂R₁₀, or —NO₂;

$R_{10}$ is —(C₁-C₄)alkyl;

each $R_{13}$ is independently —H, —(C₁-C₄)alkyl, —(C₁-C₄)alkenyl, —(C₁-C₄)alkynyl, or -phenyl;

$Ar_1$ is

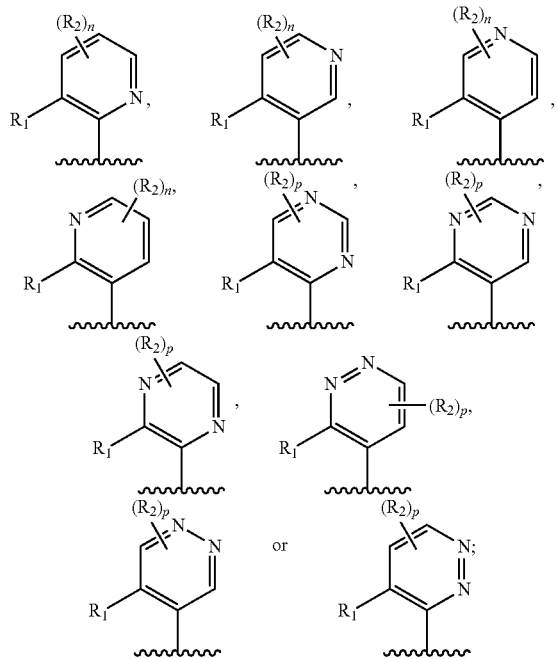

$Ar_2$ is

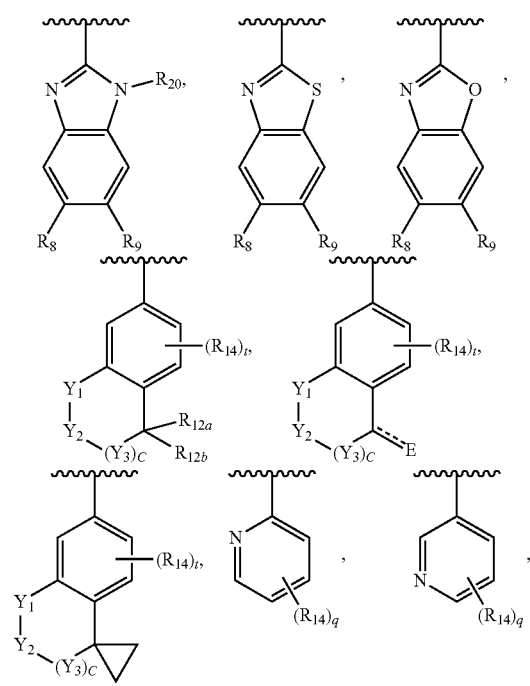

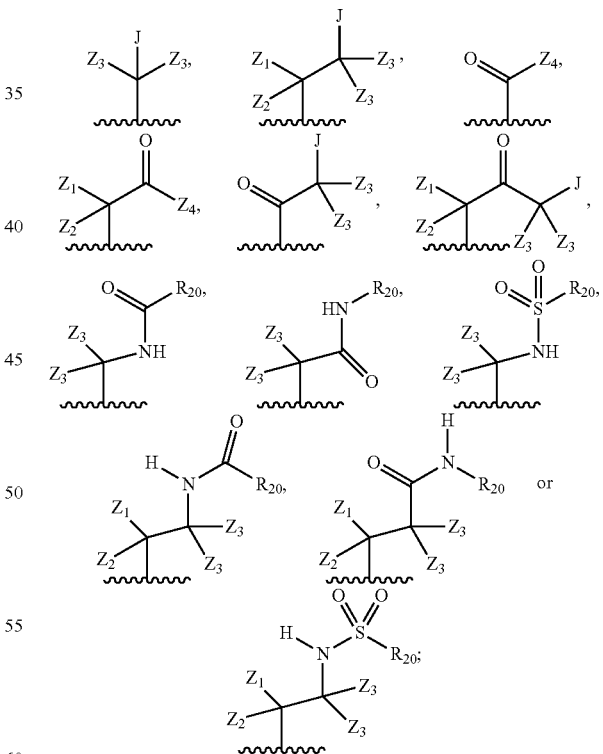

c is the integer 0, 1, or 2;

$Y_1$, $Y_2$, and $Y_3$ are independently C, N, or O; wherein no more than one of $Y_1$, $Y_2$, or $Y_3$ can be O, and for each $Y_1$, $Y_2$, and $Y_3$ that is N, the N is bonded to one $R_{21}$ group, and for each $Y_1$, $Y_2$, and $Y_3$ that is C, the C is bonded to two $R_{20}$ groups, provided that there are no more than a total of two (C₁-C₆)alkyl groups substituted on all of $Y_1$, $Y_2$, and $Y_3$;

$R_{12a}$ and $R_{12b}$ are independently —H or —(C₁-C₆)alkyl;

E is =O, =S, =CH(C₁-C₅)alkyl, =CH(C₁-C₅)alkenyl, —NH(C₁-C₆)alkyl, or =N—OR₂₀;

$R_1$ is —H, -halo, —(C₁-C₄)alkyl, —NO₂, —CN, —OH, —OCH₃, —NH₂, —C(halo)₃, —CH(halo)₂, —CH₂(halo), —OC(halo)₃, —OCH(halo)₂, or —OCH₂(halo);

each $R_2$ is independently:
(a) -halo, —OH, —O(C₁-C₄)alkyl, —CN, —NO₂, —NH₂, —(C₁-C₁₀)alkyl, —(C₂-C₁₀)alkenyl, —(C₂-C₁₀)alkynyl, or -phenyl, or
(b) a group of formula Q;
wherein Q is $Z_1$ is —H, —OR₇, —SR₇, —CH₂—OR₇, —CH₂—SR₇, —CH₂—N(R₂₀)₂, or -halo;

$Z_2$ is —H, —(C₁-C₆)alkyl, —(C₂-C₆)alkenyl, —(C₂-C₆)alkynyl, —CH₂—OR₇, -phenyl, or -halo;

each $Z_3$ is independently —H, —(C₁-C₆)alkyl, —(C₂-C₆)alkenyl, —(C₂-C₆)alkynyl, or -phenyl;

$Z_4$ is —H, —OH, —OR$_{20}$, —($C_1$-$C_6$)alkyl, or —N(R$_{20}$)$_2$;
J is —OR$_{20}$, —SR$_{20}$, —N(R$_{20}$)$_2$, or —CN;
provided that at least one R$_2$ group is a group of formula Q, and provided that when $Z_1$ is —OR$_7$ or —SR$_7$, then $Z_2$ is not -halo;
each R$_3$ is independently:
(a) —H, —CH$_2$OR$_7$, or —(C$_1$-C$_6$)alkyl; or
(b) two R$_3$ groups together form a (C$_2$-C$_6$)bridge, which is unsubstituted or substituted with 1, 2 or 3 independently selected R$_8$ groups, and which bridge optionally contains —HC═CH— within the (C$_2$-C$_6$)bridge; or
(c) two R$_3$ groups together form a —CH$_2$—N(R$_a$)—CH$_2$— bridge, a

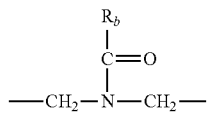

bridge, or a

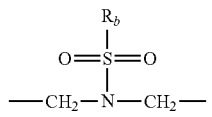

bridge;
R$_a$ is —H, —(C$_1$-C$_6$)alkyl, —(C$_3$-C$_8$)cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;
R$_b$ is:
(a) —H, —(C$_1$-C$_6$)alkyl, —(C$_3$-C$_8$)cycloalkyl, -(3- to 7-membered)heterocycle, —N(R$_c$)$_2$, —N(R$_c$)—(C$_3$-C$_8$)cycloalkyl, or —N(R$_c$)-(3- to 7-membered)heterocycle; or
(b) -phenyl, -(5- or 6-membered)heteroaryl, —N(R$_c$)-phenyl, or —N(R$_c$)-(5- to 10-membered)heteroaryl, each of which is unsubstituted or substituted with 1, 2 or 3 independently selected R$_7$ groups;
each R$_c$ is independently —H or —(C$_1$-C$_4$)alkyl;
each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$)alkyl-N(R$_{20}$)$_2$, or —CON(R$_{20}$)$_2$;
each R$_8$ and R$_9$ is independently:
(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, or -phenyl, each of which is unsubstituted or substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH═NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;
each R$_{11}$ is independently —CN, —OH, —(C$_1$-C$_6$)alkyl, —(C$_2$-C$_6$)alkenyl, -halo, —N$_3$, —NO$_2$, —N(R$_7$)$_2$, —CH═NR$_7$, —NR$_7$OH, —OR$_7$, —C(O)R$_7$, —C(O)OR$_7$, —OC(O)R$_7$, or —OC(O)OR$_7$;
each R$_{14}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, —(C$_1$-C$_6$)alkoxy-(C$_1$-C$_6$)alkyl, -phenyl, —C(halo)$_3$, —CH(halo)$_2$, —CH$_2$(halo), -(3- to 7-membered)heterocycle, —(C$_1$-C$_6$)haloalkyl, —(C$_2$-C$_6$)haloalkenyl, —(C$_2$-C$_6$)haloalkynyl, —(C$_2$-C$_6$)hydroxyalkyl, —(C$_2$-C$_6$)hydroxyalkynyl, —(C$_1$-C$_6$)alkoxy(C$_2$-C$_6$)alkyl, —(C$_1$-C$_6$)alkoxy(C$_2$-C$_6$)alkenyl, —(C$_1$-C$_6$)alkoxy(C$_2$-C$_6$)alkynyl, —(C$_1$-C$_6$)alkoxy(C$_3$-C$_8$)cycloalkyl, —CN, —OH, -halo, —OC(halo)$_3$, —N$_3$, —NO$_2$, —CH═NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)COR$_7$, —C(O)R$_7$, —C(O)OR$_7$, —OC(O)R$_7$, —OC(O)OR$_7$, —S(O)R$_7$, or —S(O)$_2$R$_7$, —S(O)$_2$N(R$_7$)$_2$, —SO$_2$C(halo)$_3$, —SO$_2$(3- to 7-membered)heterocycle, —CON(R$_7$)$_2$, —(C$_1$-C$_5$)alkyl-C═NOR$_7$, —(C$_1$-C$_5$)alkyl-C(O)—N(R$_7$)$_2$, —(C$_1$-C$_6$)alkyl-NHSO$_2$N(R$_7$)$_2$, or —(C$_1$-C$_6$)alkyl-C(═NH)—N(R$_7$)$_2$;
each R$_{20}$ is independently —H, —(C$_1$-C$_6$)alkyl, or —(C$_3$-C$_8$)cycloalkyl;
each R$_{21}$ is independently —H, —(C$_1$-C$_6$)alkyl,

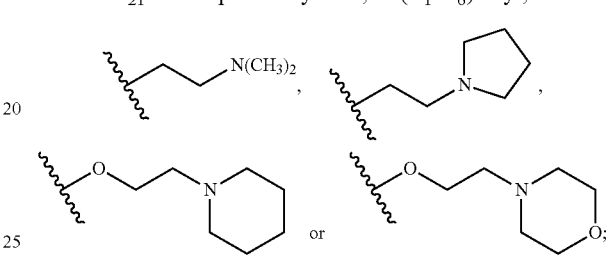

each halo is independently —F, —Cl, —Br, or —I;
n is the integer 1, 2, or 3;
p is the integer 1 or 2
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
m is the integer 0, 1, or 2.

Compounds of formula I are potent at TRPV1 receptors, and are highly soluble in aqueous solutions at either pH 6.8 or pH 1.2.

A compound of formula I, or a pharmaceutically acceptable derivative thereof, is useful for treating or preventing pain, UI, an ulcer, IBD, or IBS (each being a "Condition") in an animal.

The invention also relates to compositions comprising an effective amount of a compound of formula I, or a pharmaceutically acceptable derivative thereof, and a pharmaceutically acceptable carrier or excipient. The compositions are useful for treating or preventing a Condition in an animal.

The invention further relates to methods for treating a Condition comprising administering to an animal in need thereof an effective amount of a compound of formula I, or a pharmaceutically acceptable derivative thereof.

The invention further relates to use of a compound of formula I in the manufacture of a medicament for treating and/or preventing a Condition.

The invention further relates to methods for preventing a Condition comprising administering to an animal in need thereof an effective amount of a compound of formula I, or a pharmaceutically acceptable derivative thereof.

The invention still further relates to methods for inhibiting Transient Receptor Potential Vanilloid 1 ("TRPV1," formerly known as Vanilloid Receptor 1 or VR1) function in a cell, comprising contacting a cell capable of expressing TRPV1 with an effective amount of a compound of formula I, or a pharmaceutically acceptable derivative thereof.

The invention still further relates to a method for preparing a composition comprising the step of admixing a compound of formula I, or a pharmaceutically acceptable derivative thereof, and a pharmaceutically acceptable carrier or excipient.

The invention still further relates to a kit comprising a container containing an effective amount of a compound of formula I, or a pharmaceutically acceptable derivative thereof.

In one embodiment, preferred compounds of formula I are compounds of formula IA:

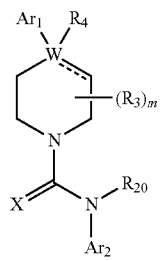
(IA)

or a pharmaceutically acceptable derivative thereof, where the dashed line, W, X, $Ar_1$, $Ar_2$, $R_3$, $R_4$, $R_{20}$, and m are as defined above for compounds of formula I, wherein Q is

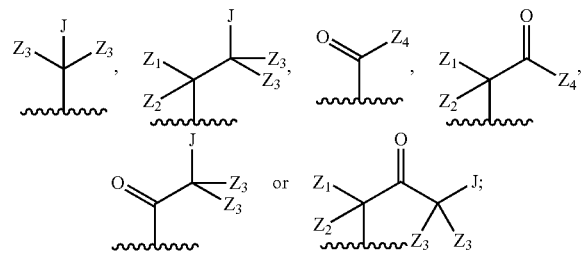

and wherein $Z_1$, $Z_2$, $Z_3$, $Z_4$, and J are as defined above for compounds of formula I.

Preferred compounds of formula I are compounds of formula II:

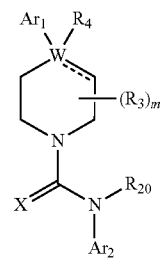
(II)

or a pharmaceutically acceptable derivative thereof, where the dashed line, W, X, $Ar_1$, $Ar_2$, $R_3$, $R_4$, $R_{20}$, and m are as defined above for compounds of formula I, wherein Q is

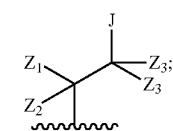

$Z_1$ is —OH, —SH, —N($R_{20}$)$_2$, —CH$_2$—OH, —CH$_2$—SH, or —CH$_2$—N($R_{20}$)$_2$;

$Z_2$ is —H, —CH$_3$, or —CH$_2$—OR$_7$;

each $Z_3$ is independently —H or —CH$_3$; and

J is —OH, —SH, or —N($R_{20}$)$_2$.

Compounds of formula II are highly soluble in aqueous solutions at either pH 6.8 or pH1.2, are very potent at the TRPV1 receptor, have good bioavailability, and have a good therapeutic index.

Preferred compounds of formula II are compounds of formula III:

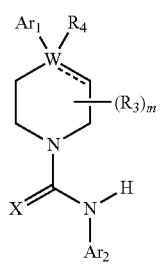
(III)

or a pharmaceutically acceptable derivative thereof, where the dashed line, W, X, $Ar_1$, $Ar_2$, $R_3$, $R_4$, and m are as defined above for compounds of formula I, wherein $Ar_1$ is:

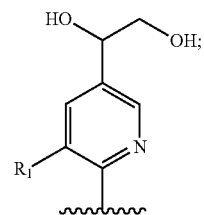

$R_1$ is —Cl, —F, or —CF$_3$;

wherein $Ar_2$ is:

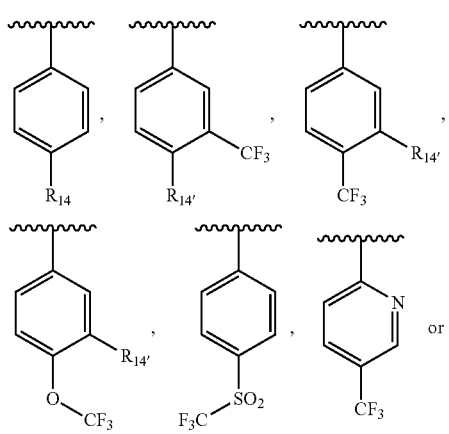

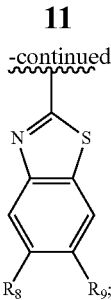

$R_{14}$ is —H, —Cl, —F, —Br, —CF$_3$, —OCF$_3$, —(C$_1$-C$_6$) alkyl, —SO$_2$CF$_3$, —SO$_2$(C$_1$-C$_6$)alkyl, —OCH$_3$, —OCH$_2$CH$_3$, or —OCH(CH$_3$)$_2$, and optionally is —H, —CF$_3$, —OCF$_3$, —Cl, or —F;

$R_{14'}$ is —H, —Cl, —F, —Br, —CF$_3$, —OCF$_3$, —(C$_1$-C$_6$) alkyl, —SO$_2$CF$_3$, —SO$_2$(C$_1$-C$_6$)alkyl, —OCH$_3$, —OCH$_2$CH$_3$, or —OCH(CH$_3$)$_2$, and optionally is —H, —CF$_3$, —OCF$_3$, —Cl, or —F; and each $R_8$ and $R_9$ is independently —H, —Cl, —Br, —F, —CH$_3$, —OCH$_3$, —OCH$_2$CH$_3$, —CF$_3$, —OCF$_3$, iso-propyl, or tert-butyl.

Compounds of formula III are highly soluble in aqueous solutions at either pH 6.8 or pH 1.2, are exceptionally potent at TRPV1 receptors, have excellent bioavailability, have a high therapeutic index, and are believed to be highly efficacious in animals for the treatment of pain.

The invention can be understood more fully by reference to the following detailed description and illustrative examples, which are intended to exemplify non-limiting embodiments of the invention.

4. BRIEF DESCRIPTION OF THE FIGURES

FIG. 1. 96-well plate with different agonist solutions (Agonist Plate). Seven different sulfuric acid solutions, or agonist solutions, with different sulfuric acid (H$_2$SO$_4$) concentrations (of from 15.0 mM to 18 mM as indicated) were used for the pH assay as indicated. For the wells in row A, measuring buffer alone was used. The final concentration of sulfuric acid in the wells for each row, after a 1:4 dilution of the agonist solution, is also indicated in each row in parenthesis.

FIG. 2. pH dependent Ca$^{2+}$ responses in TRPV1/CHO cells. Ca$^{2+}$ influx into TRPV1/CHO cells as measured by Fura-2 AM fluorescence is indicated by the graph within each rectangular field. The graph presents the fluorescence intensity over time starting from the addition of agonist solution. Each rectangular field presents one experiment performed in one well of a 96-well plate. Each row presents six experiments performed at the same final sulfuric acid concentration; the final sulfuric acid concentration is indicated at the left. Actual pH values were measured after the experiment and are indicated above the graph. No antagonists were added to the cell culture. Final sulfuric acid concentrations of 3.2 and 3.3 mM produced an appropriate Ca$^{2+}$ response and were selected for subsequent assays. These final sulfuric acid concentrations can be obtained by 1:4 dilutions of agonist solution with sulfuric acid concentrations of 16.0 mM or 16.5 mM, respectively (see FIG. 1).

Figure 3:
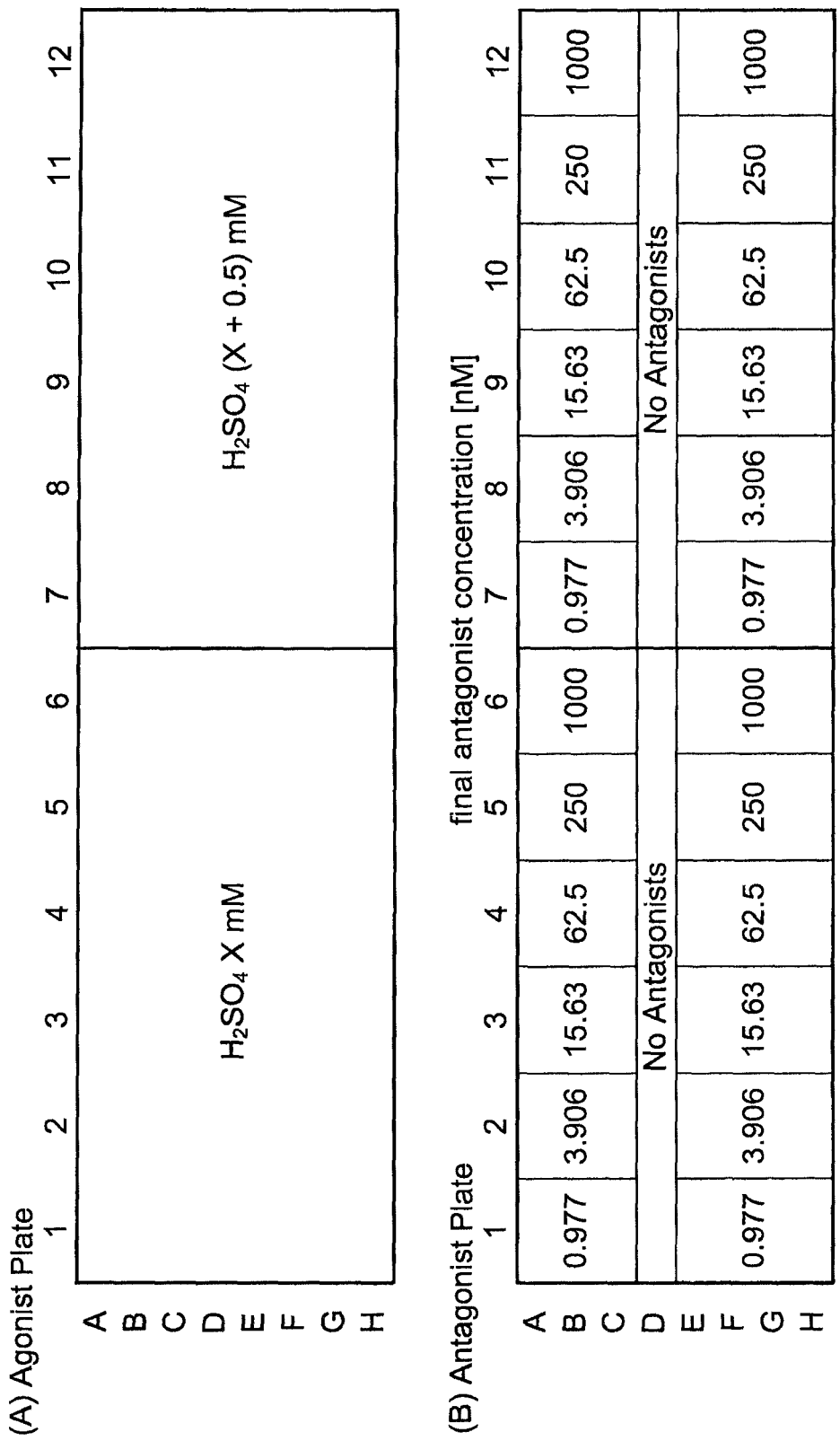

FIG. 3. (A) A 96-well plate with two different sulfuric acid concentrations. Wells in columns 1 to 6 had one final sulfuric acid concentration; wells in columns 7 to 12 had a different final sulfuric acid concentration. The final sulfuric acid concentration was reached by 1:4 dilution of two different agonist solutions with sulfuric acid concentrations of X mM and (X+0.5) mM, respectively. In the experiment described in Section 2 of Protocol 2, X was determined to be 16 mM. (B) A 96-well plate with different test compound, or antagonist, concentrations indicated in nM. Only one kind of test compound was applied per 96-well plate. Since two different sulfuric acid concentrations were used (columns 1-6 vs. columns 7-12), seven wells were tested for each combination of test compound concentration and agonist solution (e.g., wells A1, B1, C1, E1, F1, G1, and H1 were tested for test compound concentration 0.977 nM and agonist solution with sulfuric acid solution X mM). The wells in row D did not include an antagonist in order to measure the maximal Ca$^{2+}$ response.

5. DETAILED DESCRIPTION OF THE INVENTION

5.1 Compounds of Formula I

The invention encompasses compounds of formula I:

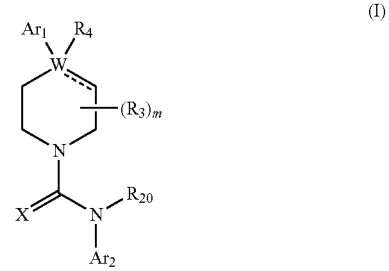

(I)

or a pharmaceutically acceptable derivative thereof, where W, X, Ar$_1$, Ar$_2$, R$_3$, R$_4$, R$_{20}$, and m are as defined above for compounds of formula I.

Certain embodiments of formula I are presented below.

In one embodiment, a compound of formula I is a pharmaceutically acceptable derivative of a compound of formula I.

In another embodiment, a compound of formula I is a compound of formula I wherein the derivative is a pharmaceutically acceptable salt.

In another embodiment, a compound of formula I is a pharmaceutically acceptable salt of a compound of formula I.

In another embodiment, Ar$_1$ is a pyridyl group.
In another embodiment, Ar$_1$ is a pyrimidinyl group.
In another embodiment, Ar$_1$ is a pyrazinyl group.
In another embodiment, Ar$_1$ is pyridazinyl group.
In another embodiment, W is C.
In another embodiment, W is N.
In another embodiment, X is O.
In another embodiment, X is S.
In another embodiment, X is N—CN.
In another embodiment, X is N—OH.
In another embodiment, X is N—OR$_{10}$.
In another embodiment, Ar$_2$ is a benzoimidazolyl group.
In another embodiment, Ar$_2$ is a benzothiazolyl group.
In another embodiment, Ar$_2$ is a benzooxazolyl group.
In another embodiment, Ar$_2$ is

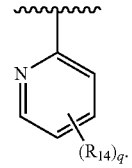

In another embodiment, Ar$_2$ is

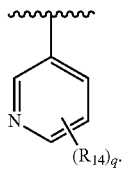

In another embodiment, Ar$_2$ is

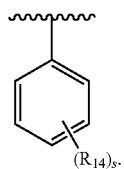

In another embodiment, Ar$_2$ is

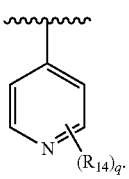

In another embodiment, Ar$_2$ is

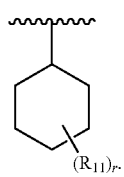

In another embodiment, Ar$_2$ is

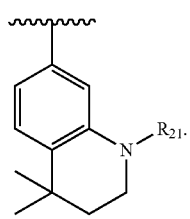

In another embodiment, Ar$_2$ is

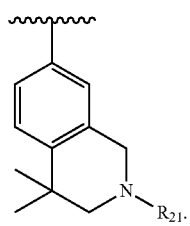

In another embodiment, Ar$_2$ is

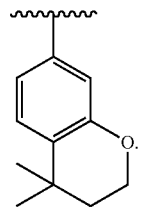

In another embodiment, n or p is 1.
In another embodiment, n or p is 2.
In another embodiment, n is 3.
In another embodiment, m is 2.
In another embodiment, each R$_3$ is independently —H, or —(C$_1$-C$_6$)alkyl.
In another embodiment, two R$_3$ groups together form a (C$_2$-C$_6$)bridge, which is unsubstituted or substituted with 1, 2 or 3 independently selected R$_8$ groups, and which bridge optionally contains —HC=CH— within the (C$_2$-C$_6$)bridge.
In another embodiment, two R$_3$ groups together form a (C$_2$-C$_6$)bridge, which is unsubstituted or substituted with an R$_8$ group, and which bridge optionally contains —HC=CH— within the (C$_2$-C$_6$)bridge.
In another embodiment, two R$_3$ groups together form a (C$_2$-C$_3$)bridge, which is unsubstituted or substituted with an R$_8$ group, and which bridge optionally contains —HC=CH— within the (C$_2$-C$_3$)bridge.
In another embodiment, two R$_3$ groups together form a (C$_2$-C$_3$)bridge, which is unsubstituted and which bridge optionally contains —HC=CH— within the (C$_2$-C$_3$)bridge.
In another embodiment, two R$_3$ groups together form a (C$_2$)bridge, a —HC=CH— bridge, or a (C$_3$)bridge each of which is unsubstituted.
In another embodiment, two R$_3$ groups together form a (C$_2$-C$_6$)bridge, which is unsubstituted or substituted with 1, 2 or 3 independently selected R$_8$ groups, which bridge optionally contains —HC=CH— within the (C$_2$-C$_6$)bridge, and which bridge joins positions 2 and 6 of the piperidine, 1,2,3,6-tetrahydropyridine or piperazine ring.
In another embodiment, two R$_3$ groups together form a (C$_2$-C$_6$)bridge, which is unsubstituted or substituted with an R$_8$ group, which bridge optionally contains —HC=CH— within the (C$_2$-C$_6$)bridge, and which bridge joins positions 2 and 6 of the piperidine, 1,2,3,6-tetrahydropyridine or piperazine ring.
In another embodiment, two R$_3$ groups together form a (C$_2$-C$_3$)bridge, which is unsubstituted or substituted with an R$_8$ group, which bridge optionally contains —HC=CH— within the (C$_2$-C$_3$)bridge, and which bridge joins positions 2 and 6 of the piperidine, 1,2,3,6-tetrahydropyridine or piperazine ring.
In another embodiment, two R$_3$ groups together form a (C$_2$-C$_3$)bridge, which is unsubstituted, which bridge optionally contains —HC=CH— within the (C$_2$-C$_3$)bridge, and which bridge joins positions 2 and 6 of the piperidine, 1,2,3,6-tetrahydropyridine or piperazine ring.
In another embodiment, two R$_3$ groups together form a (C$_2$)bridge, a —HC=CH— bridge, or a (C$_3$)bridge each of which is unsubstituted, and which bridge joins positions 2 and 6 of the piperidine, 1,2,3,6-tetrahydropyridine or piperazine ring.

In another embodiment, two $R_3$ groups together form a —$CH_2$—$N(R_a)$—$CH_2$— bridge (B1), a $$\begin{array}{c} R_b \\ | \\ C=O \\ | \\ -CH_2-N-CH_2- \end{array}$$

bridge (B2), or a $$\begin{array}{c} R_b \\ | \\ O=S=O \\ | \\ -CH_2-N-CH_2- \end{array}$$

bridge (B3);

wherein $R_a$ is —H, —$(C_1$-$C_6)$alkyl, —$(C_3$-$C_8)$cycloalkyl, —$CH_2$—C(O)—$R_c$, —$(CH_2)$—C(O)—$OR_c$, —$(CH_2)$—C(O)—$N(R_c)_2$, —$(CH_2)_2$—O—$R_c$, —$(CH_2)_2$—$S(O)_2$—$N(R_c)_2$, or —$(CH_2)_2$—$N(R_c)S(O)_2$—$R_c$;

$R_b$ is:
(a) —H, —$(C_1$-$C_6)$alkyl, —$(C_3$-$C_8)$cycloalkyl, -(3- to 7-membered)heterocycle, —$N(R_c)_2$, —$N(R_c)$—$(C_3$-$C_8)$cycloalkyl, or —$N(R_c)$-(3- to 7-membered)heterocycle; or
(b) -phenyl, -(5- or 6-membered)heteroaryl, —$N(R_c)$-phenyl, or —$N(R_c)$-(5- to 10-membered)heteroaryl, each of which is unsubstituted or substituted with 1, 2 or 3 independently selected $R_7$ groups; and each $R_c$ is independently —H or —$(C_1$-$C_4)$alkyl.

In another embodiment, $R_a$ is —H, —$(C_1$-$C_6)$alkyl, —$(C_3$-$C_8)$cycloalkyl, —$(CH_2)$—C(O)—$N(R_c)_2$, —$(CH_2)_2$—$S(O)_2$—$N(R_c)_2$, or —$(CH_2)_2$—$N(R_c)S(O)_2$—$R_c$.

In another embodiment, $R_a$ is —H, —$(C_1$-$C_6)$alkyl, —$(C_3$-$C_8)$cycloalkyl, or —$(CH_2)$—C(O)—$N(R_c)_2$.

In another embodiment, $R_a$ is —H, —$(C_1$-$C_6)$alkyl, or —$(C_3$-$C_8)$cycloalkyl.

In another embodiment, $R_b$ is —H, —$(C_3$-$C_8)$cycloalkyl, or -(3- to 7-membered)heterocycle.

In another embodiment, $R_b$ is —H, —$N(R_c)_2$, —$N(R_c)$—$(C_3$-$C_8)$cycloalkyl, or —$N(R_c)$-(3- to 7-membered)heterocycle.

In another embodiment, $R_b$ is —H, —$(C_1$-$C_6)$alkyl, or —$(C_3$-$C_8)$cycloalkyl.

In another embodiment, $R_b$ is -phenyl or —$N(R_c)$-phenyl, each of which is unsubstituted or substituted with 1, 2 or 3 independently selected $R_7$ groups.

In another embodiment, $R_b$ is -(5- or 6-membered)heteroaryl or —$N(R_c)$-(5- to 10-membered)heteroaryl, each of which is unsubstituted or substituted with 1, 2 or 3 independently selected $R_7$ groups.

In another embodiment, $R_b$ is —H, —$(C_1$-$C_6)$alkyl, -phenyl, or -(5- or 6-membered)heteroaryl.

In another embodiment, $R_a$ and $R_b$ are each independently —H or —$(C_1$-$C_6)$alkyl.

In another embodiment, $R_a$ and $R_b$ are —$CH_3$.

In another embodiment, each $R_c$ is independently —H or —$CH_3$.

In another embodiment, the B1, B2, or B3 bridge joins positions 2 and 6 of the piperidine, 1,2,3,6-tetrahydropyridine or piperazine ring.

In another embodiment, two $R_3$ groups form a bicyclo group to give one of the following structures

[Two bicyclic structures shown with substituents $Ar_1$, $R_4$, W, N, X, $R_{20}$, $Ar_2$]

In another embodiment, m is 1.
In another embodiment, m is 0.
In another embodiment, s or q is 0.
In another embodiment, s or q is 1.
In another embodiment, s or q is 2.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —$C(halo)_3$.
In another embodiment, $R_1$ is —$CF_3$.
In another embodiment, $R_1$ is —$CH(halo)_2$.
In another embodiment, $R_1$ is —$CH_2(halo)$.
In another embodiment, $Ar_1$ is a pyridyl group and n is 1.
In another embodiment, $Ar_1$ is a pyrazinyl group and p is 1.
In another embodiment, $Ar_1$ is a pyrimidinyl group and p is 1.
In another embodiment, $Ar_1$ is a pyridazinyl group and p is 1.
In another embodiment, when n and p are 1, then $R_2$ must be Q.
In another embodiment, Q is

[Chemical structures showing various Q group options with $Z_1$, $Z_2$, $Z_3$, $Z_4$, J, $R_{20}$, NH, O substituents]

or

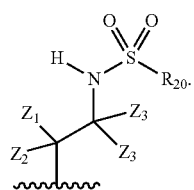
In another embodiment, Q is
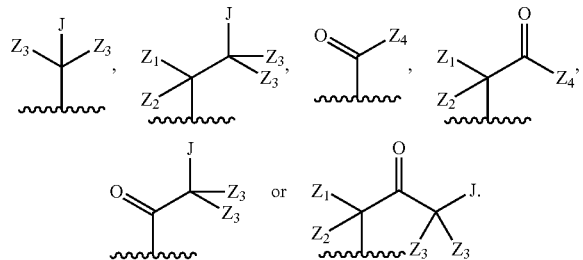
In another embodiment, Q is
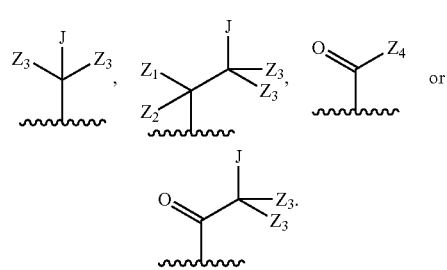
In another embodiment, Q is
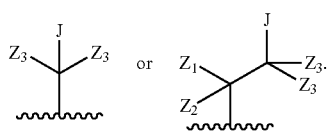
In another embodiment, Q is
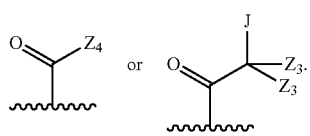
In another embodiment, Q is
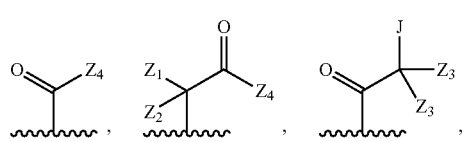
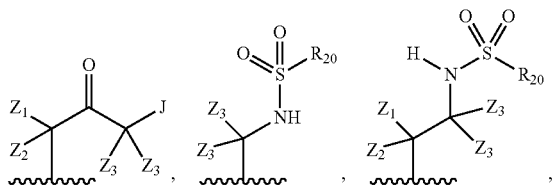
In another embodiment, Q is
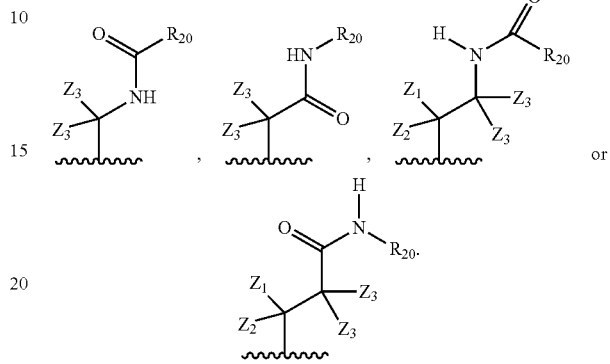
In another embodiment, Q is
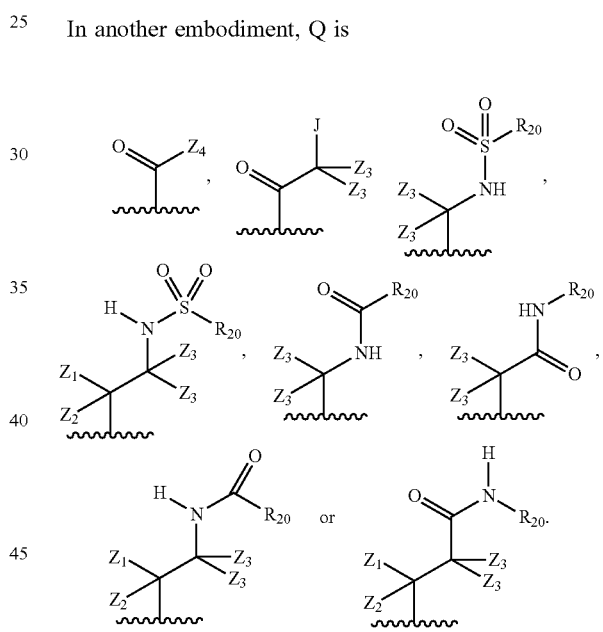
In another embodiment, Q is
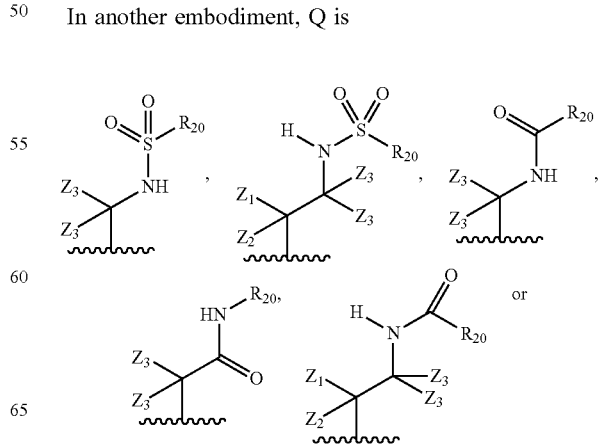

-continued

In another embodiment, Q is

In another embodiment, Q is or

In another embodiment, Q is or

In another embodiment, Q is

In another embodiment, Q is

In another embodiment, Q is

In another embodiment, Q is

In another embodiment, Q is

In another embodiment, J is —$OR_{20}$, —$SR_{20}$ or —$N(R_{20})_2$.
In another embodiment, J is —$OR_{20}$.
In another embodiment, J is —OH.
In another embodiment, J is —CN.
In another embodiment, $Z_1$ is —H.
In another embodiment, $Z_1$ is —OH.
In another embodiment, $Z_1$ is —$OCH_3$.
In another embodiment, $Z_1$ is —$CH_2OH$.
In another embodiment, $Z_2$ is —$CH_2$—$OR_7$.
In another embodiment, $Z_2$ is —$CH_2OH$.
In another embodiment, $Z_2$ is —H, —$(C_1$-$C_6)$alkyl, —$(C_2$-$C_6)$alkenyl, —$(C_2$-$C_6)$alkynyl, -phenyl, or -halo.
In another embodiment, $Z_2$ is —H.
In another embodiment, $Z_2$ is —$CH_3$.
In another embodiment, $Z_3$ is —H.
In another embodiment, $Z_3$ is —$CH_3$.
In another embodiment, $Z_4$ is —H.
In another embodiment, $Z_4$ is —$(C_1$-$C_6)$alkyl.
In another embodiment, $Z_4$ is —$N(R_{20})_2$.
In another embodiment $Z_4$ is —$OR_{20}$.
In another embodiment, $Z_4$ is —OH.
In another embodiment, Q is In another embodiment, Q is [structures shown].

In another embodiment, Q is [structures shown].

In another embodiment, Q is [structures shown].

In another embodiment, Q is [structures shown].

In another embodiment, Q is [structures shown].

In another embodiment, Q is [structure shown].

In another embodiment, m is 1 and $R_3$ is —$(C_1-C_6)$alkyl.
In another embodiment, m is 1 and $R_3$ is —$CH_3$ or —$CH_2CH_3$.
In another embodiment, m is 1 and $R_3$ is —$CH_3$.
In another embodiment, m is 1 and $R_3$ is —$CH_2OH$.
In another embodiment, m is 0.
In another embodiment, $R_4$ is —OH.
In another embodiment, $R_4$ is —$OCF_3$
In another embodiment, $R_4$ is -halo.
In another embodiment, $R_4$ is —F.
In another embodiment, $R_4$ is —Cl.
In another embodiment, $R_4$ is —$(C_1-C_6)$alkyl.
In another embodiment, $R_4$ is —$CH_3$.
In another embodiment, $R_4$ is —$CH_2OH$.
In another embodiment, $R_4$ is —$CH_2Cl$.
In another embodiment, $R_4$ is —$CH_2Br$.
In another embodiment, $R_4$ is —$CH_2I$.
In another embodiment, $R_4$ is —$CH_2F$.
In another embodiment, $R_4$ is —$CH(halo)_2$.
In another embodiment, $R_4$ is —$CF_3$.
In another embodiment, $R_4$ is —$NO_2$.
In another embodiment, $R_4$ is —$OR_{10}$.
In another embodiment, $R_4$ is —$SR_{10}$.

In another embodiment, $R_4$ is —$C(O)R_{10}$.
In another embodiment, $R_4$ is —COOH.
In another embodiment, $R_4$ is —C(O)H.
In another embodiment, $R_4$ is —$COOR_{10}$.
In another embodiment, $R_4$ is —$OC(O)R_{10}$.
In another embodiment, $R_4$ is —$SO_2R_{10}$.
In another embodiment, $R_4$ is —$OC(O)NHR_{10}$.
In another embodiment, $R_4$ is —$NHC(O)R_{13}$.
In another embodiment, $R_4$ is —$CON(R_{13})_2$.
In another embodiment, each $R_{20}$ is independently —H or —$(C_1-C_6)$alkyl.
In another embodiment, each $R_{20}$ is —H.
In another embodiment, each $R_{20}$ is —$(C_1-C_6)$alkyl.
In another embodiment, $Ar_2$ is a benzothiazolyl, benzoimidazolyl, or benzooxazolyl group; and at least one of $R_8$ and $R_9$ is —H.
In another embodiment, $Ar_2$ is a benzothiazolyl, benzoimidazolyl, or benzooxazolyl group; and at least one of $R_8$ and $R_9$ is not —H.
In another embodiment, $Ar_2$ is a benzothiazolyl, benzoimidazolyl, or benzooxazolyl group; and at least one of $R_8$ and $R_9$ is -halo.
In another embodiment, $Ar_2$ is

[structure: phenyl with $(R_{14})_s$]

s is 1 and $R_{14}$ is —$(C_1-C_6)$alkyl, -halo, —$C(halo)_3$, —$OC(halo)_3$, —$OR_7$, —$N(R_7)_2$, —$SO_2R_7$, or —$SO_2C(halo)_3$.

In another embodiment, $Ar_2$ is

[structure: phenyl with $(R_{14})_s$]

s is 2, and each $R_{14}$ is independently —$(C_1-C_6)$alkyl, -halo, —$C(halo)_3$, —$OC(halo)_3$, —$OR_7$, —$N(R_7)_2$, —$SO_2R_7$, or —$SO_2C(halo)_3$.

In another embodiment, the invention encompasses compounds of formula I.4:

(I.4)

or a pharmaceutically acceptable salt thereof, where
X is O, S, N—CN, N—OH, or N—$OR_{10}$;
W is N or C;

the dashed line denotes the presence or absence of a bond, and when the dashed line denotes the presence of a bond or W is N then $R_4$ is absent, otherwise $R_4$ is —H, —OH, —$OCF_3$, -halo, —$(C_1-C_6)$alkyl, —$CH_2OH$, —$CH_2Cl$, —$CH_2Br$, —$CH_2I$, —$CH_2F$, —$CH(halo)_2$, —$CF_3$, —$OR_{10}$, —$SR_{10}$, —COOH, —$COOR_{10}$, —$C(O)R_{10}$, —C(O)H, —$OC(O)R_{10}$, —$OC(O)NHR_{10}$, —$NHC(O)R_{13}$, —$CON(R_{13})_2$, —$S(O)_2R_{10}$, or —$NO_2$;

$R_{10}$ is —$(C_1-C_4)$alkyl;

each $R_{13}$ is independently: —H, —$(C_1-C_4)$alkyl, —$(C_1-C_4)$alkenyl, —$(C_1-C_4)$alkynyl, or -phenyl;

$Ar_1$ is

[six pyridine/pyrimidine/pyrazine/pyridazine ring structures with $(R_2)_n$ or $(R_2)_p$ and $R_1$ substituents]

,

[additional pyridazine ring structures with $(R_2)_p$ and $R_1$ substituents]

or ;

$Ar_2$ is

[benzimidazole, benzothiazole, benzoxazole structures with $R_{20}$, $R_8$, $R_9$]

, , ,

[phenyl structures with $(R_{14})_t$, $Y_1$, $Y_2$, $(Y_3)_c$, $R_{12a}$, $R_{12b}$, E]

-continued

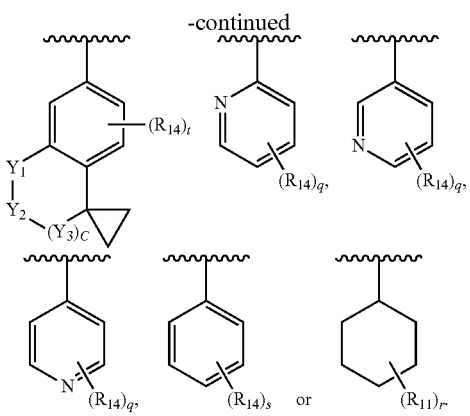

c is the integer 0, 1, or 2;
$Y_1$, $Y_2$, and $Y_3$ are independently C, N, or O;
wherein no more than one of $Y_1$, $Y_2$, or $Y_3$ can be O, and for each $Y_1$, $Y_2$, and $Y_3$ that is N, the N is bonded to one $R_{21}$ group, and for each $Y_1$, $Y_2$, and $Y_3$ that is C, the C is bonded to two $R_{20}$ groups, provided that there are no more than a total of two $(C_1-C_6)$alkyl groups substituted on all of $Y_1$, $Y_2$, and $Y_3$;
$R_{12a}$ and $R_{12b}$ are independently —H or —$(C_1-C_6)$alkyl;
E is =O, =S, =$C(C_1-C_5)$alkyl, =$C(C_1-C_5)$alkenyl, =$NH(C_1-C_6)$alkyl, or =N—$OR_{20}$;
$R_1$ is —H, -halo, —$(C_1-C_4)$alkyl, —$NO_2$, —CN, —OH, —$OCH_3$, —$NH_2$, —C(halo)$_3$, —CH(halo)$_2$, —CH$_2$(halo), —OC(halo)$_3$, —OCH(halo)$_2$, or —OCH$_2$(halo);
each $R_2$ is independently:
(a) -halo, —OH, —O$(C_1-C_4)$alkyl, —CN, —$NO_2$, —$NH_2$, —$(C_1-C_{10})$alkyl, —$(C_2-C_{10})$alkenyl, —$(C_2-C_{10})$alkynyl, or -phenyl, or
(b) a group of formula Q;
wherein Q is

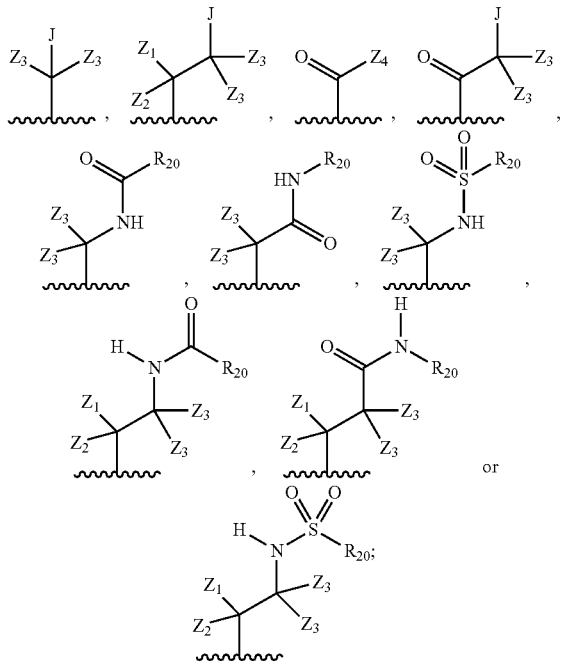

$Z_1$ is —H, —$OR_7$, —$SR_7$, —$CH_2$—$OR_7$, —$CH_2$—$SR_7$, —$CH_2$—$N(R_{20})_2$, or -halo;

$Z_2$ is —H, —$(C_1-C_6)$alkyl, —$(C_2-C_6)$alkenyl, —$(C_2-C_6)$alkynyl, -phenyl, or -halo;
each $Z_3$ is independently —H, —$(C_1-C_6)$alkyl, —$(C_2-C_6)$alkenyl, —$(C_2-C_6)$alkynyl, or -phenyl;
$Z_4$ is —H, —OH, —$OR_{20}$, —$(C_1-C_6)$alkyl, or —$NR_{20}$;
J is —$OR_{20}$, —$SR_{20}$, or —$N(R_{20})_2$;
provided that at least one $R_2$ group is a group of formula Q, and provided that when $Z_1$ is —$OR_7$ or —$SR_7$, then $Z_2$ is not -halo;
each $R_3$ is independently:
(a) —H, —$(C_1-C_6)$alkyl, or two $R_3$ groups form a bicyclo group to give one of the following structures

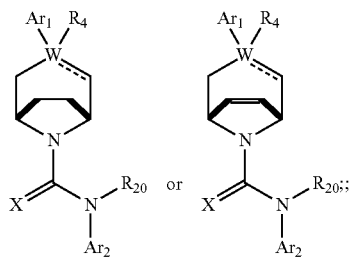

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_1-C_6)$haloalkyl, —$(C_1-C_6)$hydroxyalkyl, —$(C_1-C_6)$alkoxy$(C_1-C_6)$alkyl, —$(C_1-C_6)$alkyl-$N(R_{20})_2$, or —$CON(R_{20})_2$;
each $R_8$ and $R_9$ are independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$CH_2C$(halo)$_3$, —C(halo)$_3$, —CH(halo)$_2$, —$CH_2$(halo), —OC(halo)$_3$, —OCH(halo)$_2$, —OCH$_2$(halo), —O—CN, —OH, -halo, —$N_3$, —$NO_2$, —CH=$NR_7$, —$N(R_7)_2$, —$NR_7OH$, —$OR_7$, —C(O)$R_7$, —C(O)O$R_7$, —OC(O)$R_7$, —OC(O)O$R_7$, —$SR_7$, —S(O)$R_7$, or —S(O)$_2R_7$;
each $R_{11}$ is independently —CN, —OH, —$(C_1-C_6)$alkyl, —$(C_2-C_6)$alkenyl, -halo, —$N_3$, —$NO_2$, —$N(R_7)_2$, —CH=$NR_7$, —$NR_7OH$, —$OR_7$, —C(O)$R_7$, —C(O)O$R_7$, —OC(O)$R_7$, or —OC(O)O$R_7$;
each $R_{14}$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_1-C_6)$alkoxy-$(C_1-C_6)$alkyl, -phenyl, —C(halo)$_3$, —CH(halo)$_2$, —CH$_2$(halo), -(3- to 7-membered)heterocycle, —$(C_1-C_6)$haloalkyl, —$(C_2-C_6)$haloalkenyl, —$(C_2-C_6)$haloalkynyl, —$(C_2-C_6)$hydroxyalkenyl, —$(C_2-C_6)$hydroxyalkynyl, —$(C_1-C_6)$alkoxy$(C_2-C_6)$alkyl, —$(C_1-C_6)$alkoxy$(C_2-C_6)$alkenyl, —$(C_1-C_6)$alkoxy$(C_2-C_6)$alkynyl, —CN, —OH, -halo, OC(halo)$_3$, —$N_3$, —$NO_2$, —CH=$NR_7$, —$N(R_7)_2$, —$NR_7OH$, —$OR_7$, —$SR_7$, —O$(CH_2)_bOR_7$, —O$(CH_2)_bSR_7$, —O$(CH_2)_bN(R_7)_2$, —$N(R_7)(CH_2)_bOR_7$, —$N(R_7)(CH_2)_bSR_7$, —$N(R_7)(CH_2)_bN(R_7)_2$, —$N(R_7)COR_7$, —C(O)$R_7$, —C(O)O$R_7$, —OC(O)$R_7$, —OC(O)O$R_7$, —S(O)$R_7$, or —S(O)$_2R_7$, —S(O)$_2N(R_7)_2$, —$SO_2C$(halo)$_3$, —CON$(R_7)_2$, —$(C_1-C_5)$alkyl-C=$NOR_7$, —$(C_1-C_5)$alkyl-C(O)—$N(R_7)_2$, —$(C_1-C_6)$alkyl-NHSO$_2$N$(R_7)_2$, or —$(C_1-C_6)$alkyl-C(=NH)—$N(R_1)_2$;
each $R_{20}$ is independently —H or —$(C_1-C_6)$alkyl;
each $R_{21}$ is independently —H, —$(C_1-C_6)$alkyl,

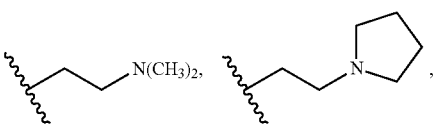

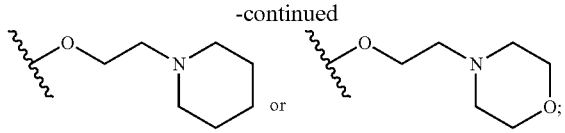

each halo is independently —F, —Cl, —Br, or —I;
n is the integer 1, 2, or 3;
p is the integer 1 or 2;
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
m is the integer 0, 1, or 2.

In another embodiment relating to formula I.4, E is =O, =S, =CH($C_1$-$C_5$)alkyl, =CH($C_1$-$C_5$)alkenyl, or =N—OR$_{20}$.

In another embodiment relating to formula I.4, E is =O, =S, or =N—OR$_{20}$.

In another embodiment, the invention encompasses compounds of formula I.3:

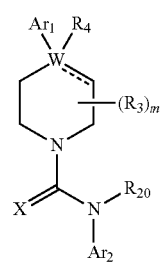

(I.3)

or a pharmaceutically acceptable salt thereof, where
X is O, S, N—CN, N—OH, or N—OR$_{10}$;
W is N or C;
the dashed line denotes the presence or absence of a bond, and when the dashed line denotes the presence of a bond or W is N then R$_4$ is absent, otherwise R$_4$ is —H, —OH, —OCF$_3$, -halo, —($C_1$-$C_6$)alkyl, —CH$_2$OH, —CH$_2$Cl, —CH$_2$Br, —CH$_2$I, —CH$_2$F, —CH(halo)$_2$, —CF$_3$, —OR$_{10}$, —SR$_{10}$, —COOH, —COOR$_{10}$, —C(O)R$_{10}$, —C(O)H, —OC(O)R$_{10}$, —OC(O)NHR$_{10}$, —NHC(O)R$_{13}$, —CON(R$_{13}$)$_2$, —S(O)$_2$R$_{10}$, or —NO$_2$;
R$_{10}$ is —($C_1$-$C_4$)alkyl;
each R$_{13}$ is independently: —H, —($C_1$-$C_4$)alkyl, —($C_1$-$C_4$)alkenyl, —($C_1$-$C_4$)alkynyl, or -phenyl;
Ar$_1$ is

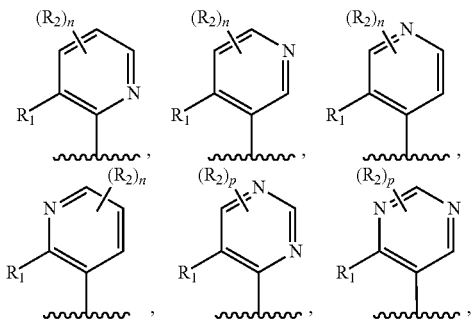

Ar$_2$ is

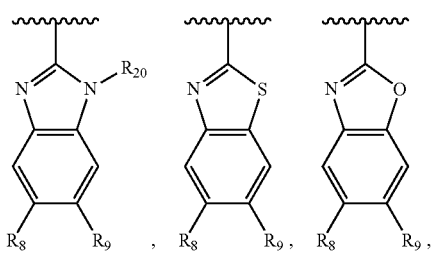

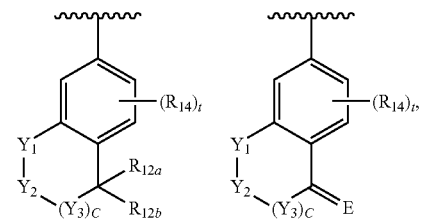

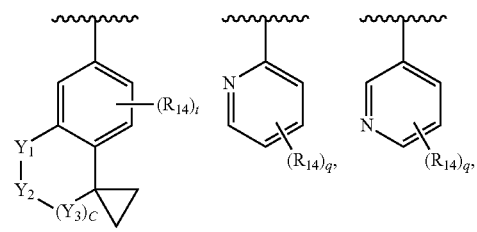

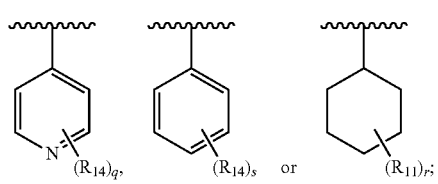

c is the integer 0, 1, or 2;
Y$_1$, Y$_2$, and Y$_3$ are independently C or N;
wherein for each Y$_1$, Y$_2$, and Y$_3$ that is N, the N is bonded to one R$_{20}$ group, and for each Y$_1$, Y$_2$, and Y$_3$ that is C, the C is bonded to two R$_{20}$ groups, provided that there are no more than a total of two ($C_1$-$C_6$)alkyl groups substituted on all of Y$_1$, Y$_2$, and Y$_3$;
R$_{12a}$ and R$_{12b}$ are independently —H or —($C_1$-$C_6$)alkyl;
E is =O, =S, =C($C_1$-$C_5$)alkyl, =C($C_1$-$C_5$)alkenyl, =NH($C_1$-$C_6$)alkyl, or =N—OR$_{20}$;

$R_1$ is —H, -halo, —$(C_1-C_4)$alkyl, —$NO_2$, —CN, —OH, —$OCH_3$, —$NH_2$, —$C(halo)_3$, —$CH(halo)_2$, —$CH_2(halo)$, —$OC(halo)_3$, —$OCH(halo)_2$, or —$OCH_2(halo)$;

each $R_2$ is independently:
(a) -halo, —OH, —$O(C_1-C_4)$alkyl, —CN, —$NO_2$, —$NH_2$, —$(C_1-C_{10})$alkyl, —$(C_2-C_{10})$alkenyl, —$(C_2-C_{10})$alkynyl, or -phenyl, or
(b) a group of formula Q;
wherein Q is

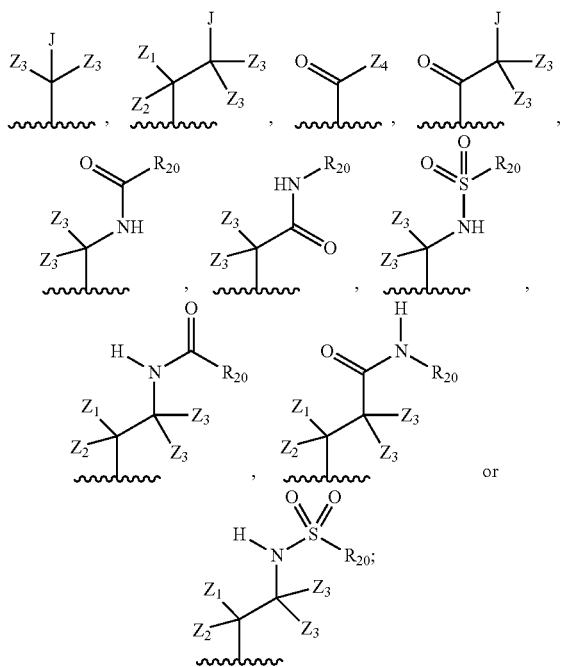

$Z_1$ is —H, —$OR_7$, —$SR_7$, —$CH_2$—$OR_7$, —$CH_2$—$SR_7$, —$CH_2$—$N(R_{20})_2$, or -halo;
$Z_2$ is —H, —$(C_1-C_6)$alkyl, —$(C_2-C_6)$alkenyl, —$(C_2-C_6)$alkynyl, -phenyl, or -halo;
each $Z_3$ is independently —H, —$(C_1-C_6)$alkyl, —$(C_2-C_6)$alkenyl, —$(C_2-C_6)$alkynyl, or -phenyl;
$Z_4$ is —H, —OH, —$OR_{20}$, —$(C_1-C_6)$alkyl, or —$NR_{20}$;
J is —$OR_{20}$, —$SR_{20}$, or —$N(R_{20})_2$;
provided that at least one $R_2$ group is a group of formula Q, and provided that when $Z_1$ is —$OR_7$ or —$SR_7$, then $Z_2$ is not -halo;

each $R_3$ is independently:
(a) —H, —$(C_1-C_6)$alkyl, or two $R_3$ groups form a bicyclo group to give one of the following structures

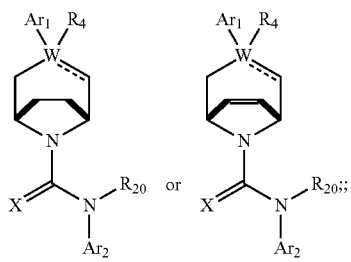

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_1-C_6)$haloalkyl, —$(C_1-C_6)$hydroxyalkyl, —$(C_1-C_6)$alkoxy$(C_1-C_6)$alkyl, —$(C_1-C_6)$alkyl-$N(R_{20})_2$, or —$CON(R_{20})_2$;

each $R_8$ and $R_9$ are independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$CH_2C(halo)_3$, —$C(halo)_3$, —$CH(halo)_2$, —$CH_2(halo)$, —$OC(halo)_3$, —$OCH(halo)_2$, —$OCH_2(halo)$, —O—CN, —OH, -halo, —$N_3$, —$NO_2$, —CH=$NR_7$, —$N(R_7)_2$, —$NR_7OH$, —$OR_7$, —$C(O)R_7$, —$C(O)OR_7$, —$OC(O)R_7$, —$OC(O)OR_7$, —$SR_7$, —$S(O)R_7$, or —$S(O)_2R_7$;

each $R_{11}$ is independently —CN, —OH, —$(C_1-C_6)$alkyl, —$(C_2-C_6)$alkenyl, -halo, —$N_3$, —$NO_2$, —$N(R_7)_2$, —CH=$NR_7$, —$NR_7OH$, —$OR_7$, —$C(O)R_7$, —$C(O)OR_7$, —$OC(O)R_7$, or —$OC(O)OR_7$;

each $R_{14}$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_1-C_6)$alkoxy-$(C_1-C_6)$alkyl, -phenyl, —$C(halo)_3$, —$CH(halo)_2$, —$CH_2(halo)$, -(3- to 7-membered)heterocycle, —$(C_1-C_6)$haloalkyl, —$(C_2-C_6)$haloalkenyl, —$(C_2-C_6)$haloalkynyl, —$(C_2-C_6)$hydroxyalkenyl, —$(C_2-C_6)$hydroxyalkynyl, —$(C_1-C_6)$alkoxy$(C_2-C_6)$alkyl, —$(C_1-C_6)$alkoxy$(C_2-C_6)$alkenyl, —$(C_1-C_6)$alkoxy$(C_2-C_6)$alkynyl, —CN, —OH, -halo, $OC(halo)_3$, —$N_3$, —$NO_2$, —CH=$NR_7$, —$N(R_7)_2$, —$NR_7OH$, —$OR_7$, —$SR_7$, —$O(CH_2)_bOR_7$, —$O(CH_2)_bSR_7$, —$O(CH_2)_bN(R_7)_2$, —$N(R_7)(CH_2)_bOR_7$, —$N(R_7)(CH_2)_bSR_7$, —$N(R_7)(CH_2)_bN(R_7)_2$, —$N(R_7)COR_7$, —$C(O)R_7$, —$C(O)OR_7$, —$OC(O)R_7$, —$OC(O)OR_7$, —$S(O)R_7$, or —$S(O)_2R_7$, —$S(O)_2N(R_7)_2$, —$SO_2C(halo)_3$, —$CON(R_7)_2$, —$(C_1-C_5)$alkyl-C=$NOR_7$, —$(C_1-C_5)$alkyl-C(O)—$N(R_7)_2$, —$(C_1-C_6)$alkyl-$NHSO_2N(R_7)_2$, or —$(C_1-C_6)$alkyl-C(=NH)—$N(R_7)_2$;

each $R_{20}$ is independently —H or —$(C_1-C_6)$alkyl;
each halo is independently —F, —Cl, —Br, or —I;
n is the integer 1, 2, or 3;
p is the integer 1 or 2;
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
m is the integer 0, 1, or 2.

In another embodiment relating to formula I.3, E is =O, =S, =CH$(C_1-C_5)$alkyl, =CH$(C_1-C_5)$alkenyl, or =N—$OR_{20}$.

In another embodiment relating to formula I.3, E is =O, =S, or =N—$OR_{20}$.

In another embodiment, the invention encompasses compounds of formula I.2:

(I.2)

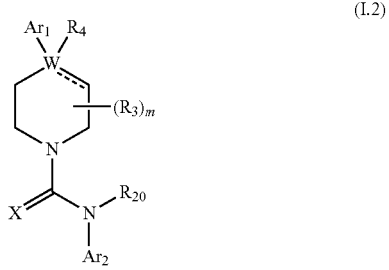

or a pharmaceutically acceptable salt thereof, where
X is O, S, N—CN, N—OH, or N—$OR_{10}$;
W is N or C;

the dashed line denotes the presence or absence of a bond, and when the dashed line denotes the presence of a bond or W is N then $R_4$ is absent, otherwise $R_4$ is —H, —OH, —OCF$_3$, -halo, —(C$_1$-C$_6$)alkyl, —CH$_2$OH, —CH$_2$Cl, —CH$_2$Br, —CH$_2$I, —CH$_2$F, —CH(halo)$_2$, —CF$_3$, —OR$_{10}$, —SR$_{10}$, —COOH, —COOR$_{10}$, —C(O)R$_{10}$, —C(O)H, —OC(O)R$_{10}$, —OC(O)NHR$_{10}$, —NHC(O)R$_{13}$, —CON(R$_{13}$)$_2$, —S(O)$_2$R$_{10}$, or —NO$_2$;

$R_{10}$ is —(C$_1$-C$_4$)alkyl;

each $R_{13}$ is independently: —H, —(C$_1$-C$_4$)alkyl, —(C$_1$-C$_4$)alkenyl, —(C$_1$-C$_4$)alkynyl, or -phenyl;

Ar$_1$ is

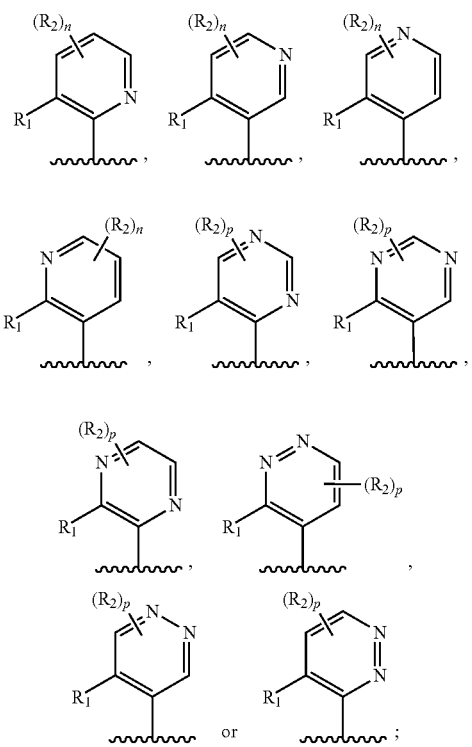

Ar$_2$ is

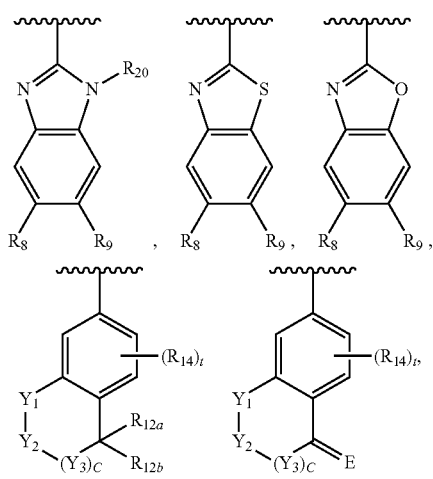

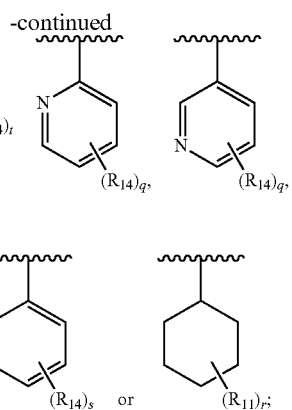

c is the integer 0, 1, or 2;

$Y_1$, $Y_2$, and $Y_3$ are independently C or N;

wherein for each $Y_1$, $Y_2$, and $Y_3$ that is N, the N is bonded to one $R_{20}$ group, and for each $Y_1$, $Y_2$, and $Y_3$ that is C, the C is bonded to two $R_{20}$ groups, provided that there are no more than a total of two (C$_1$-C$_6$)alkyl groups substituted on all of $Y_1$, $Y_2$, and $Y_3$;

$R_{12a}$ and $R_{12b}$ are independently —H or —(C$_1$-C$_6$)alkyl;

E is =O, =S, =C(C$_1$-C$_5$)alkyl, =C(C$_1$-C$_5$)alkenyl, =NH(C$_1$-C$_6$)alkyl, or =N—OR$_{20}$;

$R_1$ is —H, -halo, —(C$_1$-C$_4$)alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each $R_2$ is independently:
(a) -halo, —OH, —O(C$_1$-C$_4$)alkyl, —CN, —NO$_2$, —NH$_2$, —(C$_1$-C$_{10}$)alkyl, —(C$_2$-C$_{10}$)alkenyl, —(C$_2$-C$_{10}$)alkynyl, or -phenyl, or
(b) a group of formula Q;
wherein Q is

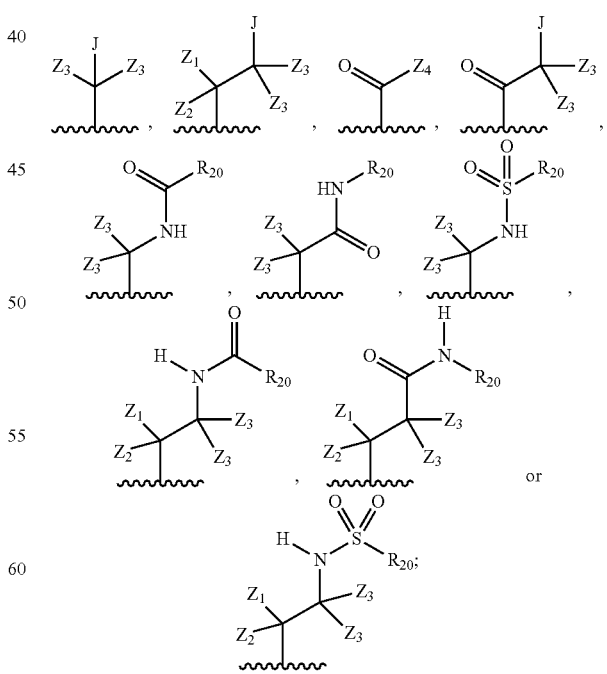

$Z_1$ is —H, —OR$_7$, —SR$_7$, —CH$_2$—OR$_7$, —CH$_2$—SR$_7$, —CH$_2$—N(R$_{20}$)$_2$, or -halo;

$Z_2$ is —H, —($C_1$-$C_6$)alkyl, —($C_2$-$C_6$)alkenyl, —($C_2$-$C_6$)alkynyl, -phenyl, or -halo;

each $Z_3$ is independently —H, —($C_1$-$C_6$)alkyl, —($C_2$-$C_6$)alkenyl, —($C_2$-$C_6$)alkynyl, or -phenyl;

$Z_4$ is —H, —OH, —$OR_{20}$, —($C_1$-$C_6$)alkyl, or —$NR_{20}$;

J is —$OR_{20}$, —$SR_{20}$, or —$N(R_{20})_2$;

provided that at least one $R_2$ group is a group of formula Q, and provided that when $Z_1$ is —$OR_7$ or —$SR_7$, then $Z_2$ is not -halo;

each $R_3$ is independently:
(a) —H, —($C_1$-$C_6$)alkyl, or two $R_3$ groups form a bicyclo group to give one of the following structures

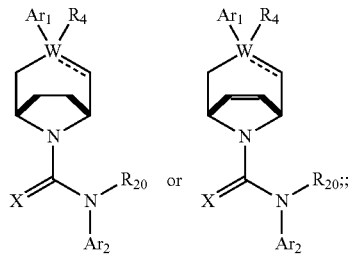

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-$N(R_{20})_2$, or —$CON(R_{20})_2$;

each $R_8$ and $R_9$ are independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —$CH_2C(halo)_3$, —$C(halo)_3$, —$CH(halo)_2$, —$CH_2(halo)$, —$OC(halo)_3$, —$OCH(halo)_2$, —$OCH_2(halo)$, —O—CN, —OH, -halo, —$N_3$, —$NO_2$, —CH=$NR_7$, —$N(R_7)_2$, —$NR_7OH$, —$OR_7$, —$C(O)R_7$, —$C(O)OR_7$, —$OC(O)R_7$, —$OC(O)OR_7$, —$SR_7$, —$S(O)R_7$, or —$S(O)_2R_7$;

each $R_{11}$ is independently —CN, —OH, —($C_1$-$C_6$)alkyl, —($C_2$-$C_6$)alkenyl, -halo, —$N_3$, —$NO_2$, —$N(R_7)_2$, —CH=$NR_7$, —$NR_7OH$, —$OR_7$, —$C(O)R_7$, —$C(O)OR_7$, —$OC(O)R_7$, or —$OC(O)OR_7$;

each $R_{14}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy-($C_1$-$C_6$)alkyl, -phenyl, —$C(halo)_3$, —$CH(halo)_2$, —$CH_2(halo)$, -(3- to 7-membered)heterocycle, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy($C_2$-$C_6$)alkenyl, —($C_1$-$C_6$)alkoxy($C_2$-$C_6$)alkynyl, —CN, —OH, -halo, $OC(halo)_3$, —$N_3$, —$NO_2$, —CH=$NR_7$, —$N(R_7)_2$, —$NR_7OH$, —$OR_7$, —$SR_7$, —$O(CH_2)_bOR_7$, —$O(CH_2)_bSR_7$, —$O(CH_2)_bN(R_7)_2$, —$N(R_7)(CH_2)_bOR_7$, —$N(R_7)(CH_2)_bSR_7$, —$N(R_7)(CH_2)_bN(R_7)_2$, —$N(R_7)COR_7$, —$C(O)R_7$, —$C(O)OR_7$, —$OC(O)R_7$, —$OC(O)OR_7$, —$S(O)R_7$, or —$S(O)_2R_7$, —$S(O)_2N(R_7)_2$, —$SO_2C(halo)_3$, —$CON(R_7)_2$, —($C_1$-$C_5$)alkyl-C=$NOR_7$, —($C_1$-$C_5$)alkyl-C(O)—$N(R_7)_2$, —($C_1$-$C_6$)alkyl-$NHSO_2N(R_7)_2$, or —($C_1$-$C_6$)alkyl-C(=NH)—$N(R_7)_2$;

each $R_{20}$ is independently —H or —($C_1$-$C_6$)alkyl;
each halo is independently —F, —Cl, —Br, or —I;
n is the integer 1, 2, or 3;
p is the integer 1 or 2;
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;

t is the integer 0, 1, 2, or 3; and
m is the integer 0, 1, or 2.

In another embodiment relating to formula I.2, E is =O, =S, =CH($C_1$-$C_5$)alkyl, =CH($C_1$-$C_5$)alkenyl, or =N—$OR_{20}$.

In another embodiment relating to formula I.2, E is =O, =S, or =N—$OR_{20}$.

In another embodiment, the invention encompasses compounds of formula I.1:

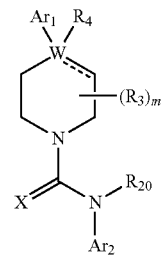

(I.1)

or a pharmaceutically acceptable salt thereof, where
X is O, S, N—CN, N—OH, or N—$OR_{10}$;
W is N or C;
the dashed line denotes the presence or absence of a bond, and when the dashed line denotes the presence of a bond or W is N then $R_4$ is absent, otherwise $R_4$ is —H, —OH, —$OCF_3$, -halo, —($C_1$-$C_6$)alkyl, —$CH_2OH$, —$CH_2Cl$, —$CH_2Br$, —$CH_2I$, —$CH_2F$, —$CH(halo)_2$, —$CF_3$, —$OR_{10}$, —$SR_{10}$, —COOH, —$COOR_{10}$, —$C(O)R_{10}$, —$C(O)H$, —$OC(O)R_{10}$, —$OC(O)NHR_{10}$, —$NHC(O)R_{13}$, —$CON(R_{13})_2$, —$S(O)_2R_{10}$, or —$NO_2$;
$R_{10}$ is —($C_1$-$C_4$)alkyl;
each $R_{13}$ is independently: —H, —($C_1$-$C_4$)alkyl, —($C_1$-$C_4$)alkenyl, —($C_1$-$C_4$)alkynyl, or -phenyl;

$Ar_1$ is

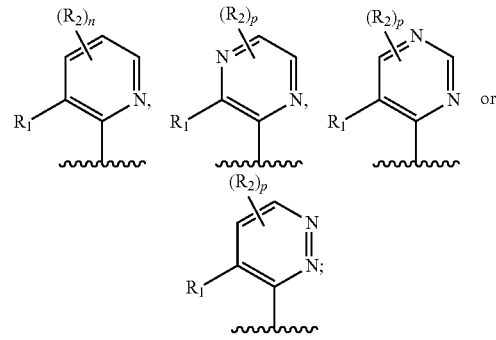

$Ar_2$ is

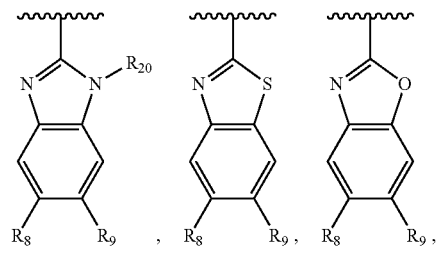

-continued

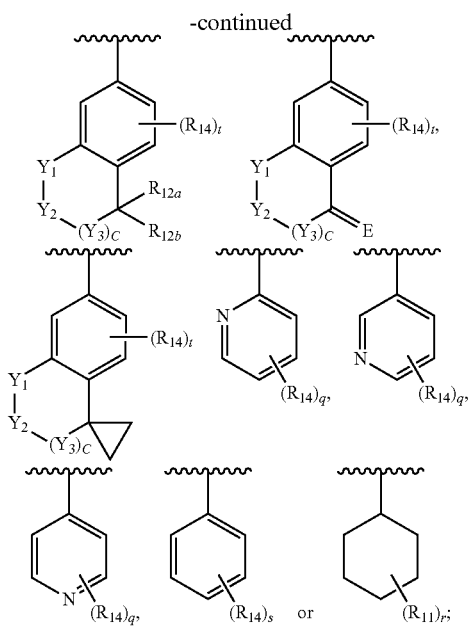

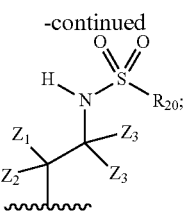

c is the integer 0, 1, or 2;

$Y_1$, $Y_2$, and $Y_3$ are independently C or N;

wherein for each $Y_1$, $Y_2$, and $Y_3$ that is N, the N is bonded to one $R_{20}$ group, and for each $Y_1$, $Y_2$, and $Y_3$ that is C, the C is bonded to two $R_{20}$ groups, provided that there are no more than a total of two $(C_1$-$C_6)$alkyl groups substituted on all of $Y_1$, $Y_2$, and $Y_3$;

$R_{12a}$ and $R_{12b}$ are independently —H or —$(C_1$-$C_6)$alkyl;

E is =O, =S, =C$(C_1$-$C_5)$alkyl, =C$(C_1$-$C_5)$alkenyl, =NH$(C_1$-$C_6)$alkyl, or =N—OR$_{20}$;

$R_1$ is —H, -halo, —$(C_1$-$C_4)$alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each $R_2$ is independently:

(a) -halo, —OH, —O$(C_1$-$C_4)$alkyl, —CN, —NO$_2$, —NH$_2$, —$(C_1$-$C_{10})$alkyl, —$(C_2$-$C_{10})$alkenyl, —$(C_2$-$C_{10})$alkynyl, or -phenyl, or (b) a group of formula Q;

wherein Q is

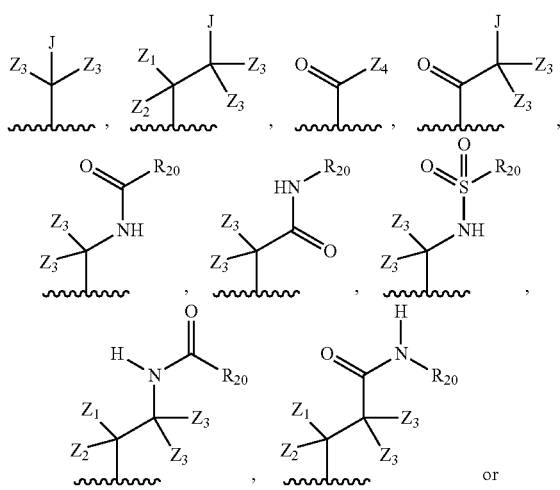

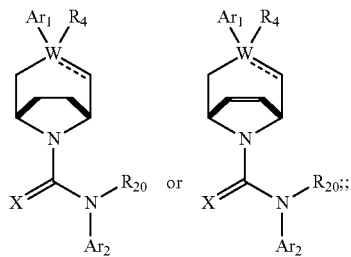

$Z_1$ is —H, —OR$_7$, —SR$_7$, —CH$_2$—OR$_7$, —CH$_2$—SR$_7$, —CH$_2$—N(R$_{20}$)$_2$, or -halo;

$Z_2$ is —H, —$(C_1$-$C_6)$alkyl, —$(C_2$-$C_6)$alkenyl, —$(C_2$-$C_6)$alkynyl, -phenyl, or -halo;

each $Z_3$ is independently —H, —$(C_1$-$C_6)$alkyl, —$(C_2$-$C_6)$alkenyl, —$(C_2$-$C_6)$alkynyl, or -phenyl;

$Z_4$ is —H, —OH, —OR$_{20}$, —$(C_1$-$C_6)$alkyl, or —NR$_{20}$;

J is —OR$_{20}$, —SR$_{20}$, or —N(R$_{20}$)$_2$;

provided that at least one $R_2$ group is a group of formula Q, and provided that when $Z_1$ is —OR$_7$ or —SR$_7$, $Z_2$ in not -halo;

each $R_3$ is independently:

(a) —H, —$(C_1$-$C_6)$alkyl, or two $R_3$ groups may form bicyclo group, which gives the following structures

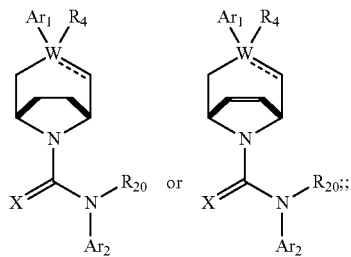

each $R_7$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-N(R$_{20}$)$_2$, or —CON(R$_{20}$)$_2$;

each $R_8$ and $R_9$ are independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each $R_{11}$ is independently —CN, —OH, —$(C_1$-$C_6)$alkyl, —$(C_2$-$C_6)$alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, or —OC(O)OR$_7$;

each $R_{14}$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, —$(C_1$-$C_6)$alkoxy-$(C_1$-$C_6)$alkyl, -phenyl, —C(halo)$_3$, —CH(halo)$_2$, —CH$_2$(halo), -(3- to 7-membered)heterocycle, —$(C_1$-$C_6)$haloalkyl, —$(C_2$-$C_6)$haloalkenyl, —$(C_2$-$C_6)$haloalkynyl, —$(C_2$-$C_6)$hydroxyalkenyl, —$(C_2$-$C_6)$hydroxyalkynyl, —$(C_1$-$C_6)$alkoxy$(C_2$-$C_6)$alkyl, —$(C_1$-$C_6)$alkoxy$(C_2$-$C_6)$alkenyl, —$(C_1$-$C_6)$alkoxy$(C_2$-$C_6)$alkynyl, —CN, —OH, -halo, OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)COR$_7$, —C(O)R$_7$, —C(O)OR$_7$, —OC(O)R$_7$, —OC(O)OR$_7$, —S(O)R$_7$, or —S(O)$_2$R$_7$, —S(O)$_2$N(R$_7$)$_2$, —SO$_2$C(halo)$_3$, —CON(R$_7$)$_2$, —(C$_1$-C$_5$)alkyl-C=NOR$_7$, —(C$_1$-C$_5$)alkyl-C(O)—N(R$_7$)$_2$, —(C$_1$-C$_6$)alkyl-NHSO$_2$N(R$_7$)$_2$, or —(C$_1$-C$_6$)alkyl-C(=NH)—N(R$_7$)$_2$;

each R$_{20}$ is independently —H or —(C$_1$-C$_6$)alkyl;
each halo is independently —F, —Cl, —Br, or —I;
n is the integer 1, 2, or 3;
p is the integer 1 or 2;
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
m is the integer 0, 1, or 2.

In another embodiment relating to formula I.1, E is =O, =S, =CH(C$_1$-C$_5$)alkyl, =CH(C$_1$-C$_5$)alkenyl, or =N—OR$_{20}$.

In another embodiment relating to formula I.1, E is =O, =S, or =N—OR$_{20}$.

In other embodiments, the compound of formula I is

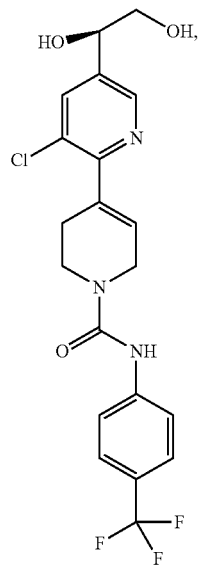
Q5

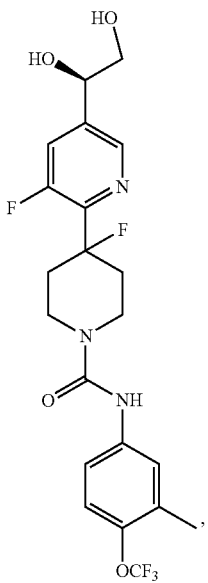
S5

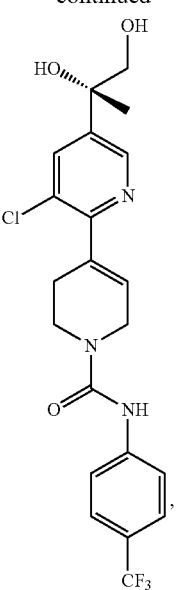
R6

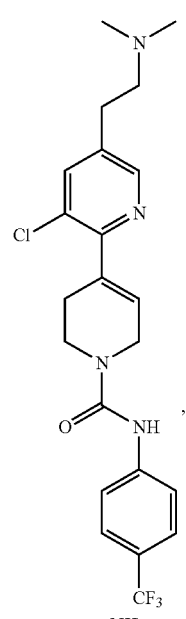
S6

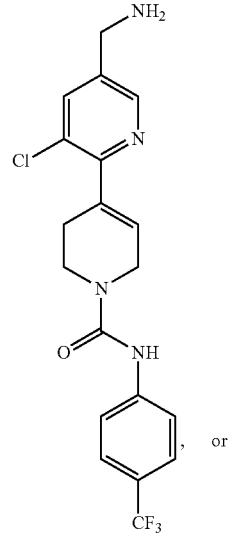
T6

, or

U6
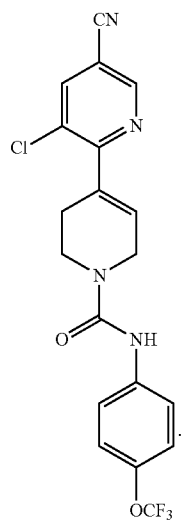
Other compounds of interest include
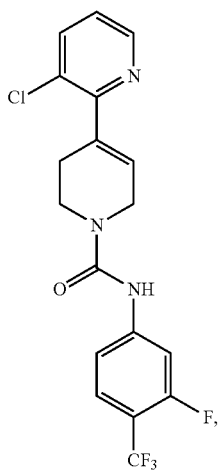
213
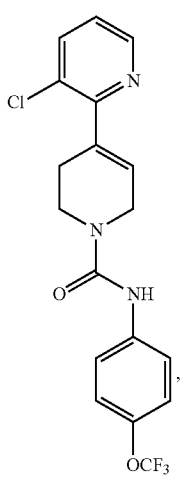
214
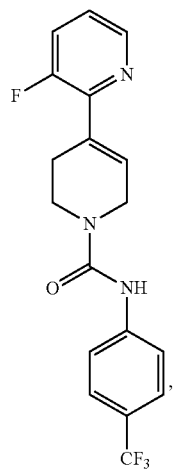
208
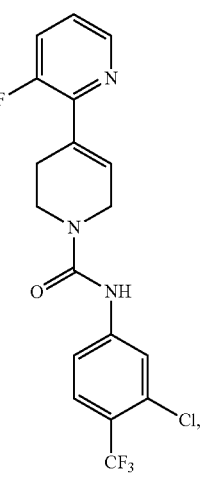
215
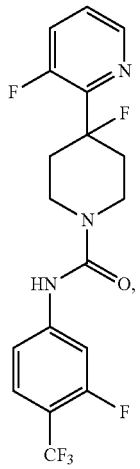
212

-continued

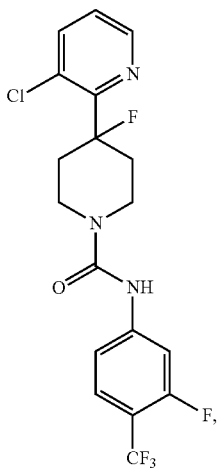

209

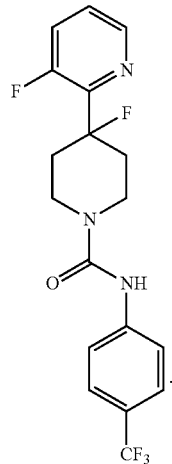

207

210

211

Aqueous solubility of compounds is often a desirable feature. For example, aqueous solubility of a compound permits that compound to be more easily formulated into a variety of dosage forms that may be administered to an animal. When a compound is not fully soluble in the blood, it may precipitate in the blood, and the animal's exposure to the drug will accordingly not correspond to the administered dose. Aqueous solubility increases the likelihood that a compound will not precipitate in an animal's blood, and increases the ability to predict exposure at the target sight of the compound.

Compounds of formula I are highly soluble in aqueous solution. For example, at either pH 6.8 or pH 1.2, compound 200 is insoluble in aqueous solution, i.e., has an aqueous solubility <0.1 µM. In contrast, the aqueous solubility at pH 6.8, in µM, of compounds of formula I F2, E6, F6, and G2 is 3.0, 9.0, 9.2, and 38.2, respectively. The aqueous solubility at pH 1.2, in µM, of compounds of formula I F2, E6, F6 and G2 is 1.0, 27.2, >50 and >50, respectively. Additionally, the aqueous solubility at either pH 6.8 or pH 1.2 of each of compounds of formula I G6, H6, J2, and Z1 is >50 µM. The following compounds are aqueous insoluble at pH 6.8: 203, 207, 200, and 208. The following compounds have very low aqueous solubility at pH 6.8: 209, 210, 211, 212, 213, 214, and 215 have aqueous solubility, in µM, of 1.0, 0.4, 0.4, 1.9, 0.8, 1.8, and 0.6, respectively. The aqueous solubility, in µM, at pH 1.2 of compounds 209, 210, 211, 212, 213, 214 and 215 is 9.3, 2.0, 1.3, 10.3, 39.6, >50 and 9.6, respectively. In contrast, the aqueous solubility at pH 6.8, in µM, of compounds of formula I N1, F1, C1, Y3, and U3 is 28.0, 22.6, 15.7, 17.4, and 26.4, respectively. At pH 1.2, compounds of formula I N1, F1, C1, Y3 and U3 all have an aqueous solubility of >50 µM. The aqueous solubility, at either pH 6.8 or pH 1.2, is >50 µM for each of the following compounds of formula I: H1, N6, Z1, S1, E2, and U1.

5.2 Compounds of Formula IA

Preferred compounds of formula I are compounds of formula IA:

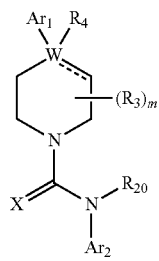

(IA)

or a pharmaceutically acceptable derivative thereof, where W, X, $Ar_1$, $Ar_2$, $R_3$, $R_4$, $R_{20}$, and m are as defined above for compounds of formula IA.

Certain embodiments of formula IA are presented below.

In one embodiment, a compound of formula IA is a pharmaceutically acceptable derivative of a compound of formula IA.

In another embodiment, a compound of formula IA is a compound of formula IA wherein the derivative is a pharmaceutically acceptable salt.

In another embodiment, a compound of formula IA is a pharmaceutically acceptable salt of a compound of formula IA.

In another embodiment, $Ar_1$ is a pyridyl group.
In another embodiment, $Ar_1$ is a pyrimidinyl group.
In another embodiment, $Ar_1$ is a pyrazinyl group.
In another embodiment, $Ar_1$ is pyridazinyl group.
In another embodiment, W is C.
In another embodiment, W is N.
In another embodiment, X is O.
In another embodiment, X is S.
In another embodiment, X is N—CN.
In another embodiment, X is N—OH.
In another embodiment, X is N—$OR_{10}$.
In another embodiment, $Ar_2$ is a benzoimidazolyl group.
In another embodiment, $Ar_2$ is a benzothiazolyl group.
In another embodiment, $Ar_2$ is a benzooxazolyl group.
In another embodiment, $Ar_2$ is

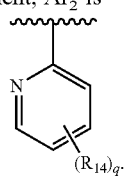

In another embodiment, $Ar_2$ is

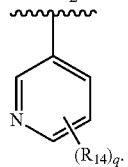

In another embodiment, $Ar_2$ is

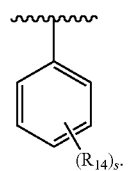

In another embodiment, $Ar_2$ is

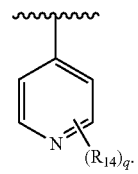

In another embodiment, $Ar_2$ is

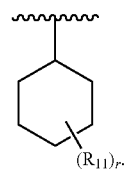

In another embodiment, $Ar_2$ is

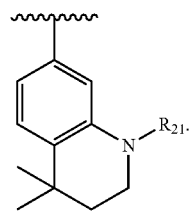

In another embodiment, $Ar_2$ is

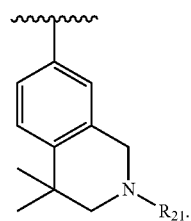

In another embodiment, $Ar_2$ is

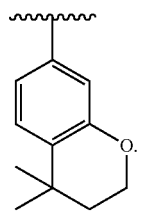

In another embodiment, n or p is 1.
In another embodiment, n or p is 2.
In another embodiment, n is 3.
In another embodiment, m is 2.
In another embodiment, each $R_3$ is independently —H, or —($C_1$-$C_6$)alkyl.
In another embodiment, two $R_3$ groups together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge.

In another embodiment, two $R_3$ groups together form a $(C_2$-$C_6)$bridge, which is unsubstituted or substituted with an $R_8$ group, and which bridge optionally contains —HC=CH— within the $(C_2$-$C_6)$bridge.

In another embodiment, two $R_3$ groups together form a $(C_2$-$C_3)$bridge, which is unsubstituted or substituted with an $R_8$ group, and which bridge optionally contains —HC=CH— within the $(C_2$-$C_3)$bridge.

In another embodiment, two $R_3$ groups together form a $(C_2$-$C_3)$bridge, which is unsubstituted and which bridge optionally contains —HC=CH— within the $(C_2$-$C_3)$bridge.

In another embodiment, two $R_3$ groups together form a $(C_2)$bridge, a —HC=CH— bridge, or a $(C_3)$bridge each of which is unsubstituted.

In another embodiment, two $R_3$ groups together form a $(C_2$-$C_6)$bridge, which is unsubstituted or substituted with 1, 2 or 3 independently selected $R_8$ groups, which bridge optionally contains —HC=CH— within the $(C_2$-$C_6)$bridge, and which bridge joins positions 2 and 6 of the piperidine, 1,2,3,6-tetrahydropyridine or piperazine ring.

In another embodiment, two $R_3$ groups together form a $(C_2$-$C_6)$bridge, which is unsubstituted or substituted with an $R_8$ group, which bridge optionally contains —HC=CH— within the $(C_2$-$C_6)$bridge, and which bridge joins positions 2 and 6 of the piperidine, 1,2,3,6-tetrahydropyridine or piperazine ring.

In another embodiment, two $R_3$ groups together form a $(C_2$-$C_3)$bridge, which is unsubstituted or substituted with an $R_8$ group, which bridge optionally contains —HC=CH— within the $(C_2$-$C_3)$bridge, and which bridge joins positions 2 and 6 of the piperidine, 1,2,3,6-tetrahydropyridine or piperazine ring.

In another embodiment, two $R_3$ groups together form a $(C_2$-$C_3)$bridge, which is unsubstituted, which bridge optionally contains —HC=CH— within the $(C_2$-$C_3)$bridge, and which bridge joins positions 2 and 6 of the piperidine, 1,2,3,6-tetrahydropyridine or piperazine ring.

In another embodiment, two $R_3$ groups together form a $(C_2)$bridge, a —HC=CH— bridge, or a $(C_3)$bridge each of which is unsubstituted, and which bridge joins positions 2 and 6 of the piperidine, 1,2,3,6-tetrahydropyridine or piperazine ring.

In another embodiment, two $R_3$ groups together form a —$CH_2$—$N(R_a)$—$CH_2$— bridge (B1), a

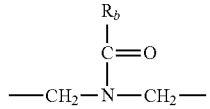

bridge (B2), or a

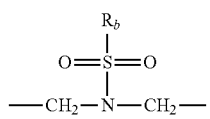

bridge (B3);

wherein $R_a$ is —H, —$(C_1$-$C_6)$alkyl, —$(C_3$-$C_8)$cycloalkyl, —$CH_2$—C(O)—$R_c$, —$(CH_2)$—C(O)—$OR_c$, —$(CH_2)$—C(O)—$N(R_c)_2$, —$(CH_2)_2$—O—$R_c$, —$(CH_2)_2$—S(O)$_2$—N$(R_c)_2$, or —$(CH_2)_2$—$N(R_c)S(O)_2$—$R_c$;

$R_b$ is:
(a) —H, —$(C_1$-$C_6)$alkyl, —$(C_3$-$C_8)$cycloalkyl, -(3- to 7-membered)heterocycle, —$N(R_c)_2$, —$N(R_c)$—$(C_3$-$C_8)$cycloalkyl, or —$N(R_c)$-(3- to 7-membered)heterocycle; or (b) -phenyl, -(5- or 6-membered)heteroaryl, —$N(R_c)$-phenyl, or —$N(R_c)$-(5- to 10-membered)heteroaryl, each of which is unsubstituted or substituted with 1, 2 or 3 independently selected $R_7$ groups; and each $R_c$ is independently —H or —$(C_1$-$C_4)$alkyl.

In another embodiment, $R_a$ is —H, —$(C_1$-$C_6)$alkyl, —$(C_3$-$C_8)$cycloalkyl, —$(CH_2)$—C(O)—$N(R_c)_2$, —$(CH_2)_2$—S(O)$_2$—N$(R_c)_2$, or —$(CH_2)_2$—$N(R_c)S(O)_2$—$R_c$.

In another embodiment, $R_a$ is —H, —$(C_1$-$C_6)$alkyl, —$(C_3$-$C_8)$cycloalkyl, or —$(CH_2)$—C(O)—$N(R_c)_2$.

In another embodiment, $R_a$ is —H, —$(C_1$-$C_6)$alkyl, or —$(C_3$-$C_8)$cycloalkyl.

In another embodiment, $R_b$ is —H, —$(C_3$-$C_8)$cycloalkyl, or -(3- to 7-membered)heterocycle.

In another embodiment, $R_b$ is —H, —$N(R_c)_2$, —$N(R_c)$—$(C_3$-$C_8)$cycloalkyl, or —$N(R_c)$-(3- to 7-membered)heterocycle.

In another embodiment, $R_b$ is —H, —$(C_1$-$C_6)$alkyl, or —$(C_3$-$C_8)$cycloalkyl.

In another embodiment, $R_b$ is -phenyl or —$N(R_c)$-phenyl, each of which is unsubstituted or substituted with 1, 2 or 3 independently selected $R_7$ groups.

In another embodiment, $R_b$ is -(5- or 6-membered)heteroaryl or —$N(R_c)$-(5- to 10-membered)heteroaryl, each of which is unsubstituted or substituted with 1, 2 or 3 independently selected $R_7$ groups.

In another embodiment, $R_b$ is —H, —$(C_1$-$C_6)$alkyl, -phenyl, or -(5- or 6-membered)heteroaryl.

In another embodiment, $R_a$ and $R_b$ are each independently —H or —$(C_1$-$C_6)$alkyl.

In another embodiment, $R_a$ and $R_b$ are —$CH_3$.

In another embodiment, each $R_c$ is independently —H or —$CH_3$.

In another embodiment, the B1, B2, or B3 bridge joins positions 2 and 6 of the piperidine, 1,2,3,6-tetrahydropyridine or piperazine ring.

In another embodiment, two $R_3$ groups form a bicyclo group to give one of the following structures

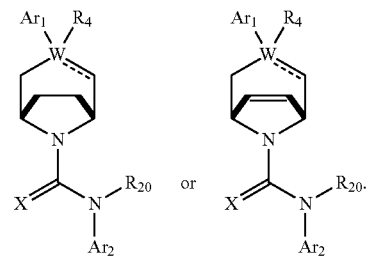

In another embodiment, m is 1.
In another embodiment, m is 0.
In another embodiment, s or q is 0.
In another embodiment, s or q is 1.
In another embodiment, s or q is 2.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.

In another embodiment, $R_1$ is —$CF_3$.
In another embodiment, $R_1$ is —$CH(halo)_2$.
In another embodiment, $R_1$ is —$CH_2(halo)$.
In another embodiment, $Ar_1$ is a pyridyl group and n is 1.
In another embodiment, $Ar_1$ is a pyrazinyl group and p is 1.
In another embodiment, $Ar_1$ is a pyrimidinyl group and p is 1.
In another embodiment, $Ar_1$ is a pyridazinyl group and p is 1.
In another embodiment, when n and p are 1, then $R_2$ must be Q.
In another embodiment, Q is

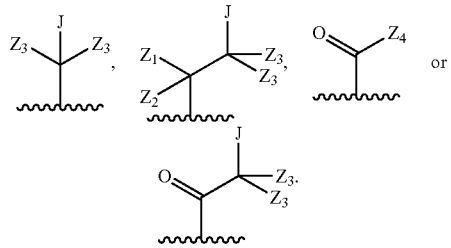

In another embodiment, Q is

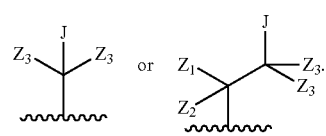

In another embodiment, Q is

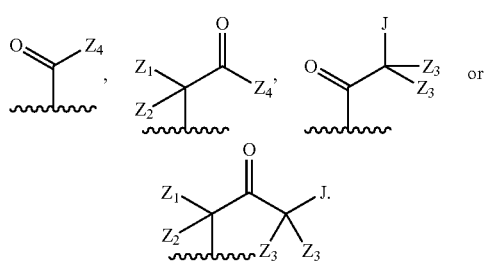

In another embodiment, Q is

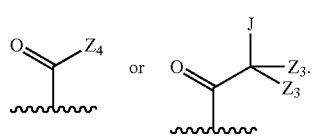

In another embodiment, Q is

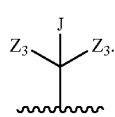

In another embodiment, Q is

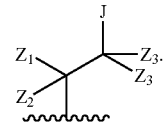

In another embodiment, Q is

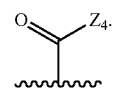

In another embodiment, Q is

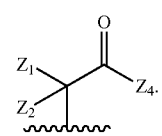

In another embodiment, Q is

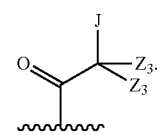

In another embodiment, Q is

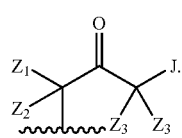

In another embodiment, J is —$OR_{20}$, —$SR_{20}$ or —$N(R_{20})_2$.
In another embodiment, J is —$OR_{20}$.
In another embodiment, J is —OH.
In another embodiment, J is —CN.
In another embodiment, $Z_1$ is —H.
In another embodiment, $Z_1$ is —OH.
In another embodiment, $Z_1$ is —$OCH_3$.
In another embodiment, $Z_1$ is —$CH_2OH$.
In another embodiment, $Z_2$ is —$CH_2$—$OR_7$.
In another embodiment, $Z_2$ is —$CH_2OH$.
In another embodiment, $Z_2$ is —H, —$(C_1$-$C_6)$alkyl, —$(C_2$-$C_6)$alkenyl, —$(C_2$-$C_6)$alkynyl, -phenyl, or -halo.
In another embodiment, $Z_2$ is —H.
In another embodiment, $Z_2$ is —$CH_3$.
In another embodiment, $Z_3$ is —H.
In another embodiment, $Z_3$ is —$CH_3$.
In another embodiment, $Z_4$ is —H.
In another embodiment, $Z_4$ is —$(C_1$-$C_6)$alkyl.
In another embodiment, $Z_4$ is —$N(R_{20})_2$.
In another embodiment $Z_4$ is —$OR_{20}$.
In another embodiment, $Z_4$ is —OH.
In another embodiment, Q is

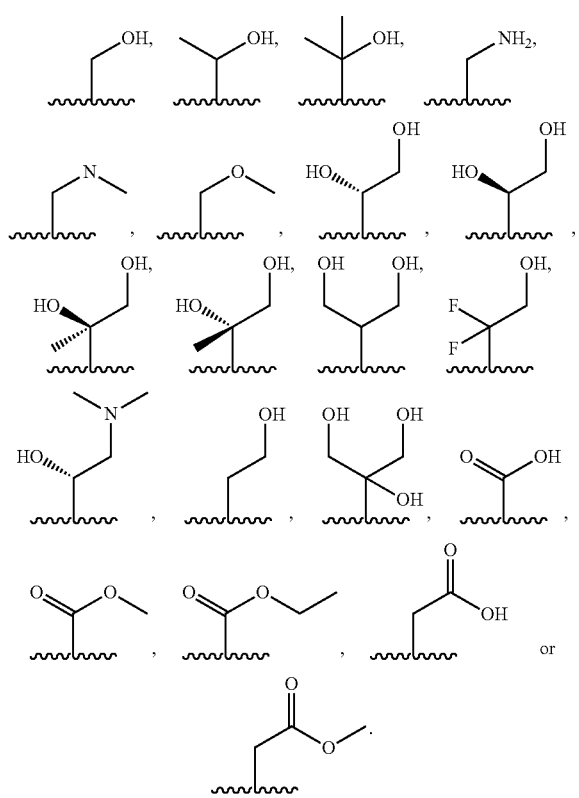

In another embodiment, Q is

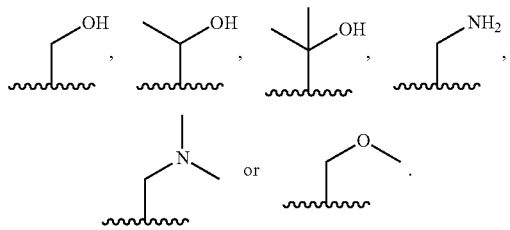

In another embodiment, Q is

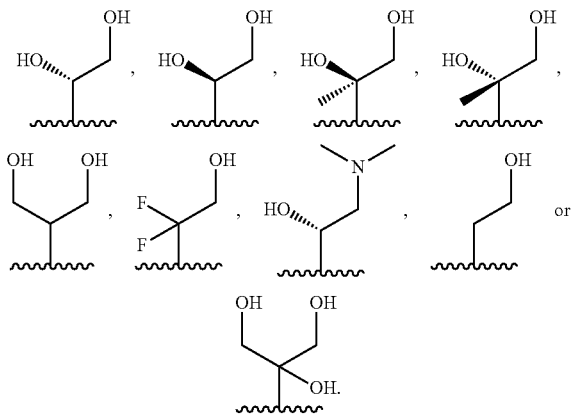

In another embodiment, Q is

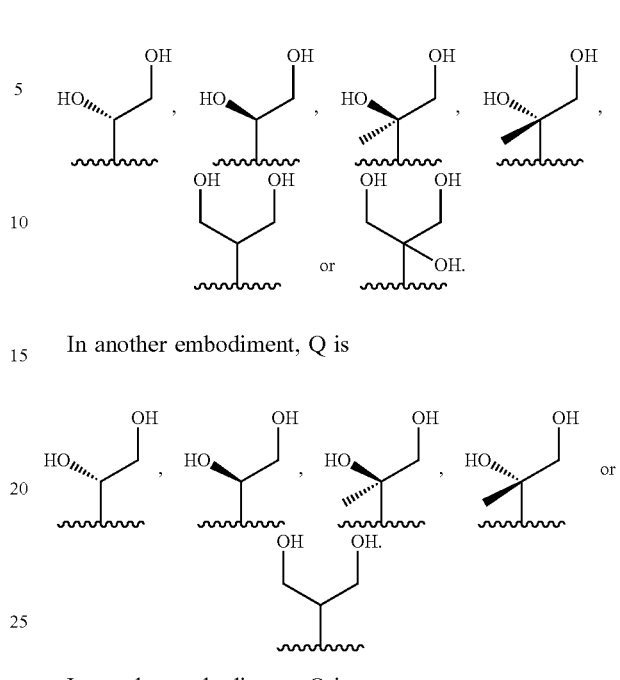

In another embodiment, Q is

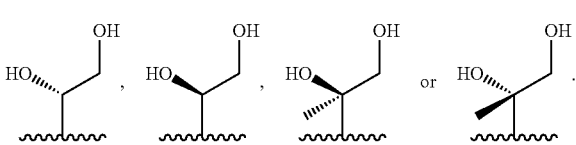

In another embodiment, Q is

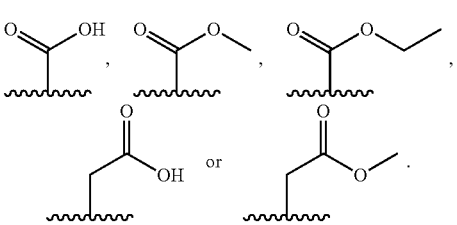

In another embodiment, m is 1 and $R_3$ is —$(C_1$-$C_6)$alkyl.
In another embodiment, m is 1 and $R_3$ is —$CH_3$ or —$CH_2CH_3$.
In another embodiment, m is 1 and $R_3$ is —$CH_3$.
In another embodiment, m is 1 and $R_3$ is —$CH_2OH$.
In another embodiment, m is 0.
In another embodiment, $R_4$ is —OH.
In another embodiment, $R_4$ is —$OCF_3$
In another embodiment, $R_4$ is -halo.
In another embodiment, $R_4$ is —F.
In another embodiment, $R_4$ is —Cl.
In another embodiment, $R_4$ is —$(C_1$-$C_6)$alkyl.
In another embodiment, $R_4$ is —$CH_3$.
In another embodiment, $R_4$ is —$CH_2OH$.
In another embodiment, $R_4$ is —$CH_2Cl$.
In another embodiment, $R_4$ is —$CH_2Br$.
In another embodiment, $R_4$ is —$CH_2I$.
In another embodiment, $R_4$ is —$CH_2F$.
In another embodiment, $R_4$ is —$CH(halo)_2$.
In another embodiment, $R_4$ is —$CF_3$.

In another embodiment, $R_4$ is —$NO_2$.
In another embodiment, $R_4$ is —$OR_{10}$.
In another embodiment, $R_4$ is —$SR_{10}$.
In another embodiment, $R_4$ is —$C(O)R_{10}$.
In another embodiment, $R_4$ is —COOH.
In another embodiment, $R_4$ is —C(O)H.
In another embodiment, $R_4$ is —$COOR_{10}$.
In another embodiment, $R_4$ is —$OC(O)R_{10}$.
In another embodiment, $R_4$ is —$SO_2R_{10}$.
In another embodiment, $R_4$ is —$OC(O)NHR_{10}$.
In another embodiment, $R_4$ is —$NHC(O)R_{13}$.
In another embodiment, $R_4$ is —$CON(R_{13})_2$.
In another embodiment, each $R_{20}$ is independently —H or —($C_1$-$C_6$)alkyl.
In another embodiment, each $R_{20}$ is —H.
In another embodiment, each $R_{20}$ is —($C_1$-$C_6$)alkyl.
In another embodiment, $Ar_2$ is a benzothiazolyl, benzoimidazolyl, or benzooxazolyl group; and at least one of $R_8$ and $R_9$ is —H.
In another embodiment, $Ar_2$ is a benzothiazolyl, benzoimidazolyl, or benzooxazolyl group; and at least one of $R_8$ and $R_9$ is not —H.
In another embodiment, $Ar_2$ is a benzothiazolyl, benzoimidazolyl, or benzooxazolyl group; and at least one of $R_8$ and $R_9$ is -halo.
In another embodiment, $Ar_2$ is

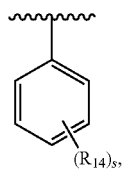

s is 1 and $R_{14}$ is —($C_1$-$C_6$)alkyl, -halo, —C(halo)$_3$, —OC(halo)$_3$, —$OR_7$, —$N(R_7)_2$, —$SO_2R_7$, or —$SO_2C(halo)_3$.

In another embodiment, $Ar_2$ is

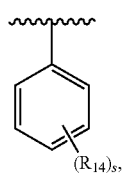

s is 2, and each $R_{14}$ is independently —($C_1$-$C_6$)alkyl, -halo, —C(halo)$_3$, —OC(halo)$_3$, —$OR_7$, —$N(R_7)_2$, —$SO_2R_7$, or —$SO_2C(halo)_3$.

In another embodiment, $R_4$ is -halo, n or p is 1, $R_2$ is Q, wherein Q is

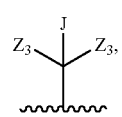

wherein J is —$OR_{20}$.
In another embodiment, $R_4$ is -halo, n or p is 1, $R_2$ is Q, wherein Q is

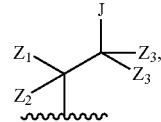

wherein J is —$OR_{20}$ and $Z_1$ is —$OR_7$.
In another embodiment, $R_4$ is -halo, n or p is 1, $R_2$ is Q, wherein Q is

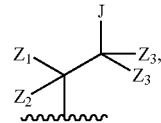

wherein J is —$OR_{20}$ and $Z_1$ is —$CH_2OR_7$.
In another embodiment, $R_4$ is -halo, n or p is 1, $R_2$ is Q, wherein Q is

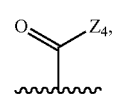

wherein $Z_4$ is —$OR_{20}$.
In another embodiment, $R_4$ is -halo, n or p is 1, $R_2$ is Q, wherein Q is

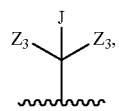

wherein J is —OH.
In another embodiment, $R_4$ is -halo, n or p is 1, $R_2$ is Q, wherein Q is

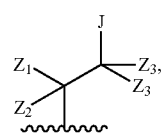

wherein J is —OH and $Z_1$ is —OH.
In another embodiment, $R_4$ is -halo, n or p is 1, $R_2$ is Q, wherein Q is

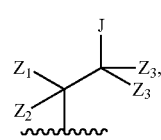

wherein J is —OH and $Z_1$ is —$CH_2OH$.
In another embodiment, $R_4$ is —F, n or p is 1, $R_2$ is Q, wherein Q is

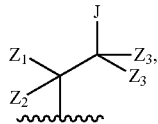

wherein J is —OH and $Z_1$ is —OH.

In another embodiment, $R_4$ is —F, n or p is 1, $R_2$ is Q, wherein Q is

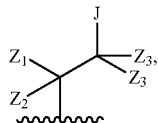

wherein J is —OH and $Z_1$ is —CH$_2$OH.

In another embodiment, $R_1$ is -halo, $R_4$ is -halo, n or p is 1, $R_2$ is Q, wherein Q is

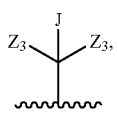

wherein J is —OR$_{20}$.

In another embodiment, $R_1$ is -halo, $R_4$ is -halo, n or p is 1, $R_2$ is Q, wherein Q is

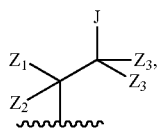

wherein J is —OR$_{20}$ and $Z_1$ is —OR$_7$.

In another embodiment, $R_1$ is -halo, $R_4$ is -halo, n or p is 1, $R_2$ is Q, wherein Q is

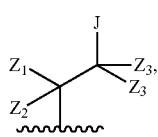

wherein J is —OR$_{20}$ and $Z_1$ is —CH$_2$OR$_7$.

In another embodiment, $R_1$ is -halo $R_4$ is -halo, n or p is 1, $R_2$ is Q, wherein Q is

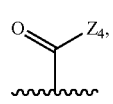

wherein $Z_4$ is —OR$_{20}$.

In another embodiment, $R_1$ is —Cl, $R_4$ is —F, n or p is 1, $R_2$ is Q, wherein Q is

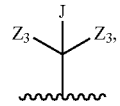

wherein J is —OR$_{20}$.

In another embodiment, $R_1$ is —Cl is —F, n or p is 1, $R_2$ is Q, wherein Q is

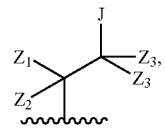

wherein J is —OR$_{20}$ and $Z_1$ is —OR$_7$.

In another embodiment, $R_1$ is —Cl, $R_4$ is —F, n or p is 1, $R_2$ is Q, wherein Q is

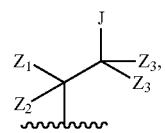

wherein J is —OR$_{20}$ and $Z_1$ is —CH$_2$OR$_7$.

In another embodiment, $R_1$ is —Cl, $R_4$ is —F, n or p is 1, $R_2$ is Q, wherein Q is

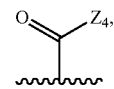

wherein $Z_4$ is —OR$_{20}$.

In another embodiment, $R_1$ is —Cl, $R_4$ is —F, n or p is 1, $R_2$ is Q, wherein Q is

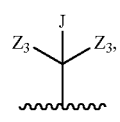

wherein J is —OH.

In another embodiment, $R_1$ is —Cl, $R_4$ is —F, n or p is 1, $R_2$ is Q, wherein Q is

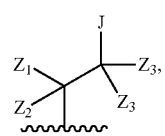

wherein J is —OH and $Z_1$ is —OH.

In another embodiment, $R_1$ is —Cl, $R_4$ is —F, n or p is 1, $R_2$ is Q, wherein Q is

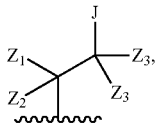

wherein J is —OH and $Z_1$ is —CH$_2$OH.

In another embodiment, Ar$_1$ is a pyridyl group, wherein n is 1, and R$_2$ is Q.

In another embodiment, Ar$_1$ is a pyridyl group, wherein n is 1, R$_2$ is Q, and Q is

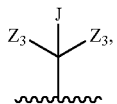

wherein J is —OH.

In another embodiment, Ar$_1$ is a pyridyl group, wherein n is 1, R$_2$ is Q, and Q is

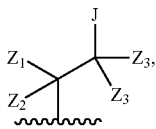

wherein J is —OR$_{20}$, and Z$_1$ is —OR$_7$.

In another embodiment, Ar$_1$ is a pyridyl group, wherein n is 1, R$_2$ is Q, and Q is

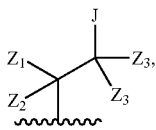

wherein J is —OH, and Z$_1$ is —OH.

In another embodiment, Ar$_1$ is a pyridyl group, wherein n is 1, R$_2$ is Q, and Q is

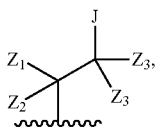

wherein J is —OR$_{20}$, and Z$_1$ is —CH$_2$OR$_7$.

In another embodiment, Ar$_1$ is a pyridyl group, wherein n is 1, R$_2$ is Q, and Q is

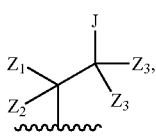

wherein J is —OH, and Z$_1$ is —CH$_2$OH.

In another embodiment, Ar$_1$ is a pyridyl group, wherein n is 1, R$_2$ is Q, and Q is

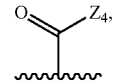

wherein Z$_4$ is —OR$_{20}$.

In another embodiment, R$_1$ is -halo, R$_4$ is -halo, and Ar$_1$ is a pyridyl group, wherein n is 1, R$_2$ is Q, and Q is

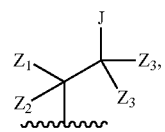

wherein J is —OR$_{20}$, Z$_1$ is —OR$_7$.

In another embodiment, R$_1$ is -halo, R$_4$ is -halo, and Ar$_1$ is a pyridyl group, wherein n is 1, R$_2$ is Q, and Q is

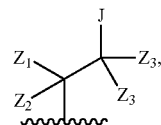

wherein J is —OH, Z$_1$ is —OH.

In another embodiment, R$_1$ is -halo, R$_4$ is -halo, and Ar$_1$ is a pyridyl group, wherein n is 1, R$_2$ is Q, and Q is

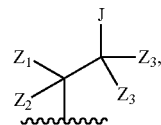

wherein J is —OR$_{20}$, Z$_1$ is —CH$_2$OR$_7$.

In another embodiment, R$_1$ is -halo, R$_4$ is -halo, and Ar$_1$ is a pyridyl group, wherein n is 1, R$_2$ is Q, and Q is

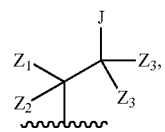

wherein J is —OH, Z$_1$ is —CH$_2$OH.

In another embodiment, R$_1$ is -halo, R$_4$ is -halo, and Ar$_1$ is a pyridyl group, wherein n is 1, R$_2$ is Q, and Q is

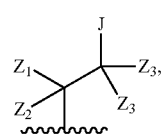

wherein J is —OH, Z$_1$ is —OH, Ar$_2$ is benzothiazolyl, wherein at least one of R$_8$ or R$_9$ is not —H.

In another embodiment, R$_1$ is -halo, R$_4$ is -halo, and Ar$_1$ is a pyridyl group, wherein n is 1, R$_2$ is Q, and Q is

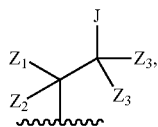

wherein J is —OH, $Z_1$ is —CH$_2$OH, Ar$_2$ is benzothiazolyl, wherein at least one of $R_8$ or $R_9$ is not —H.

In another embodiment, $R_1$ is -halo, $R_4$ is -halo, and Ar$_1$ is a pyridyl group, wherein n is 1, $R_2$ is Q, and Q is

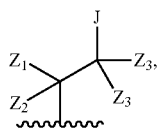

wherein J is —OH, $Z_1$ is —OH, Ar$_2$ is benzooxazolyl, wherein at least one of $R_8$ or $R_9$ is not —H.

In another embodiment, $R_1$ is -halo, $R_4$ is -halo, and Ar$_1$ is a pyridyl group, wherein n is 1, $R_2$ is Q, and Q is

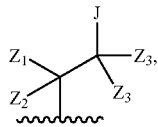

wherein J is —OH, $Z_1$ is —CH$_2$OH, Ar$_2$ is benzooxazolyl, wherein at least one of $R_8$ or $R_9$ is not —H.

In another embodiment, $R_1$ is -halo, $R_4$ is -halo, and Ar$_1$ is a pyridyl group, wherein n is 1, $R_2$ is Q, and Q is

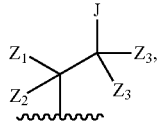

wherein J is —OH, $Z_1$ is —OH, Ar$_2$ is benzoimidazolyl, wherein at least one of $R_8$ or $R_9$ is not —H.

In another embodiment, $R_1$ is -halo, $R_4$ is -halo, and Ar$_1$ is a pyridyl group, wherein n is 1, $R_2$ is Q, and Q is

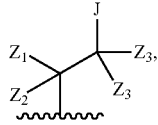

wherein J is —OH, $Z_1$ is —CH$_2$OH, Ar$_2$ is benzoimidazolyl, wherein at least one of $R_8$ or $R_9$ is not —H.

In another embodiment, $R_1$ is -halo, $R_4$ is -halo, and Ar$_1$ is a pyridyl group, wherein n is 1, $R_2$ is Q, and Q is

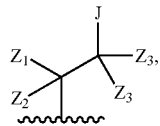

wherein J is —OH, $Z_1$ is —OH, Ar$_2$ is phenyl, wherein s is 0 or 1.

In another embodiment, $R_1$ is -halo, $R_4$ is -halo, and Ar$_1$ is a pyridyl group, wherein n is 1, $R_2$ is Q, and Q is

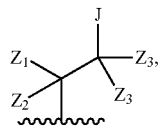

wherein J is —OH, $Z_1$ is —CH$_2$OH, Ar$_2$ is phenyl, wherein s is 0 or 1.

In another embodiment, $R_1$ is -halo, $R_4$ is -halo, and Ar$_1$ is a pyridyl group, wherein n is 1, $R_2$ is Q, and Q is

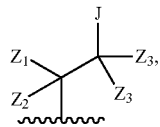

wherein J is —OH, $Z_1$ is —OH, Ar$_2$ is phenyl, wherein s is 2.

In another embodiment, $R_1$ is -halo, $R_4$ is -halo, and Ar$_1$ is a pyridyl group, wherein n is 1, $R_2$ is Q, and Q is

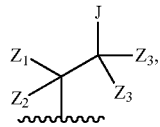

wherein J is —OH, $Z_1$ is —CH$_2$OH, Ar$_2$ is phenyl, wherein s is 2.

In another embodiment, the dashed line is a double bond, n or p is 1, $R_2$ is Q, wherein Q is

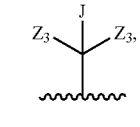

wherein J is —OR$_{20}$.

In another embodiment, the dashed line is a double bond, n or p is 1, $R_2$ is Q, wherein Q is

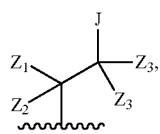

wherein J is —OR$_{20}$ and $Z_1$ is —OR$_7$.

In another embodiment, the dashed line is a double bond, n or p is 1, $R_2$ is Q, wherein Q is

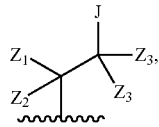

wherein J is —$OR_{20}$ and $Z_1$ is —$CH_2OR_7$.

In another embodiment, the dashed line is a double bond, n or p is 1, $R_2$ is Q, wherein Q is

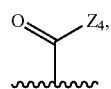

wherein $Z_4$ is —$OR_{20}$.

In another embodiment, the dashed line is a double bond, n or p is 1, $R_2$ is Q, wherein Q is

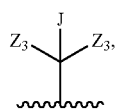

wherein J is —OH.

In another embodiment, the dashed line is a double bond, n or p is 1, $R_2$ is Q, wherein Q is

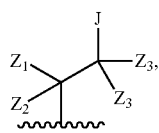

wherein J is —OH and $Z_1$ is —OH.

In another embodiment, the dashed line is a double bond, n or p is 1, $R_2$ is Q, wherein Q is

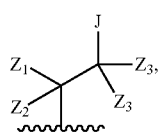

wherein J is —OH and $Z_1$ is —$CH_2OH$.

In another embodiment, the dashed line is a double bond, $R_1$ is -halo, n or p is 1, $R_2$ is Q, wherein Q is

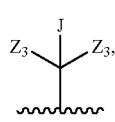

wherein J is —OH.

In another embodiment, the dashed line is a double bond, $R_1$ is -halo, n or p is 1, $R_2$ is Q, wherein Q is

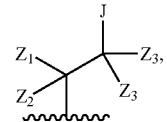

wherein J is —OH and $Z_1$ is —OH.

In another embodiment, the dashed line is a double bond, $R_1$ is -halo, n or p is 1, $R_2$ is Q, wherein Q is wherein J is —OH and $Z_1$ is —$CH_2OH$.

In another embodiment, the dashed line is a double bond, $R_1$ is -halo, and $Ar_1$ is a pyridyl group, wherein n is 1, $R_2$ is Q, and Q is wherein J is —OH, $Z_1$ is —OH.

In another embodiment, the dashed line is a double bond, $R_1$ is -halo, and $Ar_1$ is a pyridyl group, wherein n is 1, $R_2$ is Q, and Q is wherein J is —OH, $Z_1$ is —$CH_2OH$.

In another embodiment, the dashed line is a double bond, $R_1$ is -halo, and $Ar_1$ is a pyridyl group, wherein n is 1, $R_2$ is Q, and Q is

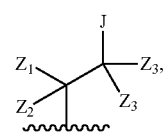

wherein J is —OH, $Z_1$ is —OH $Ar_2$ is benzothiazolyl, wherein at least one of $R_8$ or $R_9$ is not a —H.

In another embodiment, the dashed line is a double bond, $R_1$ is -halo, and $Ar_1$ is a pyridyl group, wherein n is 1, $R_2$ is Q, and Q is wherein J is —OH, $Z_1$ is —$CH_2OH$, $Ar_2$ is benzothiazolyl, wherein at least one of $R_8$ or $R_9$ is not a —H.

In another embodiment, the dashed line is a double bond, $R_1$ is -halo, and $Ar_1$ is a pyridyl group, and Q is

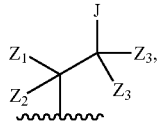

wherein J is —OH, $Z_1$ is —OH $Ar_2$ is benzooxazolyl, wherein at least one of $R_8$ or $R_9$ is not a —H.

In another embodiment, the dashed line is a double bond, $R_1$ is -halo, and $Ar_1$ is a pyridyl group, wherein n is 1, and Q is

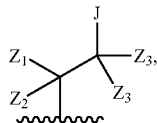

wherein J is —OH, $Z_1$ is —$CH_2OH$, $Ar_2$ is benzooxazolyl, wherein at least one of $R_8$ or $R_9$ is not a —H.

In another embodiment, the dashed line is a double bond, $R_1$ is -halo, and $Ar_1$ is a pyridyl group, wherein n is 1, $R_2$ is Q, and Q is

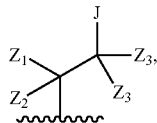

wherein J is —OH, $Z_1$ is —OH, $Ar_2$ is benzoimidazolyl, wherein at least one of $R_8$ or $R_9$ is not a —H.

In another embodiment, the dashed line is a double bond, $R_1$ is -halo, and $Ar_1$ is a pyridyl group, wherein n is 1, $R_2$ is Q, and Q is

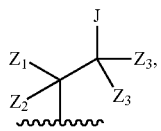

wherein J is —OH, $Z_1$ is —$CH_2OH$, $Ar_2$ is benzoimidazolyl, wherein at least one of $R_8$ or $R_9$ is not a —H.

In another embodiment, the dashed line is a double bond, $R_1$ is -halo, and $Ar_1$ is a pyridyl group, wherein n is 1, $R_2$ is Q, and Q is

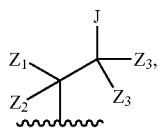

wherein J is —OH, $Z_1$ is —OH $Ar_2$ is phenyl, wherein s is 0 or 1 and $R_{14}$ is —($C_1$-$C_6$)alkyl, -halo, —C(halo)$_3$, —OC(halo)$_3$, —$OR_7$, —N($R_7$)$_2$, —$SO_2R_7$, or —$SO_2C$(halo)$_3$, and optionally is —F, —Cl, —$CF_3$, or —$OCF_3$.

In another embodiment, the dashed line is a double bond, $R_1$ is -halo, and $Ar_1$ is a pyridyl group, wherein n is 1, $R_2$ is Q, and Q is

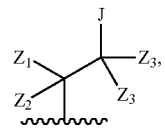

wherein J is —OH, $Z_1$ is —$CH_2OH$, $Ar_2$ is phenyl, wherein s is 0 or 1 and $R_{14}$ is —($C_1$-$C_6$)alkyl, -halo, —C(halo)$_3$, —OC(halo)$_3$, —$OR_7$, —N($R_7$)$_2$, —$SO_2R_7$, or —$SO_2C$(halo)$_3$, and optionally is —F, —Cl, —$CF_3$, or —$OCF_3$.

In another embodiment, the dashed line is a double bond, $R_1$ is -halo, and $Ar_1$ is a pyridyl group, wherein n is 1, $R_2$ is Q, and Q is

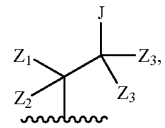

wherein J is —OH, $Z_1$ is —OH $Ar_2$ is phenyl, wherein s is 2, and each $R_{14}$ is independently —($C_1$-$C_6$)alkyl, -halo, —C(halo)$_3$, —OC(halo)$_3$, —$OR_7$, —N($R_7$)$_2$, —$SO_2R_7$, or —$SO_2C$(halo)$_3$, and optionally is —F, —Cl, —$CF_3$, or —$OCF_3$.

In another embodiment, the dashed line is a double bond, $R_1$ is -halo, and $Ar_1$ is a pyridyl group, wherein n is 1, $R_2$ is Q, and Q is

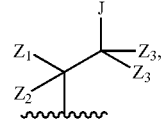

wherein J is —OH, $Z_1$ is —$CH_2OH$, $Ar_2$ is phenyl, wherein s is 2, and each $R_{14}$ is independently —($C_1$-$C_6$)alkyl, -halo, —C(halo)$_3$, —OC(halo)$_3$, —$OR_7$, —N($R_7$)$_2$, —$SO_2R_7$, or —$SO_2C$(halo)$_3$, and optionally is —F, —Cl, —$CF_3$, or —$OCF_3$.

In another embodiment Q is

wherein the compound of formula IA is racemic.

In another embodiment Q is

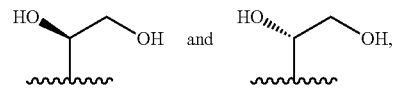

wherein the % ee of the R enantiomer is greater than 60%.

In another embodiment Q is

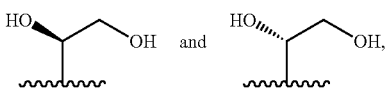 [SMILES: *[C@@H](O)CO ; "and" ; *[C@H](O)CO]

wherein the % ee of the R enantiomer is greater than 70%.
In another embodiment Q is

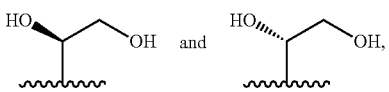 [SMILES: *[C@@H](O)CO ; "and" ; *[C@H](O)CO]

wherein the % ee of the R enantiomer is greater than 80%.
In another embodiment Q is

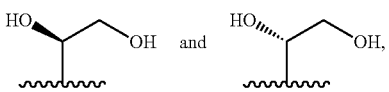

wherein the % ee of the R enantiomer is greater than 90%.
In another embodiment Q is

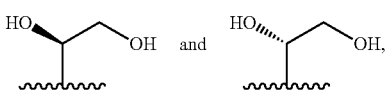 [SMILES: *[C@@H](O)CO ; "and" ; *[C@H](O)CO]

wherein the % ee of the R enantiomer is greater than 99%.
In another embodiment Q is

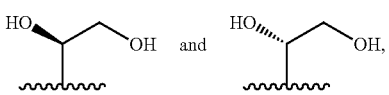 [SMILES: *[C@@H](O)CO ; "and" ; *[C@H](O)CO]

wherein the % ee of the S enantiomer is greater than 60%.
In another embodiment Q is

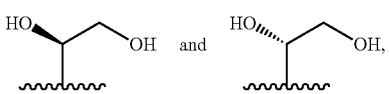

wherein the % ee of the S enantiomer is greater than 70%.
In another embodiment Q is

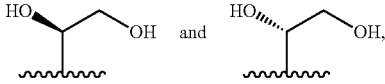 [SMILES: *[C@@H](O)CO ; "and" ; *[C@H](O)CO]

wherein the % ee of the S enantiomer is greater than 80%.
In another embodiment Q is

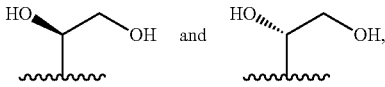 [SMILES: *[C@@H](O)CO ; "and" ; *[C@H](O)CO]

wherein the % ee of the S enantiomer is greater than 90%.

In another embodiment Q is

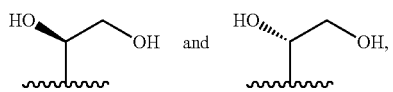 [SMILES: *[C@@H](O)CO ; "and" ; *[C@H](O)CO]

wherein the % ee of the S enantiomer is greater than 99%.
In another embodiment, the invention encompasses compounds of formula IA.1:

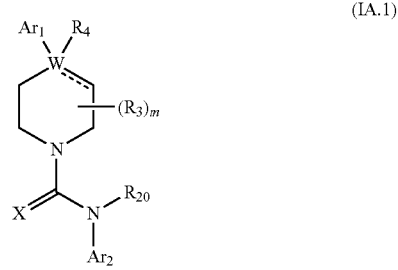

(IA.1)

or a pharmaceutically acceptable salt thereof, where
X is O, S, N—CN, N—OH, or N—OR$_{10}$;
W is N or C;
the dashed line denotes the presence or absence of a bond, and when the dashed line denotes the presence of a bond or W is N then R$_4$ is absent, otherwise R$_4$ is —H, —OH, —OCF$_3$, -halo, —(C$_1$-C$_6$)alkyl, —CH$_2$OH, —CH$_2$Cl, —CH$_2$Br, —CH$_2$I, —CH$_2$F, —CH(halo)$_2$, —CF$_3$, —OR$_{10}$, —SR$_{10}$, —COOH, —COOR$_{10}$, —C(O)R$_{10}$, —C(O)H, —OC(O)R$_{10}$, —OC(O)NHR$_{10}$, —NHC(O)R$_{13}$, —CON(R$_{13}$)$_2$, —S(O)$_2$R$_{10}$, or —NO$_2$;
R$_{10}$ is —(C$_1$-C$_4$)alkyl;
each R$_{13}$ is independently: —H, —(C$_1$-C$_4$)alkyl, —(C$_1$-C$_4$)alkenyl, —(C$_1$-C$_4$)alkynyl, or -phenyl;
Ar$_1$ is

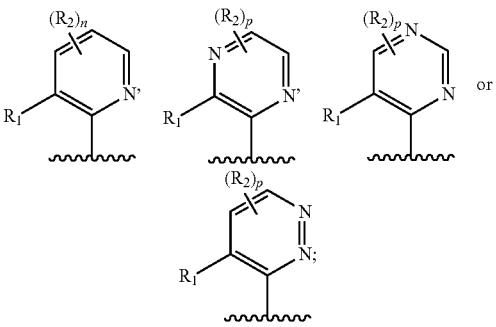

Ar$_2$ is

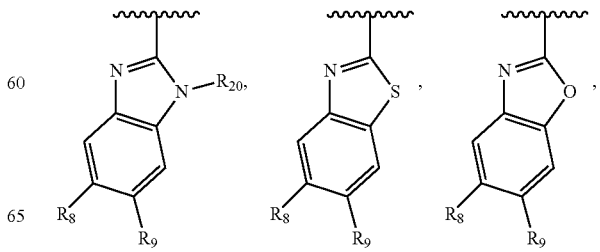

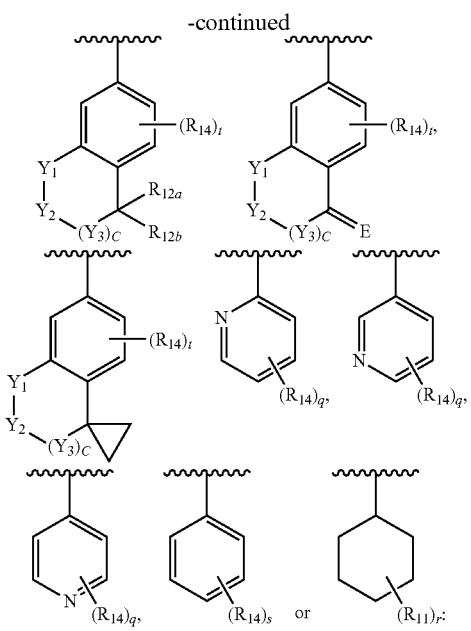

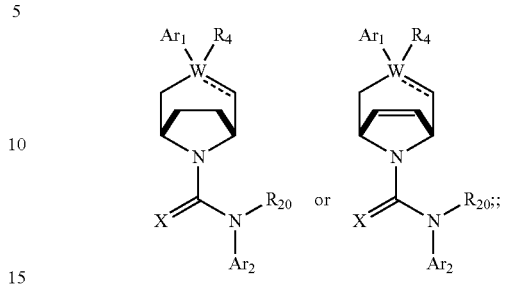

c is the integer 0, 1, or 2;
$Y_1$, $Y_2$, and $Y_3$ are independently C or N;
wherein for each $Y_1$, $Y_2$, and $Y_3$ that is N, the N is bonded to one $R_{20}$ group, and for each $Y_1$, $Y_2$, and $Y_3$ that is C, the C is bonded to two $R_{20}$ groups, provided that there are no more than a total of two $(C_1-C_6)$alkyl groups substituted on all of $Y_1$, $Y_2$, and $Y_3$;
$R_{12a}$ and $R_{12b}$ are independently —H or —$(C_1-C_6)$alkyl;
E is =O, =S, =C$(C_1-C_5)$alkyl, =C$(C_1-C_5)$alkenyl, =NH$(C_1-C_6)$alkyl, or =N—OR$_{20}$;
$R_1$ is —H, -halo, —$(C_1-C_4)$alkyl, —$NO_2$, —CN, —OH, —$OCH_3$, —$NH_2$, —C(halo)$_3$, —CH(halo)$_2$, —$CH_2$(halo), —OC(halo)$_3$, —OCH(halo)$_2$, or —$OCH_2$(halo);
each $R_2$ is independently:
(a) -halo, —OH, —O$(C_1-C_4)$alkyl, —CN, —$NO_2$, —$NH_2$, —$(C_1-C_{10})$alkyl, —$(C_2-C_{10})$alkenyl, —$(C_2-C_{10})$alkynyl, or -phenyl, or
(b) a group of formula Q;
wherein Q is

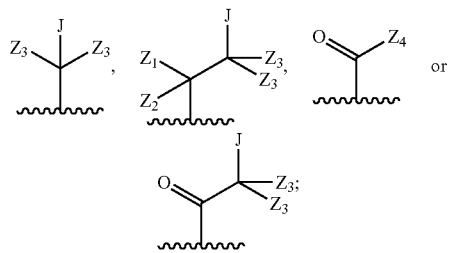

$Z_1$ is —H, —$OR_7$, —$SR_7$, —$CH_2$—$OR_7$, —$CH_2$—$SR_7$, —$CH_2$—$N(R_{20})_2$, or -halo;
$Z_2$ is —H, —$(C_1-C_6)$alkyl, —$(C_2-C_6)$alkenyl, —$(C_2-C_6)$alkynyl, -phenyl, or -halo;
each $Z_3$ is independently —H, —$(C_1-C_6)$alkyl, —$(C_2-C_6)$alkenyl, —$(C_2-C_6)$alkynyl, or -phenyl;
$Z_4$ is —H, —OH, —$OR_{20}$, —$(C_1-C_6)$alkyl, or —$NR_{20}$;
J is —$OR_{20}$, —$SR_{20}$, or —$N(R_{20})_2$;
provided that at least one $R_2$ group is a group of formula Q, and provided that when $Z_1$ is —$OR_7$ or —$SR_7$, $Z_2$ in not -halo;

each $R_3$ is independently:
(a) —H, —$(C_1-C_6)$alkyl, or two $R_3$ groups may form bicyclo group, which gives the following structures each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_1-C_6)$haloalkyl, —$(C_1-C_6)$hydroxyalkyl, —$(C_1-C_6)$alkoxy$(C_1-C_6)$alkyl, —$(C_1-C_6)$alkyl-$N(R_{20})_2$, or —$CON(R_{20})_2$;
each $R_8$ and $R_9$ are independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$CH_2$C(halo)$_3$, —C(halo)$_3$, —CH(halo)$_2$, —$CH_2$(halo), —OC(halo)$_3$, —OCH(halo)$_2$, —$OCH_2$(halo), —O—CN, —OH, -halo, —$N_3$, —$NO_2$, —CH=$NR_7$, —$N(R_7)_2$, —$NR_7$OH, —$OR_7$, —C(O)$R_7$, —C(O)O$R_7$, —OC(O)$R_7$, —OC(O)O$R_7$, —$SR_7$, —S(O)$R_7$, or —S(O)$_2R_7$;
each $R_{11}$ is independently —CN, —OH, —$(C_1-C_6)$alkyl, —$(C_2-C_6)$alkenyl, -halo, —$N_3$, —$NO_2$, —$N(R_7)_2$, —CH=$NR_7$, —$NR_7$OH, —$OR_7$, —C(O)$R_7$, —C(O)O$R_7$, —OC(O)$R_7$, or —OC(O)O$R_7$;
each $R_{14}$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_1-C_6)$alkoxy-$(C_1-C_6)$alkyl, -phenyl, —C(halo)$_3$, —CH(halo)$_2$, —$CH_2$(halo), -(3- to 7-membered)heterocycle, —$(C_1-C_6)$haloalkyl, —$(C_2-C_6)$haloalkenyl, —$(C_2-C_6)$haloalkynyl, —$(C_2-C_6)$hydroxyalkenyl, —$(C_2-C_6)$hydroxyalkynyl, —$(C_1-C_6)$alkoxy$(C_2-C_6)$alkyl, —$(C_1-C_6)$alkoxy$(C_2-C_6)$alkenyl, —$(C_1-C_6)$alkoxy$(C_2-C_6)$alkynyl, —CN, —OH, -halo, OC(halo)$_3$, —$N_3$, —$NO_2$, —CH=$NR_7$, —$N(R_7)_2$, —$NR_7$OH, —$OR_7$, —$SR_7$, —O$(CH_2)_b$O$R_7$, —O$(CH_2)_b$S$R_7$, —O$(CH_2)_b$N$(R_7)_2$, —N$(R_7)(CH_2)_b$O$R_7$, —N$(R_7)(CH_2)_b$S$R_7$, —N$(R_7)(CH_2)_b$N$(R_7)_2$, —N$(R_7)$CO$R_7$, —C(O)$R_7$, —C(O)O$R_7$, —OC(O)$R_7$, —OC(O)O$R_7$, —S(O)$R_7$, or —S(O)$_2R_7$, —S(O)$_2$N$(R_7)_2$, —$SO_2$C(halo)$_3$, —CON$(R_7)_2$, —$(C_1-C_5)$alkyl-C=NO$R_7$, —$(C_1-C_5)$alkyl-C(O)—N$(R_7)_2$, —$(C_1-C_6)$alkyl-NHSO$_2$N$(R_7)_2$, or —$(C_1-C_6)$alkyl-C(=NH)—N$(R_7)_2$;
each $R_{20}$ is independently —H or —$(C_1-C_6)$alkyl;
each halo is independently —F, —Cl, —Br, or —I;
n is the integer 1, 2, or 3;
p is the integer 1 or 2;
each b is independently the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
m is the integer 0, 1, or 2.
In another embodiment relating to formula IA.1, E is =O, =S, =CH$(C_1-C_5)$alkyl, =CH$(C_1-C_5)$alkenyl, or =N—OR$_{20}$.
In another embodiment relating to formula IA.1, E is =O, =S, or =N—OR$_{20}$.

In another embodiment relating to formula IA.1, Q is

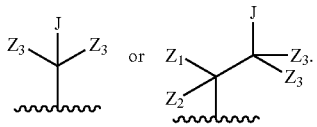

In another embodiment relating to formula IA.1, Q is

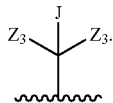

In another embodiment relating to formula IA.1, Q is

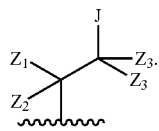

In another embodiment relating to formula IA.1, Q is

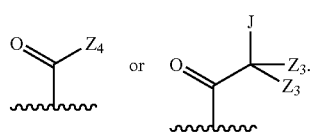

In another embodiment relating to formula IA.1, Q is

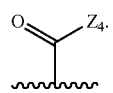

In another embodiment relating to formula IA.1, Q is

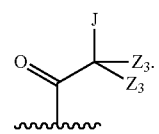

5.3 Compounds of Formula II

Preferred compounds of formula I are compounds of formula II:

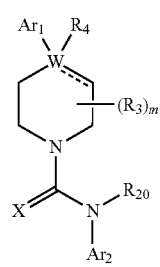

(II)

or a pharmaceutically acceptable derivative thereof, where the dashed line, W, X, $Ar_1$, $Ar_2$, $R_3$, $R_4$, $R_{20}$, and m are as defined above for compounds of formula I, wherein Q is

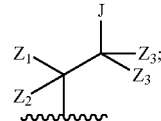

$Z_1$ is —OH, —SH, —N($R_{20}$)$_2$, —CH$_2$—OH, —CH$_2$—SH, or —CH$_2$—N($R_{20}$)$_2$;

$Z_2$ is —H, —CH$_3$, or —CH$_2$—OR$_7$;

each $Z_3$ is independently —H or —CH$_3$; and

J is —OH, —SH, or —N($R_{20}$)$_2$.

In addition to being highly soluble in aqueous solution, compounds of formula II are preferred because side effects are less severe (e.g., attenuation or removal of central nervous system side effects) in animals administered a compound of formula II. For example, muscle relaxation is attenuated or absent in animals administered a compound of formula II. Sedation is attenuated or absent in animals administered a compound of formula II. Ataxia is attenuated or absent in animals administered a compound of formula II. Flat body posture is attenuated or absent in animals administered a compound of formula II. Tremor is attenuated or absent in animals administered a compound of formula II. When a compound induces less severe side effects, the therapeutic index, which is the difference between an effective dose and a dose that causes adverse effects, is increased. Therapeutic index is a measure of the safety of a compound when administered to an animal. The greater the therapeutic index, the safer the compound.

Compounds of formula II also have excellent pharmacokinetic properties. Specifically, the plasma level of a compound of formula II in an animal is dose proportionate. Therefore, the amount of compound in the plasma of an animal can be more readily controlled according to the dose of the compound administered to the animal. Moreover, for a given dose administered, the animal plasma concentration is greater and is achieved more rapidly for a compound of formula II. For example, compound 200 achieves its maximum plasma concentration 3.1 h after administration. In contrast, compound of formula II Z1 achieves its maximum plasma concentration 2.5 h after administration and that maximum plasma concentration is 2.5 times greater than the maximum for compound 200. Additionally, compound of formula II $R_6$ achieves its maximum plasma concentration 1.85 h after administration and that maximum plasma concentration is 5.3 times greater than the maximum for compound 200. For each of compounds of formula II Z1 and $R_6$, the plasma concentration up to 24 h is consistently greater for each when compared with compound 200.

Compounds of formula II are also preferred because they have a high therapeutic index. Therapeutic index is the difference between the amount of a compound that is effective for treating a Condition and the amount of that same compound that induces adverse effects.

Other embodiments of formula II are presented below.

In one embodiment, a compound of formula II is a pharmaceutically acceptable derivative of a compound of formula II.

In another embodiment, a compound of formula I is a compound of formula II wherein the derivative is a pharmaceutically acceptable salt.

In another embodiment, a compound of formula II is a pharmaceutically acceptable salt of a compound of formula II.

In another embodiment, $Ar_1$ is a pyridyl group.
In another embodiment, $Ar_1$ is a pyrimidinyl group.
In another embodiment, $Ar_1$ is a pyrazinyl group.
In another embodiment, $Ar_1$ is pyridazinyl group.
In another embodiment, W is C.
In another embodiment, W is N.
In another embodiment, X is O.
In another embodiment, X is S.
In another embodiment, X is N—CN.
In another embodiment, X is N—OH.
In another embodiment, X is N—$OR_{10}$.
In another embodiment, $Ar_2$ is a benzoimidazolyl group.
In another embodiment, $Ar_2$ is a benzothiazolyl group.
In another embodiment, $Ar_2$ is a benzooxazolyl group.
In another embodiment, $Ar_2$ is

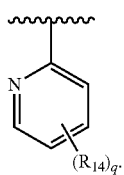

In another embodiment, $Ar_2$ is

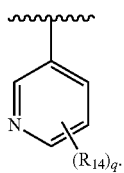

In another embodiment, $Ar_2$ is

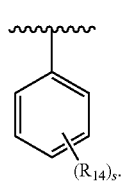

In another embodiment, $Ar_2$ is

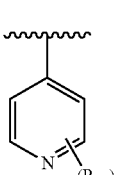

In another embodiment, $Ar_2$ is

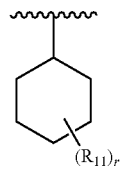

In another embodiment, n or p is 1.
In another embodiment, n or p is 2.
In another embodiment, n is 3.
In another embodiment, m is 2.
In another embodiment, two $R_3$ groups together form a $(C_2-C_6)$bridge, which is unsubstituted or substituted with 1, 2 or 3 independently selected $R_8$ groups, and which bridge optionally contains —HC=CH— within the $(C_2-C_6)$bridge.
In another embodiment, two $R_3$ groups together form a $(C_2-C_6)$bridge, which is unsubstituted or substituted with an $R_8$ group, and which bridge optionally contains —HC=CH— within the $(C_2-C_6)$bridge.
In another embodiment, two $R_3$ groups together form a $(C_2-C_3)$bridge, which is unsubstituted or substituted with an $R_8$ group, and which bridge optionally contains —HC=CH— within the $(C_2-C_3)$bridge.
In another embodiment, two $R_3$ groups together form a $(C_2-C_3)$bridge, which is unsubstituted and which bridge optionally contains —HC=CH— within the $(C_2-C_3)$bridge.
In another embodiment, two $R_3$ groups together form a $(C_2)$bridge, a —HC=CH— bridge, or a $(C_3)$bridge each of which is unsubstituted.
In another embodiment, two $R_3$ groups together form a $(C_2-C_6)$bridge, which is unsubstituted or substituted with 1, 2 or 3 independently selected $R_8$ groups, which bridge optionally contains —HC=CH— within the $(C_2-C_6)$bridge, and which bridge joins positions 2 and 6 of the piperidine, 1,2,3,6-tetrahydropyridine or piperazine ring.
In another embodiment, two $R_3$ groups together form a $(C_2-C_6)$bridge, which is unsubstituted or substituted with an $R_8$ group, which bridge optionally contains —HC=CH— within the $(C_2-C_6)$bridge, and which bridge joins positions 2 and 6 of the piperidine, 1,2,3,6-tetrahydropyridine or piperazine ring.
In another embodiment, two $R_3$ groups together form a $(C_2-C_3)$bridge, which is unsubstituted or substituted with an $R_8$ group, which bridge optionally contains —HC=CH— within the $(C_2-C_3)$bridge, and which bridge joins positions 2 and 6 of the piperidine, 1,2,3,6-tetrahydropyridine or piperazine ring.
In another embodiment, two $R_3$ groups together form a $(C_2-C_3)$bridge, which is unsubstituted, which bridge optionally contains —HC=CH— within the $(C_2-C_3)$bridge, and which bridge joins positions 2 and 6 of the piperidine, 1,2,3,6-tetrahydropyridine or piperazine ring.
In another embodiment, two $R_3$ groups together form a $(C_2)$bridge, a —HC=CH— bridge, or a $(C_3)$bridge each of which is unsubstituted, and which bridge joins positions 2 and 6 of the piperidine, 1,2,3,6-tetrahydropyridine or piperazine ring.
In another embodiment, two $R_3$ groups together form a —$CH_2$—N($R_a$)—$CH_2$— bridge (B1), a

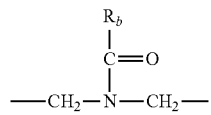

bridge (B2), or a

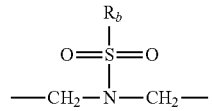

bridge (B3);

wherein $R_a$ is —H, —$(C_1$-$C_6)$alkyl, —$(C_3$-$C_8)$cycloalkyl, —$CH_2$—C(O)—$R_c$, —$(CH_2)$—C(O)—$OR_c$, —$(CH_2)$—C(O)—N$(R_c)_2$, —$(CH_2)_2$—O—$R_c$, —$(CH_2)_2$—$S(O)_2$—N$(R_c)_2$, or —$(CH_2)_2$—N$(R_c)S(O)_2$—$R_c$;

$R_b$ is:
(a) —H, —$(C_1$-$C_6)$alkyl, —$(C_3$-$C_8)$cycloalkyl, -(3- to 7-membered)heterocycle, —N$(R_c)_2$, —N$(R_c)$—$(C_3$-$C_8)$cycloalkyl, or —N$(R_c)$-(3- to 7-membered)heterocycle; or
(b) -phenyl, -(5- or 6-membered)heteroaryl, —N$(R_c)$-phenyl, or —N$(R_c)$-(5- to 10-membered)heteroaryl, each of which is unsubstituted or substituted with 1, 2 or 3 independently selected $R_7$ groups; and each $R_c$ is independently —H or —$(C_1$-$C_4)$alkyl.

In another embodiment, $R_a$ is —H, —$(C_1$-$C_6)$alkyl, —$(C_3$-$C_8)$cycloalkyl, —$(CH_2)$—C(O)—N$(R_c)_2$, —$(CH_2)_2$—$S(O)_2$—N$(R_7)_2$, or —$(CH_2)_2$—N$(R_c)S(O)_2$—$R_c$.

In another embodiment, $R_a$ is —H, —$(C_1$-$C_6)$alkyl, —$(C_3$-$C_8)$cycloalkyl, or —$(CH_2)$—C(O)—N$(R_c)_2$.

In another embodiment, $R_a$ is —H, —$(C_1$-$C_6)$alkyl, or —$(C_3$-$C_8)$cycloalkyl.

In another embodiment, $R_b$ is —H, —$(C_3$-$C_8)$cycloalkyl, or -(3- to 7-membered)heterocycle.

In another embodiment, $R_b$ is —H, —N$(R_c)_2$, —N$(R_c)$—$(C_3$-$C_8)$cycloalkyl, or —N$(R_c)$-(3- to 7-membered)heterocycle.

In another embodiment, $R_b$ is —H, —$(C_1$-$C_6)$alkyl, or —$(C_3$-$C_8)$cycloalkyl.

In another embodiment, $R_b$ is -phenyl or —N$(R_c)$-phenyl, each of which is unsubstituted or substituted with 1, 2 or 3 independently selected $R_7$ groups.

In another embodiment, $R_b$ is -(5- or 6-membered)heteroaryl or —N$(R_c)$-(5- to 10-membered)heteroaryl, each of which is unsubstituted or substituted with 1, 2 or 3 independently selected $R_7$ groups.

In another embodiment, $R_b$ is —H, —$(C_1$-$C_6)$alkyl, -phenyl, or -(5- or 6-membered)heteroaryl.

In another embodiment, $R_a$ and $R_b$ are each independently —H or —$(C_1$-$C_6)$alkyl.

In another embodiment, $R_a$ and $R_b$ are —$CH_3$.

In another embodiment, each R, is independently —H or —$CH_3$.

In another embodiment, the B1, B2, or B3 bridge joins positions 2 and 6 of the piperidine, 1,2,3,6-tetrahydropyridine or piperazine ring.

In another embodiment, two $R_3$ groups form a bicyclo group to give one of the following structures

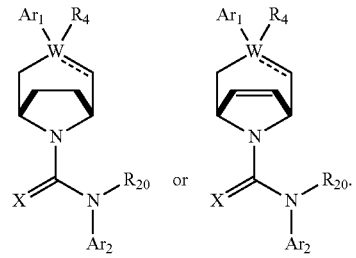

In another embodiment, m is 1.
In another embodiment, m is 0.
In another embodiment, s or q is 0.
In another embodiment, s or q is 1.
In another embodiment, s or q is 2.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is $CF_3$.
In another embodiment, $R_1$ is —CH(halo)$_2$.
In another embodiment, $R_1$ is —$CH_2$(halo).
In another embodiment, $Ar_1$ is a pyridyl group and n is 1.
In another embodiment, $Ar_1$ is a pyrazinyl group and p is 1.
In another embodiment, $Ar_1$ is a pyrimidinyl group and p is 1.
In another embodiment, $Ar_1$ is a pyridazinyl group and p is 1.
In another embodiment, Q is

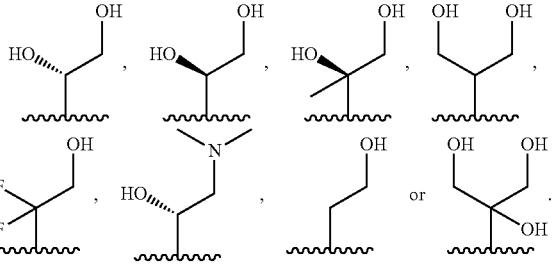

In another embodiment, J is —$OR_{20}$.
In another embodiment, J is —OH.
In another embodiment, $Z_1$ is —$OR_7$.
In another embodiment, $Z_1$ is —OH.
In another embodiment, $Z_1$ is —$CH_2$—$OR_7$.
In another embodiment, $Z_1$ is —$CH_2OH$.
In another embodiment, $Z_2$ is —$CH_2$—$OR_7$.
In another embodiment, $Z_2$ is —$CH_2OH$.
In another embodiment, $Z_2$ is —H or —$CH_3$.
In another embodiment, $Z_2$ is —H.
In another embodiment, $Z_2$ is —$CH_3$.
In another embodiment, $Z_3$ is —H.
In another embodiment, $Z_3$ is —$CH_3$.
In another embodiment, m is 1 and $R_3$ is —$(C_1$-$C_6)$alkyl.
In another embodiment, m is 1 and $R_3$ is —$CH_3$ or —$CH_2CH_3$.

In another embodiment, m is 1 and $R_3$ is —CH$_3$.
In another embodiment, m is 1 and $R_3$ is —CH$_2$OH.
In another embodiment, $R_4$ is —OH.
In another embodiment, $R_4$ is —OCF$_3$.
In another embodiment, $R_4$ is -halo.
In another embodiment, $R_4$ is —F.
In another embodiment, $R_4$ is —Cl.
In another embodiment, $R_4$ is —(C$_1$-C$_6$)alkyl.
In another embodiment, $R_4$ is —CH$_3$.
In another embodiment, $R_4$ is —CH$_2$OH.
In another embodiment, $R_4$ is —CH$_2$Cl.
In another embodiment, $R_4$ is —CH$_2$Br.
In another embodiment, $R_4$ is —CH$_2$I.
In another embodiment, $R_4$ is —CH$_2$F.
In another embodiment, $R_4$ is —CH(halo)$_2$.
In another embodiment, $R_4$ is —CF$_3$.
In another embodiment, $R_4$ is —NO$_2$.
In another embodiment, $R_4$ is —OR$_{10}$.
In another embodiment, $R_4$ is —SR$_{10}$.
In another embodiment, $R_4$ is —C(O)R$_{10}$.
In another embodiment, $R_4$ is —COOH.
In another embodiment, $R_4$ is —C(O)H.
In another embodiment, $R_4$ is —COOR$_{10}$.
In another embodiment, $R_4$ is —OC(O)R$_{10}$.
In another embodiment, $R_4$ is —SO$_2$R$_{10}$.
In another embodiment, $R_4$ is —OC(O)NHR$_{10}$.
In another embodiment, $R_4$ is —NHC(O)R$_{13}$.
In another embodiment, $R_4$ is —CON(R$_{13}$)$_2$.
In another embodiment, each $R_{20}$ is independently —H or —(C$_1$-C$_6$)alkyl.
In another embodiment, each $R_{20}$ is independently —H or —(C$_3$-C$_8$)cycloalkyl.
In another embodiment, each $R_{20}$ is independently —(C$_1$-C$_6$)alkyl or —(C$_3$-C$_8$)cycloalkyl.
In another embodiment, each $R_{20}$ is —H.
In another embodiment, each $R_{20}$ is —(C$_1$-C$_6$)alkyl.
In another embodiment, each $R_{20}$ is —(C$_3$-C$_8$)cycloalkyl.
In another embodiment, Ar$_2$ is a benzothiazolyl, benzoimidazolyl, or benzooxazolyl group; and at least one of $R_8$ and $R_9$ is —H.
In another embodiment, Ar$_2$ is a benzothiazolyl, benzoimidazolyl, or benzooxazolyl group; and at least one of $R_8$ and $R_9$ is not —H.
In another embodiment, Ar$_2$ is a benzothiazolyl, benzoimidazolyl, or benzooxazolyl group; and at least one of $R_8$ and $R_9$ is -halo.
In another embodiment, Ar$_2$ is

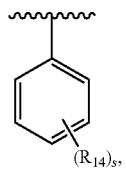

s is 1 and $R_{14}$ is —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.
In another embodiment, Ar$_2$ is

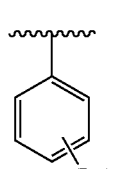

s is 2, and each $R_{14}$ is independently —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.

In another embodiment, J is —OH, and $Z_1$ is —OH.
In another embodiment, J is —OH and $Z_1$ is —CH$_2$OH.
In another embodiment, J is —OH, $Z_1$ is —OH, $Z_2$ is —H, and $Z_3$ is —H.
In another embodiment, J is —OH, $Z_1$ is —CH$_2$OH, $Z_2$ is —H, and $Z_3$ is —H.
In another embodiment, $R_4$ is -halo, J is —OH, $Z_1$ is —OH, $Z_2$ is —H, and $Z_3$ is —H.
In another embodiment, $R_4$ is -halo, J is —OH, $Z_1$ is —CH$_2$OH, $Z_2$ is —H, and $Z_3$ is —H.
In another embodiment, $R_4$ is —F, J is —OH, $Z_1$ is —OH, $Z_2$ is —H, and $Z_3$ is —H.
In another embodiment, $R_4$ is —F, J is —OH, $Z_1$ is —CH$_2$OH, $Z_2$ is —H, and $Z_3$ is —H.
In another embodiment, $R_1$ is -halo, $R_4$ is -halo, J is —OH, $Z_1$ is —OH, $Z_2$ is —H, and $Z_3$ is —H.
In another embodiment, $R_1$ is -halo, $R_4$ is -halo, J is —OH, $Z_1$ is —CH$_2$OH, $Z_2$ is —H, and $Z_3$ is —H.
In another embodiment, $R_1$ is —Cl, $R_4$ is —F, J is —OH, $Z_1$ is —OH, $Z_2$ is —H, and $Z_3$ is —H.
In another embodiment, $R_1$ is —Cl, $R_4$ is —F, J is —OH, $Z_1$ is —CH$_2$OH, $Z_2$ is —H, and $Z_3$ is —H.
In another embodiment Ar$_1$ is

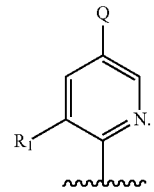

In another embodiment, $R_1$ is -halo, $R_4$ is -halo, Ar$_1$ is

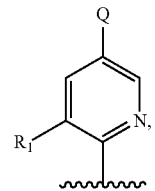

J is —OH, $Z_1$ is —OH, $Z_2$ is —H, and $Z_3$ is —H.
In another embodiment, $R_1$ is -halo, $R_4$ is -halo, Ar$_1$ is

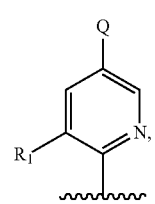

J is —OH, $Z_1$ is —CH$_2$OH, $Z_2$ is —H, and $Z_3$ is —H.

In another embodiment, $R_1$ is -halo, $R_4$ is -halo, $Ar_1$ is

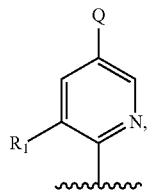

J is —OH, $Z_1$ is —OH, $Z_2$ is —H, $Z_3$ is —H, $Ar_2$ is benzooxazolyl, wherein at least one of $R_8$ or $R_9$ is not —H.

In another embodiment, $R_1$ is -halo, $R_4$ is -halo, $Ar_1$ is

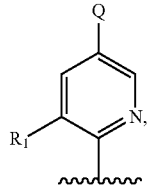

J is —OH, $Z_1$ is —CH$_2$OH, $Z_2$ is —H, $Z_3$ is —H, $Ar_2$ is benzooxazolyl, wherein at least one of $R_8$ or $R_9$ is not —H.

In another embodiment, $R_1$ is -halo, $R_4$ is -halo, $Ar_1$ is

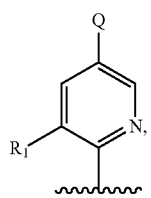

J is —OH, $Z_1$ is —OH, $Z_2$ is —H, $Z_3$ is —H, $Ar_2$ is benzothiazolyl, wherein at least one of $R_8$ or $R_9$ is not —H.

In another embodiment, $R_1$ is -halo, $R_4$ is -halo, $Ar_1$ is

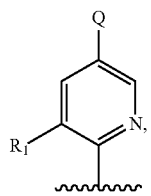

J is —OH, $Z_1$ is —CH$_2$OH, $Z_2$ is —H, $Z_3$ is —H, $Ar_2$ is benzothiazolyl, wherein at least one of $R_8$ or $R_9$ is not —H.

In another embodiment, $R_1$ is -halo, $R_4$ is -halo, $Ar_1$ is

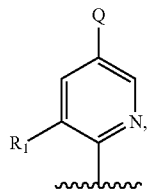

J is —OH, $Z_1$ is —OH, $Z_2$ is —H, $Z_3$ is —H, $Ar_2$ is benzoimidazolyl, wherein at least one of $R_8$ or $R_9$ is not —H.

In another embodiment, $R_1$ is -halo, $R_4$ is -halo, $Ar_1$ is

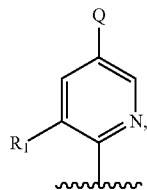

J is —OH, $Z_1$ is —CH$_2$OH, $Z_2$ is —H, $Z_3$ is —H, $Ar_2$ is benzoimidazolyl, wherein at least one of $R_8$ or $R_9$ is not —H.

In another embodiment, $R_1$ is -halo, $R_4$ is -halo, $Ar_1$ is,

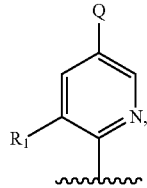

J is —OH, $Z_1$ is —OH, $Z_2$ is —H, $Z_3$ is —H, $Ar_2$ is phenyl, wherein s is 1.

In another embodiment, $R_1$ is -halo, $R_4$ is -halo, $Ar_1$ is

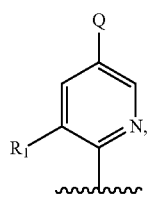

J is —OH, $Z_1$ is —CH$_2$OH, $Z_2$ is —H, $Z_3$ is —H, $Ar_2$ is phenyl, wherein s is 2.

In another embodiment, the dashed line is a double bond, $R_1$ is -halo, $Ar_1$ is

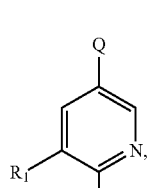

J is —OH, $Z_1$ is —OH, $Z_2$ is —H, and $Z_3$ is —H.

In another embodiment, the dashed line is a double bond, $R_1$ is -halo, $Ar_1$ is

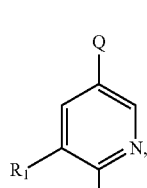

J is —OH, $Z_1$ is —CH$_2$OH, $Z_2$ is —H, and $Z_3$ is —H.

In another embodiment, the dashed line is a double bond, $R_1$ is -halo, $Ar_1$ is

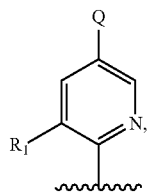

J is —OH, $Z_1$ is —OH, $Z_2$ is —H, $Z_3$ is —H, $Ar_2$ is benzooxazolyl, wherein at least one of $R_8$ or $R_9$ is not —H.

In another embodiment, the dashed line is a double bond, $R_1$ is -halo, $Ar_1$ is

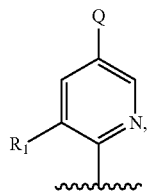

J is —OH, $Z_1$ is —CH$_2$OH, $Z_2$ is —H, $Z_3$ is —H, $Ar_2$ is benzooxazolyl, wherein at least one of $R_8$ or $R_9$ is not —H.

In another embodiment, the dashed line is a double bond, $R_1$ is -halo, $Ar_1$ is

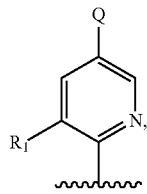

J is —OH, $Z_1$ is —OH, $Z_2$ is —H, $Z_3$ is —H, $Ar_2$ is benzothiazolyl, wherein at least one of $R_8$ or $R_9$ is not —H.

In another embodiment, the dashed line is a double bond, $R_1$ is -halo, $Ar_1$ is

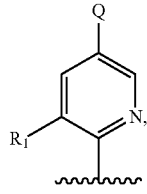

J is —OH, $Z_1$ is —CH$_2$OH, $Z_2$ is —H, $Z_3$ is —H, $Ar_2$ is benzothiazolyl, wherein at least one of $R_8$ or $R_9$ is not —H.

In another embodiment, the dashed line is a double bond, $R_1$ is -halo, $Ar_1$ is

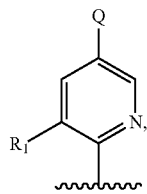

J is —OH, $Z_1$ is —OH, $Z_2$ is —H, $Z_3$ is —H, $Ar_2$ is benzoimidazolyl, wherein at least one of $R_8$ or $R_9$ is not —H.

In another embodiment, the dashed line is a double bond, $R_1$ is -halo, $Ar_1$ is

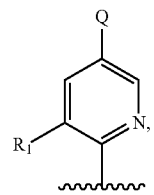

J is —OH, $Z_1$ is —CH$_2$OH, $Z_2$ is —H, $Z_3$ is —H, $Ar_2$ is benzoimidazolyl, wherein at least one of $R_8$ or $R_9$ is not —H.

In another embodiment, the dashed line is a double bond, $R_1$ is -halo, $Ar_1$ is

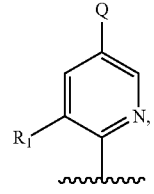

J is —OH, $Z_1$ is —OH, $Z_2$ is —H, $Z_3$ is —H, $Ar_2$ is phenyl, wherein s is 1.

In another embodiment, the dashed line is a double bond, $R_1$ is -halo, $Ar_1$ is

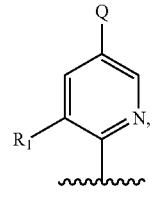

J is —OH, $Z_1$ is —OH, $Z_2$ is —H, $Z_3$ is —H, $Ar_2$ is phenyl, wherein s is 2.

In another embodiment, the dashed line is a double bond, $R_1$ is -halo, $Ar_1$ is

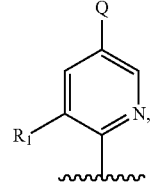

J is —OH, $Z_1$ is —CH$_2$OH, $Z_2$ is —H, $Z_3$ is —H, $Ar_2$ is phenyl, wherein s is 1.

In another embodiment, the dashed line is a double bond, $R_1$ is -halo, $Ar_1$ is

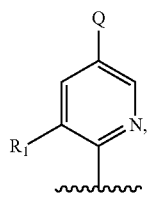

J is —OH, $Z_1$ is —CH$_2$OH, $Z_2$ is —H, $Z_3$ is —H, $Ar_2$ is phenyl, wherein s is 2.

In another embodiment, the dashed line is a double bond, $R_1$ is -halo, $Ar_1$ is

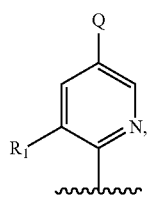

J is —OH, $Z_1$ is —OH, $Z_2$ is —H, $Z_3$ is —H, $Ar_2$ is phenyl, wherein s is 1, and $R_{14}$ is —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.

In another embodiment, the dashed line is a double bond, $R_1$ is -halo, $Ar_1$ is

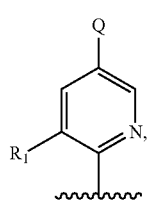

J is —OH, $Z_1$ is —CH$_2$OH, $Z_2$ is —H, $Z_3$ is —H, $Ar_2$ is phenyl, wherein s is 1, and $R_{14}$ is —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.

In another embodiment, the dashed line is a double bond, $R_1$ is -halo, $Ar_1$ is

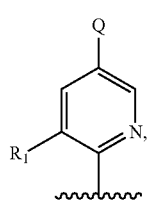

J is —OH, $Z_1$ is —OH, $Z_2$ is —H, $Z_3$ is —H, $Ar_2$ is phenyl, wherein s is 2, and each $R_{14}$ is independently —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.

In another embodiment, the dashed line is a double bond, $R_1$ is -halo, $Ar_1$ is

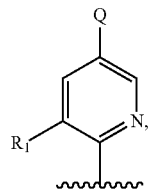

J is —OH, $Z_1$ is —CH$_2$OH, $Z_2$ is —H, $Z_3$ is —H, $Ar_2$ is phenyl, wherein s is 2, and each $R_{14}$ is independently —(C$_1$-C$_6$)alkyl, -halo, —C(halo)$_3$, —OC(halo)$_3$, —OR$_7$, —N(R$_7$)$_2$, —SO$_2$R$_7$, or —SO$_2$C(halo)$_3$.

In another embodiment Q is

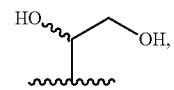

wherein the compound of formula II is racemic.

In another embodiment Q is

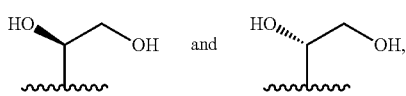

wherein the % ee of the R enantiomer is greater than 60%.

In another embodiment Q is

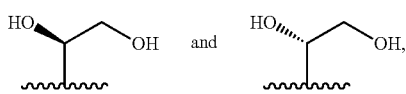 [SMILES: *[C@@H](O)CO ; *[C@H](O)CO]

wherein the % ee of the R enantiomer is greater than 70%.

In another embodiment Q is

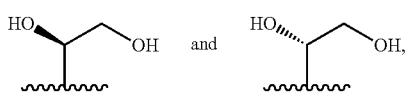 [SMILES: *[C@@H](O)CO ; *[C@H](O)CO]

wherein the % ee of the R enantiomer is greater than 80%.

In another embodiment Q is

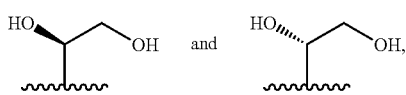 [SMILES: *[C@@H](O)CO ; *[C@H](O)CO]

wherein the % ee of the R enantiomer is greater than 90%.

In another embodiment Q is

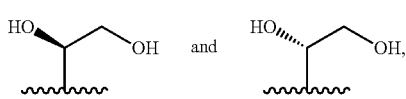

wherein the % ee of the R enantiomer is greater than 99%.

In another embodiment Q is

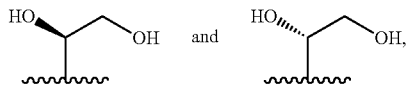

wherein the % ee of the S enantiomer is greater than 60%.

In another embodiment Q is

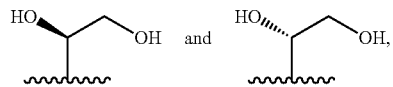 [SMILES: *[C@@H](O)CO ; "and" ; *[C@H](O)CO]

wherein the % ee of the S enantiomer is greater than 70%.

In another embodiment Q is

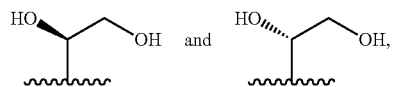 [SMILES: *[C@@H](O)CO ; "and" ; *[C@H](O)CO]

wherein the % ee of the S enantiomer is greater than 80%.

In another embodiment Q is

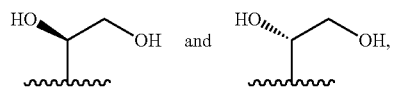 [SMILES: *[C@@H](O)CO ; "and" ; *[C@H](O)CO]

wherein the % ee of the S enantiomer is greater than 90%.

In another embodiment Q is

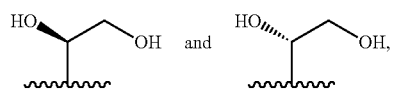 [SMILES: *[C@@H](O)CO ; "and" ; *[C@H](O)CO]

wherein the % ee of the S enantiomer is greater than 99%.

In another embodiment Q is

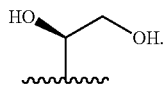

In another embodiment Q is

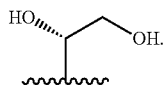

In another embodiment, the invention encompasses compounds formula II.4:

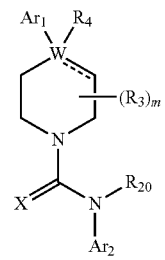

(II.4)

or a pharmaceutically acceptable salt thereof, where the dashed line, W, X, $Ar_1$, $Ar_2$, $R_3$, $R_4$, $R_{20}$, and m are as defined above for compounds of formula I.4, wherein Q is

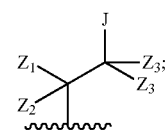

$Z_1$ is —OH, —SH, $N(R_{20})_2$, —CH$_2$—OH, —CH$_2$—SH, or —CH$_2$—N(R$_{20}$)$_2$;
$Z_2$ is —H or —CH$_3$;
each $Z_3$ is independently —H or —CH$_3$; and
J is —OH, —SH, or —N(R$_{20}$)$_2$.

In another embodiment, the invention encompasses compounds formula II.3:

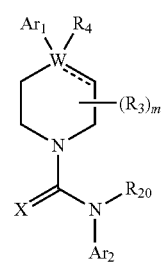

(II.3)

or a pharmaceutically acceptable salt thereof, where the dashed line, W, X, $Ar_1$, $Ar_2$, $R_3$, $R_4$, $R_{20}$, and m are as defined above for compounds of formula I.3, wherein Q is

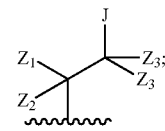

$Z_1$ is —OH, —SH, $N(R_{20})_2$, —CH$_2$—OH, —CH$_2$—SH, or —CH$_2$—N(R$_{20}$)$_2$;
$Z_2$ is —H or —CH$_3$;
each $Z_3$ is independently —H or —CH$_3$; and
J is —OH, —SH, or —N(R$_{20}$)$_2$.

In another embodiment, the invention encompasses compounds formula II.2:

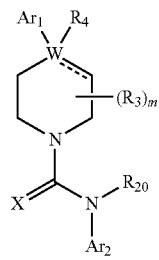

(II.2)

or a pharmaceutically acceptable salt thereof, where the dashed line, W, X, Ar$_1$, Ar$_2$, R$_3$, R$_4$, R$_{20}$, and m are as defined above for compounds of formula I.2,
  wherein Q is

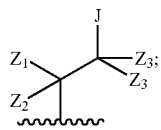

Z$_1$ is —OH, —SH, N(R$_{20}$)$_2$, —CH$_2$—OH, —CH$_2$—SH, or —CH$_2$—N(R$_{20}$)$_2$;
Z$_2$ is —H or —CH$_3$;
each Z$_3$ is independently —H or —CH$_3$; and
J is —OH, —SH, or —N(R$_{20}$)$_2$.

In another embodiment, the invention encompasses compounds formula II.1:

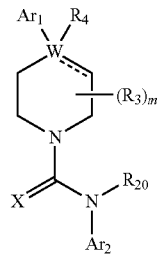

(II.1)

or a pharmaceutically acceptable salt thereof, where the dashed line, W, X, Ar$_1$, Ar$_2$, R$_3$, R$_4$, R$_{20}$, and m are defined above for compounds of formula I.1,
  wherein Q is

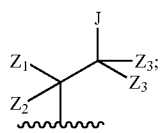

Z$_1$ is —OH, —SH, N(R$_{20}$)$_2$, —CH$_2$—OH, —CH$_2$—SH, or —CH$_2$—N(R$_{20}$)$_2$;
Z$_2$ is —H or —CH$_3$;
each Z$_3$ is independently —H or —CH$_3$; and
J is —OH, —SH, or —N(R$_{20}$)$_2$.

5.4 Compounds of Formula III

Preferred compounds of formula II are compounds of formula III:

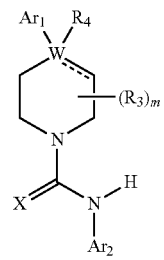

(III)

or a pharmaceutically acceptable derivative thereof, where the dashed line, W, X, R$_3$, R$_4$, and m are as defined above for compounds of formula I,
  wherein Ar$_1$ is:

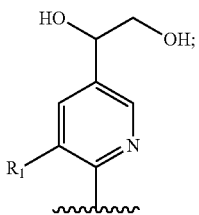

R$_1$ is —Cl, —F, —CF$_3$, or —CH$_3$;
wherein Ar$_2$ is:

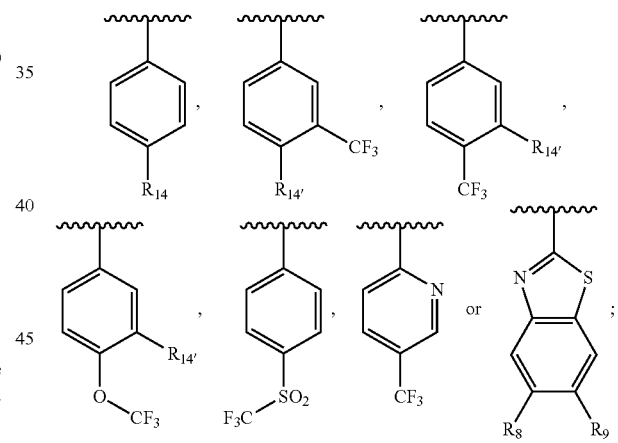

R$_{14}$ is —H, —Cl, —F, —Br, —CF$_3$, —OCF$_3$, —(C$_1$-C$_6$)alkyl, —SO$_2$CF$_3$, —SO$_2$(C$_1$-C$_6$)alkyl, —OCH$_3$, —OCH$_2$CH$_3$, or —OCH(CH$_3$)$_2$, and optionally is —H, —CF$_3$, —OCF$_3$, —Cl, or —F;
R$_{14'}$ is —H, —Cl, —F, —Br, —CF$_3$, —OCF$_3$, —(C$_1$-C$_6$)alkyl, —SO$_2$CF$_3$, —SO$_2$(C$_1$-C$_6$)alkyl, —OCH$_3$, —OCH$_2$CH$_3$, or —OCH(CH$_3$)$_2$, and optionally is —H, —CF$_3$, —OCF$_3$, —Cl, or —F; and
each R$_8$ and R$_9$ is independently —H, —Cl, —Br, —F, —CH$_3$, —OCH$_3$, —OCH$_2$CH$_3$, —CF$_3$, —OCF$_3$, iso-propyl, or tert-butyl.

In addition to being highly soluble in aqueous solution at both pH 6.8 and pH 1.2, having a very high therapeutic index, and having excellent pharmacokinetic parameters as described for formulae I and II, compounds of formula III are preferred because they are also very bioavailable, and are believed to be highly efficacious in animals for the treatment of pain. Bioavailability is a measure of how much of the dose administered reaches systemic circulation after oral administration. For example, compounds of formula III $R_6$ and G1 are 68.9% and 70.7% bioavailable following oral administration, respectively. The compound of formula III D2 produced a 78.7% maximum reversal of FCA-induced hyperalgesia at 5 hours post-administration, with an $ED_{50}$ of 1.63 mg/kg.

Certain embodiments of formula III are presented below.

In one embodiment, a compound of formula III is a pharmaceutically acceptable derivative of a compound of formula III.

In another embodiment, a compound of formula I is a compound of formula III wherein the derivative is a pharmaceutically acceptable salt.

In another embodiment, a compound of formula III is a pharmaceutically acceptable salt of a compound of formula III.

In another embodiment, $Ar_1$ is:

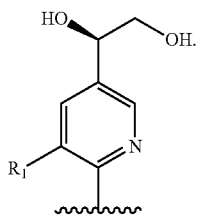

In a preferred embodiment, $Ar_1$ is:

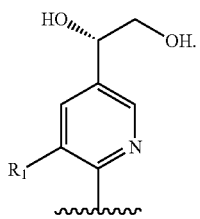

In another embodiment, m is 2.

In another embodiment, two $R_3$ groups together form a $(C_2-C_6)$bridge, which is unsubstituted or substituted with 1, 2 or 3 independently selected $R_8$ groups, and which bridge optionally contains —HC=CH— within the $(C_2-C_6)$bridge.

In another embodiment, two $R_3$ groups together form a $(C_2-C_6)$bridge, which is unsubstituted or substituted with an $R_8$ group, and which bridge optionally contains —HC=CH— within the $(C_2-C_6)$bridge.

In another embodiment, two $R_3$ groups together form a $(C_2-C_3)$bridge, which is unsubstituted or substituted with an $R_8$ group, and which bridge optionally contains —HC=CH— within the $(C_2-C_3)$bridge.

In another embodiment, two $R_3$ groups together form a $(C_2-C_3)$bridge, which is unsubstituted and which bridge optionally contains —HC=CH— within the $(C_2-C_3)$bridge.

In another embodiment, two $R_3$ groups together form a $(C_2)$bridge, a —HC=CH— bridge, or a $(C_3)$bridge each of which is unsubstituted.

In another embodiment, two $R_3$ groups together form a $(C_2-C_6)$bridge, which is unsubstituted or substituted with 1, 2 or 3 independently selected $R_8$ groups, which bridge optionally contains —HC=CH— within the $(C_2-C_6)$bridge, and which bridge joins positions 2 and 6 of the piperidine, 1,2,3,6-tetrahydropyridine or piperazine ring.

In another embodiment, two $R_3$ groups together form a $(C_2-C_6)$bridge, which is unsubstituted or substituted with an $R_8$ group, which bridge optionally contains —HC=CH— within the $(C_2-C_6)$bridge, and which bridge joins positions 2 and 6 of the piperidine, 1,2,3,6-tetrahydropyridine or piperazine ring.

In another embodiment, two $R_3$ groups together form a $(C_2-C_3)$bridge, which is unsubstituted or substituted with an $R_8$ group, which bridge optionally contains —HC=CH— within the $(C_2-C_3)$bridge, and which bridge joins positions 2 and 6 of the piperidine, 1,2,3,6-tetrahydropyridine or piperazine ring.

In another embodiment, two $R_3$ groups together form a $(C_2-C_3)$bridge, which is unsubstituted, which bridge optionally contains —HC=CH— within the $(C_2-C_3)$bridge, and which bridge joins positions 2 and 6 of the piperidine, 1,2,3,6-tetrahydropyridine or piperazine ring.

In another embodiment, two $R_3$ groups together form a $(C_2)$bridge, a —HC=CH— bridge, or a $(C_3)$bridge each of which is unsubstituted, and which bridge joins positions 2 and 6 of the piperidine, 1,2,3,6-tetrahydropyridine or piperazine ring.

In another embodiment, two $R_3$ groups together form a —$CH_2$—$N(R_a)$—$CH_2$— bridge (B1), a

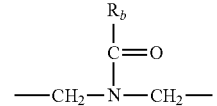

bridge (B2), or a

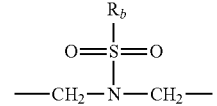

bridge (B3);

wherein $R_a$ is —H, —$(C_1-C_6)$alkyl, —$(C_3-C_8)$cycloalkyl, —$CH_2$—C(O)—$R_c$, —$(CH_2)$—C(O)—$OR_c$, —$(CH_2)$—C(O)—$N(R_c)_2$, —$(CH_2)_2$—O—$R_c$, —$(CH_2)_2$—$S(O)_2$—$N(R_c)_2$, or —$(CH_2)_2$—$N(R_c)S(O)_2$—$R_c$;

$R_b$ is:

(a) —H, —$(C_1-C_6)$alkyl, —$(C_3-C_8)$cycloalkyl, -(3- to 7-membered)heterocycle, —$N(R_c)_2$, —$N(R_c)$—$(C_3-C_8)$cycloalkyl, or —$N(R_c)$-(3- to 7-membered)heterocycle; or (b) -phenyl, -(5- or 6-membered)heteroaryl, —$N(R_c)$-phenyl, or —$N(R_c)$-(5- to 10-membered)heteroaryl, each of which is unsubstituted or substituted with 1, 2 or 3 independently selected $R_7$ groups; and each $R_c$ is independently —H or —$(C_1-C_4)$alkyl.

In another embodiment, $R_a$ is —H, —$(C_1-C_6)$alkyl, —$(C_3-C_8)$cycloalkyl, —$(CH_2)$—C(O)—$N(R_c)_2$, —$(CH_2)_2$—$S(O)_2$—$N(R_c)_2$, or —$(CH_2)_2$—$N(R_c)S(O)_2$—$R_c$.

In another embodiment, $R_a$ is —H, —$(C_1-C_6)$alkyl, —$(C_3-C_8)$cycloalkyl, or —$(CH_2)$—C(O)—$N(R_c)_2$.

In another embodiment, $R_a$ is —H, —$(C_1-C_6)$alkyl, or —$(C_3-C_8)$cycloalkyl.

In another embodiment, $R_b$ is —H, —$(C_3-C_8)$cycloalkyl, or -(3- to 7-membered)heterocycle.

In another embodiment, $R_b$ is —H, —N($R_c$)$_2$, —N($R_c$)—($C_3$-$C_8$)cycloalkyl, or —N($R_c$)-(3- to 7-membered)heterocycle.

In another embodiment, $R_b$ is —H, —($C_1$-$C_6$)alkyl, or —($C_3$-$C_8$)cycloalkyl.

In another embodiment, $R_b$ is -phenyl or —N($R_c$)-phenyl, each of which is unsubstituted or substituted with 1, 2 or 3 independently selected $R_7$ groups.

In another embodiment, $R_b$ is -(5- or 6-membered)heteroaryl or —N($R_c$)-(5- to 10-membered)heteroaryl, each of which is unsubstituted or substituted with 1, 2 or 3 independently selected $R_7$ groups.

In another embodiment, $R_b$ is —H, —($C_1$-$C_6$)alkyl, -phenyl, or -(5- or 6-membered)heteroaryl.

In another embodiment, $R_a$ and $R_b$ are each independently —H or —($C_1$-$C_6$)alkyl.

In another embodiment, $R_a$ and $R_b$ are —CH$_3$.

In another embodiment, each $R_c$ is independently —H or —CH$_3$.

In another embodiment, the B1, B2, or B3 bridge joins positions 2 and 6 of the piperidine, 1,2,3,6-tetrahydropyridine or piperazine ring.

In another embodiment, two $R_3$ groups form a bicyclo group to give one of the following structures

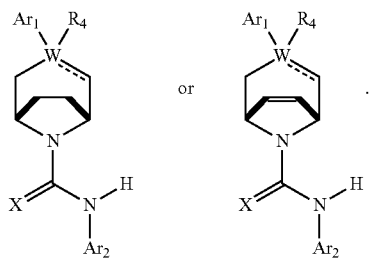

In another embodiment, $R_1$ is —Cl, —F, or —CF$_3$.
In another embodiment, m is 1.
In another embodiment, m is 1 and $R_3$ is —CH$_3$ or —CH$_2$CH$_3$.
In another embodiment, m is 1 and $R_3$ is —CH$_3$.
In another embodiment, m is 1 and $R_3$ is —CH$_2$OH.
In another embodiment, m is 0.
In another embodiment X is O.
In another embodiment the dashed line denotes the presence of a bond and $R_4$ is absent.
In another embodiment W is N and $R_4$ is absent.
In another embodiment $R_4$ is —H, —OH, —Cl, or F.
In another embodiment, each $R_{20}$ is independently —H or —($C_1$-$C_6$)alkyl.
In another embodiment, each $R_{20}$ is —H.
In another embodiment, each $R_{20}$ is —($C_1$-$C_6$)alkyl.
In another embodiment Ar$_2$ is

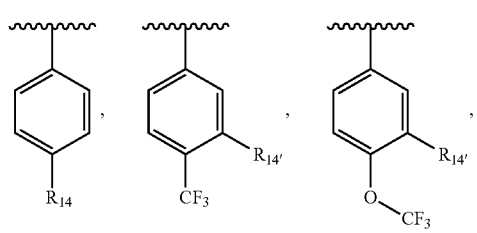

-continued

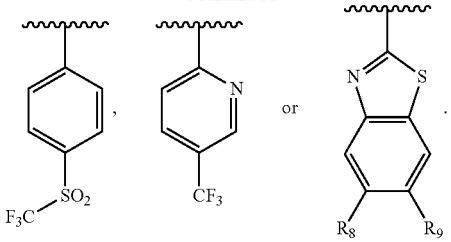

In another embodiment Ar$_1$ is

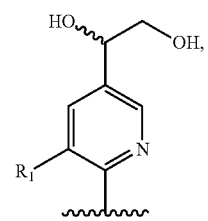

wherein the compound of formula III is racemic.
In another embodiment Ar$_1$ is

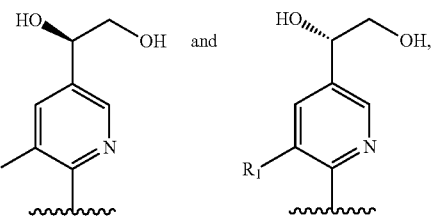

wherein the % ee of the R enantiomer is greater than 60%.
In another embodiment Ar$_1$ is

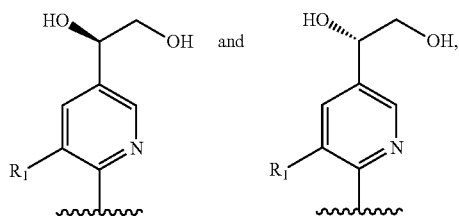

wherein the % ee of the R enantiomer is greater than 70%.
In another embodiment Ar$_1$ is

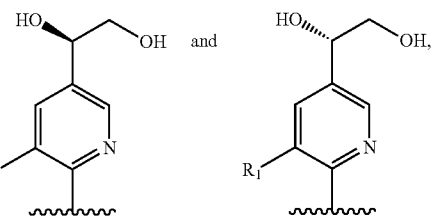

wherein the % ee of the R enantiomer is greater than 80%.

In another embodiment Ar₁ is

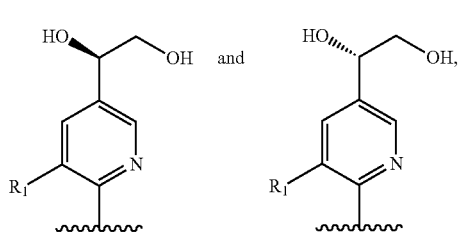

wherein the % ee of the R enantiomer is greater than 90%.
In another embodiment Ar₁ is

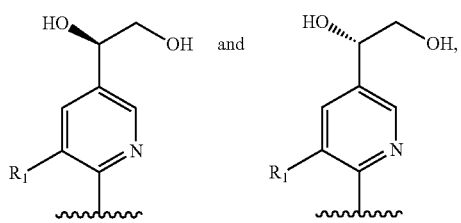

wherein the % ee of the R enantiomer is greater than 99%.
In another embodiment Ar₁ is

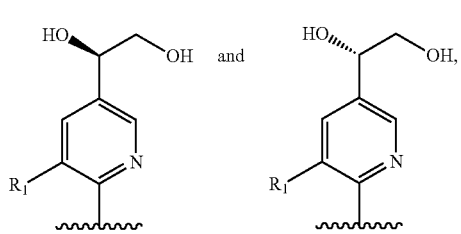

wherein the % ee of the S enantiomer is greater than 60%.
In another embodiment Ar₁ is

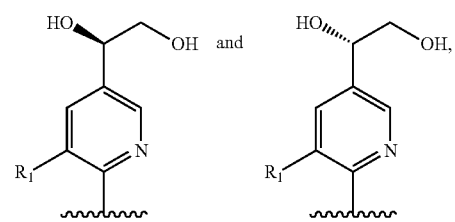

wherein the % ee of the S enantiomer is greater than 70%.

In another embodiment Ar₁ is

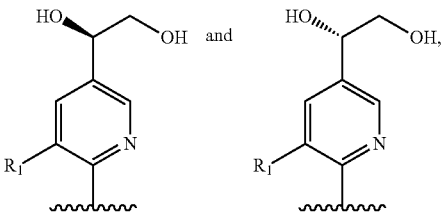

wherein the % ee of the S enantiomer is greater than 80%.
In another embodiment Ar₁ is

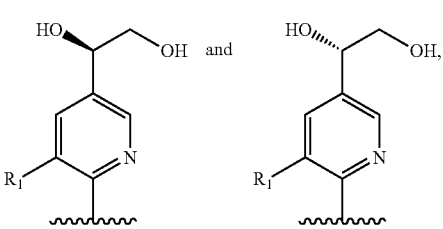

wherein the % ee of the S enantiomer is greater than 90%.
In another embodiment Ar₁ is

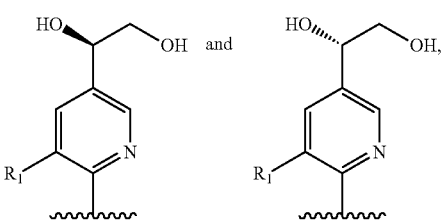

wherein the % ee of the S enantiomer is greater than 99%.
In another embodiment Ar₁ is

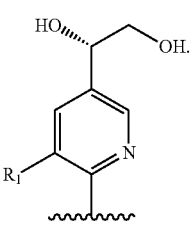

In another embodiment Ar₁ is

In another embodiment the compound of formula III is

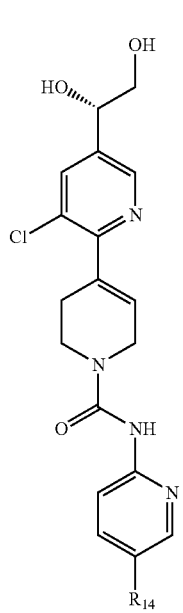

or a pharmaceutically acceptable derivative thereof, where $R_{14}$ is as defined above for the compounds of formula I.

In another embodiment the compound of formula III is

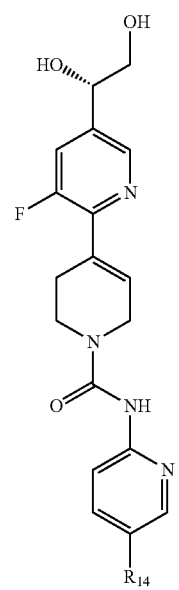

or a pharmaceutically acceptable derivative thereof, where $R_{14}$ is as defined above for the compounds of formula I.

In another embodiment the compound of formula III is

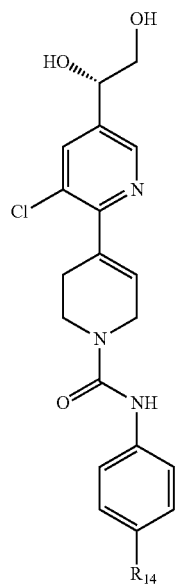

or a pharmaceutically acceptable derivative thereof, where $R_{14}$ is as defined above for the compounds of formula I.

In another embodiment the compound of formula III is

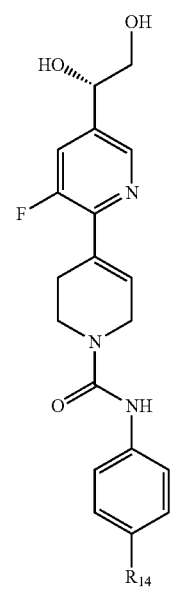

or a pharmaceutically acceptable derivative thereof, where $R_{14}$ is as defined above for the compounds of formula I.

In another embodiment the compound of formula III is

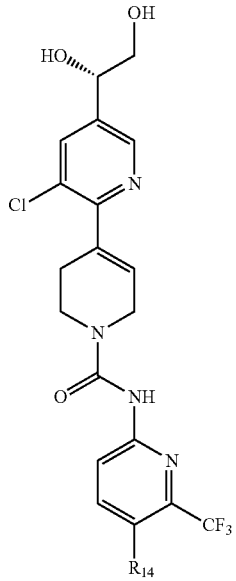

or a pharmaceutically acceptable derivative thereof, where $R_{14}$ is as defined above for the compounds of formula I.

In another embodiment the compound of formula III is

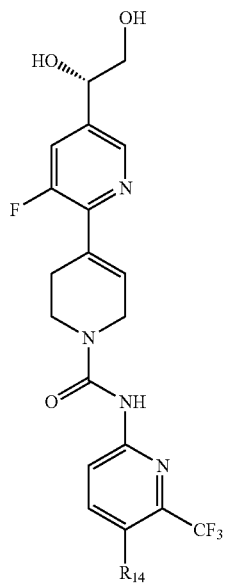

or a pharmaceutically acceptable derivative thereof, where $R_{14}$ is as defined above for the compounds of formula I.

In another embodiment the compound of formula III is

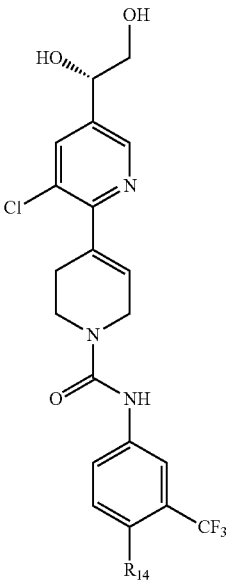

or a pharmaceutically acceptable derivative thereof, where $R_{14}$ is as defined above for the compounds of formula I.

In another embodiment the compound of formula III is

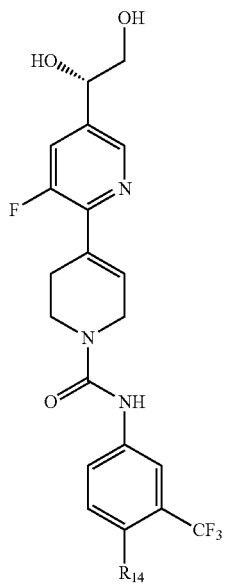

or a pharmaceutically acceptable derivative thereof, where $R_{14}$ is as defined above for the compounds of formula I.

In another embodiment the compound of formula III is

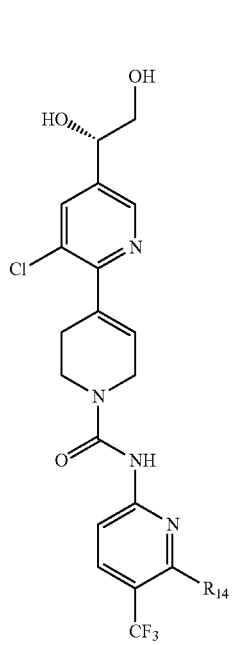

or a pharmaceutically acceptable derivative thereof, where $R_{14}$ is as defined above for the compounds of formula I.

In another embodiment the compound of formula III is

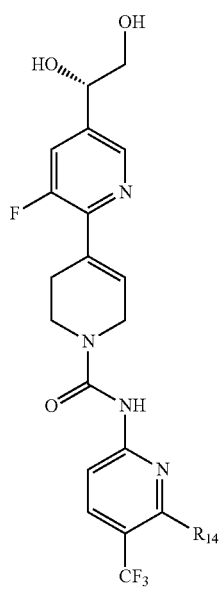

or a pharmaceutically acceptable derivative thereof, where $R_{14}$ is as defined above for the compounds of formula I.

In another embodiment the compound of formula III is

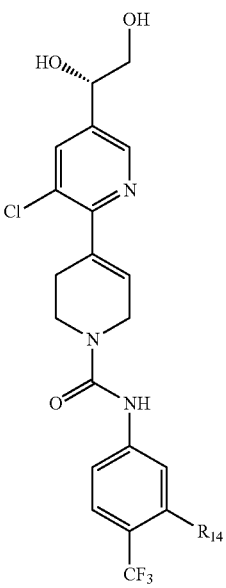

or a pharmaceutically acceptable derivative thereof, where $R_{14}$ is as defined above for the compounds of formula I.

In another embodiment the compound of formula III is

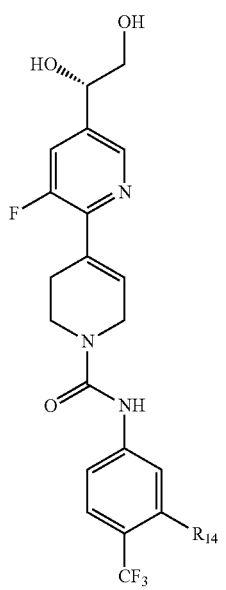

or a pharmaceutically acceptable derivative thereof, where $R_{14}$ is as defined above for the compounds of formula I.

In another embodiment the compound of formula III is

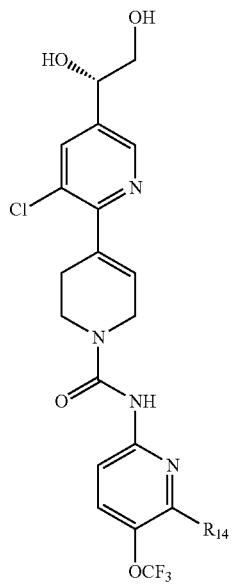

or a pharmaceutically acceptable derivative thereof, where R$_{14}$ is as defined above for the compounds of formula I.

In another embodiment the compound of formula III is

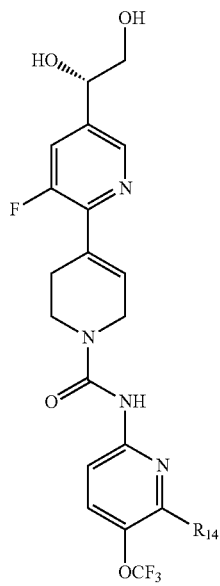

or a pharmaceutically acceptable derivative thereof, where R$_{14}$ is as defined above for the compounds of formula I.

In another embodiment the compound of formula III is

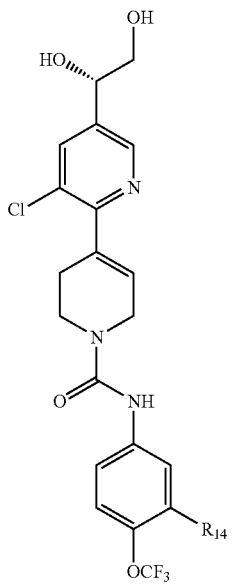

or a pharmaceutically acceptable derivative thereof, where R$_{14}$ is as defined above for the compounds of formula I.

In another embodiment the compound of formula III is

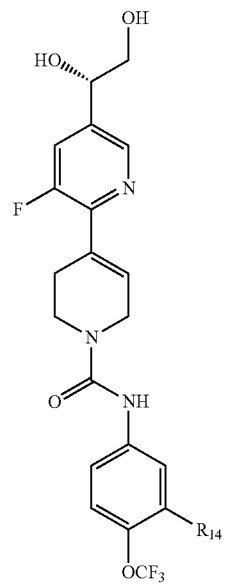

or a pharmaceutically acceptable derivative thereof, where R$_{14}$ is as defined above for the compounds of formula I.

In another embodiment the compound of formula III is

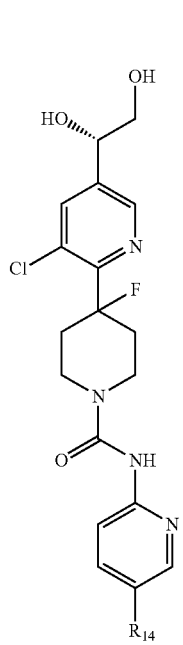

or a pharmaceutically acceptable derivative thereof, where $R_{14}$ is as defined above for the compounds of formula I.

In another embodiment the compound of formula III is

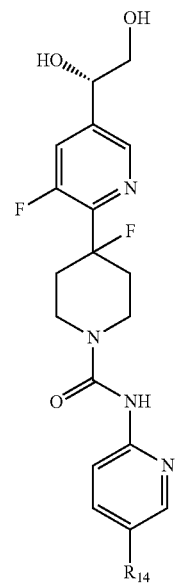

or a pharmaceutically acceptable derivative thereof, where $R_{14}$ is as defined above for the compounds of formula I.

In another embodiment the compound of formula III is

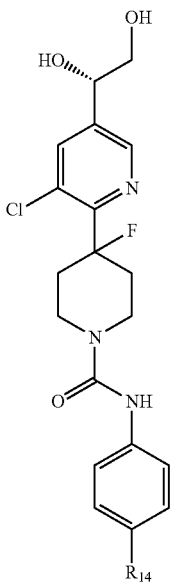

or a pharmaceutically acceptable derivative thereof, where $R_{14}$ is as defined above for the compounds of formula I.

In another embodiment the compound of formula III is

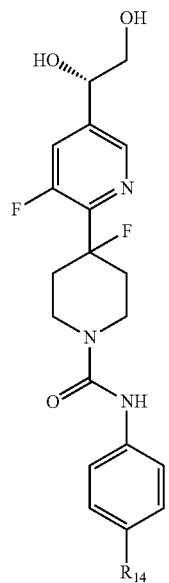

or a pharmaceutically acceptable derivative thereof, where $R_{14}$ is as defined above for the compounds of formula I.

In another embodiment the compound of formula III is

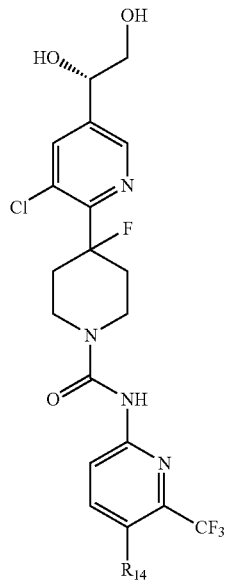

or a pharmaceutically acceptable derivative thereof, where $R_{14}$ is as defined above for the compounds of formula I.

In another embodiment the compound of formula III is

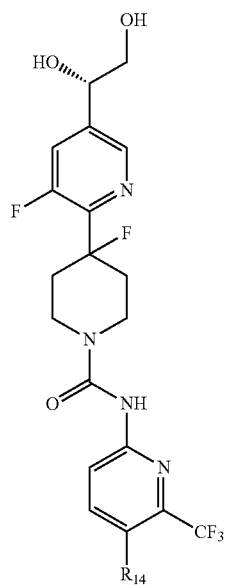

or a pharmaceutically acceptable derivative thereof, where $R_{14}$ is as defined above for the compounds of formula I.

In another embodiment the compound of formula III is

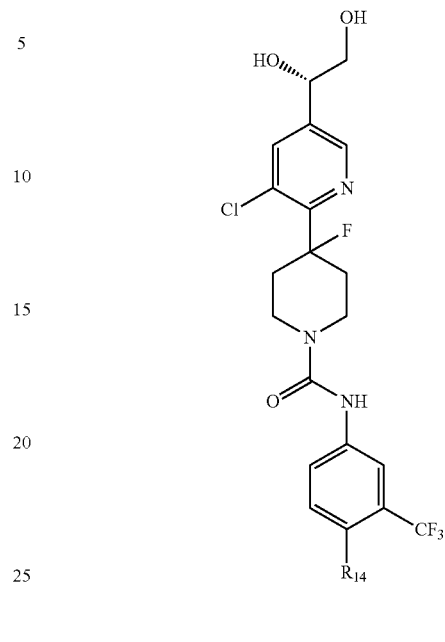

or a pharmaceutically acceptable derivative thereof, where $R_{14}$ is as defined above for the compounds of formula I.

In another embodiment the compound of formula III is

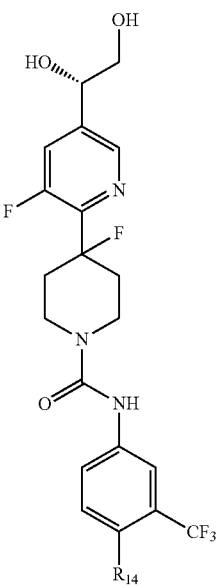

or a pharmaceutically acceptable derivative thereof, where $R_{14}$ is as defined above for the compounds of formula I.

In another embodiment the compound of formula III is

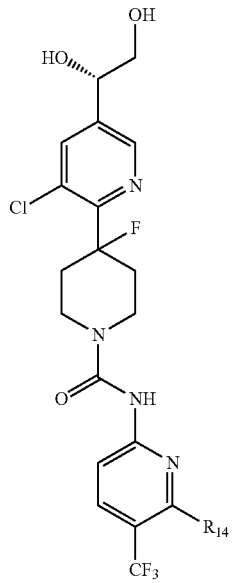

or a pharmaceutically acceptable derivative thereof, where $R_{14}$ is as defined above for the compounds of formula I.

In another embodiment the compound of formula III is

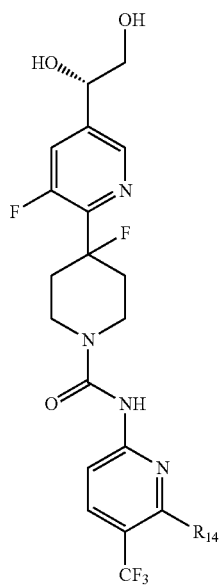

or a pharmaceutically acceptable derivative thereof, where $R_{14}$ is as defined above for the compounds of formula I.

In another embodiment the compound of formula III is

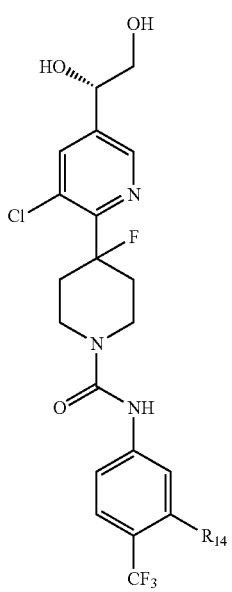

or a pharmaceutically acceptable derivative thereof, where $R_{14}$ is as defined above for the compounds of formula I.

In another embodiment the compound of formula III is

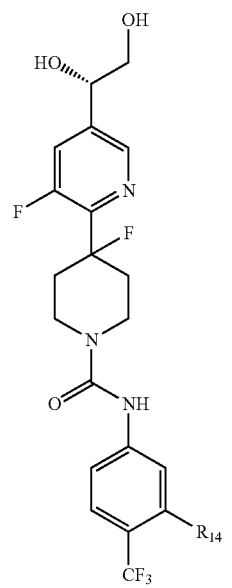

or a pharmaceutically acceptable derivative thereof, where $R_{14}$ is as defined above for the compounds of formula I.

In another embodiment the compound of formula III is

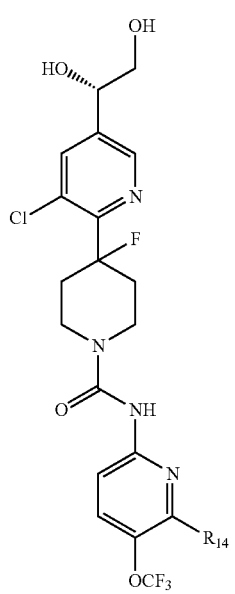

or a pharmaceutically acceptable derivative thereof, where $R_{14}$ is as defined above for the compounds of formula I.

In another embodiment the compound of formula III is

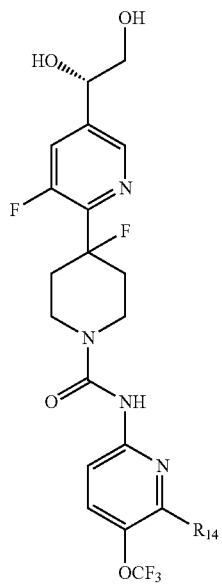

or a pharmaceutically acceptable derivative thereof, where $R_{14}$ is as defined above for the compounds of formula I.

In another embodiment the compound of formula III is

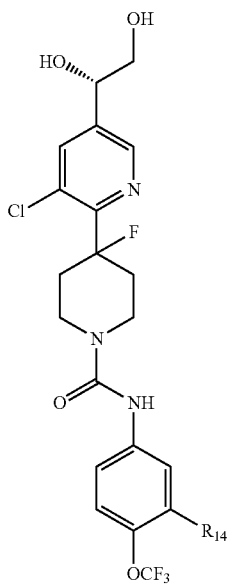

or a pharmaceutically acceptable derivative thereof, where $R_{14}$ is as defined above for the compounds of formula I.

In another embodiment the compound of formula III is

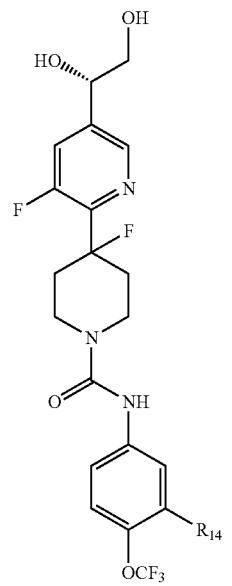

or a pharmaceutically acceptable derivative thereof, where $R_{14}$ is as defined above for the compounds of formula I.

In another embodiment the compound of formula III is

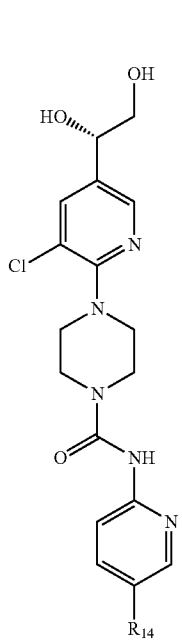

or a pharmaceutically acceptable derivative thereof, where $R_{14}$ is as defined above for the compounds of formula I.

In another embodiment the compound of formula III is

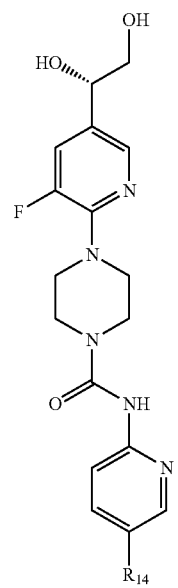

or a pharmaceutically acceptable derivative thereof, where $R_{14}$ is as defined above for the compounds of formula I.

In another embodiment the compound of formula III is

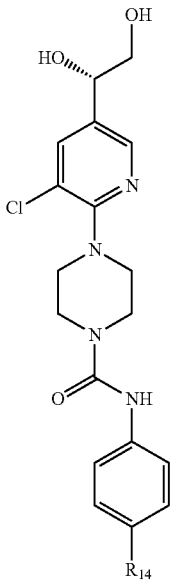

or a pharmaceutically acceptable derivative thereof, where $R_{14}$ is as defined above for the compounds of formula I.

In another embodiment the compound of formula III is

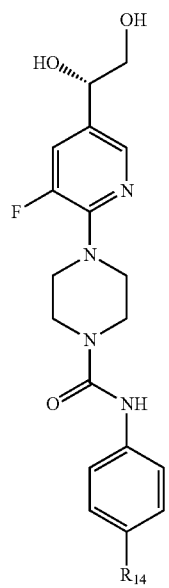

or a pharmaceutically acceptable derivative thereof, where $R_{14}$ is as defined above for the compounds of formula I.

In another embodiment the compound of formula III is

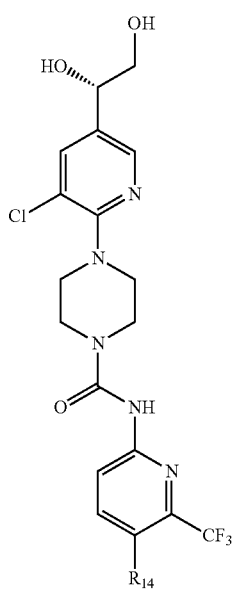

or a pharmaceutically acceptable derivative thereof, where $R_{14}$ is as defined above for the compounds of formula I.

In another embodiment the compound of formula III is

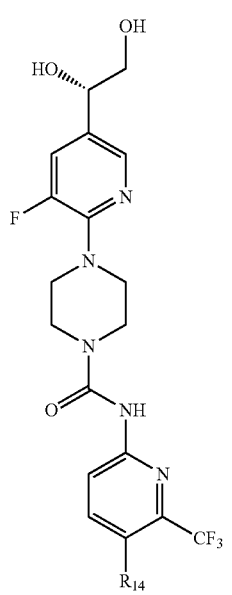

or a pharmaceutically acceptable derivative thereof, where $R_{14}$ is as defined above for the compounds of formula I.

In another embodiment the compound of formula III is

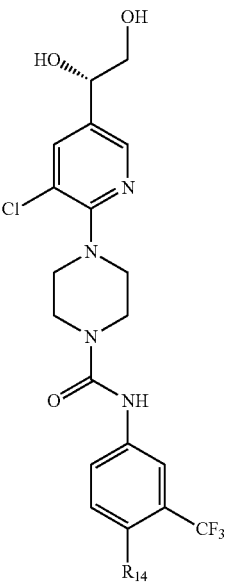

or a pharmaceutically acceptable derivative thereof, where $R_{14}$ is as defined above for the compounds of formula I.

In another embodiment the compound of formula III is

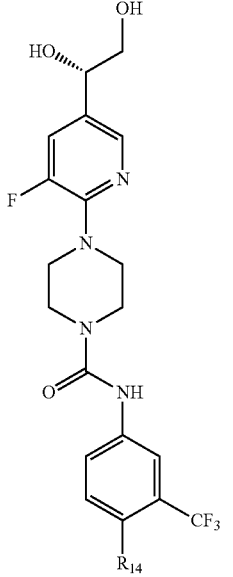

or a pharmaceutically acceptable derivative thereof, where $R_{14}$ is as defined above for the compounds of formula I.

In another embodiment the compound of formula III is

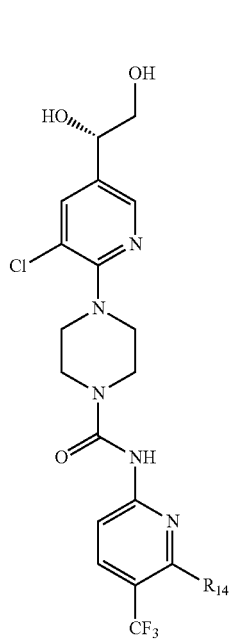

or a pharmaceutically acceptable derivative thereof, where $R_{14}$ is as defined above for the compounds of formula I.

In another embodiment the compound of formula III is

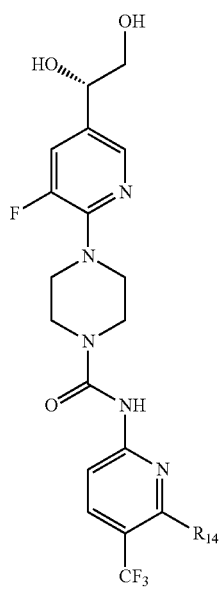

or a pharmaceutically acceptable derivative thereof, where $R_{14}$ is as defined above for the compounds of formula I.

In another embodiment the compound of formula III is

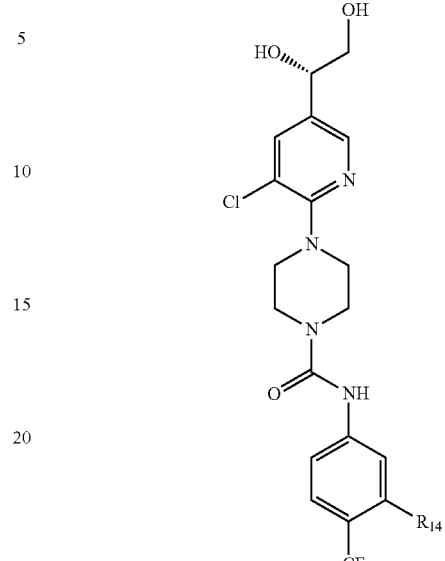

or a pharmaceutically acceptable derivative thereof, where $R_{14}$ is as defined above for the compounds of formula I.

In another embodiment the compound of formula III is

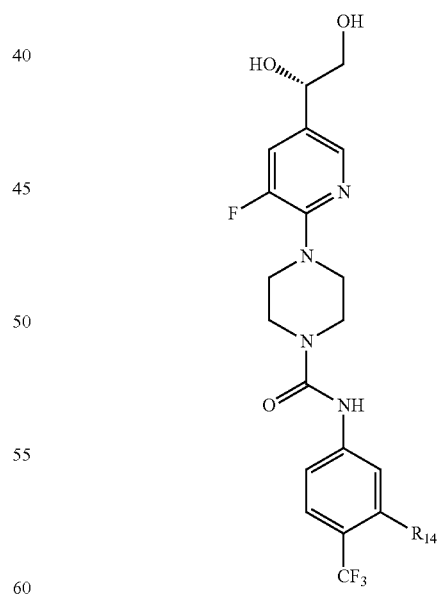

or a pharmaceutically acceptable derivative thereof, where $R_{14}$ is as defined above for the compounds of formula I.

In another embodiment the compound of formula III is

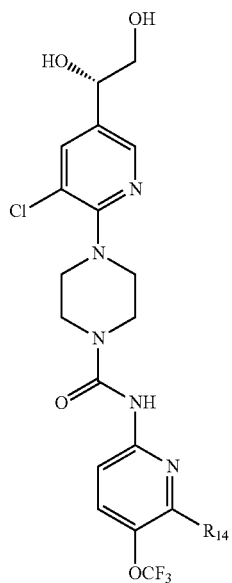

or a pharmaceutically acceptable derivative thereof, where $R_{14}$ is as defined above for the compounds of formula I.

In another embodiment the compound of formula III is

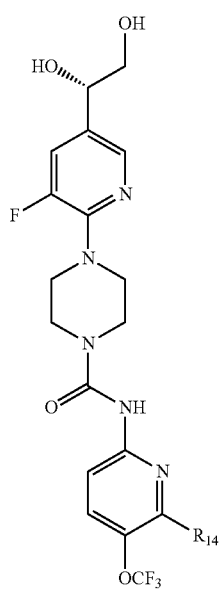

or a pharmaceutically acceptable derivative thereof, where $R_{14}$ is as defined above for the compounds of formula I.

In another embodiment the compound of formula III is

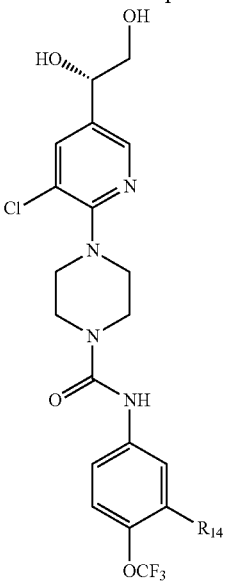

or a pharmaceutically acceptable derivative thereof, where $R_{14}$ is as defined above for the compounds of formula I.

In another embodiment the compound of formula III is

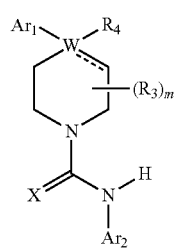

or a pharmaceutically acceptable derivative thereof, where $R_{14}$ is as defined above for the compounds of formula I.

In another embodiment, the invention encompasses compounds of formula III.4:

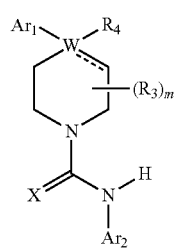

(III.4)

or a pharmaceutically acceptable salt thereof, where the dashed line, W, X, Ar$_1$, Ar$_2$, R$_3$, R$_4$, and m are as defined above for compounds of formula I.4,
wherein Ar$_1$ is:

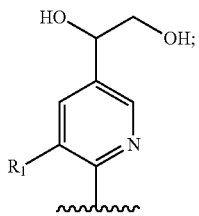

R$_1$ is —Cl, —F, or —CF$_3$;
wherein Ar$_2$ is:

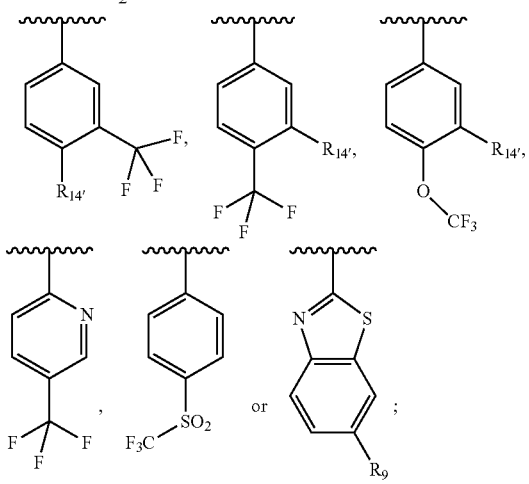

R$_{14'}$ is —H, —Cl, —F, —Br, —CH$_3$, —CH$_2$CH$_3$, —OCH$_3$, or —OCH$_2$CH$_3$;
R$_9$ is —Cl, F, or CH$_3$.

In another embodiment, the invention encompasses compounds of formula III.3:

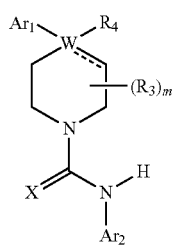

(III.3)

or a pharmaceutically acceptable salt thereof, where the dashed line, W, X, Ar$_1$, Ar$_2$, R$_3$, R$_4$, and m are as defined above for compounds of formula I.3,
wherein Ar$_1$ is:

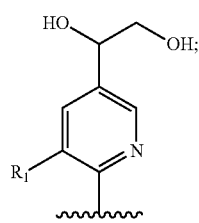

R$_1$ is —Cl, —F, or —CF$_3$;

wherein Ar$_2$ is:

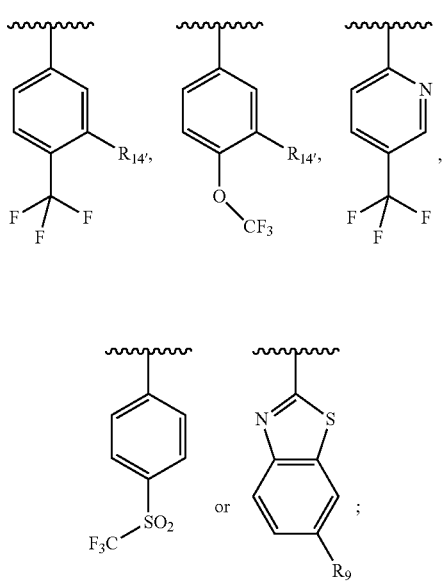

R$_{14}$ is —Cl, —F, —CH$_3$, —CH$_2$CH$_3$, —OCH$_3$, or —OCH$_2$CH$_3$;
R$_9$ is —Cl, F, or CH$_3$.

Illustrative compounds of formula III are listed below in Tables 1-36:

TABLE 1

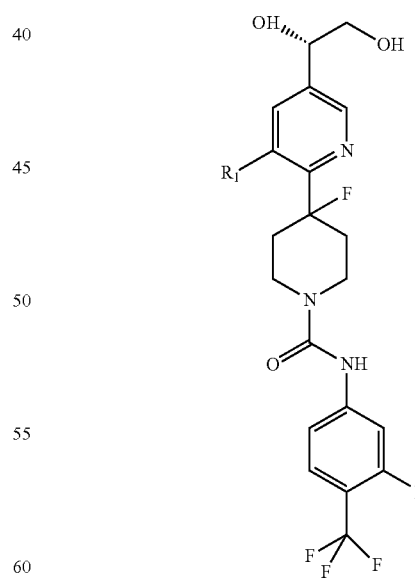

(IIIa)

and pharmaceutically acceptable derivatives thereof, where:

| Compound | R$_1$ | R$_{14'}$ |
|---|---|---|
| AAA | —Cl | —Cl |
| AAB | —Cl | —F |

TABLE 1-continued

| Compound | | |
|---|---|---|
| AAC | —Cl | —OCH₃ |
| AAD | —Cl | —OCH₂CH₃ |
| AAE | —F | —Cl |
| AAF | —F | —F |
| AAG | —F | —OCH₃ |
| AAH | —F | —OCH₂CH₃ |
| AAI | —CF₃ | —Cl |
| AAJ | —CF₃ | —F |
| AAK | —CF₃ | —OCH₃ |
| AAL | —CF₃ | —OCH₂CH₃ |

TABLE 2

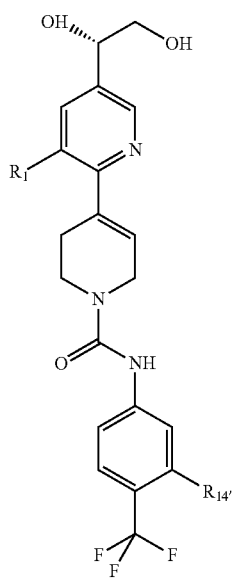

(IIIb)

and pharmaceutically acceptable derivatives thereof, where:

| Compound | R₁ | R₁₄' |
|---|---|---|
| AAM | —Cl | —Cl |
| AAN | —Cl | —F |
| AAO | —Cl | —OCH₃ |
| AAP | —Cl | —OCH₂CH₃ |

TABLE 2-continued

| Compound | R₁ | R₁₄' |
|---|---|---|
| AAQ | —F | —Cl |
| AAR | —F | —F |
| AAS | —F | —OCH₃ |
| AAT | —F | —OCH₂CH₃ |
| AAU | —CF₃ | —Cl |
| AAV | —CF₃ | —F |
| AAW | —CF₃ | —OCH₃ |
| AAX | —CF₃ | —OCH₂CH₃ |

TABLE 3

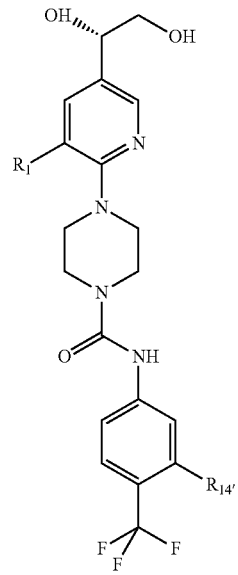

(IIIc)

and pharmaceutically acceptable derivatives thereof, where:

| Compound | R₁ | R₁₄' |
|---|---|---|
| AAY | —Cl | —Cl |
| AAZ | —Cl | —F |
| ABA | —Cl | —OCH₃ |
| ABB | —Cl | —OCH₂CH₃ |
| ABC | —F | —Cl |
| ABD | —F | —F |

TABLE 3-continued

| Compound | R₁ | R₁₄' |
|---|---|---|
| ABE | —F | —OCH₃ |
| ABF | —F | —OCH₂CH₃ |
| ABG | —CF₃ | —Cl |
| ABH | —CF₃ | —F |
| ABI | —CF₃ | —OCH₃ |
| ABJ | —CF₃ | —OCH₂CH₃ |

TABLE 4

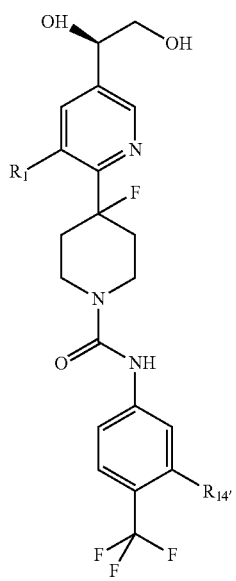

(IIId)

and pharmaceutically acceptable derivatives thereof, where:

| Compound | R₁ | R₁₄' |
|---|---|---|
| ABK | —Cl | —Cl |
| ABL | —Cl | —F |
| ABM | —Cl | —OCH₃ |
| ABN | —Cl | —OCH₂CH₃ |
| ABO | —F | —Cl |
| ABP | —F | —F |
| ABQ | —F | —OCH₃ |
| ABR | —F | —OCH₂CH₃ |

TABLE 4-continued

| Compound | R₁ | R₁₄' |
|---|---|---|
| ABS | —CF₃ | —Cl |
| ABT | —CF₃ | —F |
| ABU | —CF₃ | —OCH₃ |
| ABV | —CF₃ | —OCH₂CH₃ |

TABLE 5

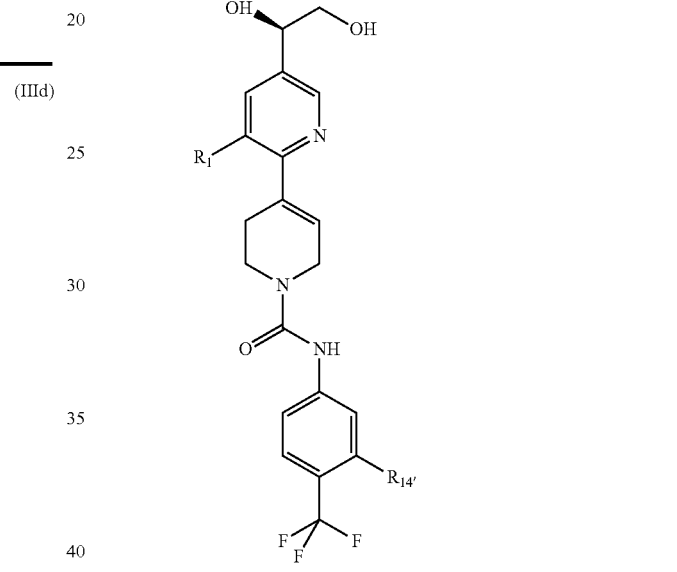

(IIIe)

and pharmaceutically acceptable derivatives thereof, where:

| Compound | R₁ | R₁₄' |
|---|---|---|
| ABW | —Cl | —Cl |
| ABX | —Cl | —F |
| ABY | —Cl | —OCH₃ |
| ABZ | —Cl | —OCH₂CH₃ |
| ACA | —F | —Cl |
| ACB | —F | —F |
| ACC | —F | —OCH₃ |
| ACD | —F | —OCH₂CH₃ |
| ACE | —CF₃ | —Cl |

TABLE 5-continued

| Compound | | |
|---|---|---|
| ACF | —CF₃ | —F |
| ACG | —CF₃ | —OCH₃ |
| ACH | —CF₃ | —OCH₂CH₃ |

TABLE 6

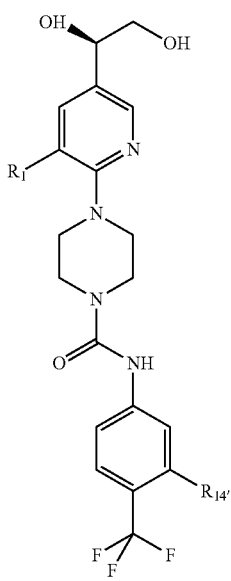

(IIIf)

and pharmaceutically acceptable derivatives thereof, where:

| Compound | R₁ | R₁₄' |
|---|---|---|
| ACI | —Cl | —Cl |
| ACJ | —Cl | —F |
| ACK | —Cl | —OCH₃ |
| ACL | —Cl | —OCH₂CH₃ |
| ACM | —F | —Cl |
| ACN | —F | —F |
| ACO | —F | —OCH₃ |
| ACP | —F | —OCH₂CH₃ |
| ACQ | —CF₃ | —Cl |
| ACR | —CF₃ | —F |
| ACS | —CF₃ | —OCH₃ |
| ACT | —CF₃ | —OCH₂CH₃ |

TABLE 7

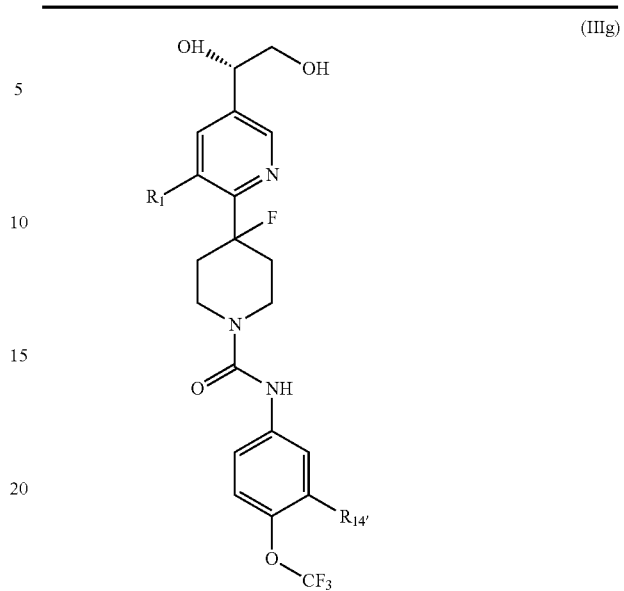

(IIIg)

and pharmaceutically acceptable derivatives thereof, where:

| Compound | R₁ | R₁₄' |
|---|---|---|
| BAA | —Cl | —CH₃ |
| BAB | —Cl | —CH₂CH₃ |
| BAC | —Cl | —Cl |
| BAD | —F | —CH₃ |
| BAE | —F | —CH₂CH₃ |
| BAF | —F | —Cl |
| BAG | —CF₃ | —CH₃ |
| BAH | —CF₃ | —CH₂CH₃ |
| BAI | —CF₃ | —Cl |

TABLE 8

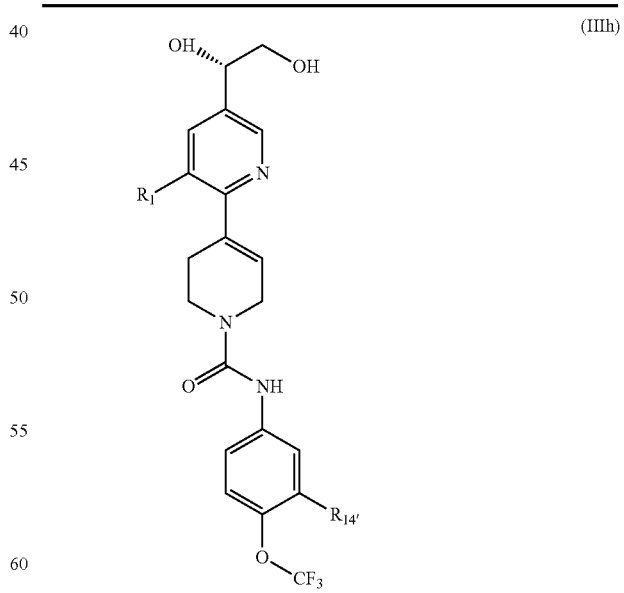

(IIIh)

and pharmaceutically acceptable derivatives thereof, where:

| Compound | R₁ | R₁₄' |
|---|---|---|
| BAJ | —Cl | —CH₃ |
| BAK | —Cl | —CH₂CH₃ |

TABLE 8-continued

| | | |
|---|---|---|
| BAL | —Cl | —Cl |
| BAM | —F | —CH₃ |
| BAN | —F | —CH₂CH₃ |
| BAO | —F | —Cl |
| BAP | —CF₃ | —CH₃ |
| BAQ | —CF₃ | —CH₂CH₃ |
| BAR | —CF₃ | —Cl |

TABLE 9

(IIIi)

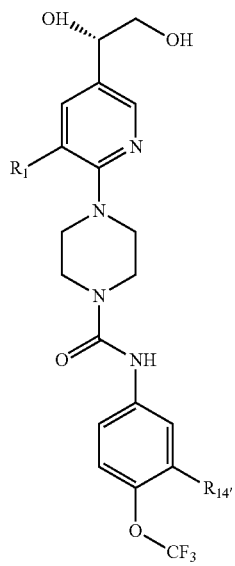

and pharmaceutically acceptable derivatives thereof, where:

| Compound | R₁ | R₁₄' |
|---|---|---|
| BAS | —Cl | —CH₃ |
| BAT | —Cl | —CH₂CH₃ |
| BAU | —Cl | —Cl |
| BAV | —F | —CH₃ |
| BAW | —F | —CH₂CH₃ |
| BAX | —F | —Cl |
| BAY | —CF₃ | —CH₃ |
| BAZ | —CF₃ | —CH₂CH₃ |
| BBA | —CF₃ | —Cl |

TABLE 10

(IIIj)

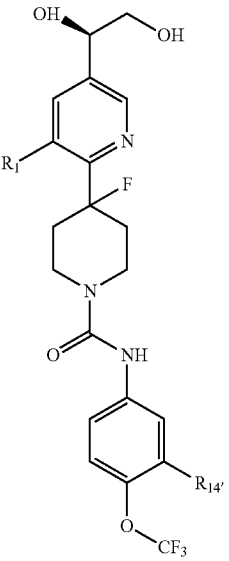

and pharmaceutically acceptable derivatives thereof, where:

| Compound | R₁ | R₁₄' |
|---|---|---|
| BBB | —Cl | —CH₃ |
| BBC | —Cl | —CH₂CH₃ |
| BBD | —Cl | —Cl |
| BBE | —F | —CH₃ |
| BBF | —F | —CH₂CH₃ |
| BBG | —F | —Cl |
| BBH | —CF₃ | —CH₃ |
| BBI | —CF₃ | —CH₂CH₃ |
| BBJ | —CF₃ | —Cl |

TABLE 11

(IIIk)

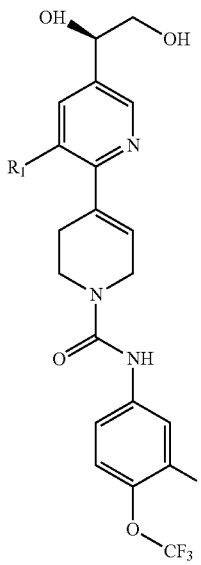

and pharmaceutically acceptable derivatives thereof, where:

| Compound | R₁ | R₁₄' |
|---|---|---|
| BBK | —Cl | —CH₃ |
| BBL | —Cl | —CH₂CH₃ |

TABLE 11-continued

| Compound | | |
|---|---|---|
| BBM | —Cl | —Cl |
| BBN | —F | —CH₃ |
| BBO | —F | —CH₂CH₃ |
| BBP | —F | —Cl |
| BBQ | —CF₃ | —CH₃ |
| BBR | —CF₃ | —CH₂CH₃ |
| BBS | —CF₃ | —Cl |

TABLE 12

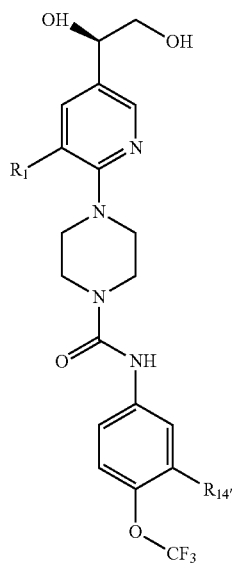

(III)

and pharmaceutically acceptable derivatives thereof, where:

| Compound | R₁ | R₁₄' |
|---|---|---|
| BBT | —Cl | —CH₃ |
| BBU | —Cl | —CH₂CH₃ |
| BBV | —Cl | —Cl |
| BBW | —F | —CH₃ |
| BBX | —F | —CH₂CH₃ |
| BBY | —F | —Cl |
| BBZ | —CF₃ | —CH₃ |
| BCA | —CF₃ | —CH₂CH₃ |
| BCB | —CF₃ | —Cl |

In other embodiments, substituent R₁₄' of Tables 1-12 can be H.

TABLE 13

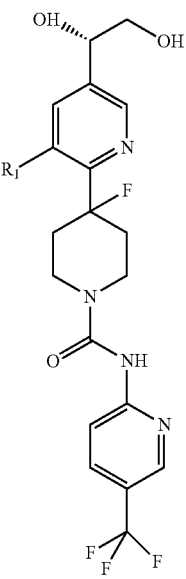

(IIIm)

and pharmaceutically acceptable derivatives thereof, where:

| Compound | R₁ |
|---|---|
| CAA | —Cl |
| CAB | —F |
| CAC | —CF₃ |

TABLE 14

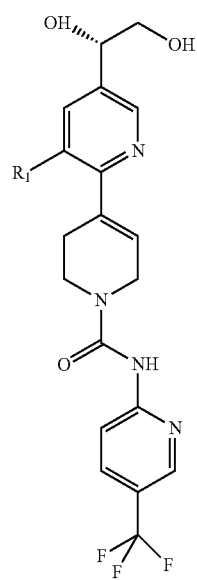

(IIIn)

and pharmaceutically acceptable derivatives thereof, where:

| Compound | R₁ |
|---|---|
| CAD | —Cl |
| CAE | —F |
| CAF | —CF₃ |

TABLE 15

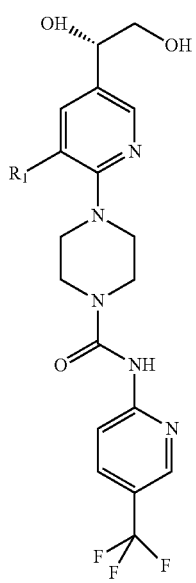

(IIIo)

and pharmaceutically acceptable derivatives thereof, where:

| Compound | R₁ |
|---|---|
| CAG | —Cl |
| CAH | —F |
| CAI | —CF₃ |

TABLE 16

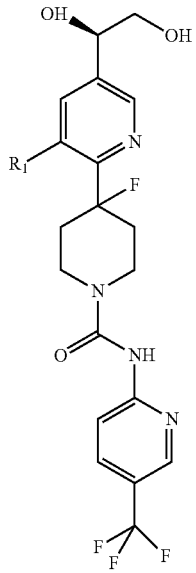

(IIIp)

and pharmaceutically acceptable derivatives thereof, where:

| Compound | R₁ |
|---|---|
| CAJ | —Cl |
| CAK | —F |
| CAL | —CF₃ |

TABLE 17

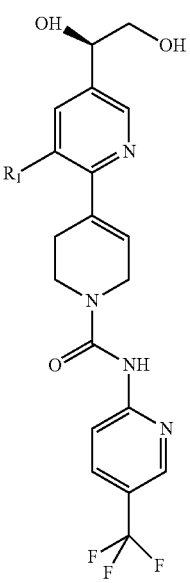

(IIIq)

and pharmaceutically acceptable derivatives thereof, where:

| Compound | R₁ |
|---|---|
| CAM | —Cl |
| CAN | —F |
| CAO | —CF₃ |

TABLE 18

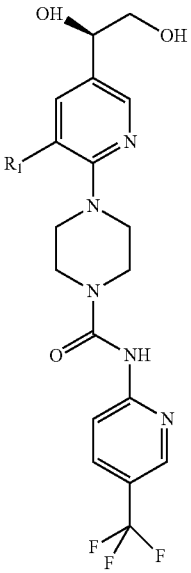

(IIIr)

and pharmaceutically acceptable derivatives thereof, where:

| Compound | R₁ |
|---|---|
| CAP | —Cl |
| CAQ | —F |
| CAR | —CF₃ |

TABLE 19

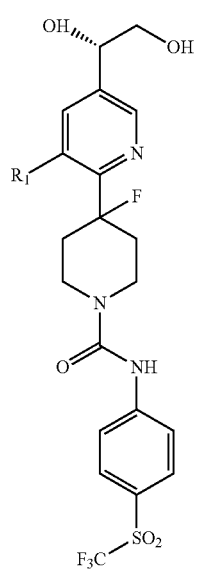

(IIIs)

and pharmaceutically acceptable derivatives thereof, where:

| Compound | R₁ |
|---|---|
| DAA | —Cl |
| DAB | —F |
| DAC | —CF₃ |

TABLE 20

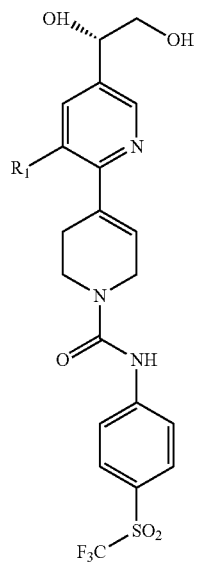

(IIIt)

and pharmaceutically acceptable derivatives thereof, where:

| Compound | R₁ |
|---|---|
| DAD | —Cl |
| DAE | —F |
| DAF | —CF₃ |

TABLE 21

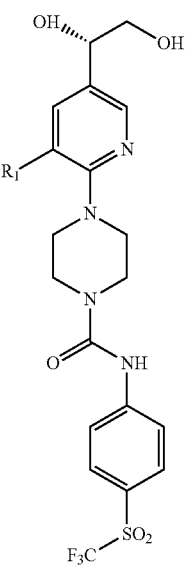

(IIIu)

and pharmaceutically acceptable derivatives thereof, where:

| Compound | R₁ |
|---|---|
| DAG | —Cl |
| DAH | —F |
| DAI | —CF₃ |

TABLE 22

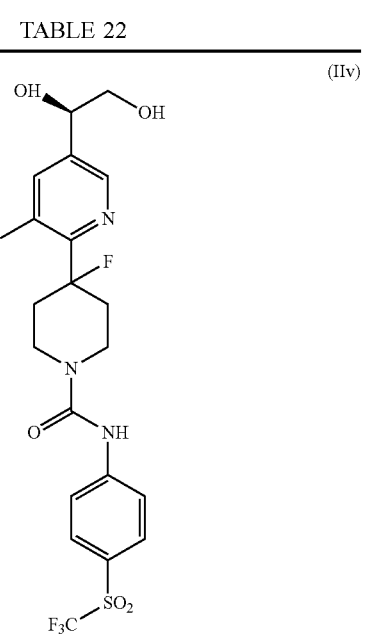

(IIv)

and pharmaceutically acceptable derivatives thereof, where:

| Compound | R₁ |
|---|---|
| DAJ | —Cl |
| DAK | —F |
| DAL | —CF₃ |

TABLE 23

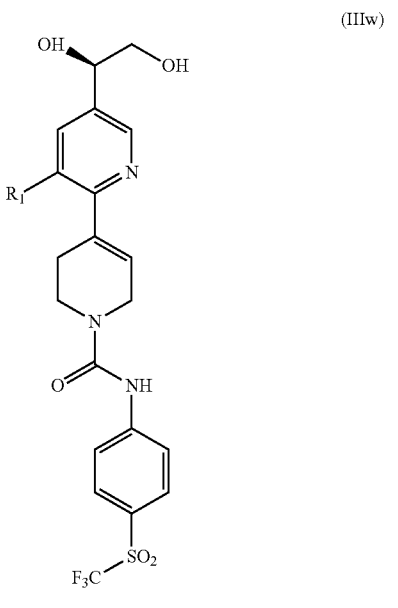

(IIIw)

and pharmaceutically acceptable derivatives thereof, where:

| Compound | $R_1$ |
|---|---|
| DAM | —Cl |
| DAN | —F |
| DAO | —CF$_3$ |

TABLE 24

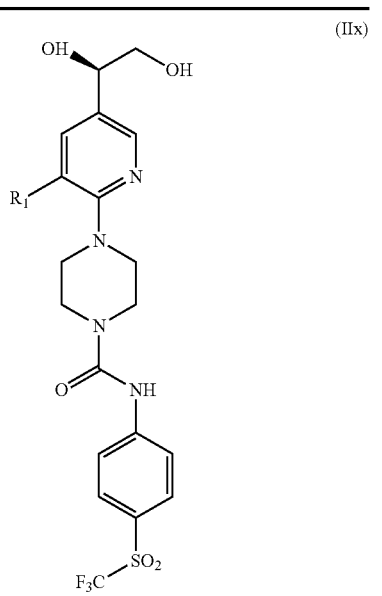

(IIx)

and pharmaceutically acceptable derivatives thereof, where:

| Compound | $R_1$ |
|---|---|
| DAP | —Cl |
| DAQ | —F |
| DAR | —CF$_3$ |

TABLE 25

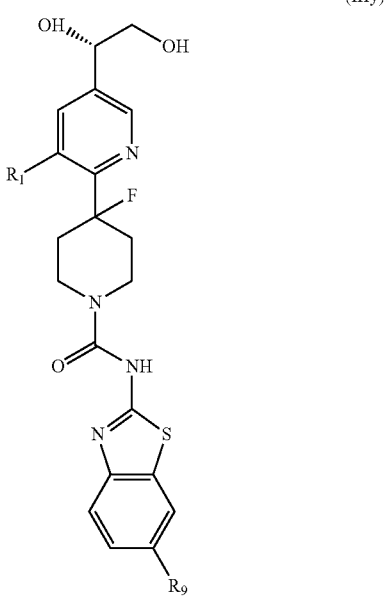

(IIIy)

and pharmaceutically acceptable derivatives thereof, where:

| Compound | $R_1$ | $R_9$ |
|---|---|---|
| EAA | —Cl | —Cl |
| EAB | —Cl | —F |
| EAC | —Cl | —CH$_3$ |
| EAD | —F | —Cl |
| EAE | —F | —F |
| EAF | —F | —CH$_3$ |
| EAG | —CF$_3$ | —Cl |
| EAH | —CF$_3$ | —F |
| EAI | —CF$_3$ | —CH$_3$ |

TABLE 26

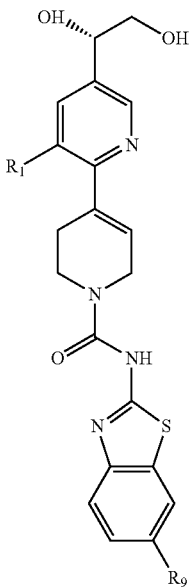

(IIIz)

and pharmaceutically acceptable derivatives thereof, where:

| Compound | R₁ | R₉ |
|---|---|---|
| EAJ | —Cl | —Cl |
| EAK | —Cl | —F |
| EAL | —Cl | —CH₃ |
| EAM | —F | —Cl |
| EAN | —F | —F |
| EAO | —F | —CH₃ |
| EAP | —CF₃ | —Cl |
| EAQ | —CF₃ | —F |
| EAR | —CF₃ | —CH₃ |

TABLE 27

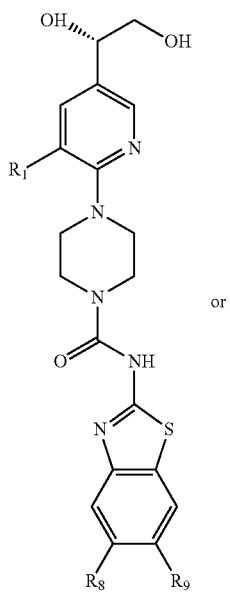

(IIIaa)

or

TABLE 27-continued

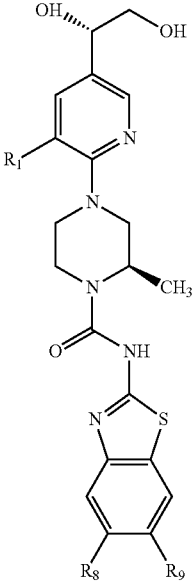

(IIIab)

and pharmaceutically acceptable derivatives thereof, where:

| Compound | R₁ | R₈ | R₉ |
|---|---|---|---|
| EAS1 aa or ab | —Cl | —H | —H |
| EAS2 aa or ab | —Cl | —H | —Cl |
| EAS3 aa or ab | —Cl | —H | —Br |
| EAS4 aa or ab | —Cl | —H | —F |
| EAS5 aa or ab | —Cl | —H | —CH₃ |
| EAS6 aa or ab | —Cl | —H | —OCH₃ |
| EAS7 aa or ab | —Cl | —H | —OCH₂CH₃ |
| EAS8 aa or ab | —Cl | —H | —CF₃ |
| EAS9 aa or ab | —Cl | —H | —OCF₃ |
| EAS10 aa or ab | —Cl | —H | iso-propyl |
| EAS11 aa or ab | —Cl | —H | tert-butyl |
| EAS12 aa or ab | —Cl | —Cl | —H |
| EAS13 aa or ab | —Cl | —Cl | —Cl |
| EAS14 aa or ab | —Cl | —Cl | —Br |
| EAS15 aa or ab | —Cl | —Cl | —F |
| EAS16 aa or ab | —Cl | —Cl | —CH₃ |
| EAS17 aa or ab | —Cl | —Cl | —OCH₃ |
| EAS18 aa or ab | —Cl | —Cl | —OCH₂CH₃ |
| EAS19 aa or ab | —Cl | —Cl | —CF₃ |
| EAS20 aa or ab | —Cl | —Cl | —OCF₃ |
| EAS21 aa or ab | —Cl | —Cl | iso-propyl |
| EAS22 aa or ab | —Cl | —Cl | tert-butyl |
| EAS23 aa or ab | —Cl | —Br | —H |
| EAS24 aa or ab | —Cl | —Br | —Cl |
| EAS25 aa or ab | —Cl | —Br | —Br |
| EAS26 aa or ab | —Cl | —Br | —F |
| EAS27 aa or ab | —Cl | —Br | —CH₃ |
| EAS28 aa or ab | —Cl | —Br | —OCH₃ |
| EAS29 aa or ab | —Cl | —Br | —OCH₂CH₃ |
| EAS30 aa or ab | —Cl | —Br | —CF₃ |
| EAS31 aa or ab | —Cl | —Br | —OCF₃ |
| EAS32 aa or ab | —Cl | —Br | iso-propyl |
| EAS33 aa or ab | —Cl | —Br | tert-butyl |
| EAS34 aa or ab | —Cl | —F | —H |
| EAS35 aa or ab | —Cl | —F | —Cl |
| EAS36 aa or ab | —Cl | —F | —Br |
| EAS37 aa or ab | —Cl | —F | —F |
| EAS38 aa or ab | —Cl | —F | —CH₃ |
| EAS39 aa or ab | —Cl | —F | —OCH₃ |
| EAS40 aa or ab | —Cl | —F | —OCH₂CH₃ |
| EAS41 aa or ab | —Cl | —F | —CF₃ |
| EAS42 aa or ab | —Cl | —F | —OCF₃ |
| EAS43 aa or ab | —Cl | —F | iso-propyl |
| EAS44 aa or ab | —Cl | —F | tert-butyl |
| EAS45 aa or ab | —Cl | —CH₃ | —H |
| EAS46 aa or ab | —Cl | —CH₃ | —Cl |

TABLE 27-continued

| | | | |
|---|---|---|---|
| EAS47 aa or ab | —Cl | —CH₃ | —Br |
| EAS48 aa or ab | —Cl | —CH₃ | —F |
| EAS49 aa or ab | —Cl | —CH₃ | —CH₃ |
| EAS50 aa or ab | —Cl | —CH₃ | —OCH₃ |
| EAS51 aa or ab | —Cl | —CH₃ | —OCH₂CH₃ |
| EAS52 aa or ab | —Cl | —CH₃ | —CF₃ |
| EAS53 aa or ab | —Cl | —CH₃ | —OCF₃ |
| EAS54 aa or ab | —Cl | —CH₃ | iso-propyl |
| EAS55 aa or ab | —Cl | —CH₃ | tert-butyl |
| EAS56 aa or ab | —Cl | —OCH₃ | —H |
| EAS57 aa or ab | —Cl | —OCH₃ | —Cl |
| EAS58 aa or ab | —Cl | —OCH₃ | —Br |
| EAS59 aa or ab | —Cl | —OCH₃ | —F |
| EAS60 aa or ab | —Cl | —OCH₃ | —CH₃ |
| EAS61 aa or ab | —Cl | —OCH₃ | —OCH₃ |
| EAS62 aa or ab | —Cl | —OCH₃ | —OCH₂CH₃ |
| EAS63 aa or ab | —Cl | —OCH₃ | —CF₃ |
| EAS64 aa or ab | —Cl | —OCH₃ | —OCF₃ |
| EAS65 aa or ab | —Cl | —OCH₃ | iso-propyl |
| EAS66 aa or ab | —Cl | —OCH₃ | tert-butyl |
| EAS67 aa or ab | —Cl | —OCH₂CH₃ | —H |
| EAS68 aa or ab | —Cl | —OCH₂CH₃ | —Cl |
| EAS69 aa or ab | —Cl | —OCH₂CH₃ | —Br |
| EAS70 aa or ab | —Cl | —OCH₂CH₃ | —F |
| EAS71 aa or ab | —Cl | —OCH₂CH₃ | —CH₃ |
| EAS72 aa or ab | —Cl | —OCH₂CH₃ | —OCH₃ |
| EAS73 aa or ab | —Cl | —OCH₂CH₃ | —OCH₂CH₃ |
| EAS74 aa or ab | —Cl | —OCH₂CH₃ | —CF₃ |
| EAS75 aa or ab | —Cl | —OCH₂CH₃ | —OCF₃ |
| EAS76 aa or ab | —Cl | —OCH₂CH₃ | iso-propyl |
| EAS77 aa or ab | —Cl | —OCH₂CH₃ | tert-butyl |
| EAS78 aa or ab | —Cl | —CF₃ | —H |
| EAS79 aa or ab | —Cl | —CF₃ | —Cl |
| EAS80 aa or ab | —Cl | —CF₃ | —Br |
| EAS81 aa or ab | —Cl | —CF₃ | —F |
| EAS82 aa or ab | —Cl | —CF₃ | —CH₃ |
| EAS83 aa or ab | —Cl | —CF₃ | —OCH₃ |
| EAS84 aa or ab | —Cl | —CF₃ | —OCH₂CH₃ |
| EAS85 aa or ab | —Cl | —CF₃ | —CF₃ |
| EAS86 aa or ab | —Cl | —CF₃ | —OCF₃ |
| EAS87 aa or ab | —Cl | —CF₃ | iso-propyl |
| EAS88 aa or ab | —Cl | —CF₃ | tert-butyl |
| EAS89 aa or ab | —Cl | —OCF₃ | —H |
| EAS90 aa or ab | —Cl | —OCF₃ | —Cl |
| EAS91 aa or ab | —Cl | —OCF₃ | —Br |
| EAS92 aa or ab | —Cl | —OCF₃ | —F |
| EAS93 aa or ab | —Cl | —OCF₃ | —CH₃ |
| EAS94 aa or ab | —Cl | —OCF₃ | —OCH₃ |
| EAS95 aa or ab | —Cl | —OCF₃ | —OCH₂CH₃ |
| EAS96 aa or ab | —Cl | —OCF₃ | —CF₃ |
| EAS97 aa or ab | —Cl | —OCF₃ | —OCF₃ |
| EAS98 aa or ab | —Cl | —OCF₃ | iso-propyl |
| EAS99 aa or ab | —Cl | —OCF₃ | tert-butyl |
| EAS100 aa or ab | —Cl | iso-propyl | —H |
| EAS101 aa or ab | —Cl | iso-propyl | —Cl |
| EAS102 aa or ab | —Cl | iso-propyl | —Br |
| EAS103 aa or ab | —Cl | iso-propyl | —F |
| EAS104 aa or ab | —Cl | iso-propyl | —CH₃ |
| EAS105 aa or ab | —Cl | iso-propyl | —OCH₃ |
| EAS106 aa or ab | —Cl | iso-propyl | —OCH₂CH₃ |
| EAS107 aa or ab | —Cl | iso-propyl | —CF₃ |
| EAS108 aa or ab | —Cl | iso-propyl | —OCF₃ |
| EAS109 aa or ab | —Cl | iso-propyl | iso-propyl |
| EAS110 aa or ab | —Cl | iso-propyl | tert-butyl |
| EAS111 aa or ab | —Cl | tert-butyl | —H |
| EAS112 aa or ab | —Cl | tert-butyl | —Cl |
| EAS113 aa or ab | —Cl | tert-butyl | —Br |
| EAS114 aa or ab | —Cl | tert-butyl | —F |
| EAS115 aa or ab | —Cl | tert-butyl | —CH₃ |
| EAS116 aa or ab | —Cl | tert-butyl | —OCH₃ |
| EAS117 aa or ab | —Cl | tert-butyl | —OCH₂CH₃ |
| EAS118 aa or ab | —Cl | tert-butyl | —CF₃ |
| EAS119 aa or ab | —Cl | tert-butyl | —OCF₃ |
| EAS120 aa or ab | —Cl | tert-butyl | iso-propyl |
| EAS121 aa or ab | —Cl | tert-butyl | tert-butyl |
| EAT1 aa or ab | —F | —H | —H |
| EAT2 aa or ab | —F | —H | —Cl |
| EAT3 aa or ab | —F | —H | —Br |
| EAT4 aa or ab | —F | —H | —F |
| EAT5 aa or ab | —F | —H | —CH₃ |
| EAT6 aa or ab | —F | —H | —OCH₃ |
| EAT7 aa or ab | —F | —H | —OCH₂CH₃ |
| EAT8 aa or ab | —F | —H | —CF₃ |
| EAT9 aa or ab | —F | —H | —OCF₃ |
| EAT10 aa or ab | —F | —H | iso-propyl |
| EAT11 aa or ab | —F | —H | tert-butyl |
| EAT12 aa or ab | —F | —Cl | —H |
| EAT13 aa or ab | —F | —Cl | —Cl |
| EAT14 aa or ab | —F | —Cl | —Br |
| EAT15 aa or ab | —F | —Cl | —F |
| EAT16 aa or ab | —F | —Cl | —CH₃ |
| EAT17 aa or ab | —F | —Cl | —OCH₃ |
| EAT18 aa or ab | —F | —Cl | —OCH₂CH₃ |
| EAT19 aa or ab | —F | —Cl | —CF₃ |
| EAT20 aa or ab | —F | —Cl | —OCF₃ |
| EAT21 aa or ab | —F | —Cl | iso-propyl |
| EAT22 aa or ab | —F | —Cl | tert-butyl |
| EAT23 aa or ab | —F | —Br | —H |
| EAT24 aa or ab | —F | —Br | —Cl |
| EAT25 aa or ab | —F | —Br | —Br |
| EAT26 aa or ab | —F | —Br | —F |
| EAT27 aa or ab | —F | —Br | —CH₃ |
| EAT28 aa or ab | —F | —Br | —OCH₃ |
| EAT29 aa or ab | —F | —Br | —OCH₂CH₃ |
| EAT30 aa or ab | —F | —Br | —CF₃ |
| EAT31 aa or ab | —F | —Br | —OCF₃ |
| EAT32 aa or ab | —F | —Br | iso-propyl |
| EAT33 aa or ab | —F | —Br | tert-butyl |
| EAT34 aa or ab | —F | —F | —H |
| EAT35 aa or ab | —F | —F | —Cl |
| EAT36 aa or ab | —F | —F | —Br |
| EAT37 aa or ab | —F | —F | —F |
| EAT38 aa or ab | —F | —F | —CH₃ |
| EAT39 aa or ab | —F | —F | —OCH₃ |
| EAT40 aa or ab | —F | —F | —OCH₂CH₃ |
| EAT41 aa or ab | —F | —F | —CF₃ |
| EAT42 aa or ab | —F | —F | —OCF₃ |
| EAT43 aa or ab | —F | —F | iso-propyl |
| EAT44 aa or ab | —F | —F | tert-butyl |
| EAT45 aa or ab | —F | —CH₃ | —H |
| EAT46 aa or ab | —F | —CH₃ | —Cl |
| EAT47 aa or ab | —F | —CH₃ | —Br |
| EAT48 aa or ab | —F | —CH₃ | —F |
| EAT49 aa or ab | —F | —CH₃ | —CH₃ |
| EAT50 aa or ab | —F | —CH₃ | —OCH₃ |
| EAT51 aa or ab | —F | —CH₃ | —OCH₂CH₃ |
| EAT52 aa or ab | —F | —CH₃ | —CF₃ |
| EAT53 aa or ab | —F | —CH₃ | —OCF₃ |
| EAT54 aa or ab | —F | —CH₃ | iso-propyl |
| EAT55 aa or ab | —F | —CH₃ | tert-butyl |
| EAT56 aa or ab | —F | —OCH₃ | —H |
| EAT57 aa or ab | —F | —OCH₃ | —Cl |
| EAT58 aa or ab | —F | —OCH₃ | —Br |
| EAT59 aa or ab | —F | —OCH₃ | —F |
| EAT60 aa or ab | —F | —OCH₃ | —CH₃ |
| EAT61 aa or ab | —F | —OCH₃ | —OCH₃ |
| EAT62 aa or ab | —F | —OCH₃ | —OCH₂CH₃ |
| EAT63 aa or ab | —F | —OCH₃ | —CF₃ |
| EAT64 aa or ab | —F | —OCH₃ | —OCF₃ |
| EAT65 aa or ab | —F | —OCH₃ | iso-propyl |
| EAT66 aa or ab | —F | —OCH₃ | tert-butyl |
| EAT67 aa or ab | —F | —OCH₂CH₃ | —H |
| EAT68 aa or ab | —F | —OCH₂CH₃ | —Cl |
| EAT69 aa or ab | —F | —OCH₂CH₃ | —Br |
| EAT70 aa or ab | —F | —OCH₂CH₃ | —F |
| EAT71 aa or ab | —F | —OCH₂CH₃ | —CH₃ |
| EAT72 aa or ab | —F | —OCH₂CH₃ | —OCH₃ |
| EAT73 aa or ab | —F | —OCH₂CH₃ | —OCH₂CH₃ |
| EAT74 aa or ab | —F | —OCH₂CH₃ | —CF₃ |
| EAT75 aa or ab | —F | —OCH₂CH₃ | —OCF₃ |
| EAT76 aa or ab | —F | —OCH₂CH₃ | iso-propyl |
| EAT77 aa or ab | —F | —OCH₂CH₃ | tert-butyl |
| EAT78 aa or ab | —F | —CF₃ | —H |
| EAT79 aa or ab | —F | —CF₃ | —Cl |
| EAT80 aa or ab | —F | —CF₃ | —Br |
| EAT81 aa or ab | —F | —CF₃ | —F |
| EAT82 aa or ab | —F | —CF₃ | —CH₃ |
| EAT83 aa or ab | —F | —CF₃ | —OCH₃ |
| EAT84 aa or ab | —F | —CF₃ | —OCH₂CH₃ |
| EAT85 aa or ab | —F | —CF₃ | —CF₃ |

TABLE 27-continued

| | | | |
|---|---|---|---|
| EAT86 aa or ab | —F | —CF$_3$ | —OCF$_3$ |
| EAT87 aa or ab | —F | —CF$_3$ | iso-propyl |
| EAT88 aa or ab | —F | —CF$_3$ | tert-butyl |
| EAT89 aa or ab | —F | —OCF$_3$ | —H |
| EAT90 aa or ab | —F | —OCF$_3$ | —Cl |
| EAT91 aa or ab | —F | —OCF$_3$ | —Br |
| EAT92 aa or ab | —F | —OCF$_3$ | —F |
| EAT93 aa or ab | —F | —OCF$_3$ | —CH$_3$ |
| EAT94 aa or ab | —F | —OCF$_3$ | —OCH$_3$ |
| EAT95 aa or ab | —F | —OCF$_3$ | —OCH$_2$CH$_3$ |
| EAT96 aa or ab | —F | —OCF$_3$ | —CF$_3$ |
| EAT97 aa or ab | —F | —OCF$_3$ | —OCF$_3$ |
| EAT98 aa or ab | —F | —OCF$_3$ | iso-propyl |
| EAT99 aa or ab | —F | —OCF$_3$ | tert-butyl |
| EAT100 aa or ab | —F | iso-propyl | —H |
| EAT101 aa or ab | —F | iso-propyl | —Cl |
| EAT102 aa or ab | —F | iso-propyl | —Br |
| EAT103 aa or ab | —F | iso-propyl | —F |
| EAT104 aa or ab | —F | iso-propyl | —CH$_3$ |
| EAT105 aa or ab | —F | iso-propyl | —OCH$_3$ |
| EAT106 aa or ab | —F | iso-propyl | —OCH$_2$CH$_3$ |
| EAT107 aa or ab | —F | iso-propyl | —CF$_3$ |
| EAT108 aa or ab | —F | iso-propyl | —OCF$_3$ |
| EAT109 aa or ab | —F | iso-propyl | iso-propyl |
| EAT110 aa or ab | —F | iso-propyl | tert-butyl |
| EAT111 aa or ab | —F | tert-butyl | —H |
| EAT112 aa or ab | —F | tert-butyl | —Cl |
| EAT113 aa or ab | —F | tert-butyl | —Br |
| EAT114 aa or ab | —F | tert-butyl | —F |
| EAT115 aa or ab | —F | tert-butyl | —CH$_3$ |
| EAT116 aa or ab | —F | tert-butyl | —OCH$_3$ |
| EAT117 aa or ab | —F | tert-butyl | —OCH$_2$CH$_3$ |
| EAT118 aa or ab | —F | tert-butyl | —CF$_3$ |
| EAT119 aa or ab | —F | tert-butyl | —OCF$_3$ |
| EAT120 aa or ab | —F | tert-butyl | iso-propyl |
| EAT121 aa or ab | —F | tert-butyl | tert-butyl |
| EAU1 aa or ab | —CF$_3$ | —H | —H |
| EAU2 aa or ab | —CF$_3$ | —H | —Cl |
| EAU3 aa or ab | —CF$_3$ | —H | —Br |
| EAU4 aa or ab | —CF$_3$ | —H | —F |
| EAU5 aa or ab | —CF$_3$ | —H | —CH$_3$ |
| EAU6 aa or ab | —CF$_3$ | —H | —OCH$_3$ |
| EAU7 aa or ab | —CF$_3$ | —H | —OCH$_2$CH$_3$ |
| EAU8 aa or ab | —CF$_3$ | —H | —CF$_3$ |
| EAU9 aa or ab | —CF$_3$ | —H | —OCF$_3$ |
| EAU10 aa or ab | —CF$_3$ | —H | iso-propyl |
| EAU11 aa or ab | —CF$_3$ | —H | tert-butyl |
| EAU12 aa or ab | —CF$_3$ | —Cl | —H |
| EAU13 aa or ab | —CF$_3$ | —Cl | —Cl |
| EAU14 aa or ab | —CF$_3$ | —Cl | —Br |
| EAU15 aa or ab | —CF$_3$ | —Cl | —F |
| EAU16 aa or ab | —CF$_3$ | —Cl | —CH$_3$ |
| EAU17 aa or ab | —CF$_3$ | —Cl | —OCH$_3$ |
| EAU18 aa or ab | —CF$_3$ | —Cl | —OCH$_2$CH$_3$ |
| EAU19 aa or ab | —CF$_3$ | —Cl | —CF$_3$ |
| EAU20 aa or ab | —CF$_3$ | —Cl | —OCF$_3$ |
| EAU21 aa or ab | —CF$_3$ | —Cl | iso-propyl |
| EAU22 aa or ab | —CF$_3$ | —Cl | tert-butyl |
| EAU23 aa or ab | —CF$_3$ | —Br | —H |
| EAU24 aa or ab | —CF$_3$ | —Br | —Cl |
| EAU25 aa or ab | —CF$_3$ | —Br | —Br |
| EAU26 aa or ab | —CF$_3$ | —Br | —F |
| EAU27 aa or ab | —CF$_3$ | —Br | —CH$_3$ |
| EAU28 aa or ab | —CF$_3$ | —Br | —OCH$_3$ |
| EAU29 aa or ab | —CF$_3$ | —Br | —OCH$_2$CH$_3$ |
| EAU30 aa or ab | —CF$_3$ | —Br | —CF$_3$ |
| EAU31 aa or ab | —CF$_3$ | —Br | —OCF$_3$ |
| EAU32 aa or ab | —CF$_3$ | —Br | iso-propyl |
| EAU33 aa or ab | —CF$_3$ | —Br | tert-butyl |
| EAU34 aa or ab | —CF$_3$ | —F | —H |
| EAU35 aa or ab | —CF$_3$ | —F | —Cl |
| EAU36 aa or ab | —CF$_3$ | —F | —Br |
| EAU37 aa or ab | —CF$_3$ | —F | —F |
| EAU38 aa or ab | —CF$_3$ | —F | —CH$_3$ |
| EAU39 aa or ab | —CF$_3$ | —F | —OCH$_3$ |
| EAU40 aa or ab | —CF$_3$ | —F | —OCH$_2$CH$_3$ |
| EAU41 aa or ab | —CF$_3$ | —F | —CF$_3$ |
| EAU42 aa or ab | —CF$_3$ | —F | —OCF$_3$ |
| EAU43 aa or ab | —CF$_3$ | —F | iso-propyl |
| EAU44 aa or ab | —CF$_3$ | —F | tert-butyl |
| EAU45 aa or ab | —CF$_3$ | —CH$_3$ | —H |
| EAU46 aa or ab | —CF$_3$ | —CH$_3$ | —Cl |
| EAU47 aa or ab | —CF$_3$ | —CH$_3$ | —Br |
| EAU48 aa or ab | —CF$_3$ | —CH$_3$ | —F |
| EAU49 aa or ab | —CF$_3$ | —CH$_3$ | —CH$_3$ |
| EAU50 aa or ab | —CF$_3$ | —CH$_3$ | —OCH$_3$ |
| EAU51 aa or ab | —CF$_3$ | —CH$_3$ | —OCH$_2$CH$_3$ |
| EAU52 aa or ab | —CF$_3$ | —CH$_3$ | —CF$_3$ |
| EAU53 aa or ab | —CF$_3$ | —CH$_3$ | —OCF$_3$ |
| EAU54 aa or ab | —CF$_3$ | —CH$_3$ | iso-propyl |
| EAU55 aa or ab | —CF$_3$ | —CH$_3$ | tert-butyl |
| EAU56 aa or ab | —CF$_3$ | —OCH$_3$ | —H |
| EAU57 aa or ab | —CF$_3$ | —OCH$_3$ | —Cl |
| EAU58 aa or ab | —CF$_3$ | —OCH$_3$ | —Br |
| EAU59 aa or ab | —CF$_3$ | —OCH$_3$ | —F |
| EAU60 aa or ab | —CF$_3$ | —OCH$_3$ | —CH$_3$ |
| EAU61 aa or ab | —CF$_3$ | —OCH$_3$ | —OCH$_3$ |
| EAU62 aa or ab | —CF$_3$ | —OCH$_3$ | —OCH$_2$CH$_3$ |
| EAU63 aa or ab | —CF$_3$ | —OCH$_3$ | —CF$_3$ |
| EAU64 aa or ab | —CF$_3$ | —OCH$_3$ | —OCF$_3$ |
| EAU65 aa or ab | —CF$_3$ | —OCH$_3$ | iso-propyl |
| EAU66 aa or ab | —CF$_3$ | —OCH$_3$ | tert-butyl |
| EAU67 aa or ab | —CF$_3$ | —OCH$_2$CH$_3$ | —H |
| EAU68 aa or ab | —CF$_3$ | —OCH$_2$CH$_3$ | —Cl |
| EAU69 aa or ab | —CF$_3$ | —OCH$_2$CH$_3$ | —Br |
| EAU70 aa or ab | —CF$_3$ | —OCH$_2$CH$_3$ | —F |
| EAU71 aa or ab | —CF$_3$ | —OCH$_2$CH$_3$ | —CH$_3$ |
| EAU72 aa or ab | —CF$_3$ | —OCH$_2$CH$_3$ | —OCH$_3$ |
| EAU73 aa or ab | —CF$_3$ | —OCH$_2$CH$_3$ | —OCH$_2$CH$_3$ |
| EAU74 aa or ab | —CF$_3$ | —OCH$_2$CH$_3$ | —CF$_3$ |
| EAU75 aa or ab | —CF$_3$ | —OCH$_2$CH$_3$ | —OCF$_3$ |
| EAU76 aa or ab | —CF$_3$ | —OCH$_2$CH$_3$ | iso-propyl |
| EAU77 aa or ab | —CF$_3$ | —OCH$_2$CH$_3$ | tert-butyl |
| EAU78 aa or ab | —CF$_3$ | —CF$_3$ | —H |
| EAU79 aa or ab | —CF$_3$ | —CF$_3$ | —Cl |
| EAU80 aa or ab | —CF$_3$ | —CF$_3$ | —Br |
| EAU81 aa or ab | —CF$_3$ | —CF$_3$ | —F |
| EAU82 aa or ab | —CF$_3$ | —CF$_3$ | —CH$_3$ |
| EAU83 aa or ab | —CF$_3$ | —CF$_3$ | —OCH$_3$ |
| EAU84 aa or ab | —CF$_3$ | —CF$_3$ | —OCH$_2$CH$_3$ |
| EAU85 aa or ab | —CF$_3$ | —CF$_3$ | —CF$_3$ |
| EAU86 aa or ab | —CF$_3$ | —CF$_3$ | —OCF$_3$ |
| EAU87 aa or ab | —CF$_3$ | —CF$_3$ | iso-propyl |
| EAU88 aa or ab | —CF$_3$ | —CF$_3$ | tert-butyl |
| EAU89 aa or ab | —CF$_3$ | —OCF$_3$ | —H |
| EAU90 aa or ab | —CF$_3$ | —OCF$_3$ | —Cl |
| EAU91 aa or ab | —CF$_3$ | —OCF$_3$ | —Br |
| EAU92 aa or ab | —CF$_3$ | —OCF$_3$ | —F |
| EAU93 aa or ab | —CF$_3$ | —OCF$_3$ | —CH$_3$ |
| EAU94 aa or ab | —CF$_3$ | —OCF$_3$ | —OCH$_3$ |
| EAU95 aa or ab | —CF$_3$ | —OCF$_3$ | —OCH$_2$CH$_3$ |
| EAU96 aa or ab | —CF$_3$ | —OCF$_3$ | —CF$_3$ |
| EAU97 aa or ab | —CF$_3$ | —OCF$_3$ | —OCF$_3$ |
| EAU98 aa or ab | —CF$_3$ | —OCF$_3$ | iso-propyl |
| EAU99 aa or ab | —CF$_3$ | —OCF$_3$ | tert-butyl |
| EAU100 aa or ab | —CF$_3$ | iso-propyl | —H |
| EAU101 aa or ab | —CF$_3$ | iso-propyl | —Cl |
| EAU102 aa or ab | —CF$_3$ | iso-propyl | —Br |
| EAU103 aa or ab | —CF$_3$ | iso-propyl | —F |
| EAU104 aa or ab | —CF$_3$ | iso-propyl | —CH$_3$ |
| EAU105 aa or ab | —CF$_3$ | iso-propyl | —OCH$_3$ |
| EAU106 aa or ab | —CF$_3$ | iso-propyl | —OCH$_2$CH$_3$ |
| EAU107 aa or ab | —CF$_3$ | iso-propyl | —CF$_3$ |
| EAU108 aa or ab | —CF$_3$ | iso-propyl | —OCF$_3$ |
| EAU109 aa or ab | —CF$_3$ | iso-propyl | iso-propyl |
| EAU110 aa or ab | —CF$_3$ | iso-propyl | tert-butyl |
| EAU111 aa or ab | —CF$_3$ | tert-butyl | —H |
| EAU112 aa or ab | —CF$_3$ | tert-butyl | —Cl |
| EAU113 aa or ab | —CF$_3$ | tert-butyl | —Br |
| EAU114 aa or ab | —CF$_3$ | tert-butyl | —F |
| EAU115 aa or ab | —CF$_3$ | tert-butyl | —CH$_3$ |
| EAU116 aa or ab | —CF$_3$ | tert-butyl | —OCH$_3$ |
| EAU117 aa or ab | —CF$_3$ | tert-butyl | —OCH$_2$CH$_3$ |
| EAU118 aa or ab | —CF$_3$ | tert-butyl | —CF$_3$ |
| EAU119 aa or ab | —CF$_3$ | tert-butyl | —OCF$_3$ |
| EAU120 aa or ab | —CF$_3$ | tert-butyl | iso-propyl |
| EAU121 aa or ab | —CF$_3$ | tert-butyl | tert-butyl |
| EAV1 aa or ab | —CH$_3$ | —H | —H |
| EAV2 aa or ab | —CH$_3$ | —H | —Cl |
| EAV3 aa or ab | —CH$_3$ | —H | —Br |

TABLE 27-continued

| | | | |
|---|---|---|---|
| EAV4 aa or ab | —CH₃ | —H | —F |
| EAV5 aa or ab | —CH₃ | —H | —CH₃ |
| EAV6 aa or ab | —CH₃ | —H | —OCH₃ |
| EAV7 aa or ab | —CH₃ | —H | —OCH₂CH₃ |
| EAV8 aa or ab | —CH₃ | —H | —CF₃ |
| EAV9 aa or ab | —CH₃ | —H | —OCF₃ |
| EAV10 aa or ab | —CH₃ | —H | iso-propyl |
| EAV11 aa or ab | —CH₃ | —H | tert-butyl |
| EAV12 aa or ab | —CH₃ | —Cl | —H |
| EAV13 aa or ab | —CH₃ | —Cl | —Cl |
| EAV14 aa or ab | —CH₃ | —Cl | —Br |
| EAV15 aa or ab | —CH₃ | —Cl | —F |
| EAV16 aa or ab | —CH₃ | —Cl | —CH₃ |
| EAV17 aa or ab | —CH₃ | —Cl | —OCH₃ |
| EAV18 aa or ab | —CH₃ | —Cl | —OCH₂CH₃ |
| EAV19 aa or ab | —CH₃ | —Cl | —CF₃ |
| EAV20 aa or ab | —CH₃ | —Cl | —OCF₃ |
| EAV21 aa or ab | —CH₃ | —Cl | iso-propyl |
| EAV22 aa or ab | —CH₃ | —Cl | tert-butyl |
| EAV23 aa or ab | —CH₃ | —Br | —H |
| EAV24 aa or ab | —CH₃ | —Br | —Cl |
| EAV25 aa or ab | —CH₃ | —Br | —Br |
| EAV26 aa or ab | —CH₃ | —Br | —F |
| EAV27 aa or ab | —CH₃ | —Br | —CH₃ |
| EAV28 aa or ab | —CH₃ | —Br | —OCH₃ |
| EAV29 aa or ab | —CH₃ | —Br | —OCH₂CH₃ |
| EAV30 aa or ab | —CH₃ | —Br | —CF₃ |
| EAV31 aa or ab | —CH₃ | —Br | —OCF₃ |
| EAV32 aa or ab | —CH₃ | —Br | iso-propyl |
| EAV33 aa or ab | —CH₃ | —Br | tert-butyl |
| EAV34 aa or ab | —CH₃ | —F | —H |
| EAV35 aa or ab | —CH₃ | —F | —Cl |
| EAV36 aa or ab | —CH₃ | —F | —Br |
| EAV37 aa or ab | —CH₃ | —F | —F |
| EAV38 aa or ab | —CH₃ | —F | —CH₃ |
| EAV39 aa or ab | —CH₃ | —F | —OCH₃ |
| EAV40 aa or ab | —CH₃ | —F | —OCH₂CH₃ |
| EAV41 aa or ab | —CH₃ | —F | —CF₃ |
| EAV42 aa or ab | —CH₃ | —F | —OCF₃ |
| EAV43 aa or ab | —CH₃ | —F | iso-propyl |
| EAV44 aa or ab | —CH₃ | —F | tert-butyl |
| EAV45 aa or ab | —CH₃ | —CH₃ | —H |
| EAV46 aa or ab | —CH₃ | —CH₃ | —Cl |
| EAV47 aa or ab | —CH₃ | —CH₃ | —Br |
| EAV48 aa or ab | —CH₃ | —CH₃ | —F |
| EAV49 aa or ab | —CH₃ | —CH₃ | —CH₃ |
| EAV50 aa or ab | —CH₃ | —CH₃ | —OCH₃ |
| EAV51 aa or ab | —CH₃ | —CH₃ | —OCH₂CH₃ |
| EAV52 aa or ab | —CH₃ | —CH₃ | —CF₃ |
| EAV53 aa or ab | —CH₃ | —CH₃ | —OCF₃ |
| EAV54 aa or ab | —CH₃ | —CH₃ | iso-propyl |
| EAV55 aa or ab | —CH₃ | —CH₃ | tert-butyl |
| EAV56 aa or ab | —CH₃ | —OCH₃ | —H |
| EAV57 aa or ab | —CH₃ | —OCH₃ | —Cl |
| EAV58 aa or ab | —CH₃ | —OCH₃ | —Br |
| EAV59 aa or ab | —CH₃ | —OCH₃ | —F |
| EAV60 aa or ab | —CH₃ | —OCH₃ | —CH₃ |
| EAV61 aa or ab | —CH₃ | —OCH₃ | —OCH₃ |
| EAV62 aa or ab | —CH₃ | —OCH₃ | —OCH₂CH₃ |
| EAV63 aa or ab | —CH₃ | —OCH₃ | —CF₃ |
| EAV64 aa or ab | —CH₃ | —OCH₃ | —OCF₃ |
| EAV65 aa or ab | —CH₃ | —OCH₃ | iso-propyl |
| EAV66 aa or ab | —CH₃ | —OCH₃ | tert-butyl |
| EAV67 aa or ab | —CH₃ | —OCH₂CH₃ | —H |
| EAV68 aa or ab | —CH₃ | —OCH₂CH₃ | —Cl |
| EAV69 aa or ab | —CH₃ | —OCH₂CH₃ | —Br |
| EAV70 aa or ab | —CH₃ | —OCH₂CH₃ | —F |
| EAV71 aa or ab | —CH₃ | —OCH₂CH₃ | —CH₃ |
| EAV72 aa or ab | —CH₃ | —OCH₂CH₃ | —OCH₃ |
| EAV73 aa or ab | —CH₃ | —OCH₂CH₃ | —OCH₂CH₃ |
| EAV74 aa or ab | —CH₃ | —OCH₂CH₃ | —CF₃ |
| EAV75 aa or ab | —CH₃ | —OCH₂CH₃ | —OCF₃ |
| EAV76 aa or ab | —CH₃ | —OCH₂CH₃ | iso-propyl |
| EAV77 aa or ab | —CH₃ | —OCH₂CH₃ | tert-butyl |
| EAV78 aa or ab | —CH₃ | —CF₃ | —H |
| EAV79 aa or ab | —CH₃ | —CF₃ | —Cl |
| EAV80 aa or ab | —CH₃ | —CF₃ | —Br |
| EAV81 aa or ab | —CH₃ | —CF₃ | —F |
| EAV82 aa or ab | —CH₃ | —CF₃ | —CH₃ |
| EAV83 aa or ab | —CH₃ | —CF₃ | —OCH₃ |
| EAV84 aa or ab | —CH₃ | —CF₃ | —OCH₂CH₃ |
| EAV85 aa or ab | —CH₃ | —CF₃ | —CF₃ |
| EAV86 aa or ab | —CH₃ | —CF₃ | —OCF₃ |
| EAV87 aa or ab | —CH₃ | —CF₃ | iso-propyl |
| EAV88 aa or ab | —CH₃ | —CF₃ | tert-butyl |
| EAV89 aa or ab | —CH₃ | —OCF₃ | —H |
| EAV90 aa or ab | —CH₃ | —OCF₃ | —Cl |
| EAV91 aa or ab | —CH₃ | —OCF₃ | —Br |
| EAV92 aa or ab | —CH₃ | —OCF₃ | —F |
| EAV93 aa or ab | —CH₃ | —OCF₃ | —CH₃ |
| EAV94 aa or ab | —CH₃ | —OCF₃ | —OCH₃ |
| EAV95 aa or ab | —CH₃ | —OCF₃ | —OCH₂CH₃ |
| EAV96 aa or ab | —CH₃ | —OCF₃ | —CF₃ |
| EAV97 aa or ab | —CH₃ | —OCF₃ | —OCF₃ |
| EAV98 aa or ab | —CH₃ | —OCF₃ | iso-propyl |
| EAV99 aa or ab | —CH₃ | —OCF₃ | tert-butyl |
| EAV100 aa or ab | —CH₃ | iso-propyl | —H |
| EAV101 aa or ab | —CH₃ | iso-propyl | —Cl |
| EAV102 aa or ab | —CH₃ | iso-propyl | —Br |
| EAV103 aa or ab | —CH₃ | iso-propyl | —F |
| EAV104 aa or ab | —CH₃ | iso-propyl | —CH₃ |
| EAV105 aa or ab | —CH₃ | iso-propyl | —OCH₃ |
| EAV106 aa or ab | —CH₃ | iso-propyl | —OCH₂CH₃ |
| EAV107 aa or ab | —CH₃ | iso-propyl | —CF₃ |
| EAV108 aa or ab | —CH₃ | iso-propyl | —OCF₃ |
| EAV109 aa or ab | —CH₃ | iso-propyl | iso-propyl |
| EAV110 aa or ab | —CH₃ | iso-propyl | tert-butyl |
| EAV111 aa or ab | —CH₃ | tert-butyl | —H |
| EAV112 aa or ab | —CH₃ | tert-butyl | —Cl |
| EAV113 aa or ab | —CH₃ | tert-butyl | —Br |
| EAV114 aa or ab | —CH₃ | tert-butyl | —F |
| EAV115 aa or ab | —CH₃ | tert-butyl | —CH₃ |
| EAV116 aa or ab | —CH₃ | tert-butyl | —OCH₃ |
| EAV117 aa or ab | —CH₃ | tert-butyl | —OCH₂CH₃ |
| EAV118 aa or ab | —CH₃ | tert-butyl | —CF₃ |
| EAV119 aa or ab | —CH₃ | tert-butyl | —OCF₃ |
| EAV120 aa or ab | —CH₃ | tert-butyl | iso-propyl |
| EAV121 aa or ab | —CH₃ | tert-butyl | tert-butyl |

TABLE 28

(IIIbb)

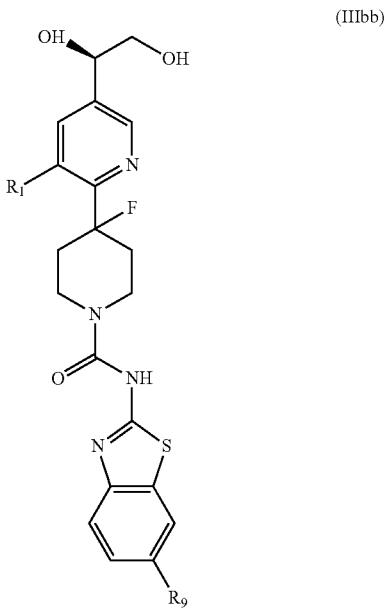

and pharmaceutically acceptable derivatives thereof, where:

| Compound | R₁ | R₉ |
|---|---|---|
| EBB | —Cl | —Cl |
| EBC | —Cl | —F |

TABLE 28-continued

| Compound | R | R |
|---|---|---|
| EBD | —Cl | —CH₃ |
| EBE | —F | —Cl |
| EBF | —F | —F |
| EBG | —F | —CH₃ |
| EBH | —CF₃ | —Cl |
| EBI | —CF₃ | —F |
| EBJ | —CF₃ | —CH₃ |

TABLE 29

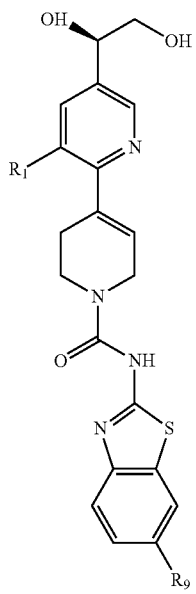

(IIIcc)

and pharmaceutically acceptable derivatives thereof, where:

| Compound | R₁ | R₉ |
|---|---|---|
| EBK | —Cl | —Cl |
| EBL | —Cl | —F |
| EBM | —Cl | —CH₃ |
| EBN | —F | —Cl |
| EBO | —F | —F |

TABLE 29-continued

| Compound | R₁ | R₉ |
|---|---|---|
| EBP | —F | —CH₃ |
| EBQ | —CF₃ | —Cl |
| EBR | —CF₃ | —F |
| EBS | —CF₃ | —CH₃ |

TABLE 30

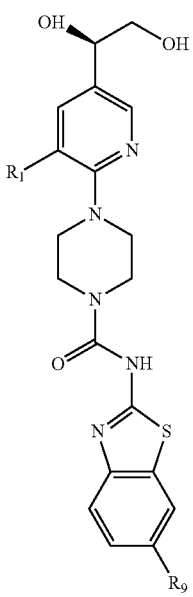

(IIIdd)

and pharmaceutically acceptable derivatives thereof, where:

| Compound | R₁ | R₉ |
|---|---|---|
| EBT | —Cl | —Cl |
| EBU | —Cl | —F |
| EBV | —Cl | —CH₃ |
| EBW | —F | —Cl |
| EBX | —F | —F |
| EBY | —F | —CH₃ |
| EBZ | —CF₃ | —Cl |

TABLE 30-continued

| | | |
|---|---|---|
| ECA | —CF₃ | —F |
| ECB | —CF₃ | —CH₃ |

TABLE 31

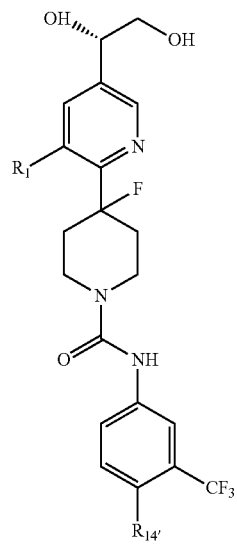

(IIIee)

and pharmaceutically acceptable derivatives thereof, where:

| Compound | $R_1$ | $R_{14'}$ |
|---|---|---|
| FAA | —Cl | —Cl |
| FAB | —Cl | —F |
| FAC | —Cl | —Br |
| FAD | —Cl | —OCH₃ |
| FAE | —Cl | —OCH₂CH₃ |
| FAF | —F | —Cl |
| FAG | —F | —F |
| FAH | —F | —Br |
| FAI | —F | —OCH₃ |
| FAJ | —F | —OCH₂CH₃ |
| FAK | —CF₃ | —Cl |

TABLE 31-continued

| | | |
|---|---|---|
| FAL | —CF₃ | —F |
| FAM | —CF₃ | —Br |
| FAN | —CF₃ | —OCH₃ |
| FAO | —CF₃ | —OCH₂CH₃ |

TABLE 32

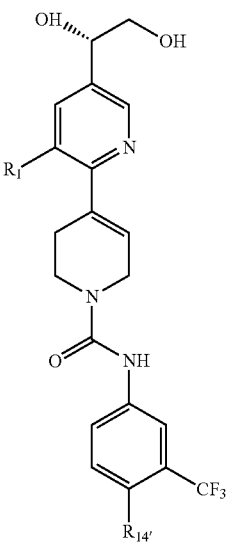

(IIIff)

and pharmaceutically acceptable derivatives thereof, where:

| Compound | $R_1$ | $R_{14'}$ |
|---|---|---|
| FAP | —Cl | —Cl |
| FAQ | —Cl | —F |
| FAR | —Cl | —Br |
| FAS | —Cl | —OCH₃ |
| FAT | —Cl | —OCH₂CH₃ |
| FAU | —F | —Cl |
| FAV | —F | —F |
| FAW | —F | —Br |
| FAX | —F | —OCH₃ |
| FAY | —F | —OCH₂CH₃ |

TABLE 32-continued

| | | |
|---|---|---|
| FAZ | —CF₃ | —Cl |
| FBA | —CF₃ | —F |
| FBB | —CF₃ | —Br |
| FBC | —CF₃ | —OCH₃ |
| FBD | —CF₃ | —OCH₂CH₃ |

TABLE 33

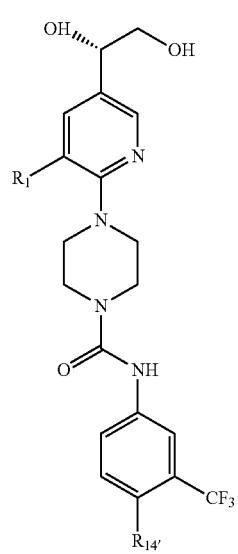

(IIIgg)

and pharmaceutically acceptable derivatives thereof, where:

| Compound | R₁ | R₁₄' |
|---|---|---|
| FBE | —Cl | —Cl |
| FBF | —Cl | —F |
| FBG | —Cl | —Br |
| FBH | —Cl | —OCH₃ |
| FBI | —Cl | —OCH₂CH₃ |
| FBJ | —F | —Cl |
| FBK | —F | —F |
| FBL | —F | —Br |
| FBM | —F | —OCH₃ |
| FBN | —F | —OCH₂CH₃ |

TABLE 33-continued

| | | |
|---|---|---|
| FBO | —CF₃ | —Cl |
| FBP | —CF₃ | —F |
| FBQ | —CF₃ | —Br |
| FBR | —CF₃ | —OCH₃ |
| FBS | —CF₃ | —OCH₂CH₃ |

TABLE 34

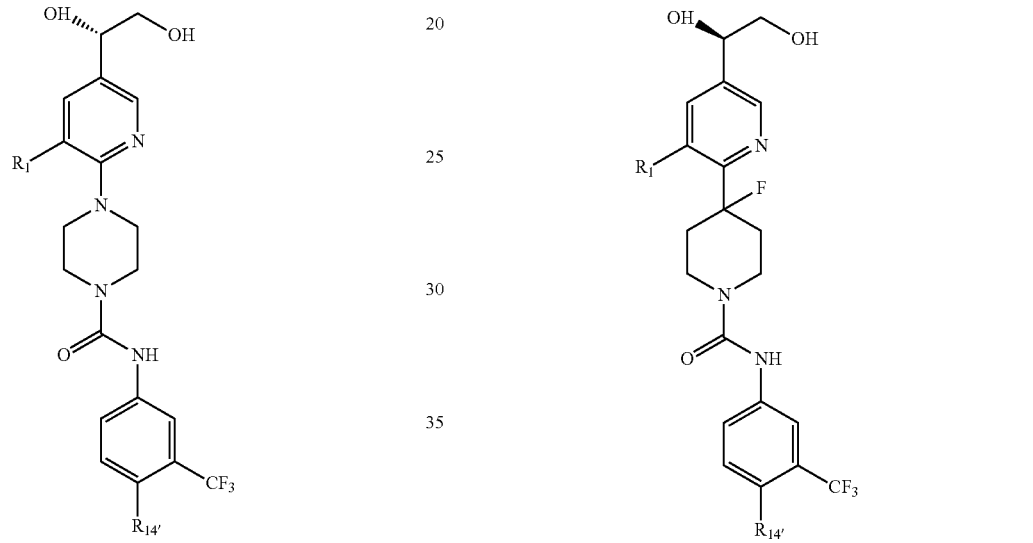

(IIIhh)

and pharmaceutically acceptable derivatives thereof, where:

| Compound | R₁ | R₁₄' |
|---|---|---|
| FBT | —Cl | —Cl |
| FBU | —Cl | —F |
| FBV | —Cl | —Br |
| FBW | —Cl | —OCH₃ |
| FBX | —Cl | —OCH₂CH₃ |
| FBY | —F | —Cl |
| FBZ | —F | —F |
| FCA | —F | —Br |
| FCB | —F | —OCH₃ |
| FCC | —F | —OCH₂CH₃ |
| FCD | —CF₃ | —Cl |
| FCE | —CF₃ | —F |
| FCF | —CF₃ | —Br |

TABLE 34-continued

| | | |
|---|---|---|
| FCG | —CF$_3$ | —OCH$_3$ |
| FCH | —CF$_3$ | —OCH$_2$CH$_3$ |

TABLE 35

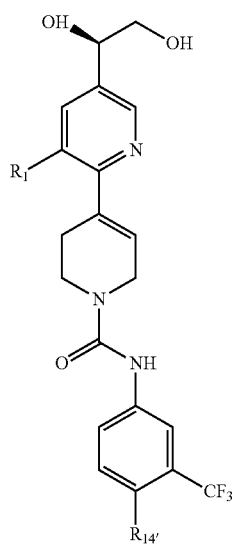

(IIIii)

and pharmaceutically acceptable derivatives thereof, where:

| Compound | R$_1$ | R$_{14'}$ |
|---|---|---|
| FCI | —Cl | —Cl |
| FCJ | —Cl | —F |
| FCK | —Cl | —Br |
| FCL | —Cl | —OCH$_3$ |
| FCM | —Cl | —OCH$_2$CH$_3$ |
| FCN | —F | —Cl |
| FCO | —F | —F |
| FCP | —F | —Br |
| FCQ | —F | —OCH$_3$ |
| FCR | —F | —OCH$_2$CH$_3$ |
| FCS | —CF$_3$ | —Cl |
| FCT | —CF$_3$ | —F |
| FCU | —CF$_3$ | —Br |
| FCV | —CF$_3$ | —OCH$_3$ |
| FCW | —CF$_3$ | —OCH$_2$CH$_3$ |

TABLE 36

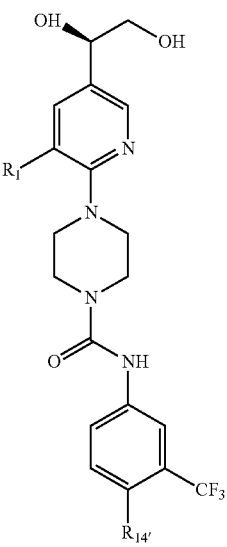

(IIIjj)

and pharmaceutically acceptable derivatives thereof, where:

| Compound | R$_1$ | R$_{14'}$ |
|---|---|---|
| FCX | —Cl | —Cl |
| FCY | —Cl | —F |
| FCZ | —Cl | —Br |
| FDA | —Cl | —OCH$_3$ |
| FDB | —Cl | —OCH$_2$CH$_3$ |
| FDC | —F | —Cl |
| FDD | —F | —F |
| FDE | —F | —Br |
| FDF | —F | —OCH$_3$ |
| FDG | —F | —OCH$_2$CH$_3$ |
| FDH | —CF$_3$ | —Cl |
| FDI | —CF$_3$ | —F |
| FDJ | —CF$_3$ | —Br |
| FDK | —CF$_3$ | —OCH$_3$ |
| FDL | —CF$_3$ | —OCH$_2$CH$_3$ |

5.5 Definitions

As used herein, the terms used above having following meaning:

"—(C$_1$-C$_{10}$)alkyl" means a straight chain or branched non-cyclic hydrocarbon having from 1 to 10 carbon atoms. Representative straight chain —(C$_1$-C$_{10}$)alkyls include -methyl, -ethyl, -n-propyl, -n-butyl, -n-pentyl, -n-hexyl, -n-heptyl, -n-octyl, -n-nonyl, and -n-decyl. Representative branched —(C$_1$-C$_{10}$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_1$-C$_6$)alkyl" means a straight chain or branched non-cyclic hydrocarbon having from 1 to 6 carbon atoms. Representative straight chain —(C$_1$-C$_6$)alkyls include -methyl, -ethyl, -n-propyl, -n-butyl, -n-pentyl, and -n-hexyl.

Representative branched —($C_1$-$C_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—($C_1$-$C_6$)haloalkyl" means a straight chain or branched non-cyclic hydrocarbon having from 1 to 6 carbon atoms as defined above for —($C_1$-$C_6$)alkyl that is substituted with 1, 2 or 3 independently selected halo groups.

"—($C_1$-$C_6$)hydroxyalkyl" means a straight chain or branched non-cyclic hydrocarbon having from 1 to 6 carbon atoms as defined above for —($C_1$-$C_6$)alkyl that is substituted with 1, 2 or 3 hydroxyl groups.

"—($C_1$-$C_4$)alkyl" means a straight chain or branched non-cyclic hydrocarbon having from 1 to 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_2$-$C_{10}$)alkenyl" means a straight chain or branched non-cyclic hydrocarbon having from 2 to 10 carbon atoms and including at least one carbon-carbon double bond. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—($C_2$-$C_6$)alkenyl" means a straight chain or branched non-cyclic hydrocarbon having from 2 to 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—($C_2$-$C_6$)haloalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 independently selected halo groups.

"—($C_2$-$C_6$)hydroxyalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 hydroxyl groups.

"—($C_2$-$C_{10}$)alkynyl" means a straight chain or branched non-cyclic hydrocarbon having from 2 to 10 carbon atoms and including at least one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—($C_2$-$C_6$)haloalkynyl" means a straight chain or branched non-cyclic hydrocarbon having from 2 to 6 carbon atoms and including at least one carbon-carbon triple bond that is substituted with 1, 2 or 3 independently selected halo groups.

"—($C_2$-$C_6$)hydroxyalkynyl" means a straight chain or branched non-cyclic hydrocarbon having from 2 to 6 carbon atoms and including at least one carbon-carbon triple bond that is substituted with 1, 2 or 3 hydroxyl groups.

"—($C_1$-$C_6$)alkoxy" means a straight chain or branched non cyclic hydrocarbon having one or more ether groups and from 1 to 6 carbon atoms. Representative straight chain and branched —($C_1$-$C_6$)alkoxys include methoxy, ethoxy, propoxy, butoxy, pentoxy, hexoxy, methoxymethyl, 2-methoxyethyl, 5-methoxypentyl, 3-ethoxybutyl, and the like.

"—($C_1$-$C_6$)alkoxy($C_2$-$C_6$)alkyl" means a straight chain or branched non cyclic hydrocarbon having one or more ether groups and from 1 to 6 carbon atoms as defined above for —($C_1$-$C_6$)alkoxy group that is substituted with a —($C_2$-$C_6$) alkyl group.

"—($C_1$-$C_6$)alkoxy($C_2$-$C_6$)alkenyl" means a straight chain or branched non cyclic hydrocarbon having one or more ether groups and from 1 to 6 carbon atoms as defined above for —($C_1$-$C_6$)alkoxy group that is substituted with a —($C_2$-$C_6$)alkenyl group.

"—($C_1$-$C_6$)alkoxy($C_2$-$C_6$)alkynyl" means a straight chain or branched non cyclic hydrocarbon having one or more ether groups and from 1 to 6 carbon atoms that is substituted with a —($C_2$-$C_6$)alkynyl group.

"—($C_1$-$C_6$)alkoxy($C_3$-$C_8$)cycloalkyl" means a straight chain or branched non cyclic hydrocarbon having one or more ether groups and from 1 to 6 carbon atoms as defined above for —($C_1$-$C_6$)alkyl group that is substituted with a —($C_3$-$C_8$)cycloalkyl group "—($C_3$-$C_{10}$)cycloalkyl" means a saturated cyclic hydrocarbon having from 3 to 10 carbon atoms. Representative ($C_3$-$C_{10}$)cycloalkyls are -cyclopropyl, -cyclobutyl, -cyclopentyl, -cyclohexyl, -cycloheptyl, -cyclooctyl, -cyclononyl, and -cyclodecyl.

"—($C_3$-$C_8$)cycloalkyl" means a saturated cyclic hydrocarbon having from 3 to 8 carbon atoms. Representative —($C_3$-$C_8$)cycloalkyls include -cyclopropyl, -cyclobutyl, -cyclopentyl, -cyclohexyl, -cycloheptyl, and -cyclooctyl.

"—($C_3$-$C_8$)cycloalkenyl" means a cyclic non-aromatic hydrocarbon having at least one carbon-carbon double bond in the cyclic system and from 5 to 8 carbon atoms. Representative —($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized;

oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, CHBrCl, CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, and —Cl$_3$.

"-Halogen" or "—Halo" means —F, —Cl, —Br, or —I.

"(C$_2$-C$_6$)bridge" as used herein means a hydrocarbon chain containing 2 to 6 carbon atoms joining two atoms of the piperidine, 1,2,3,6-tetrahydropyridine or piperazine ring of the compounds of formula I, IA, II and/or III to form a fused bicyclic ring system. The positions of the piperidine, 1,2,3,6-tetrahydropyridine or piperazine ring are denoted as follows:

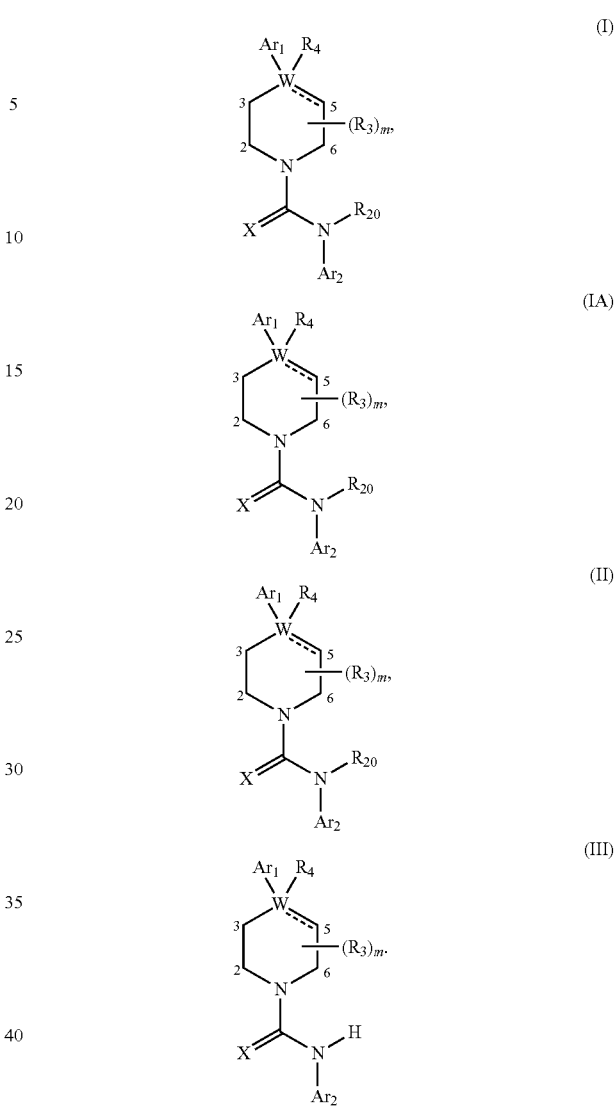

For example, compounds of the invention can comprise a (C$_2$-C$_6$)bridge joining positions 2 and 6 of the piperidine, 1,2,3,6-tetrahydropyridine or piperazine ring (two R$_3$ groups can together form a (C$_2$-C$_6$)bridge). Examples of compounds where two R$_3$ groups can together form a (C$_2$-C$_6$) bridge include compounds comprising the following ring systems: 8-aza-bicyclo[3.2.1]octane; 8-azabicyclo[3.2.1]oct-3-ene; 3,8-diazabicyclo[3.2.1]octane; 8-azabicyclo[3.2.1]oct-6-ene; 8-azabicyclo[3.2.1]octa-3,6-diene; 3,8-diazabicyclo[3.2.1]oct-6-ene; 9-aza-bicyclo[3.3.1]nonane; 9-azabicyclo[3.3.1]non-3-ene; 9-azabicyclo[3.3.1]non-6-ene; 9-azabicyclo[3.3.1]nona-3,6-diene; 9-azabicyclo[3.3.1]nona-3,7-diene; 3,9-diazabicyclo[3.3.1]nonane; 3,9-diazabicyclo[3.3.1]non-6-ene; 3,9-diazabicyclo[3.3.1]non-7-ene; 10-aza-bicyclo[4.3.1]decane; 10-azabicyclo[4.3.1]dec-8-ene; 8,10-diazabicyclo[4.3.1]decane; 8,10-diazabicyclo[4.3.1]dec-3-ene; 8,10-diazabicyclo[4.3.1]dec-4-ene; 8-azabicyclo[4.3.1]dec-4-ene; 8-azabicyclo[4.3.1]dec-3-ene; 8-azabicyclo[4.3.1]deca-2,6(10)-diene; 8-azabicyclo[4.3.1]deca-3,6(10)-diene; 8-azabicyclo[4.3.1]deca-4,6(10)-diene; 11-aza-bicyclo[5.3.1]undecane; 11-azabicyclo[5.3.1]undec-8-ene; 9,11-diazabicyclo[5.3.1]undecane; 12-azabicyclo[6.3.1]dodecane; 12-azabicyclo[6.3.1]dodec-9-ene; and 10,12-diazabicyclo[6.3.1]dodecane.

In connection with the Ar$_2$ group

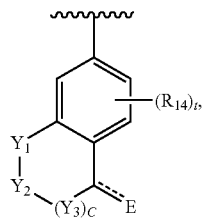

when E is —NH(C$_1$-C$_6$)alkyl it is to be understood that the dashed line in the above Ar$_2$ group is absent, i.e., the Ar$_2$ group is

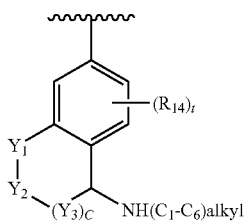

where Y$_1$, Y$_2$, Y$_3$, R$_{14}$, c and t are as defined above for compounds of formula I. When E is =O, =S, =C(C$_1$-C$_5$)alkyl, =C(C$_1$-C$_5$)alkenyl, or =N—OR$_{20}$, it is to be understood that the dashed line in the above Ar$_2$ group is present, i.e., the Ar$_2$ group is

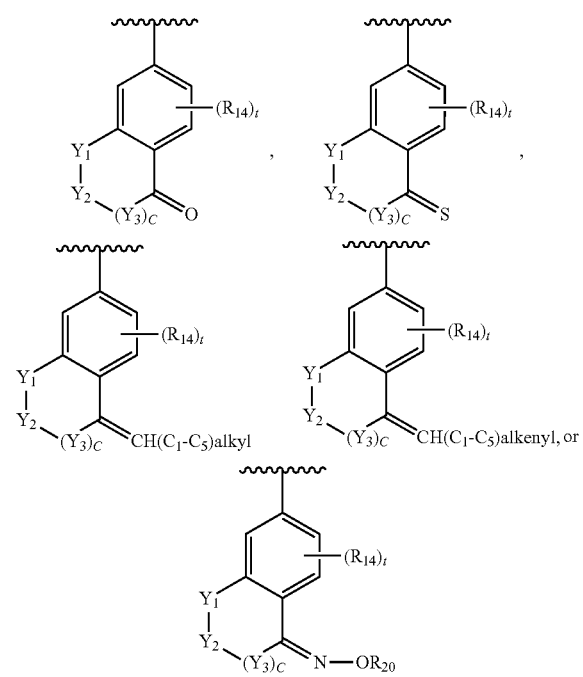

respectively, where Y$_1$, Y$_2$, Y$_3$, R$_{14}$, R$_{20}$, c and t are as defined above for compounds of formula I.

The phrase "pyridyl group" means

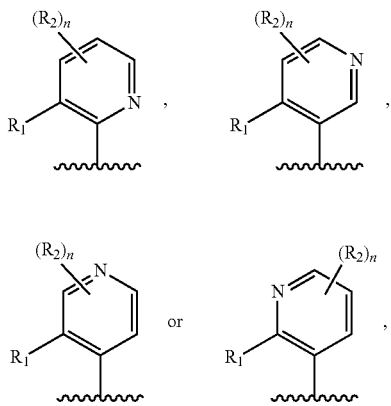

where R$_1$, R$_2$, and n are as defined above for compounds of formula I, and where the numbers designate the position of each atom in the ring.

The phrase "pyrazinyl group" means

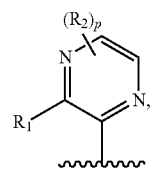

where R$_1$, R$_2$, and p are as defined above for compounds of formula I.

The phrase "pyrimidinyl group" means

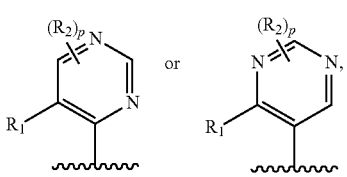

where R$_1$, R$_2$, and p are as defined above for compounds of formula I.

The phrase "pyridazinyl group" means

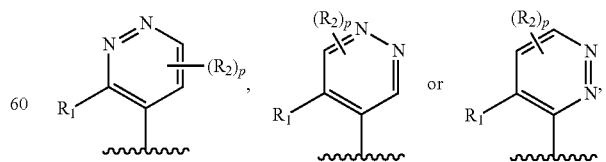

where R$_1$, R$_2$, and p are as defined above for compounds of formula I.

The phrase "benzoimidazolyl group" means

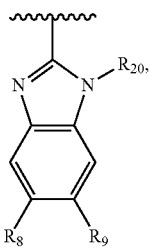

where $R_8$, $R_9$, and $R_{20}$ are as defined above for compounds of formula I.

The phrase "benzothiazolyl group" means

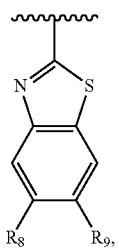

where $R_8$ and $R_9$ are as defined above for compounds of formula I.

The phrase "benzooxazolyl group" means

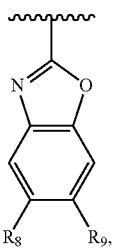

where $R_8$ and $R_9$ are as defined above for compounds of formula I.

The phrase phenyl group means

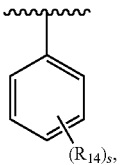

where $R_{14}$ and s are as defined for compounds of formula I.

The phrase "tetrahydropyridyl ring" means

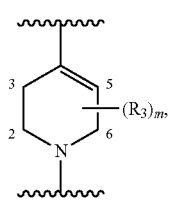

where the numbers designate the position of each atom of the tetrahydropyridyl ring.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative," as used herein, includes any pharmaceutically acceptable salt, solvate, radiolabeled, stereoisomer, enantiomer, diastereomer, other stereoisomeric form, racemic mixture, geometric isomer, and/or tautomer, e.g., of a compound of formula I of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a compound of formula I of the invention. In another embodiment, the pharmaceutically acceptable derivative is a pharmaceutically acceptable salt, e.g., of a compound of formula I of the invention.

The phrase "pharmaceutically acceptable salt," as used herein, is any pharmaceutically acceptable salt that can be prepared from a compound of formula I including a salt formed from an acid and a basic functional group, such as a nitrogen group, of a compound of formula I. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of formula I having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl, N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxytert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a compound of formula I can be prepared by reaction of the compounds with the appropriate acid via a variety of known methods.

Compounds of formula I encompass all solvates of compounds of formula I. "Solvates" are known in the art and are considered to be a combination, physical association and/or solvation of a compound of formula I with a solvent molecule, e.g., a disolvate, monosolvate or hemisolvate when the ratio of the solvent molecule to the molecule of the compound of formula I is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate," as used herein, encompasses both solution-phase and isolatable solvates. A compound of formula I of the invention may be present as a solvated form with a pharmaceutically acceptable solvent, such as water, methanol, ethanol, and the like, and it is intended that the invention include both solvated and unsolvated compound of formula I forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1), article 12 (2004), and A. L. Bingham et al., *Chem. Commun.*, 603-604 (2001). A typical, non-limiting, process involves dissolving the compound of formula I in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the compounds of the invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a compound of formula I which is readily convertible in vivo, e.g., by being metabolized, into the required compound of formula I. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a compound of formula I can be replaced by an isotope of the hydrogen, carbon or other atoms. Compounds of formula I include all radiolabeled forms of compounds of formula I. Such a "radiolabeled," "radiolabeled form", and the like of a compound of formula I, each of which is encompassed by the invention, is useful as a research and/or diagnostic tool in metabolism pharmacokinetic studies and in binding assays. Examples of isotopes that can be incorporated into a compound of formula I of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Radiolabeled compounds of the invention can be prepared by methods known in the art. For example, tritiated compounds of formula I can be prepared by introducing tritium into the particular compound of Formula I, for example, by catalytic dehalogenation with tritium. This method may include reacting a suitably halogen-substituted precursor of a compound of Formula I with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

A compound of formula I can contain one or more asymmetric centers and may thus give rise to enantiomers, diastereomers, and other stereoisomeric forms. Compounds of formula I encompass all such possible forms as well as their racemic and resolved forms or any mixture thereof. When a compound of formula I contains an olefinic double bond or other center of geometric asymmetry, and unless specified otherwise, it is intended to include all "geometric isomers," e.g., both E and Z geometric isomers. All "tautomers," e.g., ketone-enol, amide-imidic acid, lactam-lactim, enamine-imine, amine-imine, and enamine-enimine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a compound of formula I can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%.$$

The phrase "effective amount," when used in connection with a compound of formula I means an amount effective for: (a) treating or preventing a Condition; or (b) inhibiting TRPV1 function in a cell.

The phrase "effective amount," when used in connection with the another therapeutic agent means an amount for providing the therapeutic effect of the therapeutic agent.

The phrase "therapeutic index," describes the gap between the dose that is effective, and the dose that induces adverse effects.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The term "MeOH" means methanol, i.e., methyl alcohol.

The term "EtOH" means ethanol, i.e., ethyl alcohol.

The term "t-BuOH" means tert-butyl alcohol, i.e., 2-methylpropan-2-ol.

The term "THF" means tetrahydrofuran.

The term "DMF" means N,N-dimethylformamide.

The term "DCM" means methylene chloride, i.e., dichloromethane.

The term "DCE" means dichloroethane.

The term "DME" means 1,2-dimethoxyethane, i.e., ethylene glycol dimethyl ether.

The term "EtOAc" means ethyl acetate.

The term "NH$_4$OH" means ammonium hydroxide.

The term "TEA" means triethylamine.

The term "MeCN" means acetonitrile.

The term "NaH" means sodium hydride.

The term "AcOH" means acetic acid.

The term "DIEA" means N,N-diisopropylethylamine or N-ethyldiisopropylamine, i.e., N-ethyl-N-isopropylpropan-2-amine.

The term "DMSO" means dimethylsulfoxide, i.e., methylsulfinylmethane.

The term "DAST" means (diethylamino) sulfur trifluoride.

The term "LiHMDS" means lithium hexamethyldisilazide.

The term "BuLi" means butyl lithium.

The term "DPPP" means 1,3-bis(diphenylphosphino)propane.

The term "BOC" means tert-butyloxycarbonyl:

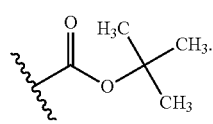

The term "TBS" means tert-butyldimethylsilyl:

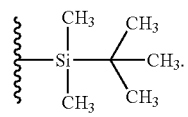

The term "TsOH" means p-toluenesulfonic acid or toluene-4-sulfonic acid.

The term "TMSBr" means trimethylsilyl bromide or (CH$_3$)$_3$SiBr.

The term "TMSCl" means trimethylsilyl chloride or (CH$_3$)$_3$SiCl.

The term "IBD" means inflammatory-bowel disease.

The term "IBS" means irritable-bowel syndrome.

The term "ALS" means amyotrophic lateral sclerosis.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

5.6 Methods for Making Compounds of Formula I

The compounds of formula I can be made using conventional organic synthesis or by the illustrative methods shown in the schemes below.

5.6.1 Methods for Making Compounds of Formula I where W is C and the Dashed Line is Absent The compounds of formula I where W is C and the dashed line is absent, i.e., "Piperidine Compounds," can be made using conventional organic synthesis or by the illustrative methods shown in the schemes below.

5.6.1.1 Methods for Making the Piperidine Compounds where X is O and R$_4$ is —OH or —F The compounds of formula I where X is O and R$_4$ is —OH can be obtained by the illustrative method shown below in scheme 1.1:

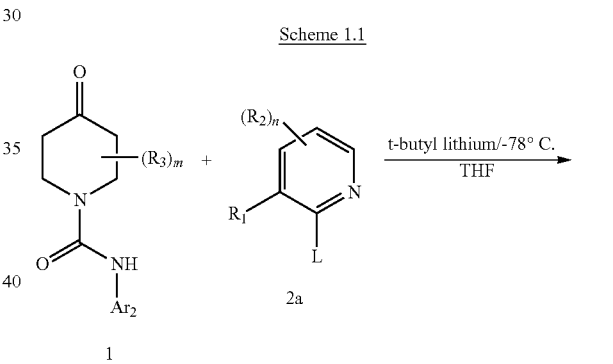

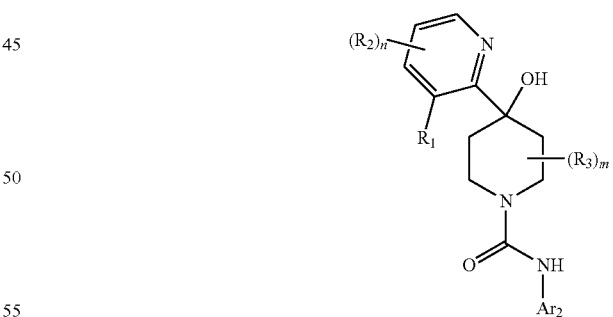

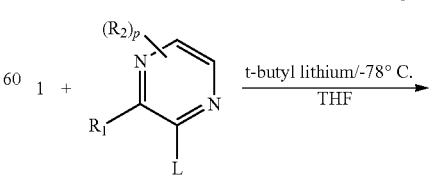

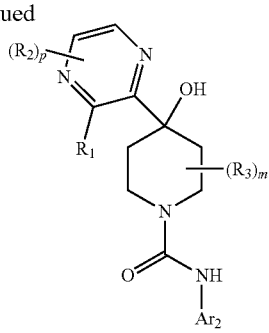

Piperidine Compound 3b

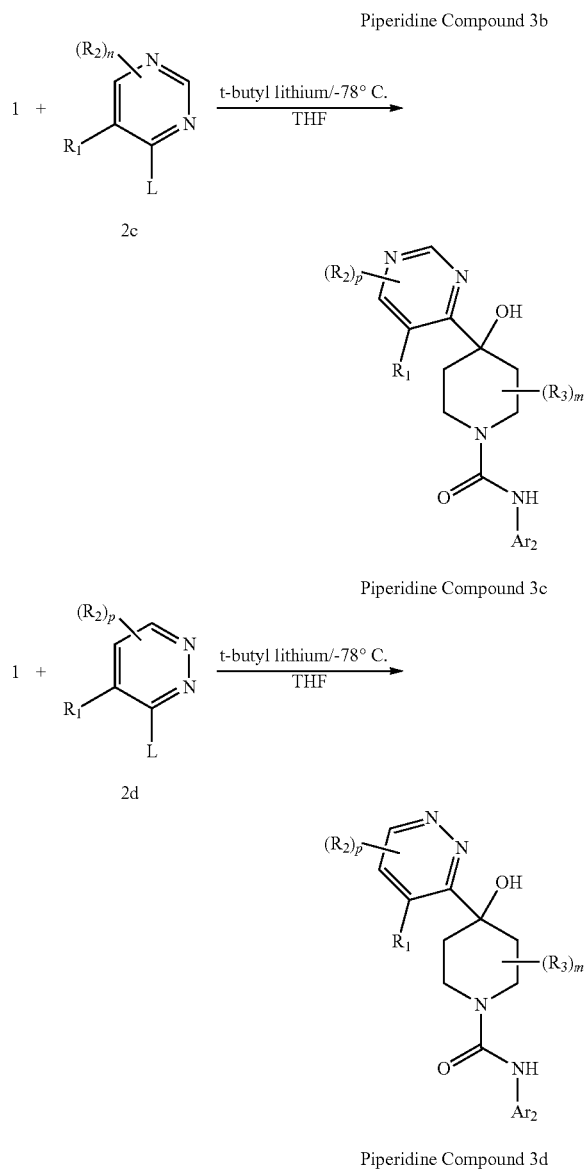

Piperidine Compound 3c

Piperidine Compound 3d where $Ar_2$, $R_1$, $R_2$, $R_3$, n, m, and p are as defined for compounds of formula I and L is a halogen.

To a solution of 2a-d in the presence of tert-butyl lithium (1.7M in heptane, 6.45 mL, 11.12 mmol) in THF (20 mL) at −78° C. is added dropwise compound 1 in anhydrous THF (10 mL). The reaction mixture is stirred at −78° C. for about 3 h and is quenched with aqueous $NH_4Cl$ at about 0° C., and then the organic and aqueous layers are separated. The aqueous layer is extracted with THF, the organic portions are combined, and dried ($Na_2SO_4$). The resulting solution is concentrated under reduced pressure to provide a residue. The residue is chromatographed using silica gel column chromatography that is eluted with ethyl acetate/hexane (gradient elution from 30:70 to 70:30) to provide a Piperidine Compound where X is O and $R_4$ is —OH (3a-d).

The compounds of formula 2a-d are commercially available or can be prepared by methods known in the art.

Compound 1 can be obtained by reacting 4 with an isocyanate as shown below in scheme 1.2:

Scheme 1.2

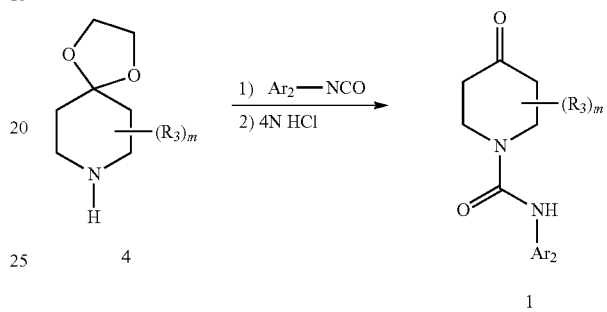

where $R_3$, and m are as defined above and R is $Ar_2$.

Compound 4 (20 mmol) in chloroform is added to a solution of an isocyanate of formula R—NCO in chloroform (30 mL) at about 25° C. The resultant reaction mixture is stirred for about 3 h at about 25° C. then concentrated under reduced pressure to provide a residue. The residue is suspended in THF (50 mL) and 4N HCl (50 mL) is added to the resulting solution. The reaction mixture allowed to stir for about 12 h. The reaction mixture is then poured into water (200 mL), and the pH is adjusted to 10 or greater with aqueous potassium carbonate base. The resulting solution is extracted with ethyl acetate and the ethyl acetate layers are combined, dried ($MgSO_4$) and concentrated under reduced pressure to provide a residue that can be chromatographed using flash chromatography on a silica gel column eluted with ethyl acetate/hexane (gradient elution from 30:70 to 70:30) to provide compound 1.

Isocyanates of formula $Ar_2$—NCO are commercially available or are can be prepared by reacting an amine $Ar_2NH_2$ with phosgene according to known methods (See, e.g., H. Eckert and B. Foster, *Angew. Chem. Int. Ed. Engl.*, 26, 894 (1987); H. Eckert, Ger. Offen. DE 3 440 141; *Chem. Abstr.* 106, 4294d (1987); and L. Contarca et al., *Synthesis*, 553-576 (1996). For example, an amine $Ar_2NH_2$ can be reacted with triphosgene as shown below.

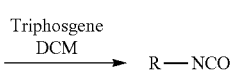

Typically a solution of triphosgene (about 0.3 equivalents or 0.3 eq.) in DCM (about 0.3M) is slowly added to a stirred solution of the amine (about 1.0 eq.) in DCM (about 0.3M) at about 25° C. The reaction mixture is then stirred at about 25° C. for about 10 min. and the temperature is raised to about 70° C. After stirring at 70° C. for 3 h., the reaction mixture is cooled to 25° C., filtered, and the filtrate is concentrated to provide the isocyanate.

Cyclic acetals of formula 4 are commercially available or can be prepared by methods known in the art.

The Piperidine Compounds where X is O and $R_4$ is —OH can also be obtained by the illustrative method shown below in schemes 1.3 and 1.4:

Scheme 1.3

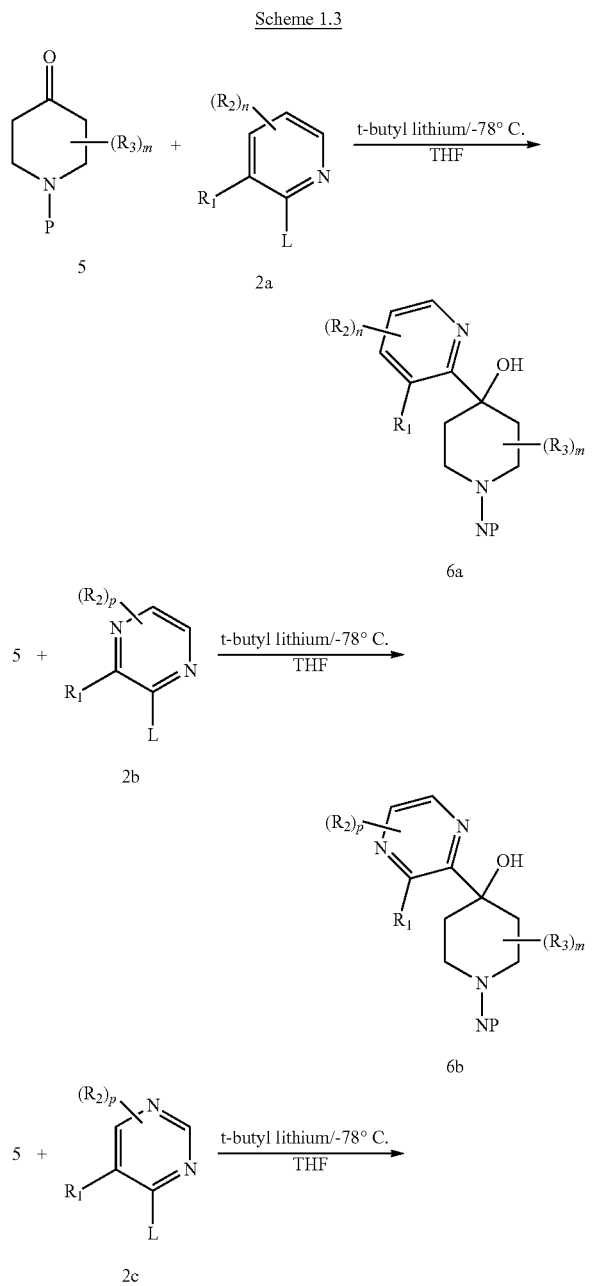

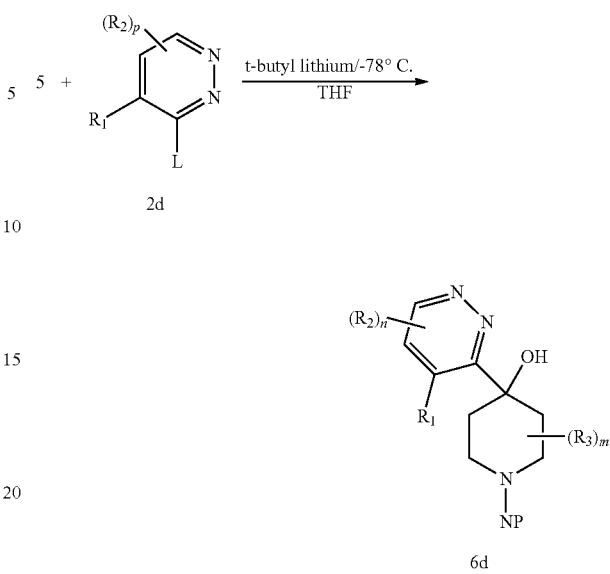

where $R_1$, $R_2$, $R_3$, n, m, and p are as defined above, L is a halogen, and NP is a nitrogen protecting group (see, for example, T. W. Greene et al., *Protective Groups in Organic Synthesis* 494-653 (3d ed. 1999).

To a solution of t-BuLi (1.7M in heptane, 18.4 mL, 31.3 mmol) or n-BuLi (1.6M in heptane, 19.5 mL, 31.3 mmol) in ether (30 mL) is added dropwise a solution of a compound of formula 2a-d (31.3 mmol) in ether (20 mL) at −78° C. under a nitrogen atmosphere. The resulting solution is stirred at −78° C. for about 1 hour. To the resulting solution is added dropwise a compound of formula 5 (25.0 mmol) dissolved in ether (20 mL) at −78° C. and the resulting mixture is allowed to stir at about −50° C. for 3 h. The reaction mixture is then quenched with aqueous $NH_4Cl$ at 0° C. and the reaction mixture is extracted with ether. The organic portions are combined, dried ($Na_2SO_4$), and concentrated under reduced pressure to provide a residue that can be chromatographed using flash chromatography on a silica gel column eluted with ethyl acetate/hexane (gradient elution 30/70 to 70/30) to provide a compound of formula 6a-d. The nitrogen protecting group is then removed to provide a compound of formula 7a-d, respectively. The compound of formula 7a-d is then reacted with an isocyanate of formula R—NCO to provide the compound of formula 3a-d, as shown below in scheme 1.4:

Scheme 1.4

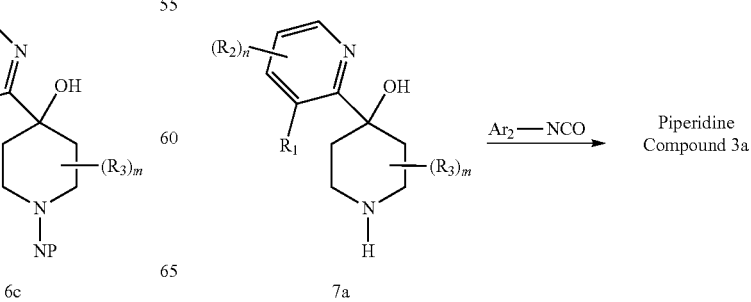

-continued

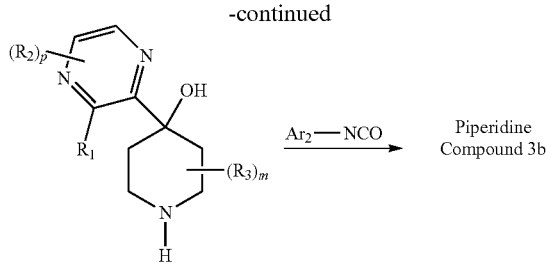

7b

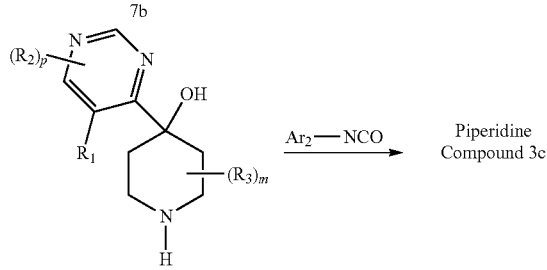

7c

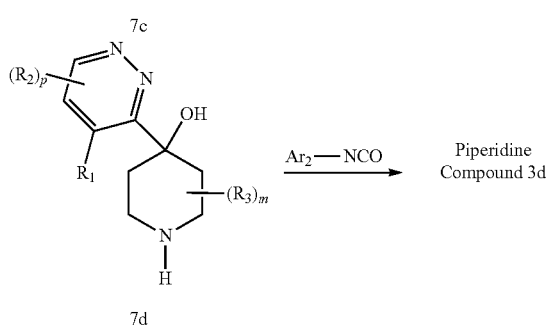

7d where $Ar_2$, $R_1$, $R_2$, $R_3$, n, m, and p are as defined above.

To a solution of a compound of formula 7a-d (1 mmol) in DCM (1 mL) is added dropwise a solution of isocyanate $Ar_2$—NCO (1 mmol) in DCM (1 mL) at the about 25° C. The resultant mixture is allowed to stir at 25° C. for 3 h and concentrated under reduced pressure to provide a residue that can be chromatographed using a silica gel column eluted with ethyl acetate/hexane (gradient elution 10/90 to 70/30) to provide a compound of formula 3a-d.

A compound of formula 5 is commercially available or can be prepared by protecting the nitrogen atom of a compound of formula 8, shown below:

8

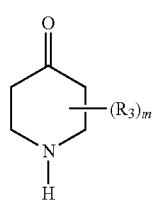

Compounds of formula 8 are commercially available or can be prepared by methods known in the art.

Any nitrogen protecting group known in the art can be used to protect the nitrogen atom in the compound of formula 8. Suitable protecting groups are described in T. W. Greene et al., *Protective Groups in Organic Synthesis*, 494-653 (3d ed. 1999). Isocyanates of formula $Ar_2$—NCO are commercially available or can be prepared as described above.

5.6.1.2 Methods for Making Piperidine Compounds where X is S and $R_4$ is —OH

The Piperidine Compound where X is S and $R_4$ is —OH can be obtained by a method analogous to that described above in Scheme 1.1 to provide the Piperidine Compounds where X is O and $R_4$ is —OH (3a-d) except that a compound of formula 9, shown below,

9

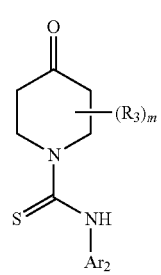

where $R_3$ and m are as defined above, is used in place of compound 1.

The compound of formula 9 can be obtained by a method analogous to that described above in Scheme 1.2 to provide 1 except that an isothiocyanate of formula $Ar_2$—NCS is used in place of the isocyanate $Ar_2$—NCO.

Isothiocyanates are commercially available or can be prepared by reacting an amine of formula $Ar_2NH_2$ with thiophosgene as shown in the scheme below (See, e.g., *Tett. Lett.*, 41(37), 7207-7209 (2000); *Org. Prep. Proced., Int.*, 23(6), 729-734 (1991); *J. Heterocycle Chem.*, 28(4), 1091-1097 (1991); *J. Fluorine Chem.*, 41(3), 303-310 (1988); and *Tett. Lett.*, 42(32), 5414-5416 (2001).

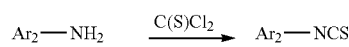

Alternatively, isothiocyanates of formula $Ar_2$—NCS can be prepared by reacting an amine of formula $Ar_2NH_2$ with carbon disulfide in the presence of triethylamine (TEA) in THF, followed by reaction with hydrogen peroxide and hydrochloric acid in water as shown in the scheme below (See, e.g., *J. Org. Chem.*, 62(13), 4539-4540 (1997)).

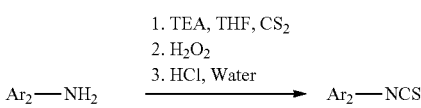

The Piperidine Compound where X is S and $R_4$ is —OH can be obtained by a method analogous to that described above in Schemes 1.3 and 1.4 to provide the Piperidine Compounds where X is O and $R_4$ is —OH (3a-d) except that an isothiocyanate of formula $Ar_2$—NCS is used in place of the isocyanate of formula $Ar_2$—NCO.

5.6.1.3 Methods for Making Piperidine Compounds where X is N—CN and $R_4$ is —OH The Piperidine Compound where X is N—CN and $R_4$ is —OH can be obtained as shown below in scheme 1.5:

Scheme 1.5

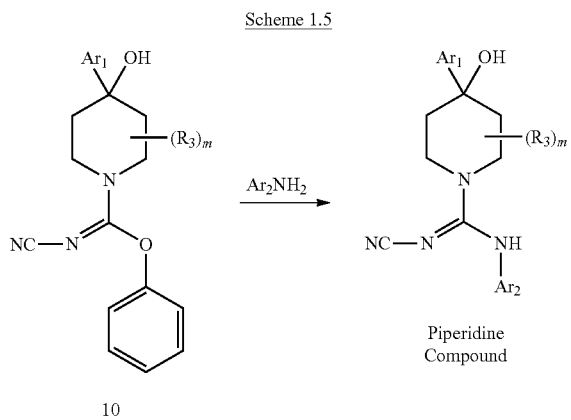

where $Ar_1$, $Ar_2$, $R_3$ and m are as defined above.

A compound of formula 10 is reacted with an amine of formula $Ar_2$—$NH_2$ in an aprotic organic solvent such as diethyl ether, di-n-propyl ether, THF, DCM, or toluene at a temperature of from about 25° C. to about the reflux temperature of the solvent for a period of from about 0.5 h to about 24 h to provide the Piperidine Compound where X is N—CN and $R_4$ is —OH. In one embodiment, the aprotic organic solvent is di-n-propyl ether. In another embodiment, a reaction mixture of di-n-propyl ether, a compound of formula 10 and the amine of formula $Ar_2$—$NH_2$ is heated at a temperature of about 70° to about 80° C. In another embodiment, the reaction mixture of di-n-propyl ether, a compound of formula 10 and the amine of formula $Ar_2$—$NH_2$ is heated at a temperature of about 75° C. for about 12 h.

The compound of formula 10 can be obtained as shown below in scheme 1.6:

Scheme 1.6

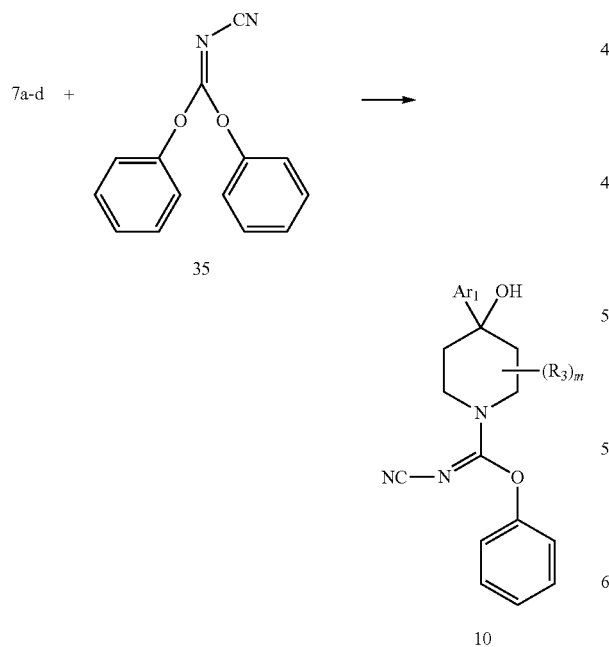

where $Ar_1$ is defined above for the Piperidine Compounds.

A compound of formula 7a-d is reacted with diphenyl cyanocarbonimidate 35 (commercially available from Sigma-Aldrich, St. Louis, Mo.) in an aprotic solvent such as diethyl ether, di-n-propyl ether, THF, DCM, or toluene to provide the compound of formula 10. In one embodiment, the aprotic solvent is DCM and the reaction mixture of the compound of formula 7a-d and diphenyl cyanocarbonimidate 35 is allowed to react at about 25° C. In another embodiment, the aprotic solvent is toluene and the reaction mixture of the compound of formula 7a-d and diphenyl cyanocarbonimidate 35 is allowed to react at about 110° C. The compound of formula 7a-d and diphenyl cyanocarbonimidate 35 is typically allowed to react for a period of about 0.5 h to about 24 h. Typically the compound of formula 10 is used without further purification.

The compounds of formula 7a-d can be obtained as described above in section 5.6.1.1.

5.6.1.4 Methods for Making Piperidine Compounds where X is N—OH and $R_4$ is —OH The Piperidine Compound where X is N—OH and $R_4$ is —OH can be prepared by a method analogous to that described above in Scheme 1.1 to provide the Piperidine Compounds where X is O and $R_4$ is —OH (3a-d) except that a compound of formula 11, shown below,

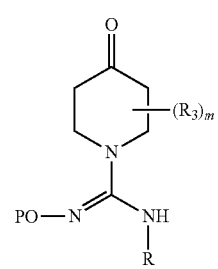

11 where $R_3$ and m are as defined above, R is $Ar_2$, and P is an oxygen/hydroxyl protecting group, is used in place of compound 1 followed by removal of the oxygen/hydroxyl protecting group.

The compound of formula 11 can be obtained as shown below in scheme 1.7:

Scheme 1.7

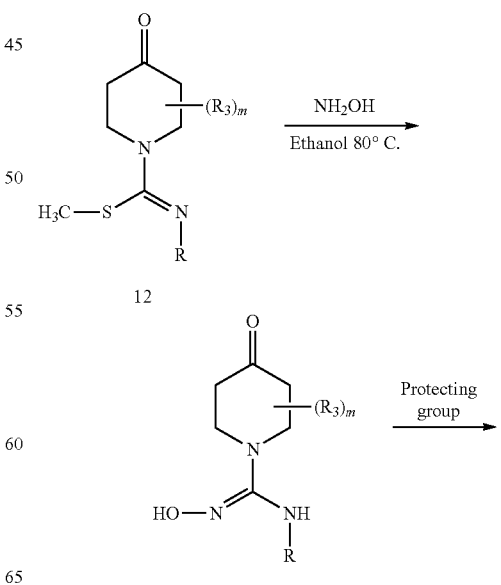

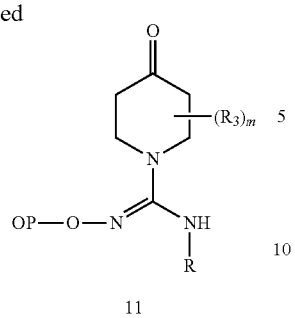

11 where $R_3$ and m are as defined above, R is $Ar_2$, and OP is an oxygen/hydroxyl protecting group.

A compound of formula 12 (about 0.3 mmol) is reacted with hydroxylamine (50 weight percent in water, about 5.8 mmol) in about 1.5 mL of ethanol with stirring at a temperature of about 80° C. for about 2 h. The mixture is then concentrated under reduced pressure to provide a compound of formula 13. The hydroxyl group of the compound of formula 13 is then protected using an oxygen/hydroxyl protecting group to provide the compound of formula 11. An oxygen/hydroxyl protecting group known in the art can be used to protect the oxygen atom in the compound of formula 13. Suitable oxygen/hydroxyl protecting groups are disclosed in T. W. Greene et al., *Protective Groups in Organic Synthesis* 17-200 (3d ed. 1999). In one embodiment, the compound of formula 11 is further treated using column chromatography or recrystallized.

The compound of formula 12 can be obtained as shown below in scheme 1.8:

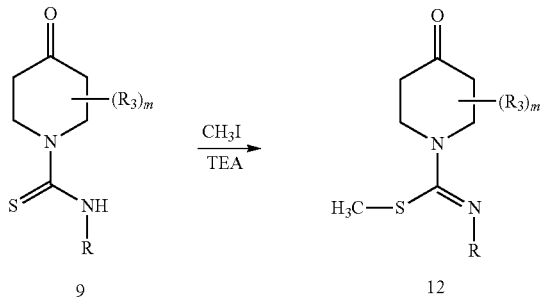

Scheme 1.8 where $R_3$ and m are as defined above and R is $Ar_2$.

A solution of a compound of formula 9 (about 0.6 mmol), obtained as descried above, in DCM is reacted with iodomethane (about 0.9 mmol) in about 3 mL of tetrahydrofuran with stirring at about 25° C. for about 12 h. Excess iodomethane is removed from the mixture under reduced pressure. A solution of triethylamine (about 1.74 mmol) in about 2.5 mL of ethyl acetate is then added to the mixture and the mixture is allowed to stir for about 2 h. The mixture is then concentrated under reduced pressure to provide the compound of formula 12 that can then be further treated if desired. In one embodiment, the compound of formula 12 is further treated using column chromatography or recrystallization.

5.6.1.5 Methods for Making Piperidine Compounds where X is N—$OR_{10}$ and $R_4$ is —OH The Piperidine Compound where X is N—$OR_{10}$ and $R_4$ is —OH can be obtained by a method analogous to that described above in Scheme 1.1 to provide the Piperidine Compounds where X is O and $R_4$ is —OH (3a-d) except that a compound of formula 14, shown below,

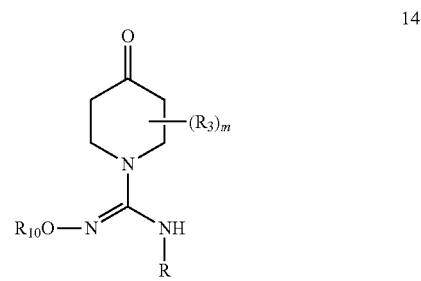

14 where $R_3$, $R_{10}$ and m are as defined above and R is $Ar_2$ is used in place of compound 1.

The compound of formula 14 can be prepared by reacting the compound of formula 13, obtained as described above in Scheme 1.7, with L-($C_1$-$C_4$)alkyl, where L is —I, —Br, —Cl, or —F in the presence of sodium hydride in DMF at about 25° C. In one embodiment, L is —I or —Br.

5.6.1.6 Methods for Making Piperidine Compounds where $R_4$ is a Group Other than —OH The Piperidine Compounds where $R_4$ is -halo, —$OCF_3$, —($C_1$-$C_6$)alkyl, —$CH_2OH$, —$CH_2Cl$, —$CH_2Br$, —$CH_2I$, —$CH_2F$, —CH(halo)$_2$, —$CF_3$, —$OR_{10}$, —$SR_{10}$, —COOH, —$COOR_{10}$, —C(O)$R_{10}$, —C(O)H, —OC(O)$R_{10}$, —OC(O)NH$R_{10}$, —NHC(O)$R_{13}$, —$SO_2R_{10}$, —CON($R_{13}$)$_2$ or —$NO_2$ can be obtained from the Piperidine Compounds where $R_4$ is —OH.

The Piperidine Compounds where $R_4$ is —F can be obtained by reacting a Piperidine Compound where $R_4$ is —OH with fluorinating reagents such as DAST, Deoxo-Fluor, $SF_4$, HF, KF, CsF, Yarovenko's reagent, Ishikawa's reagent, according to the procedure described in M. Schlosser et al., *Tetrahedron* 52(24):8257-8262 (1996).

The Piperidine Compounds where $R_4$ is —Cl can be obtained by reacting a Piperidine Compound where $R_4$ is —OH with $SOCl_2$ or $PCl_5$ according to the procedure described in *J. Amer. Chem. Soc.* 120(4):673-679 (1998) or with $CH_3COCl$ according to the procedure described in *Tett. Lett.* 41(47):9037-9042 (2000).

The Piperidine Compounds where $R_4$ is —Br can be obtained by reacting a Piperidine Compound where $R_4$ is —OH with pyridine and $SOBr_2$ according to the procedure described in *J. Organometallic Chemistry* 627(2):179-88 (2001) or by reacting a Piperidine Compound where $R_4$ is —OH with pyridine and $PPh_3/Br_2$ according to the procedure described in *J. Amer. Chem. Soc.* 112 (9):3607-14 (1990).

The Piperidine Compounds where $R_4$ is —I can be obtained by reacting a Piperidine Compound where $R_4$ is —OH with HI in acetic anhydride according to the procedure described in *J. Amer. Chem. Soc.* 87(3):539-542 (1965).

The Piperidine Compounds where $R_4$ is —$CH_3$ can be obtained by reacting a Piperidine Compound where $R_4$ is —OH with $PCl_5$ and $CH_3TiCl_3$ according to the procedure described in *Angewandte Chemie*, 92(11), 933-4 (1980).

The Piperidine Compounds where $R_4$ is —($C_1$-$C_6$)alkyl can be obtained by reacting a Piperidine Compound where $R_4$ is —OH with p-toluenesulfonic acid in toluene followed by n-butyl lithium and X—($C_1$-$C_6$)alkyl, where X is a halogen, according to the procedure described in Charles J. Barnett, et al, *J. Org. Chem.*, 54(20) 4795-4800 (1989) followed by hydrogenating the product according to the procedure described in Thomas E. D'Ambra et al, *J. Org. Chem.*, 54(23) 5632-5 (1989) as described below.

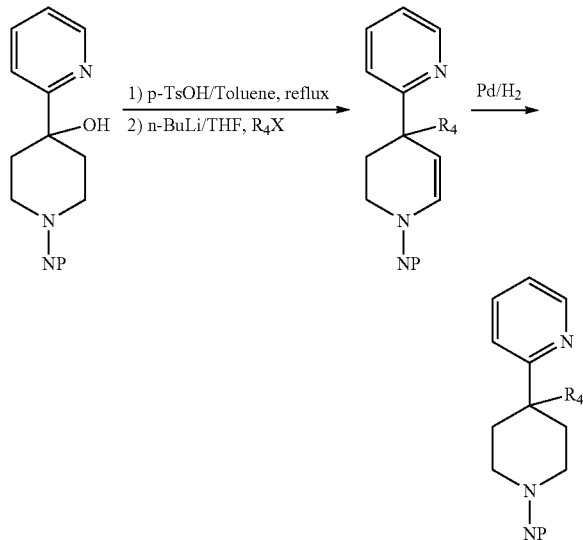

The Piperidine Compounds where $R_4$ is —$CH_2OH$ can be obtained by reacting a Piperidine Compound where $R_4$ is —COOH with $LiAlH_4$ according to procedures known in the art. The Piperidine Compounds where $R_4$ is —$CH_2OH$ can be obtained by reacting a Piperidine Compound where $R_4$ is —C(O)H with $NaBH_4$ according to procedures known in the art.

The Piperidine Compounds where $R_4$ is —COOH can be obtained by reacting a Piperidine Compound where $R_4$ is —CN with KOH according to procedures known in the art.

The Piperidine Compounds where $R_4$ is —CN can be obtained by reacting a Piperidine Compound where $R_4$ is —OH with KCN and $SOCl_2$ according to the procedure described in *Armyanskii Khimicheskii Zhurnal.* 30(9):723-727 (1977).

The Piperidine Compounds where $R_4$ is —C(O)H can be obtained by reacting a Piperidine Compound where $R_4$ is —CN with di-iso-butylaluminum hydride (DIBAL-H) according to procedures known in the art.

The Piperidine Compounds where $R_4$ is —$OCF_3$ can be obtained by reacting a Piperidine Compound where $R_4$ is —OH with $CS_2$; methyl iodide; and bromosuccinimide and pyridine/HF in DCM according to the procedure described in *Chemical Communications (Cambridge)* 3:309-310 (1997) or *Bulletin of the Chemical Society of Japan*, 732): 471-484 (2000).

The Piperidine Compounds where $R_4$ is —$CH_2Cl$ can be obtained by reacting a Piperidine Compound where $R_4$ is —$CH_2OH$, obtained as described above, with $PCl_5$ according to the procedure described in *J. Amer. Chem. Soc.*, 120(4):673-679 (1998).

The Piperidine Compounds where $R_4$ is —$CH_2Br$ can be obtained by reacting a Piperidine Compound where $R_4$ is —$CH_2OH$, obtained as described above, with $SOBr_2$ according to the procedure described in *J. Organomet. Chem.*, 627(2):179-188 (2001) or with $PPh_3/Br_2$ according to the procedure described in *J. Amer. Chem. Soc.*, 112(9): 3607-3614 (1990).

The Piperidine Compounds where $R_4$ is —$CH_2F$ can be obtained by reacting a Piperidine Compound where $R_4$ is —$CH_2OH$, obtained as described above, with 1 eq. of DAST according to the procedure described in M. Schlosser et al., *Tetrahedron* 52(24):8257-8262 (1996) and *Organic Letters.* 3(17):2713-2715 (2001).

The Piperidine Compounds where $R_4$ is —$CH_2I$ can be obtained by reacting a Piperidine Compound where $R_4$ is —$CH_2OH$, obtained as described above, with $PPh_3/I_2$ according to the procedure described in *Organic Process Research and Development* 6(2):190-191 (2002).

The Piperidine Compounds where $R_4$ is —$CH(halo)_2$ can be obtained by reacting a Piperidine Compound where $R_4$ is —C(O)H, obtained as described above, with $(F_3CSO_2)_2O$ followed by $Mg(halo)_2$ in $CS_2$ according to the procedure described in *Synthesis* 12:1076-1078 (1986).

The Piperidine Compounds where $R_4$ is —$CHF_2$ can also be obtained by reacting a Piperidine Compound where $R_4$ is —C(O)H, obtained as described above, with 2 eq. of DAST according to the procedure described in M. Schlosser et al., *Tetrahedron* 52(24):8257-8262 (1996) and *Organic Letters.* 3(17):2713-2715 (2001).

The Piperidine Compounds where $R_4$ is —$CF_3$ can be obtained by reacting a Piperidine Compound where $R_4$ is —C(O)H, obtained as described above, with copper (I) iodide and sodium trifluoroacetate according to the procedure described in U.S. Pat. No. 4,866,197 to Bauman.

The Piperidine Compounds where $R_4$ is —$OR_{10}$ can be obtained by reacting a Piperidine Compound where $R_4$ is —OH, obtained as described above, with $R_{10}$—X where X is a halogen in the presence of NaOH according to the procedure described in *European Journal of Medicinal Chemistry* 24(4):391-396 (1989).

The Piperidine Compounds where $R_4$ is —$SR_{13}$ can be obtained by reacting a Piperidine Compound where $R_4$ is —OH, obtained as described above, with $R_{13}$—SH according to the procedure described in U.S. Pat. No. 4,409,229 to Ong et al. or *Journal of Medicinal Chemistry* 24(1):74-79 (1981).

The Piperidine Compounds where $R_4$ is —$COOR_{10}$ can be obtained by esterifying a Piperidine Compound where $R_4$ is —COOH, obtained as described above, with $R_{10}$—OH. Methods to esterify carboxylic acids are known in the art.

The Piperidine Compounds where $R_4$ is —$OC(O)R_{10}$ can be obtained by reacting a Piperidine Compound where $R_4$ is —OH, obtained as described above, with $R_{10}C(O)Cl$ according to the procedure described in *European Journal of Medicinal Chemistry* 24(4):391-396 (1989). The acid chlorides, $R_{10}C(O)Cl$, can be prepared from the corresponding carboxylic acid, $R_{10}COOH$, using procedures known in the art.

The Piperidine Compounds where $R_4$ is —$NHC(O)R_{13}$ can be obtained by reacting a Piperidine Compound where $R_4$ is —OH with $R_{10}CN$ in the presence of $H_2SO_4$ followed by $K_2CO_3$ in DCM as described in *Bioorganic and Medicinal Chemistry Letters* 10(17:2001-2014 (2000).

The Piperidine Compounds where $R_4$ is —$OC(O)NH_2$ can be obtained by reacting a Piperidine Compound where $R_4$ is —OH with $Cl_3CCONCO$ in DCM at 0° C. with stirring for about 2 h and then adding to the resulting mixture $K_2CO_3$ in methanol-water and allowing the resulting mixture to stir for about 4 h at 0° C. and about 2 h at about 25° C. according to the procedure described in Christopher P. Holmes et al, *J. Org. Chem.*, 54(1):98-108 (1989).

The Piperidine Compounds where $R_4$ is —$OC(O)NHR_{10}$ can be obtained by reacting a Piperidine Compound where $R_4$ is —OH with an isocyanate of formula $R_{10}NCO$ in refluxing THF for about 24 h at about 25° C. according to the procedure described in Andre Hallot et al, *J. Med. Chem.*, 29(3):369-375 (1986).

The Piperidine Compounds where $R_4$ is $-SO_2R_{10}$, $-NO_2$, $-CN$, $-COR_{10}$, $-COOR_{10}$, and $CON(R_{13})_2$ can be prepared by the illustrative methods described below.

A compound of formula 15 is reacted with a compound of formula 16a-d in the presence of a base according to the procedure described in *Journal of Heterocycle Chemistry*, 23(1):73-75 (1986) or *Organic Chemistry and Procedures International* 28(4:478-480 (1996) to provide a compound of formula 17a-d, as described below in scheme 1.9:

where $R_1$, $R_2$, $R_3$, n, m, and p are as defined above; Y is $-SO_2R_{10}$, $-NO_2$, $-CN$, $-COR_{10}$, $-COOR_{10}$, or $CON(R_{13})_2$; and NP is a nitrogen protecting group.

The nitrogen protecting group is then removed from the compound of formula 17a-d to provide a compound of formula 18a-d. Any nitrogen protecting group known in the art can be used to protect the nitrogen in the compound of formula 15.

To provide the Piperidine compounds of formula I where X is O and $R_4$ is $-SO_2R_{10}$, $-NO_2$, $-CN$, $-COR_{10}$, $-COOR_{10}$, or $CON(R_{13})_2$, the compound of formula 18a-d is then reacted with an isocyanate of formula R—NCO according to a procedure analogous to that described above in scheme 1.4 and described below in Scheme 1.10:

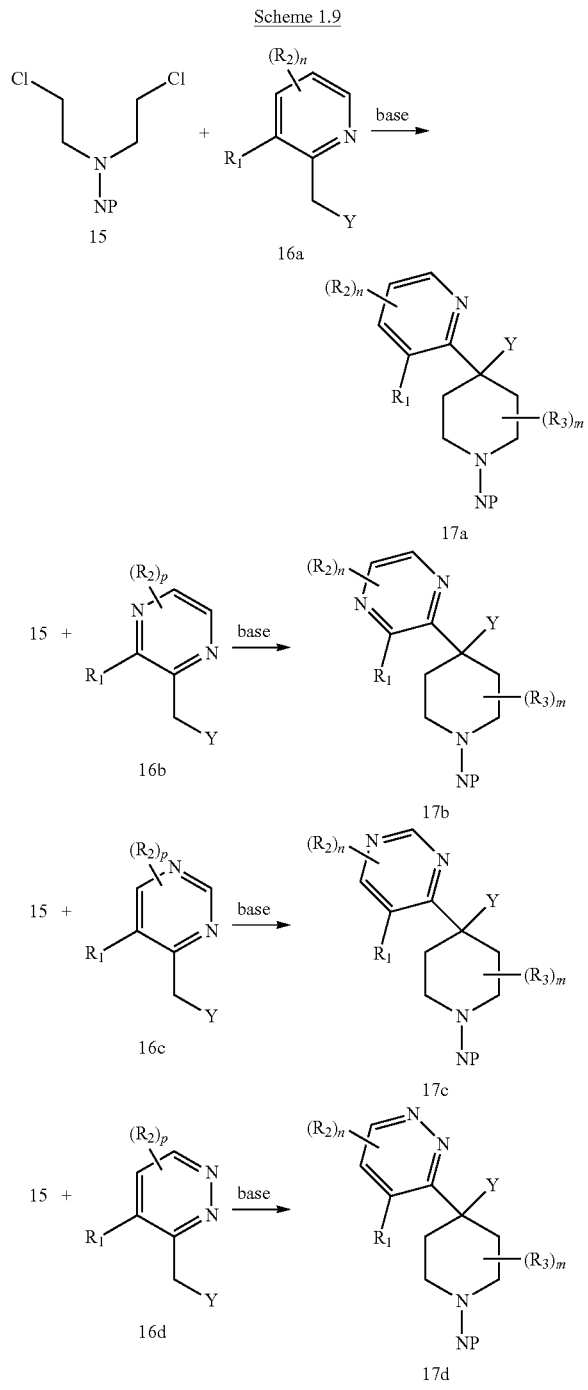

Scheme 1.9

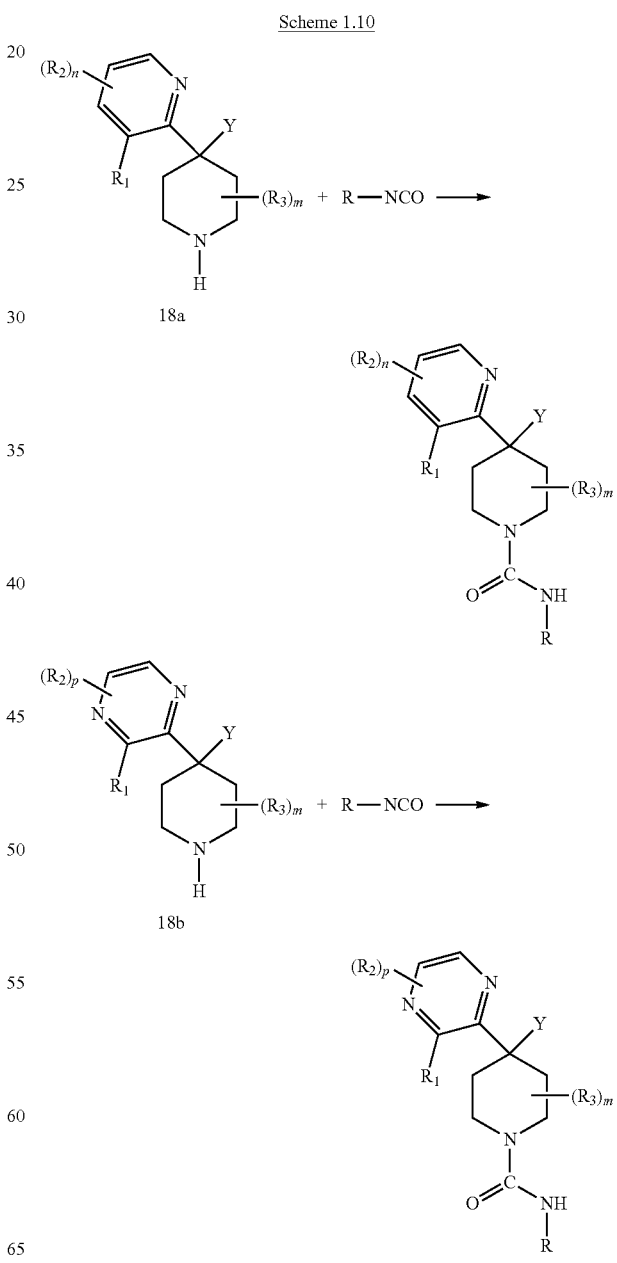

Scheme 1.10

-continued

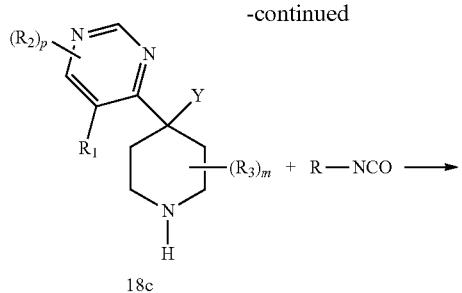

18c

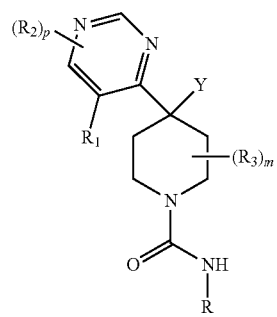

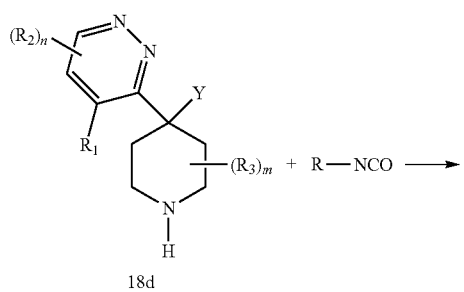

18d

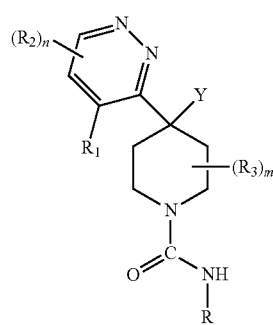

where $R_1$, $R_2$, $R_3$, n, m, and p are as defined above; Y is —$SO_2R_{10}$, —$NO_2$, —$COR_{10}$, or —$CON(R_{13})_2$; and R is $Ar_2$.

A compound of formula 18a-d is reacted with a compound of formula R—NCO according to a procedure analogous to that described above in Scheme 1.4.

To provide the Piperidine Compounds where X is S and $R_4$ is —$SO_2R_{10}$, —$NO_2$, —CN, —$COR_{10}$, —$COOR_{10}$, or $CON(R_{13})_2$, the compound of formula 18a-d is reacted with an isothiocyanate of formula R—NCS according to a procedure analogous to that described above in Section 5.6.1.2.

To provide the Piperidine Compounds where X is N—CN and $R_4$ is —$SO_2R_{10}$, —$NO_2$, —CN, —$COR_{10}$, —$COOR_{10}$, or $CON(R_{13})_2$, the compound of formula 18a-d is reacted with diphenyl cyanocarbonimidate 35 and then an amine of formula R—$NH_2$ according to a procedure analogous to that described above in Section 5.6.1.3.

To provide the Piperidine Compounds where X is N—OH and $R_4$ is —$SO_2R_{10}$, —$NO_2$, —CN, —$COR_{10}$, —$COOR_{10}$, or $CON(R_{13})_2$, the Piperidine Compound where X is S and $R_4$ is —$SO_2R_{10}$, —$NO_2$, —CN, —$COR_{10}$, —$COOR_{10}$, and $CON(R_{13})_2$ is reacted with methyl iodide according to a procedure analogous to that described above in scheme 1.8 to provide a compound of formula 19,

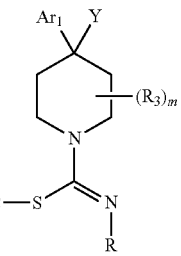

where $Ar_1$, $R_3$, m, and Y are as defined above and R is $Ar_2$.

The compound of formula 19 is then reacted with hydroxylamine in ethanol according to a procedure analogous to that described above in Scheme 1.8 to provide the Piperidine Compounds where X is N—OH and $R_4$ is —$SO_2R_{10}$, —$NO_2$, —CN, —$COR_{10}$, —$COOR_{10}$, or $CON(R_{13})_2$.

To provide the Piperidine Compounds where X is N—$OR_{10}$ and $R_4$ is —$SO_2R_{10}$, —$NO_2$, —CN, —$COR_{10}$, —$COOR_{10}$, or $CON(R_{13})_2$, the Piperidine Compound where X is NOH and $R_4$ is —$SO_2R_{10}$, —$NO_2$, —CN, —$COR_{10}$, —$COOR_{10}$, and $CON(R_{13})_2$ is reacted with X—($C_1$-$C_4$) alkyl, where X is —I, —Br, —Cl, or —F in the presence of triethylamine according to a procedure analogous to that described above in Section 5.6.1.6.

The compound of formula 15 is commercially available or can be prepared by methods known in the art.

The compounds of formula 16a-d where Y is —$SO_2R_{10}$ can be obtained by reacting a compound of formula 16a-d, where Y is a halogen, with $R_{10}SO_2H$ according to the procedure described in *J. Org. Chem.* 67(13:4387-4391 (2002) or international publication no. WO 02/48098.

The compounds of formula 16a-d where Y is —CN can be obtained by reacting a compound of formula 16a-d, where Y is a halogen, with potassium cyanide according to the procedure described in *Farmaco* 45(9):945-953 (1990).

The compounds of formula 16a-d where Y is —$COOR_{10}$ can be obtained by reacting a compound of formula 16a-d, where Y is a halogen, with (a) potassium cyanide, (b) water, and (c) $R_{10}OH$ and $SO_2Cl$ according to the procedure described in *Farmaco* 45(9):945-953 (1990).

The compounds of formula 16a-d where Y is —$COR_{10}$ can be obtained by reacting a compound of formula 16a-d, where Y is a halogen, with $R_{10}C(O)H$ and trimethylsilyl cyanide according to the procedure described in international publication no. WO 01/81333.

The compounds of formula 16a-d where Y is —$CON(R_{13})_2$ can be obtained by reacting a compound of formula 16a-d, where Y is a halogen, with (a) potassium cyanide, (b) water, and (c) $NH(R_{13})_2$ and $SO_2Cl$ according to the procedure described in *Farmaco* 45(9):945-953 (1990).

The compounds of formula 16a-d where Y is —$NO_2$ can be obtained by reacting a compound of formula 2a-d where X is —$CH_3$ with $NaNH_2$ in liquid $NH_3$ followed by $CH_3CH_2CH_3$—$ONO_2$ at a temperature of less than −33° C. to provide a nitronate that is then reacted under acidic condition to provide the compound of formula 16a-d where Y is —$NO_2$ according to the procedure described in H. Feuer et al., *J. Am. Chem. Soc.* 91(7):1856-1857 (1969) and as described in scheme 1.11 below, where $R_1$, $R_2$, n and p are as defined above.

Scheme 1.11

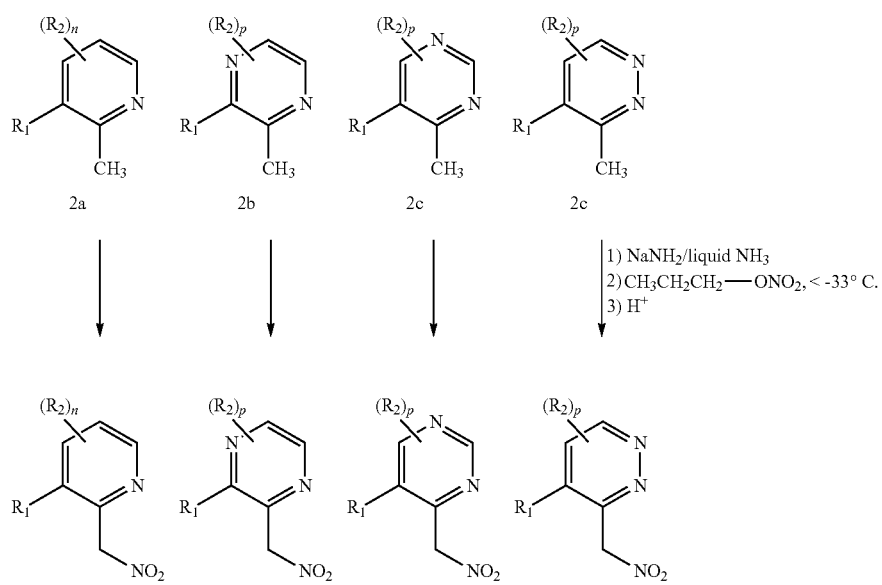

The compounds of formula 16a-d where Y is -halo are commercially available or can be prepared by methods known in the art.

Certain Piperidine Compounds can have one or more asymmetric centers and therefore exist in different enantiomeric and diastereomeric forms. A Piperidine Compound can be in the form of an optical isomer or a diastereomer. Accordingly, the invention encompasses Piperidine Compounds and their uses as described herein in the form of their optical isomers, diastereomers, and mixtures thereof, including a racemic mixture. Optical isomers of the Piperidine Compounds can be obtained by known techniques such as chiral chromatography or formation of diastereomeric salts from an optically active acid or base.

In addition, one or more hydrogen, carbon or other atoms of a Piperidine Compound can be replaced by an isotope of the hydrogen, carbon or other atoms. Such compounds, which are encompassed by the invention, are useful as research and diagnostic tools in metabolism pharmacokinetic studies and in binding assays.

5.6.1.7 Methods for Installing $R_2$ Groups on $Ar_1$ when $R_2$ is O

The conversion of a halide, L to a vinyl group via a Suzuki cross-coupling reaction is exemplified in scheme 1.12 below, where $R_1$, $R_2$, $R_4$ and p are as defined above, L is defined as -halo, and NP is a nitrogen protecting group known in the art. While this example demonstrates the conversion when L is in the 5-position of the pyridyl ring of 20, the transformation can be carried out when L is in other positions on the aryl ring as well. Moreover, the same technique can be used when $Ar_1$ is another pyridyl ring, pyrimidinyl, pyrazinyl or pyridazinyl ring.

Scheme 1.12

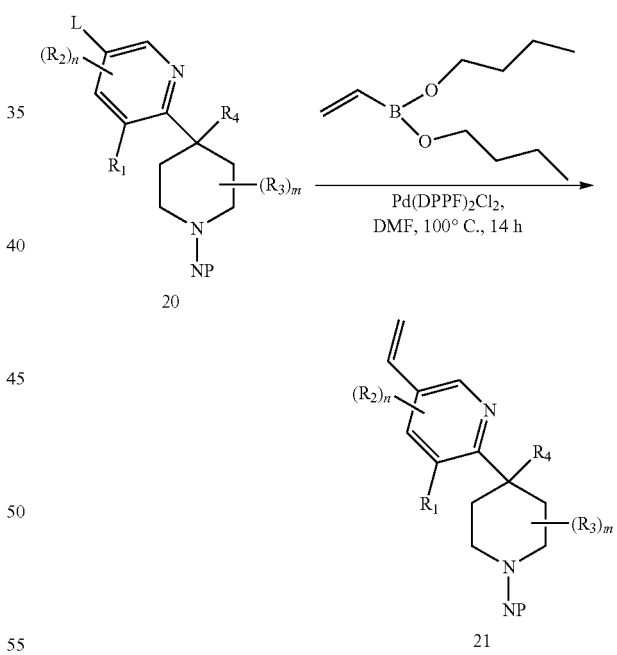

To a degassed DMF solution of compound 20 (1.6 mmol) in a 100 mL round bottom flask, is added CsF (3.2 mmol), di-n-butyl vinyl boronic ester (0.388 mL, 1.76 mmol) and palladium diphenylphosphinoferrocene dichloride (Pd(DPPF)$_2$Cl$_2$, 0.128 mmol). The resulting mixture is stirred at 100° C. for 14 hr, then cooled to a temperature of about 25° C. and diluted with 100 mL ethyl acetate, which was washed with brine (3×50 mL). The organic layer was isolated, dried, and concentrated under reduced pressure. Silica gel column chromatography gives the product, 21.

Other techniques for the installation of the vinyl group are shown in schemes 1.13a and 1.13b. In scheme 1.13a, the first step involves the oxidation of a benzylic alcohol to an aldehyde. This is followed by a Wittig olefination, to yield the vinyl group. Once again, while this example demonstrates the conversion when the starting benzylic alcohol is in the 5-position of a pyridyl ring, similar conversions can be carried out at other positions. Moreover, the same technique can be used when $Ar_1$ is another pyridyl ring, pyrimidinyl, pyrazinyl or pyridazinyl.

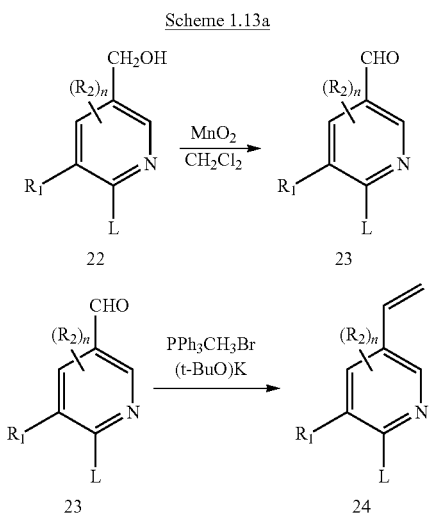

Scheme 1.13a

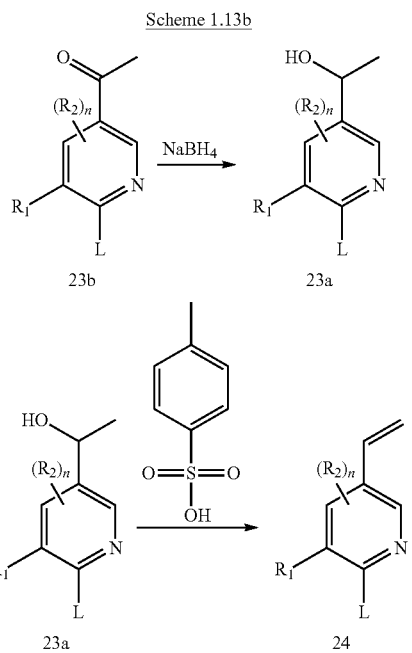

Scheme 1.13b

To a 500 mL round-bottom flask, manganese oxide (0.50 mol) is added to a solution of 22 (50.0 mmol) in anhydrous $CH_2Cl_2$ (150 mL). The resulting mixture is stirred at a temperature of about 25° C. for 48 h and then the reaction mixture is filtered through CELITE and concentrated. The resulting mixture is chromatographed by silica gel column chromatography eluting with a gradient of ethyl acetate (0%-40%)/hexanes to provide aldehyde 23.

To a cooled 0° C., stirred slurry of methyltriphenylphosphonium bromide (10.0 g) in toluene (200 mL) is added potassium t-butoxide (3.07 g) portionwise to produce a yellow slurry. After 1 hr, the reaction mixture is cooled to −20° C., and 23 (22.72 mmol) dissolved in tetrahydrofuran (6 mL) is added dropwise to produce a purple colored slurry. The reaction mixture is heated to 0° C. and stirred for additional 1 hr. Then the reaction mixture is treated with saturated aqueous brine (150 mL) and diluted with ethyl acetate (200 mL). The resulting organic layer is washed with brine, dried over anhydrous sodium sulfate and concentrated under reduced pressure. The resulting product is chromatographed by silica gel column chromatography column, eluting with a gradient of ethyl acetate (0%-10%)/hexanes to provide product 24.

In scheme 1.13b, the first step involves the reduction of a benzylic ketone to a hydroxyl. This is followed by a dehydration reaction to yield the vinyl group. Once again, while this example demonstrates the conversion when the starting benzylic ketone is in the 5-position of a pyridyl ring, similar conversions can be carried out at other positions. Moreover, the same technique can be used when $Ar_1$ is another pyridyl ring, pyrimidinyl, pyrazinyl or pyridazinyl.

To a well-stirred suspension of 23b (665 g, 3.5 mol) in methanol (3.5 L) at 0° C. is added sodium borohydride (66.21 g, 1.75 mol) portionwise at a rate such that the reaction mixture temperature does not exceed 5° C. After the addition is complete, the reaction mixture is warmed to a temperature of about 25° C. and stirred an additional 1 h. The reaction mixture is concentrated under reduced pressure and the residue mixed with 2 L diethyl ether and 2 L 1N HCl. The layers are separated and the aqueous layer extracted twice with diethyl ether (250 mL for each extraction). The organic portions are combined, dried ($MgSO_4$), and concentrated under reduced pressure to provide 23a.

To a solution of 23a (311 g, 1.62 mol) in chlorobenzene (3 L) is added p-toluene sulfonic acid (431 g, 2.5 mol). The reaction mixture is heated to reflux, about 140° C., and water is removed concurrently. At the completion of the reaction, the mixture is concentrated under reduced pressure to about 500 mL, diluted with 2 L of water, and extracted three times with ethyl acetate (1 L for each extraction). The organic portions are combined, dried ($Na_2SO_4$), and concentrated under reduced pressure under mild heating to provide a residue. The residue is added to 500 mL of methylene chloride and applied to the top of column packed with 2 kg silica eluted with a 0% to 10% gradient of ethyl acetate in hexane to provide 24.

Vinyl groups are highly versatile, because they are a synthetic handle that can be further modified. It is well known in synthetic organic chemistry that olefin hydrolysis yields a benzylic hydroxyl group, hydroboration gives a primary hydroxyl group, ozonolysis gives an aldehyde or ketone, oxidation gives a carboxylic acid, olefin metathesis extends the chain, and dihydroxylation gives a 1,2-diol. Many additional olefin functionalization techniques are available to those skilled in organic synthesis. Once functionalized, the group can undergo further transformations. Exemplified in scheme 1.14 is the vinyl group of 21 undergoing an asymmetric dihydroxylation.

Scheme 1.14

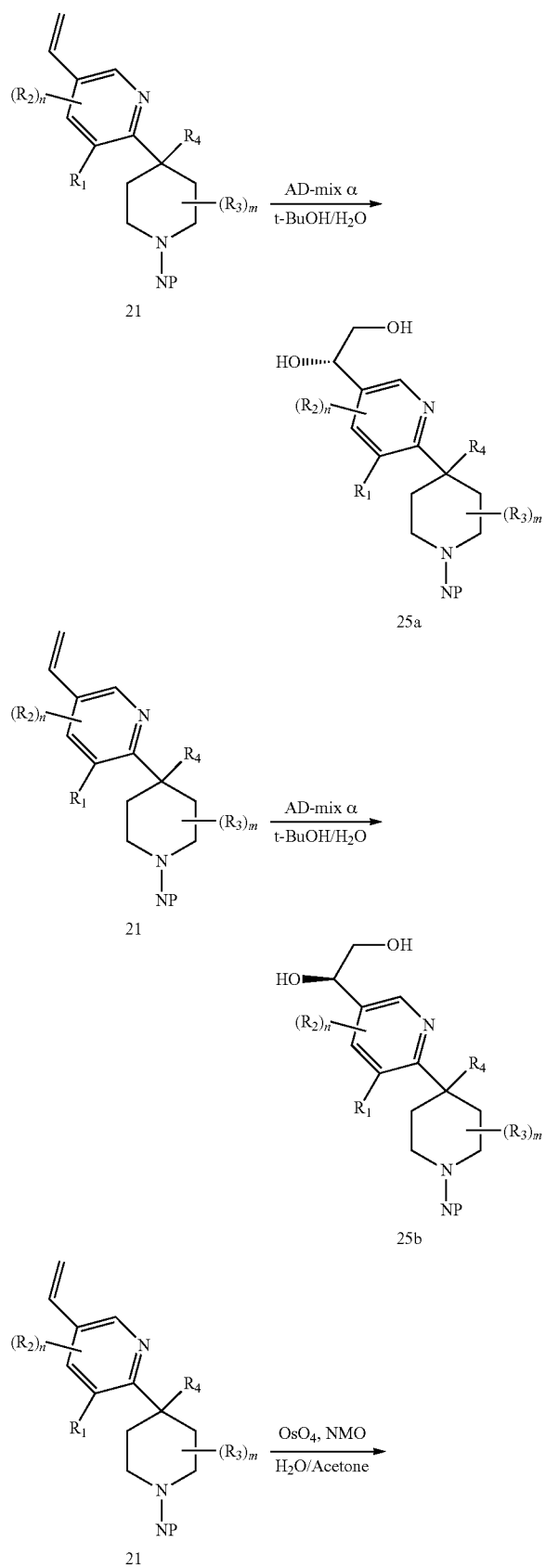

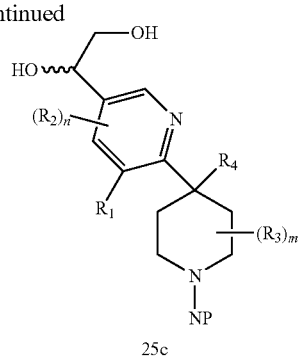

In a 100 mL round bottom flask, AD-mix α (0.5 g) is added to a mixture of t-butanol and water (2 mL/2 mL) and the mixture is stirred at a temperature of about 25° C. for 0.5 hr, and then cooled to 0° C. This solution is quickly poured into another ice chilled flask, which contains compound 21 (0.41 mmol). The mixture is stirred vigorously in an ice bath for 96 h, and then diluted with ethyl acetate (50 mL) and 2 mL saturated $Na_2S_2O_5$. The ethyl acetate layer is isolated, dried, and concentrated under reduced pressure with a rotary evaporator to provide 25a. The other enantiomer, can be synthesized by the reaction of 21 with AD-mix β to yield 25b. As demonstrated in scheme 1.14, the stereochemistry (R or S) of the resulting diol, is dependent upon the chirality of the ligand used in the AD mix as described in Sharpless et al., *J. Org. Chem.* 57:2768-2771 (1992). AD-mix is composed of the following components: potassium osmate ($K_2OsO_2(OH)_4$), potassium ferricyanide ($K_3Fe(CN)_6$), potassium carbonate ($K_2CO_3$), and the chiral ligands are shown in scheme 1.15.

Scheme 1.15

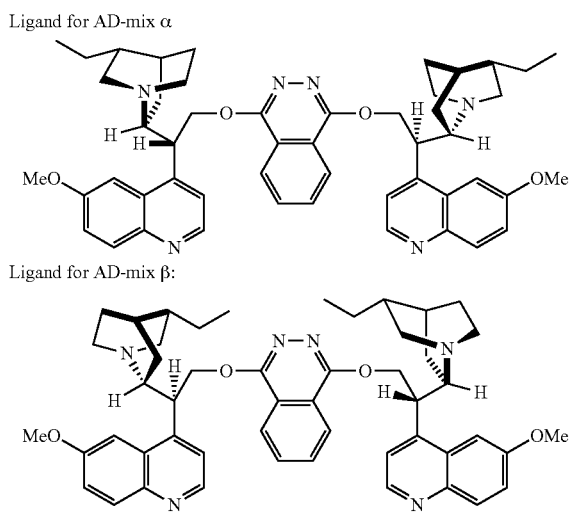

The racemic diol, 25c, can be synthesized by methods known in the art, using osmium tetroxide ($OsO_4$) and N-methyl morpholine N-oxide (NMO) in an aqueous acetone solution.

5.6.2 Methods for Making Compounds of Formula I where W is C and the Dashed Line is Present The compounds of formula 1 where W is C and the dashed line is present, i.e., "Tetrahydropyridyl Compounds," can be made using conventional organic synthesis or by the following illustrative methods shown in the schemes below.

5.6.2.1 Methods for Making the Tetrahydropyridyl Compounds where X is O

The Tetrahydropyridyl Compounds where X is O can be obtained by the following illustrative method shown below in Schemes 2.1 and 2.2, where $R_3$, $Ar_2$, and m are as defined above.

Scheme 2.1

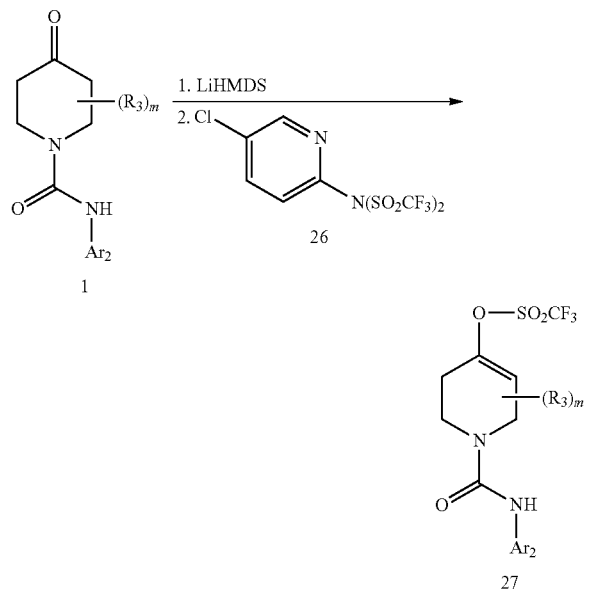

Referring to scheme 2.1 above, compound 1 (about 3.6 mmol) is dissolved in THF (100 mL) and the resulting solution cooled to −78° C. To the cooled solution is added LiHMDS (8.75 mmol) and the reaction mixture is stirred at −78° C. for 2 h. Compound 26 (about 3.6 mmol, Sigma-Aldrich) is then added to the reaction mixture and the reaction mixture is stirred at −78° C. for 2 h. The reaction mixture is then allowed to warm to 25° C. and concentrated under reduced pressure to provide a compound of formula 27.

The compound of formula 27 is then reacted with a compound of formula 28a-d to provide the Tetrahydropyridyl Compound where X is O as shown below in scheme 2.2:

Scheme 2.2

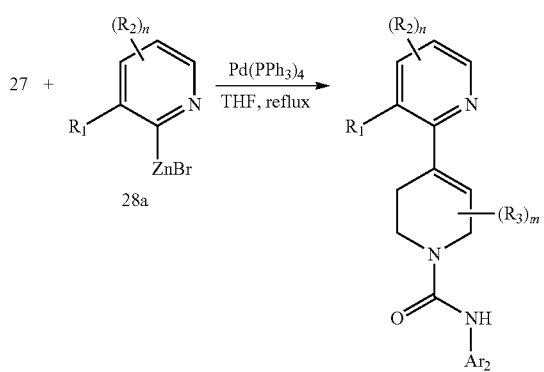

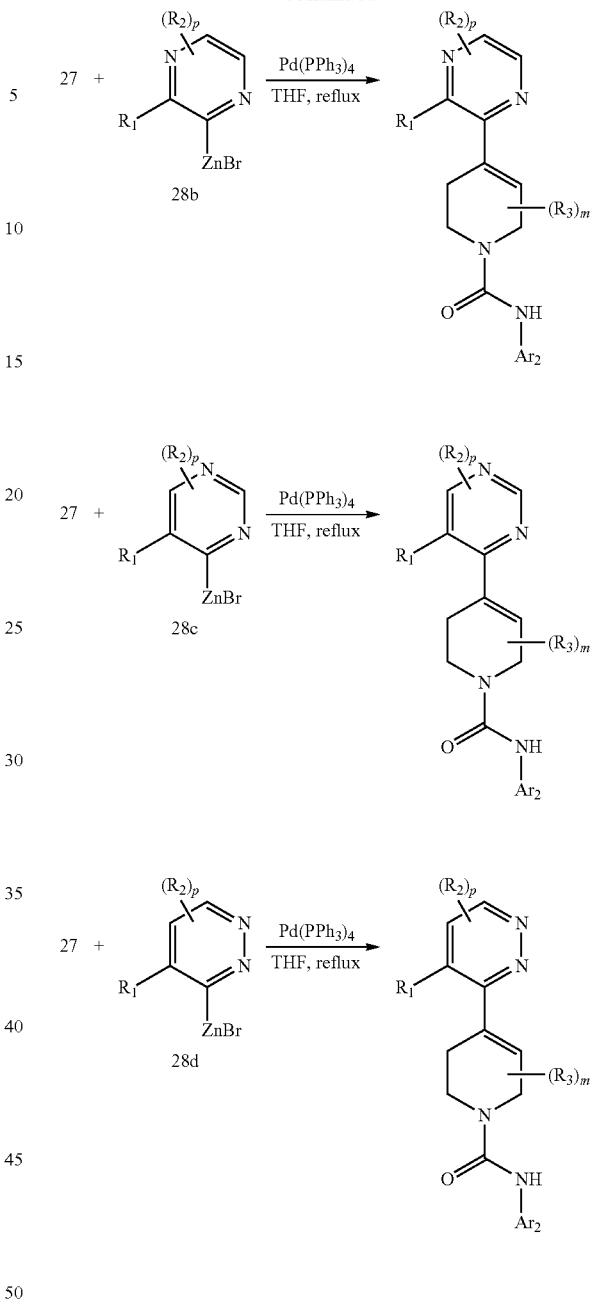

where $R_1$, $R_2$, $R_3$, $Ar_1$, n, m, and p are as defined above.

$Pd(PPh_3)_4$ (0.11 mmol) is dissolved in THF (about 50 mL) and the compound of formula 27 (about 2.2 mmol) is added to the resulting solution followed by a compound of formula 28a-d (about 6.6 mmol as a 0.5M solution in THF).

The reaction mixture is then heated for 1 h at the reflux temperature of the solvent. The reaction mixture is allowed to cool to 25° C. and concentrated under reduced pressure to provide the Tetrahydropyridyl Compound where X is O. The Tetrahydropyridyl Compound where k is O can be further treated if desired. In one embodiment, the Tetrahydropyridyl Compound where X is O is chromatographed using silica gel column chromatography followed by trituration with ethyl acetate.

Where in =1, $R_3$ is bonded to an sp3 carbon, and 27 is either racemic or a mixture of enantiomers, the resulting Tetrahydropyridyl Compound in scheme 2.2 will also be racemic or an enantiomeric mixture. If a single stereoisomer is desired, it is possible to use chiral separation techniques known in the art, such as chiral chromatography or chiral resolution, to isolate a single isomer.

Another technique that can be used to couple the tetrahydropyridyl group and An is the Suzuki cross-coupling reaction. This is accomplished by a catalyst mediated reaction of 2a with the tetrahydropyridyl borane, 29 as exemplified in scheme 2.3 below. While the reaction shown has An as a pyridyl group, the same technique can be used when $Ar_1$ is a pyrazinyl (2b), pyrimidinyl (2c), pyridazinyl (2d) or other pyrazinyl rings.

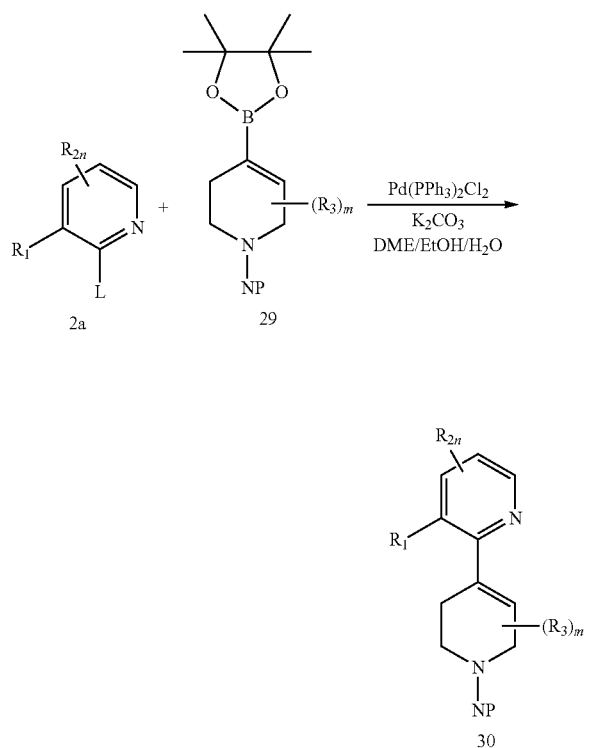

Scheme 2.3

A 150 mL sealed vessel is charged with 2a (3.37 mmol), 29 (4.04 mmol), Pd(PPh$_3$)$_2$Cl$_2$ (0.27 mmol), potassium carbonate (6.40 mmol), and a mixture of DME/EtOH/H$_2$O (8 mL/4 mL/8 mL). The resulting mixture is purged with nitrogen, sealed, and heated at 90° C. with a vigorous stirring. After 2 hrs, the reaction mixture is cooled to a temperature of about 25° C. and diluted with EtOAc (50 mL). The organic layer is washed with brine, dried (Na$_2$SO$_4$), and concentrated under reduced pressure. The residue is chromatographed by silica gel column chromatography with a gradient of ethyl acetate (0%-30%)/hexanes to provide product 30.

The boronate ester, 29 can be synthesized by the method demonstrated below in scheme 2.4.

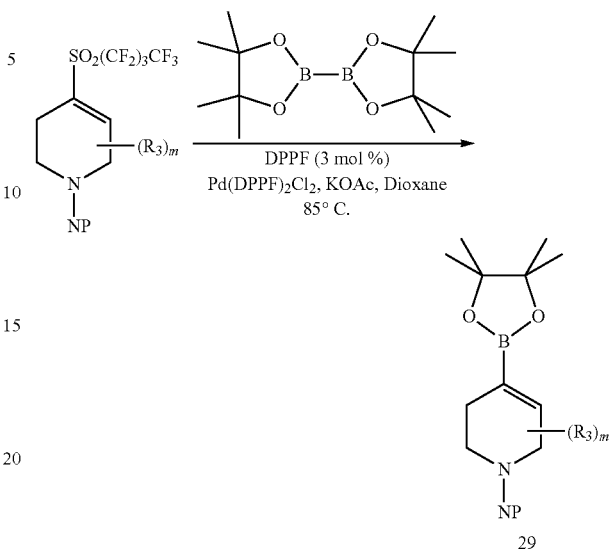

Scheme 2.4

Bis(pinacolato)diboron (333.6 mmol), diphenylphosphino ferrocene (9.1 mmol), palladium diphenylphosphinoferrocene dichloride (1:1 complex with dichloromethane) (9.1 mmol), and potassium acetate (909.9 mmol) are suspended in dry dioxane (900 mL) under argon with mechanical stirring. 4-(Nonafluorobutane-1-sulfonyloxy)-3,6-dihydro-2H-pyridine-1-carboxylic acid tert-butyl ester (303.3 mmol) in dry dioxane (500 mL) is added and the mixture is heated to 85° C. for 16 h. The mixture is cooled, filtered through CELITE, and the filter cake is washed with dichloromethane (2 L). The filtrate is concentrated under reduced pressure to provide a black solid. This is adsorbed onto silica gel (250 g) and applied to the head of a 4" silica gel column, and it is then eluted with hexanes (5 L) followed by 20:1 hexanes:ethyl acetate, and finally ethyl acetate (10 L) to yield 29.

5.6.2.2 Methods for Making the Tetrahydropyridyl Compounds where X is S

The Tetrahydropyridyl Compounds where X is S can be obtained by methods analogous to that described above in schemes 2.1 and 2.2 to provide the Tetrahydropyridyl Compounds where X is O, except that an isothiocyanate of formula Ar$_2$—NCS is used in place of the isocyanate Ar$_2$—NCO.

5.6.2.3 Methods for Making the Tetrahydropyridyl Compounds where X is N—CN

The Tetrahydropyridyl Compounds where X is N—CN can be obtained as shown below in Schemes 2.5 and 2.6 where Ar$_2$, R$_3$, and m are as defined above.

Scheme 2.5

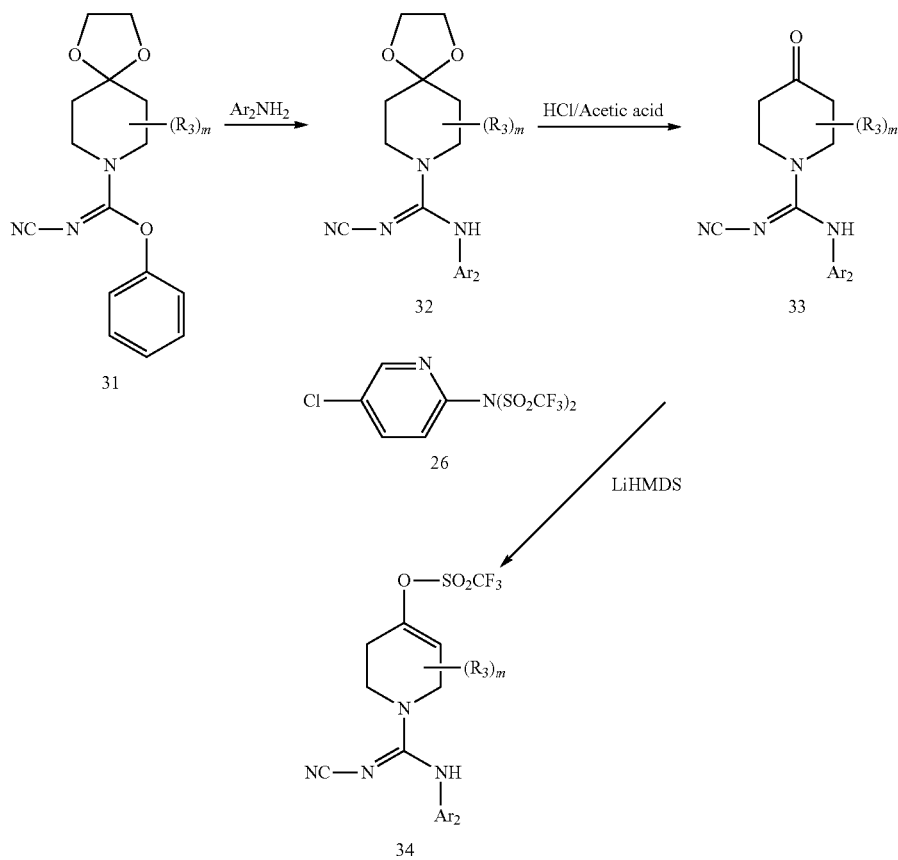

A ketal of formula 31 (about 14 mmol) is reacted with an amine of formula Ar—NH$_2$ (about 14 mmol) in an aprotic organic solvent (about 7 mL) such as diethyl ether, di-n-propyl ether, THF, DCM, or toluene at a temperature of from about 25° C. to about the reflux temperature of the solvent for a period of from about 0.5 h to about 24 h. The reaction mixture is then concentrated under reduced pressure to provide a compound of formula 32. In one embodiment, the aprotic organic solvent is di-n-propyl ether. In another embodiment, a reaction mixture of di-n-propyl ether, a compound of formula 31 and the amine of formula Ar—NH$_2$ is heated at a temperature of about 70° to about 80° C.

The compound of formula 32 is then dissolved in THF (about 20 mL). About 1N HCl in acetic acid (about 30 mL) is added to the THF solution of the compound of formula 32 and the resulting mixture is heated at the reflux temperature of the solvent. Typically, the reaction mixture is heated at the reflux temperature of the solvent for about 3 h. The reaction mixture is then cooled and concentrated under reduced pressure to provide a residue that is dissolved in DCM. The DCM solution is then extracted with aqueous Na$_2$CO$_3$. The aqueous and organic layers are separated and the aqueous layer is extracted three times with DCM. The organic portions are combined, dried (MgSO$_4$), and concentrated under reduced pressure to provide a compound of formula 33. The compound of formula 33 can be further treated if desired. In one embodiment, the compound of formula 33 is chromatographed using silica gel column chromatography.

The compound of formula 33 (about 3.6 mmol) is then dissolved in THF (about 100 mL) and the resulting solution cooled to about −78° C. To the cooled solution is added LiHMDS (about 8.75 mmol) and the reaction mixture is stirred at about −78° C. for about 2 h. A compound of formula 26 (about 3.6 mmol, Sigma-Aldrich) is then added to the reaction mixture and the reaction mixture stirred at about −78° C. for about 2 h. The reaction mixture is then allowed to warm to about 25° C. and concentrated under reduced pressure to provide a compound of formula 34.

The compound of formula 34 is then reacted with a compound of formula 28a-d as shown below in scheme 2.6 below to provide the Tetrahydropyridyl Compound where X is N—CN.

Scheme 2.6

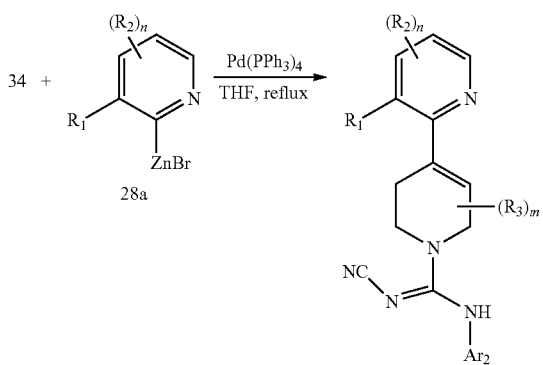

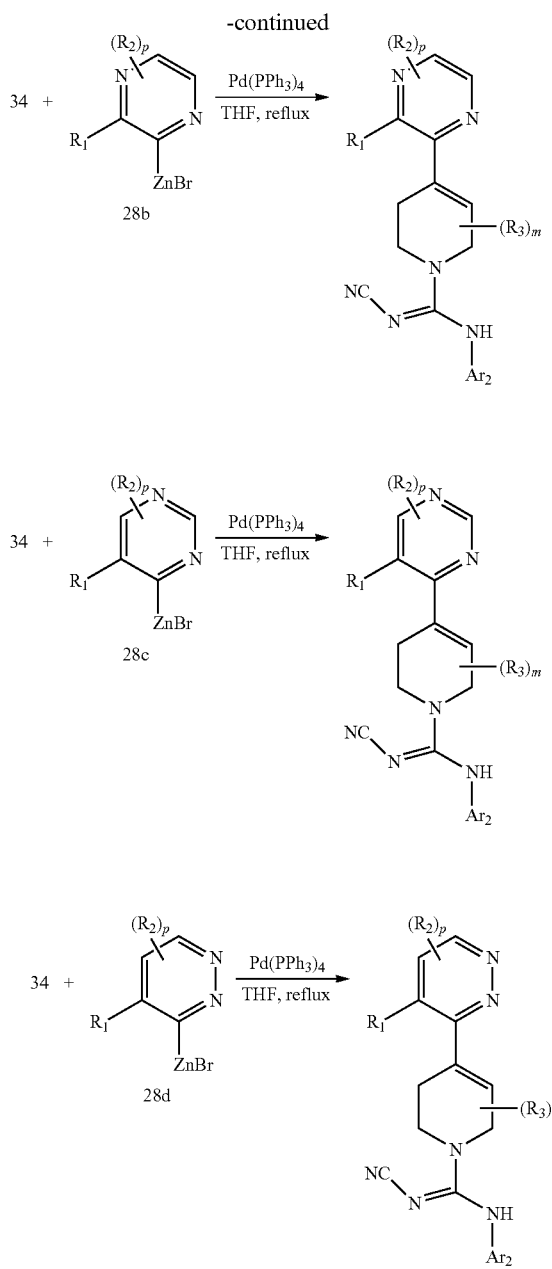

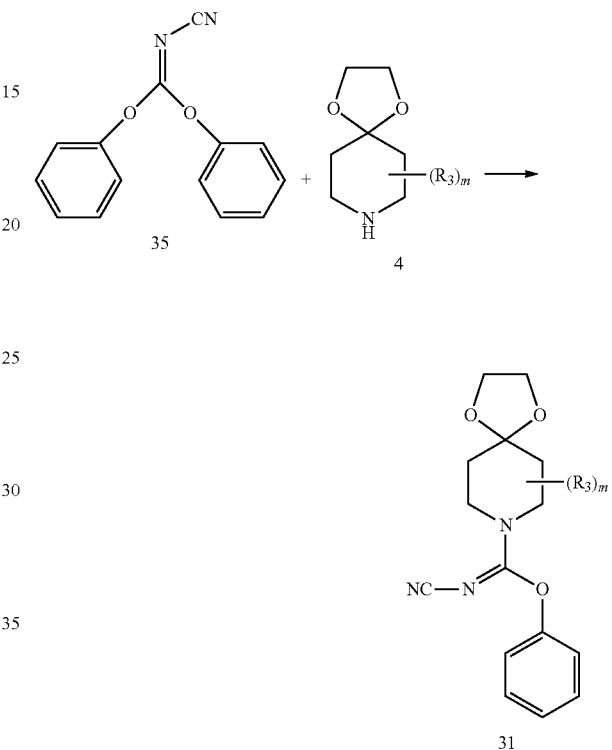

where Ar$_2$, R$_1$, R$_2$, R$_3$, n, m, and p are as defined above.

Pd(PPh$_3$)$_4$ is dissolved in THF (about 50 mL) and the compound of formula 34 (about 2.2 mmol) is added to the resulting mixture followed by a compound of formula 28a-d (about 6.6 mmol as a 0.5M solution in THF). The reaction mixture is then heated for about 1 h at the reflux temperature of the solvent. The reaction mixture is allowed to cool to about 25° C. and concentrated under reduced pressure to provide the Tetrahydropyridyl Compound where X is N—CN. The Tetrahydropyridyl Compound where X is N—CN can be further treated if desired. In one embodiment, the Tetrahydropyridyl Compound where X is N—CN is chromatographed by silica gel column chromatography.

Where m=1, R$_3$ is bonded to an sp3 carbon, and 34 is either racemic or a mixture of enantiomers, the resulting Tetrahydropyridyl Compound in scheme 2.6 will also be racemic or an enantiomeric mixtures. If a single stereoisomer is desired, it is possible to use chiral separation techniques known in the art, such as chiral chromatography or chiral resolution, to isolate a single isomer.

The compound of formula 31 can be obtained as shown below in scheme 2.7.

where R$_3$, and m are as defined above.

Compound 4 is reacted with diphenyl cyanocarbonimidate 35 (Sigma-Aldrich) in an aprotic solvent such as diethyl ether, di-n-propyl ether, THF, DCM, or toluene to provide the compound of formula 31. In one embodiment, the aprotic solvent is DCM and the reaction mixture of compound 4 and diphenyl cyanocarbonimidate 35 is allowed to react at about 25° C. In another embodiment, the aprotic solvent is toluene and the reaction mixture of compound 4 and diphenyl cyanocarbonimidate 35 is allowed to react at about 110° C. Compound 4 and diphenyl cyanocarbonimidate 35 are typically allowed to react for a period of about 0.5 h to about 24 h.

The compounds of formula 28a-d can be obtained as described above by methods known in the art.

5.6.2.4 Methods for Making the Tetrahydropyridyl Compounds where X is N—OH

The Tetrahydropyridyl Compounds where X is N—OH can be obtained in a manner analogous to schemes 2.6 and 2.7 in section 5.5.2.3, which is shown in scheme 2.8.

Scheme 2.8
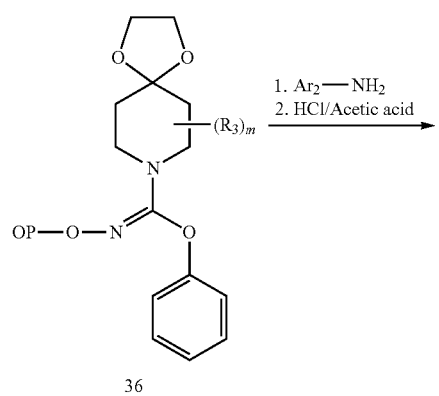
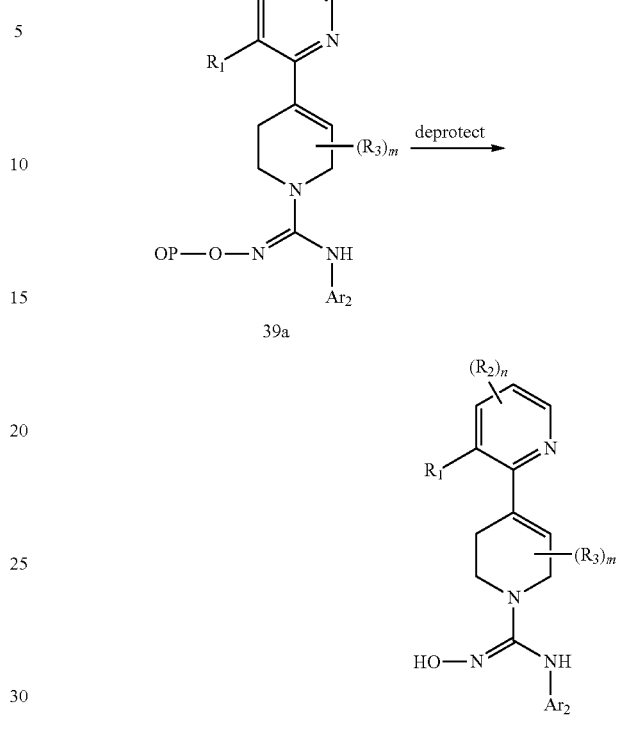
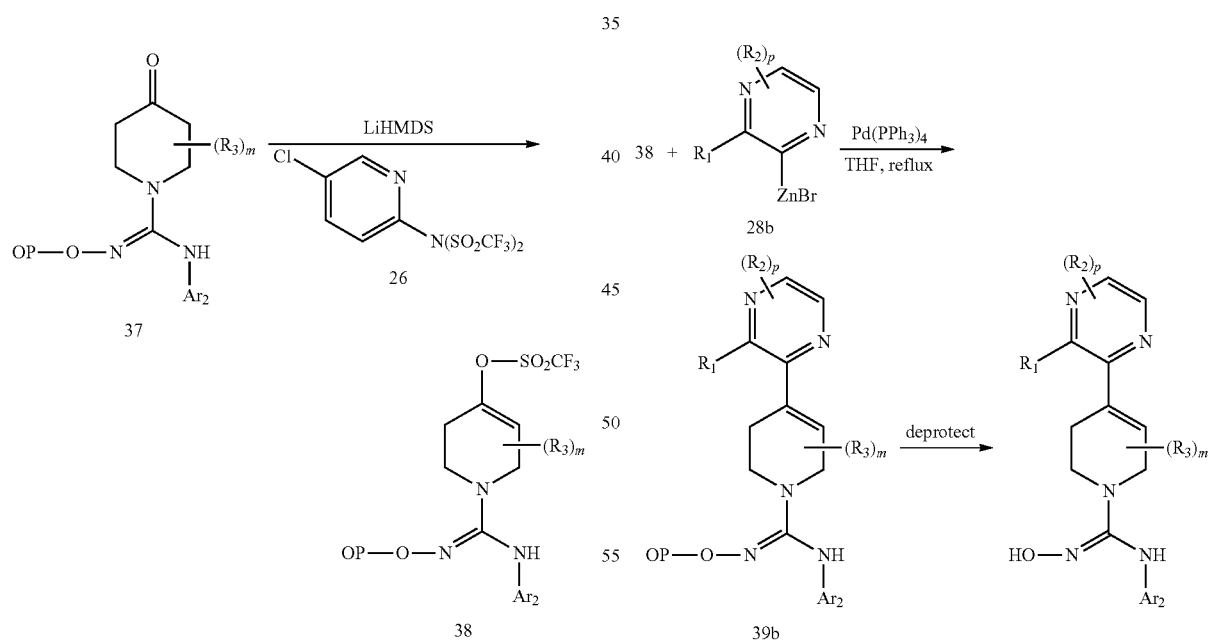

-continued

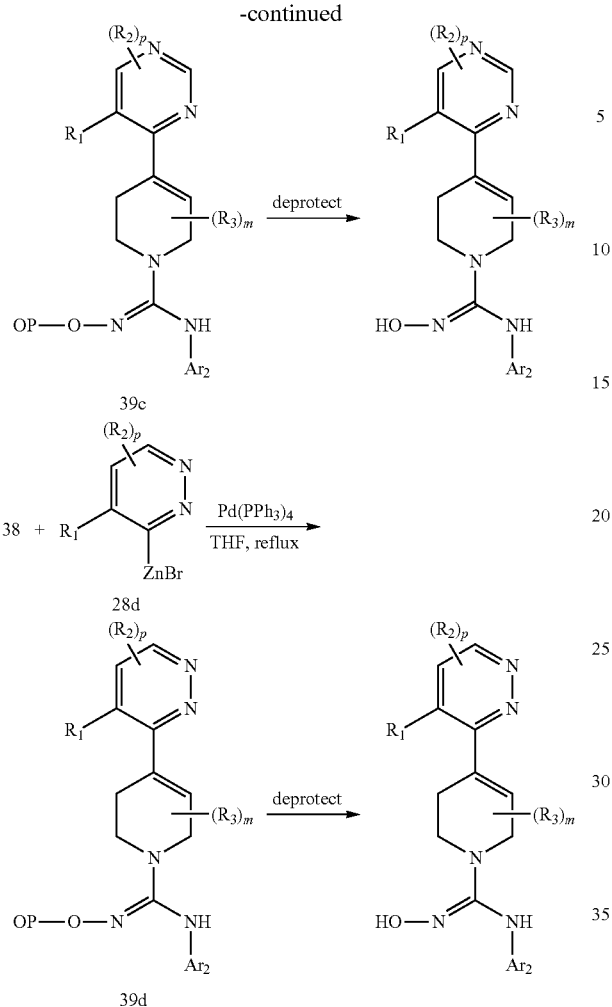

where $Ar_2$, $R_1$, $R_2$, $R_3$, n, m, and p are as defined above and P is an oxygen/hydroxyl protecting group.

The method for obtaining the Tetrahydropyridyl Compounds where X is N—OH as described above in scheme 2.8 is analogous to that described above in Schemes 2.5 and 2.6 to provide the Tetrahydropyridyl Compounds where X is N—CN except that a compound of formula 38 is used in place of the compound of formula 34.

The compound of formula 36 can be obtained as described below in scheme 2.9.

Scheme 2.9

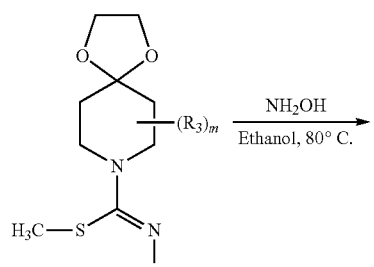

-continued

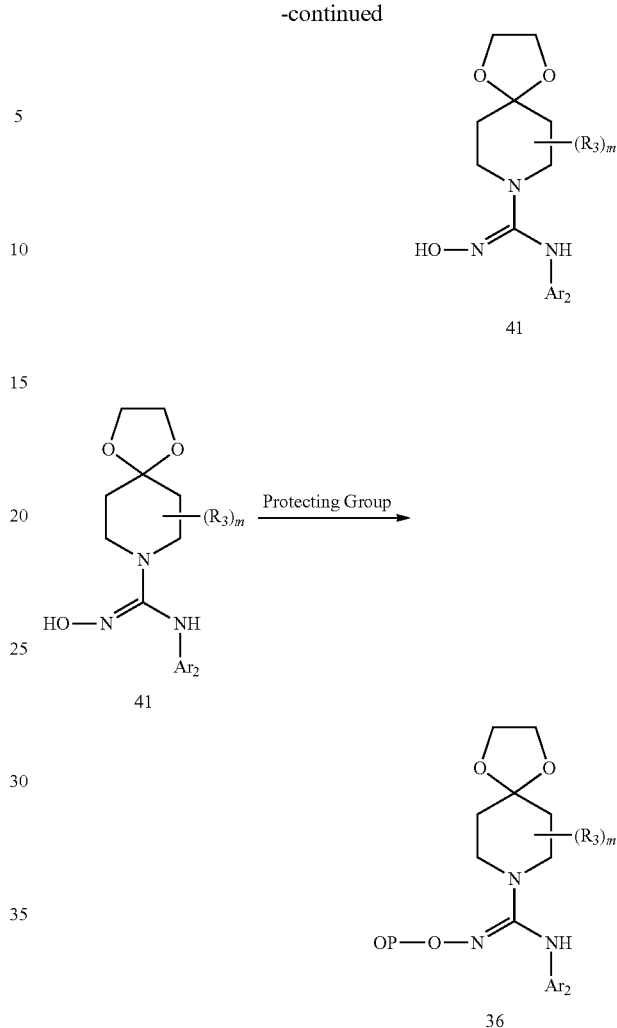

where $Ar_2$, $R_3$, and m are as defined above and P is an oxygen/hydroxyl protecting group.

A compound of formula 40 (about 0.3 mmol) is reacted with hydroxylamine (50 weight percent in water, about 5.8 mmol) in about 1.5 mL of ethanol with stirring at a temperature of about 80° C. for about 2 h. The mixture is then concentrated under reduced pressure to provide a compound of formula 41. The hydroxyl group of the compound of formula 41 is then protected using an hydroxyl protecting group to provide the compound of formula 36. Any hydroxyl protecting group known in the art can be used to protect the hydroxyl group in the compound of formula 41. Suitable hydroxyl protecting groups and methods for their removal are disclosed in T. W. Greene et al, *Protective Groups in Organic Synthesis* 17-200 (3d ed. 1999).

Where m=1, $R_3$ is bonded to an sp3 carbon, and 38 is either racemic or a mixture of enantiomers, the resulting Tetrahydropyridyl Compound in scheme 2.8 will also be racemic or enantiomeric mixtures. If a single stereoisomer is desired, it is possible to use chiral separation techniques known in the art, such as chiral chromatography or chiral resolution, to isolate a single isomer.

The compound of formula 40 can be obtained as shown below in scheme 2.10.

195

Scheme 2.10

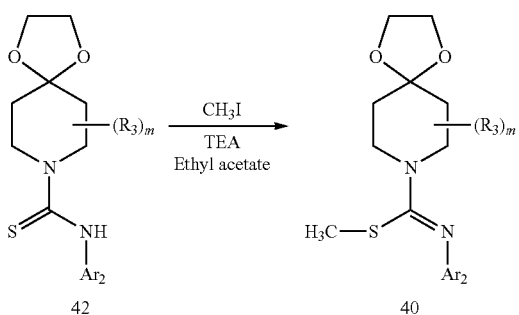

where $Ar_2$, $R_3$, and m are as defined above.

A solution of a compound of formula 42 (about 0.6 mmol), obtained as described above in section 4.4.2.2, in DCM is reacted with iodomethane (about 0.9 mmol) in about 3 mL of tetrahydrofuran with stirring at about 25° C. for about 12 h. Excess iodomethane is removed from the mixture under reduced pressure. A solution of triethylamine (about 1.74 mmol) in about 2.5 mL of ethyl acetate is then added to the mixture and the mixture is allowed to stir for about 2 h. The mixture is then concentrated under reduced pressure to provide the compound of formula 40 which can then be further treated if desired. In one embodiment, the compound of formula 40 is chromatographed using column chromatography or recrystallized.

5.6.2.5 Methods for Making the Tetrahydropyridyl Compounds where X is N—$OR_{10}$ The Tetrahydropyridyl Compounds where X is N—$OR_{10}$ can be obtained by reacting a Tetrahydropyridyl Compounds where X is N—OH, obtained as described above in Scheme 2.8, with L-($C_1$-$C_4$)alkyl, where L is —I, —Br, —Cl, or —F, in the presence of about 3 eq. of triethylamine in THF, with stirring at about 25° C. for about 12 h or at about 50° C. for about 3 h. The reaction mixture is concentrated under reduced pressure to provide a residue. The residue is then chromatographed using silica gel column chromatography eluted with a gradient elution of from 100:0 hexane:ethyl acetate to 25:75 hexane:ethyl acetate to provide the Tetrahydropyridyl Compounds where X is N—$OR_{10}$. In one embodiment, L is —I or —Br.

5.6.3 Methods for Making Compounds of Formula I where W is N and the Dashed Line is Absent The compounds of formula I where W is N and the dashed line is absent, i.e., "Piperazine Compounds," can be made using conventional organic synthesis or by the following illustrative methods shown in the schemes below.

196

5.6.3.1 Methods for Making Piperazine Compounds where X is O and $Ar_2$ is a Benzothiazolyl Group Piperazine Compounds where X is O, $Ar_2$ is a benzothiazolyl group, and $R_{20}$ is —H, can be obtained by the following illustrative method shown in scheme 3.1:

Scheme 3.1

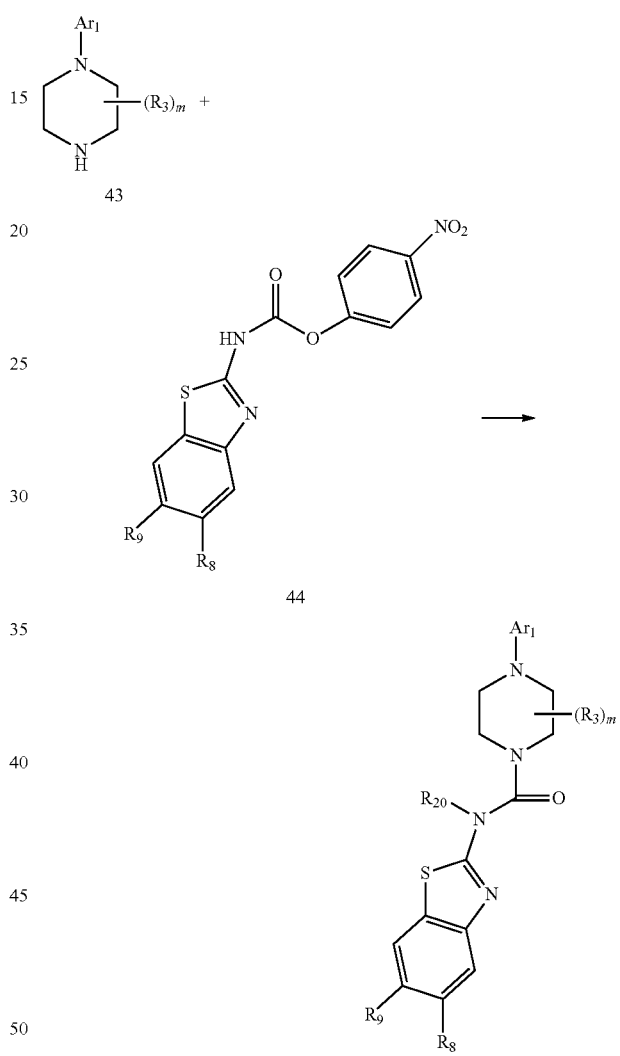

Piperazine Compounds where $Ar_1$, $R_3$, $R_8$, $R_9$ and m are as defined above.

A compound of formula 44 (about 2 mmol) is dissolved in an aprotic organic solvent (about 3 mL). To the resulting solution is added a compound of formula 43 (about 2 mmol) and the reaction mixture allowed to stir for about 10 min. The reaction mixture is concentrated under reduced pressure to provide the Piperazine Compounds where X is O, $Ar_2$ is a benzothiazolyl group, and $R_{20}$ is —H. Such Piperazine Compounds can be chromatographed on a silica column eluted with 5:95 ethyl acetate:hexane.

The compound of formula 44 can be obtained as shown below in scheme 3.2:

Scheme 3.2

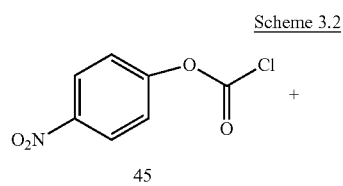

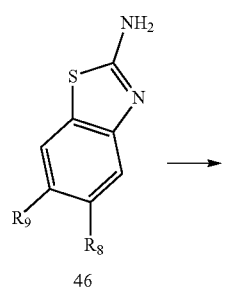

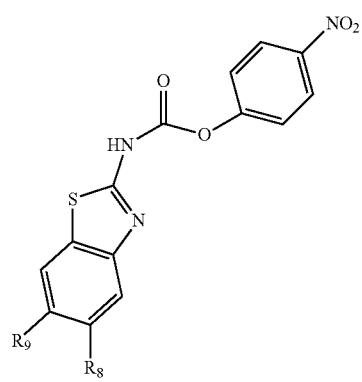

where $R_8$ and $R_9$ are as defined above.

A compound of formula 45 (about 0.75 mmol) in an aprotic organic solvent (about 0.04M) is cooled to about 0° C. To the cooled solution is slowly added a solution of a compound of formula 46 (about 0.75 mmol) in an aprotic organic solvent (about 0.4M). The reaction mixture is stirred at 0° C. for about 5 min. and about 0.75 mmol of triethylamine are added to the reaction mixture. The reaction mixture is then allowed to warm to a temperature of about 25° C. and concentrated under reduced pressure to provide the compound of formula 44. The compound of formula 45 is commercially available, e.g., from Sigma-Aldrich. Compounds of formula 46 are commercially available or can be prepared by the following illustrative method shown below in scheme 3.3:

Scheme 3.3

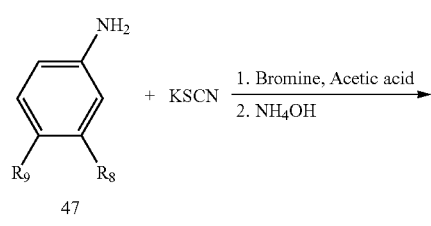

where $R_8$ and $R_9$ are as defined above.

To a stirred solution of aniline 47 (about 74 mmol) and potassium thiocyanate (about 148 mmol) in about 100 mL of glacial acetic acid is added dropwise a solution of bromine (about 74 mmol) in about 25 mL of glacial acetic acid. The flask containing the bromine in acetic acid is then rinsed with about 15 mL of acetic acid which is combined with the solution of aniline 47. The reaction mixture is vigorously stirred at a temperature of about 25° C. for between about 2 h and about 24 h. The reaction mixture is then poured over crushed ice (about 500 mL) and the pH of the resulting mixture adjusted to a value of about 10 using ammonium hydroxide to provide a precipitate. The resulting precipitate is collected by filtration and recrystallized from toluene to provide the compound of formula 46. Compounds of formula 47 are commercially available or can be prepared by methods known in the art.

The compound of formula 50a-d can be obtained as shown below in scheme 3.4:

Scheme 3.4

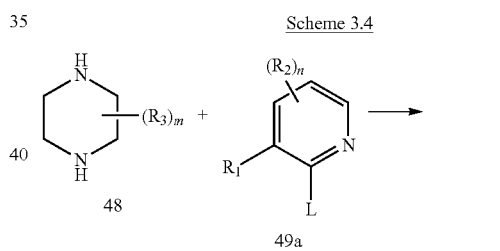

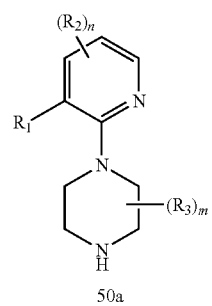

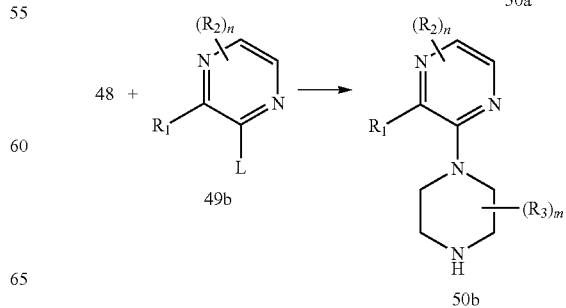

-continued

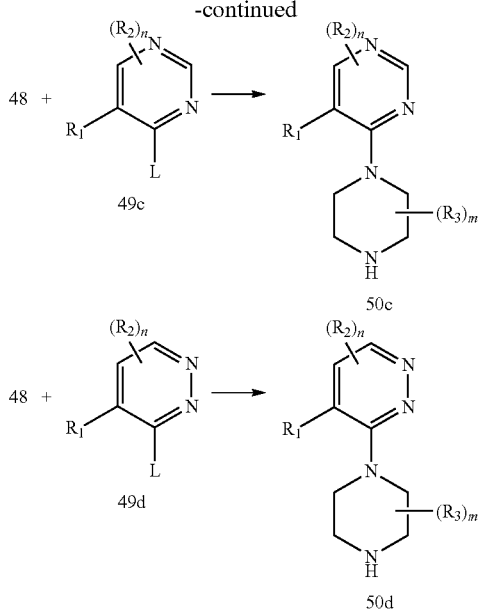

where $R_1$, $R_2$, $R_3$, m, n, and p are as defined above and L is a halogen.

A compound of formula 49a-d (about 20 mmol) is reacted with a compound of formula 48 (about 27.5 mmol) in about 15 mL of DMSO in the presence of triethylamine (about 30 mmol), optionally with heating, for about 24 h to provide a compound of formula 50a-d. The compound of formula 50a-d is isolated from the reaction mixture and further treated if desired. In one embodiment, the compound of formula 50a-d is chromatographed using column chromatography or recrystallized.

Compounds of formula 48 and 49a-d are commercially available or can be prepared by methods known in the art. The compound of formula 48 where m is 0 and the compound of formula 48 where m is 1 and $R_3$ is (R)—$CH_3$ or (S)—$CH_3$ are commercially available, e.g., from Sigma-Aldrich. In one embodiment, L is bromide, chloride, or iodide.

Piperazine Compounds where X is O, $Ar_2$ is a benzothiazolyl group, and $R_{20}$ is —($C_1$-$C_4$)alkyl can be obtained by the following illustrative method shown below in scheme 3.5:

Scheme 3.5

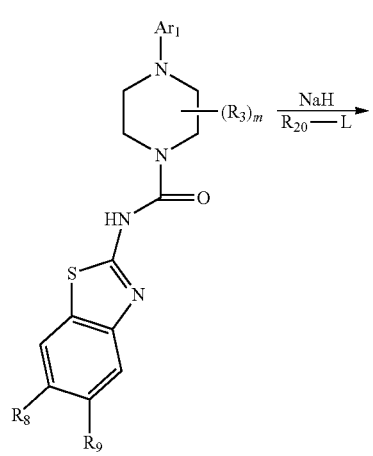

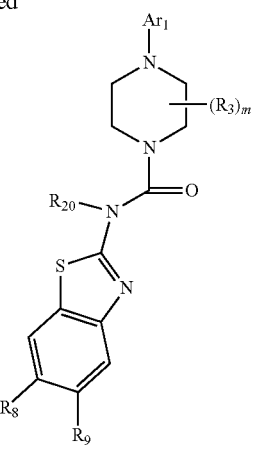

where $Ar_1$, $R_3$, $R_8$, $R_9$, $R_{20}$, and m are as defined above and L is a halogen.

To a solution of a Piperazine Compound where X is O, $Ar_2$ is a benzothiazolyl group, and $R_{20}$ is —H (about 1 eq.), obtained as described above in Scheme 3.1, in DMF at 0° C., is added a DMF solution of NaH (about 2 eq.). The reaction mixture is allowed to warm to a temperature of about 25° C. over about 1 h. To the resulting mixture is added about 1.2 eq. of an alkyl halide, $R_{20}$-L, and the reaction mixture allowed to stir until the Piperazine Compounds where X is O, $Ar_2$ is a benzothiazolyl group, and $R_{20}$ is —($C_1$-$C_4$)alkyl form. The progress of the reaction can be monitored using conventional analytical techniques including, but not limited to, high pressure liquid chromatography (HPLC), column chromatography, thin-layer chromatography (TLC), column chromatography, gas chromatography, mass spectrometry, and nuclear magnetic resonance spectroscopy such as $^1$H and $^{13}$C NMR. Piperazine Compounds can be isolated and further treated if desired. In one embodiment, the Piperazine Compound is isolated by removing the solvent under reduced pressure. In another embodiment, the Piperazine Compound is isolated by extraction. Piperazine Compounds can be further treated, for example, by column chromatography or recrystallization.

5.6.3.2 Methods for Making Piperazine Compounds where X is S and $Ar_2$ is a Benzothiazolyl Group Piperazine Compounds where X is S, $Ar_2$ is a benzothiazolyl group, and $R_{20}$ is —H can be obtained by the following illustrative method in scheme 3.6.

Scheme 3.6

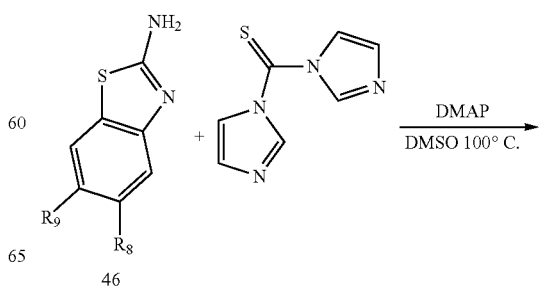

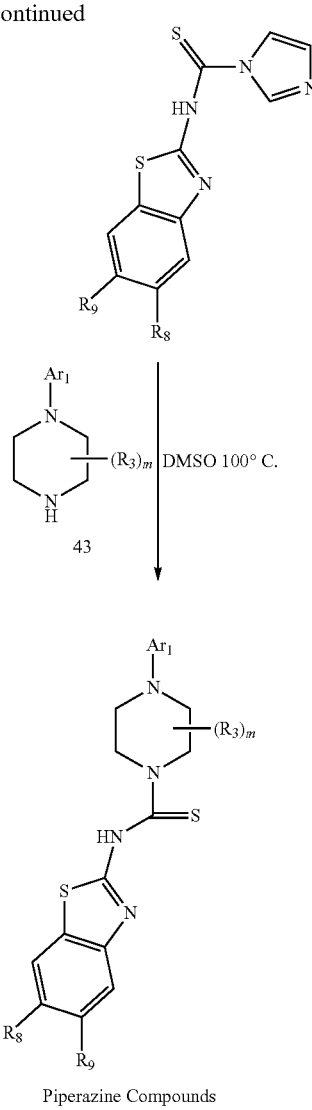

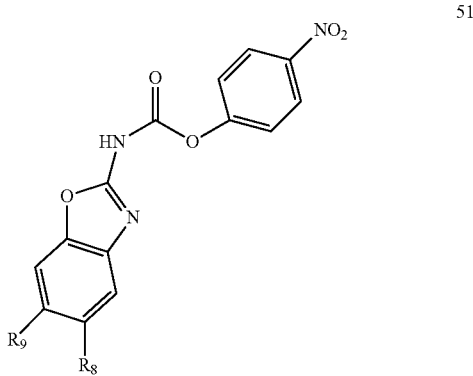

where $Ar_1$, $R_3$, $R_8$, $R_9$ and m are as defined above.

A compound of formula 46 (about 2 mmol), 1,1'-thiocarbonyldiimidazole (about mmol) (Sigma-Aldrich), and 4-dimethylaminopyridine (DMAP) (Sigma-Aldrich) are suspended in DMSO (about 3 mL) at a temperature of about 25° C. and the resulting mixture is heated at about 100° C. for about 6 h. The reaction mixture is then cooled to a temperature of about 25° C. and a compound of formula 43 (about 2 mmol) is added to the reaction mixture and the reaction mixture is heated to about 100° C. for about 16 h. The reaction mixture is concentrated under reduced pressure to provide Piperazine Compounds where X is S, $Ar_2$ is a benzothiazolyl group, and $R_{20}$ is —H. Piperazine Compounds can be chromatographed on a silica column eluted with 5:95 ethyl acetate:hexane.

Piperazine Compounds where X is S, $Ar_2$ is a benzothiazolyl group, and $R_{20}$ is —($C_1$-$C_4$)alkyl can be obtained by a method analogous to the method used to obtain Piperazine Compounds where X is O, $Ar_2$ is a benzothiazolyl group, and $R_{20}$ is —($C_1$-$C_4$)alkyl as described above in Scheme 3.5 except that a Piperazine Compound where X is S, $Ar_2$ is a benzothiazolyl group, and $R_{20}$ is —H, obtained as described above in Scheme 3.6, is used in place of the Piperazine Compound where X is O, $Ar_2$ is a benzothiazolyl group, and $R_{20}$ is —H.

5.6.3.3 Methods for Making Piperazine Compounds where X is O and $Ar_2$ is a Benzooxazolyl Group Piperazine Compounds where X is O, $Ar_2$ is a benzooxazolyl group, and $R_{20}$ is —H can be obtained by a method analogous to that used to obtain the Piperazine Compounds where X is O, $Ar_2$ is a benzothiazolyl, and $R_{20}$ is —H as described in section 5.6.3.1, scheme 3.1, except that a compound of formula 51, shown below:

51

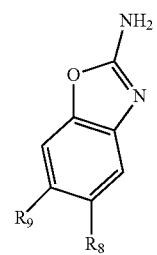

where $R_8$ and $R_9$ are as defined above, is used in place of the compound of formula 44.

The compound of formula 51 can be obtained by a method analogous to that used to obtain the compound of formula 44 as described above in Scheme 3.2 except that a compound of formula 52, shown below,

52

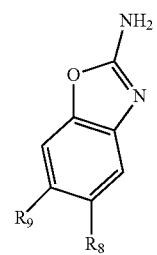

where $R_8$ and $R_9$ are as defined above, is used in place of compound 46.

5.6.3.4 Methods for Making Piperazine Compounds Where X is S and $Ar_2$ is a Benzooxazolyl Group Piperazine Compounds where X is S, $Ar_2$ is a benzooxazolyl group, and $R_{20}$ is —H can be obtained by a method analogous to that used to obtain the Piperazine Compounds described above in Scheme 3.6 except that a compound of formula 53 is used in place of the compound of formula 44. The compound of Formula 53 can be obtained as described above.

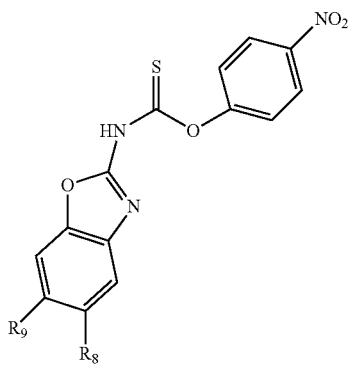

53

Piperazine Compounds where X is S, $Ar_2$ is a benzooxazolyl group, and $R_{20}$ is —$(C_1$-$C_4)$alkyl can be obtained by a method analogous to the method used to obtain the Piperazine Compounds described above in Scheme 3.5 except that a Piperazine Compound where X is S, $Ar_2$ is a benzooxazolyl group, and $R_{20}$ is —H, obtained as described above, is used in place of the Piperazine Compound where X is O, $Ar_2$ is a benzothiazolyl group, and $R_{20}$ is —H.

5.6.3.5 Methods for Making Piperazine Compounds where X is O and $Ar_2$ is a Benzoimidazolyl Group Piperazine Compounds where X is O, $Ar_2$ is a benzoimidazolyl group, the amide $R_{20}$ is —H, and the benzoimidazolyl group $R_{20}$ is —H can be obtained by a method analogous to that used to obtain the Piperazine Compounds described above in Scheme 3.1 except that a compound of formula 54, shown below,

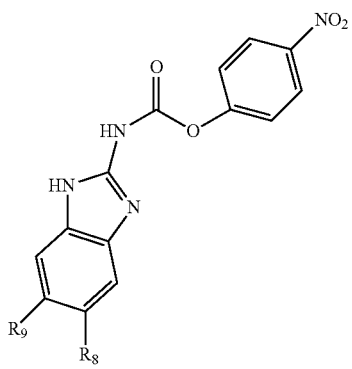

54 where $R_8$ and $R_9$ are as defined above, is used in place of the compound of formula 44.

The Compound of formula 54 can be obtained by a method analogous to that used to obtain the compound of formula 44 as described in section 5.6.3.1, Scheme 3.2, except that a compound of formula 55, shown below,

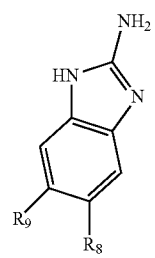

55 where $R_8$ and $R_9$ are as defined above, is used in place of the compound of formula 46. Compounds of formula 55 are commercially available or can be prepared by procedures known in the art. An illustrative procedure for obtaining compound 55 is shown below in Scheme 3.7:

Scheme 3.7 where $R_8$ and $R_9$ are as defined above.

A compound of formula 56 (about 1 mmol), prepared as described below in Scheme 3.11, is dissolved in excess aqueous ammonia in a sealed tube and heated at a temperature of between about 140° C. and 150° C. for about 72 h. The mixture is cooled to a temperature of about 25° C. and concentrated under reduced pressure to provide a residue. In another embodiment, the mixture is cooled to a temperature of about 25° C., extracted with an organic solvent, the organic phase separated from the aqueous phase, and the organic phase is concentrated under reduced pressure to provide a residue. If desired, the residue is then further treated to provide the compound of formula 55. In one embodiment, the residue is recrystallized. In another embodiment, the residue is chromatographed using flash chromatography.

Compounds of formula 56 are commercially available or can be prepared by procedures known in the art. An illustrative method for preparing the compound of formula 56 is shown below in scheme 3.8:

Scheme 3.8

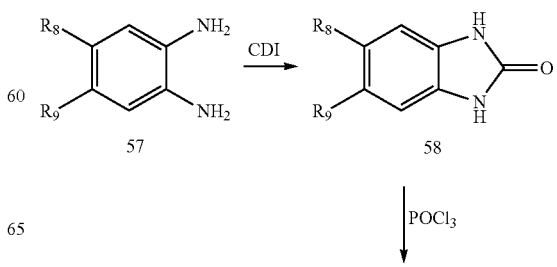

| POCl₃

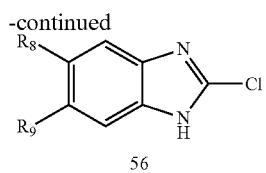

where $R_8$ and $R_9$ are as defined above.

A compound of formula 57 (about 5 mmol to about 10 mmol) and di(1H-imidazol-1-yl)methanone (CDI, about 2 eq) is dissolved in THF (about 50 mL to about 70 mL) and the reaction mixture is heated at reflux temperature for about 4 hours. The reaction mixture is then concentrated under reduced pressure to provide a residue. Ethyl acetate (about 50 mL) is added to the residue and the resulting insoluble material is collected by filtration and washed with ethyl acetate to provide a compound of formula 58. The compound of formula 58 is then reacted with POCl$_3$ according to the procedure described in *J. Med. Chem.* 40:586-593 (1997) to provide the compound of formula 56.

The compounds of formula 57 are commercially available or can be prepared by procedures known in the art. An illustrative procedure for obtaining a compound of formula 57 is shown below in scheme 3.9:

Scheme 3.9

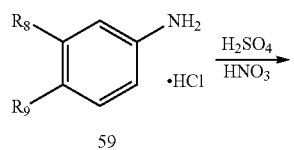

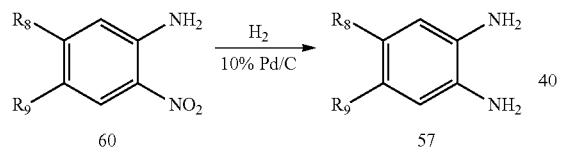

where $R_8$ and $R_9$ are as defined above.

Aniline hydrochloride 59 (about 12 mmol) is dissolved in concentrated sulfuric acid (about 10 mL) at 0° C. and the resulting solution cooled to a temperature of about −13° C. to about −15° C. About 1 mL of 70% nitric acid is added to the resulting solution over a time period of about 30 min. and the reaction mixture allowed to stir for about 2 h at a temperature of from about −13° C. to about −15° C. The reaction mixture is then poured into ice water (about 100 mL), neutralized with 5% to 10% aqueous sodium hydroxide, and extracted with about 50 mL of chloroform. The chloroform layer is separated from the aqueous layer. Concentration under reduced pressure provides a residue that is chromatographed using flash chromatography (silica column and chloroform eluent) to provide a compound of formula 60. The compound of formula 60 is dissolved in ethanol (about 50 mL) and hydrogenated for about 12 h at a temperature of about 25° C. using 10% palladium on carbon as a catalyst. The catalyst is removed by filtration and the ethanol is removed under reduced pressure to provide a residue that is chromatographed using flash chromatography (silica gel eluted with 20:1 dichloromethane:methanol) to provide the compound of formula 57. The compounds of formula 59 are commercially available or can be prepared by procedures known in the art.

Piperazine Compounds where X is O, Ar$_2$ is a benzoimidazolyl group, the amide R$_{20}$ is —H, and the benzoimidazolyl group R$_{20}$ is —(C$_1$-C$_4$)alkyl can be obtained by a method analogous to that used to obtain the Piperazine Compounds where X is O, Ar$_2$ is a benzoimidazolyl group, the amide R$_{20}$ is —H, and the benzoimidazolyl group R$_{20}$ is —H except that a compound of formula 61, shown below,

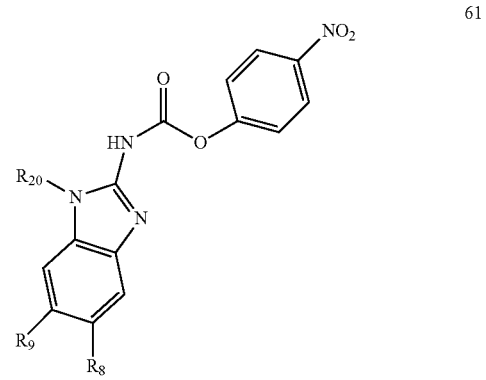

where $R_8$, $R_9$, and $R_{20}$ are as defined above, is used in place of the compound of formula 54. The compound of formula 61 can be obtained by a method analogous to that used to obtain the compound of formula 54 except that a compound of formula 62, shown below,

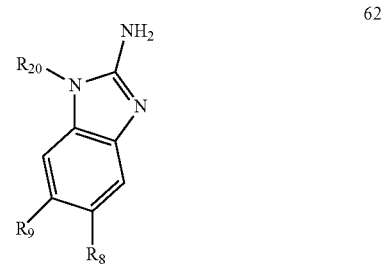

where $R_8$, $R_9$, and $R_{20}$ are as defined above, is used in place of the compound of formula 55. The compound of formula 62 can be obtained as shown below in scheme 3.10.

Scheme 3.10

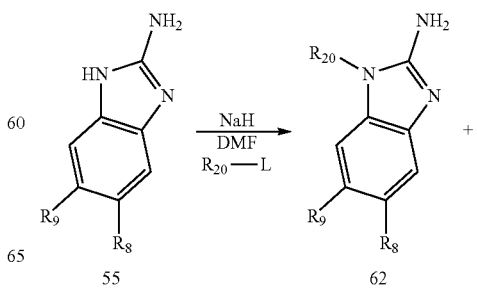

-continued

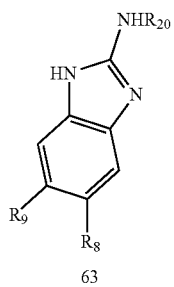

where $R_8$, $R_9$, and $R_{20}$ are as defined above and L is a halogen.

NaH (about 2 eq) is added to a solution of a compound of formula 55 in DMF at 0° C. and the resulting mixture is allowed to stir and to warm to a temperature of about 25° C. over a period of about one hour. An alkyl halide, $R_{20}$-L, (about 1 eq.) is then added to the solution and the reaction mixture allowed to stir until a mixture of a compound of formula 62 and a compound of formula 63 is produced. In one embodiment, the alkyl halide is an alkyl iodide. The formation of the compound of formula 62 and the compound of formula 63 can be monitored by analytical methods known in the art including, but not limited to, those described above. Water is then added to the reaction mixture to produce a precipitate of the compound of formula 62 and the compound of formula 63, which are collected by filtration. The compound of formula 62 and the compound of formula 63 are then separated to provide the compound of formula 62. The compound of formula 62 and the compound of formula 63 can be separated by methods known in the art including, but not limited to, column chromatography, preparative TLC, preparative HPLC, and preparative GC.

5.6.3.6 Methods for Making Piperazine Compounds where X is S and $Ar_2$ is a Benzoimidazolyl Group Piperazine Compounds where X is S, $Ar_2$ is a benzoimidazolyl group, the thioamide $R_{20}$ is —H, and the benzoimidazolyl group $R_{20}$ is —H can be obtained by a method analogous to that used to obtain the Piperazine Compounds described above in scheme 3.6 except that a compound of formula 55 is used in place of the compound of formula 46. The compound of formula 55 can be obtained as described above.

Piperazine Compounds where X is S, $Ar_2$ is a benzoimidazolyl group, the thioamide $R_{20}$ is —H, and the benzoimidazolyl group $R_{20}$ is —$(C_1-C_4)$alkyl can be obtained by a method analogous to that used to obtain Piperazine Compounds as described in section 5.6.3.2, scheme 3.6, except that a compound of formula 62 is used in place of the compound of formula 46. The compound of formula 62 can be obtained as described above.

Piperazine Compounds where X is S, $Ar_2$ is a benzoimidazolyl group, the thioamide $R_{20}$ is —$(C_1-C_4)$alkyl, and the benzoimidazolyl group $R_{20}$ is —H can be obtained by a method analogous to that used to obtain the Piperazine Compounds as described above in scheme 3.5 except that a Piperazine Compound where X is S and each $R_{20}$ is —H, prepared as described above, is used in place of the Piperazine Compounds where X is O and the amide $R_{20}$ is —H.

Piperazine Compounds where X is S, $Ar_2$ is a benzoimidazolyl group, the thioamide $R_{20}$ is —$(C_1-C_4)$alkyl, and the benzoimidazolyl group $R_{20}$ is —$(C_1-C_4)$alkyl can be obtained by a method analogous to that used to obtain the Piperazine Compounds where X is O and $R_{20}$ is —$(C_1-C_4)$ alkyl as described above in scheme 3.5 except that the Piperazine Compound where X is S, the thioamide $R_{20}$ is —H, and the benzoimidazolyl group $R_{20}$ is —$(C_1-C_4)$alkyl, prepared as described above, is used in place of the Piperazine Compound where X is O and $R_{20}$ is —H.

Suitable aprotic organic solvents for use in the illustrative methods include, but are not limited to, DCM, DMSO, chloroform, toluene, benzene, acetonitrile, carbon tetrachloride, pentane, hexane, ligroin, and diethyl ether. In one embodiment, the aprotic organic solvent is DCM.

Certain Piperazine Compounds can have one or more asymmetric centers and therefore exist in different enantiomeric and diastereomeric forms. A Piperazine Compound can be in the form of an optical isomer or a diastereomer. Accordingly, the invention encompasses Piperazine Compounds and their uses as described herein in the form of their optical isomers, diastereomers, and mixtures thereof, including a racemic mixture.

In addition, one or more hydrogen, carbon or other atoms of a Piperazine Compound can be replaced by an isotope of the hydrogen, carbon or other atoms. Such compounds, which are encompassed by the invention, are useful as research and diagnostic tools in metabolism pharmacokinetic studies and in binding assays.

5.7 Therapeutic Uses of Compounds of Formula I

In accordance with the invention, the compounds of formula I are administered to an animal in need of treatment or prevention of a Condition.

In one embodiment, an effective amount of a compound of formula I can be used to treat or prevent any condition treatable or preventable by inhibiting TRPV1. Examples of Conditions that are treatable or preventable by inhibiting TRPV1 include, but are not limited to, pain, UI, an ulcer, IBD, and IBS.

The compounds of formula I, or a pharmaceutically acceptable derivative thereof, can be used to treat or prevent acute or chronic pain. Examples of pain treatable or preventable using the compounds of formula I include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The compounds of formula I, or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the compounds of formula I can be used to treat or prevent pain associated with inflammatory diseases including, but not limited to: organ transplant rejection; reoxygenation injury resulting from organ transplantation (see Grupp et al., J. Mol. Cell Cardiol. 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The compounds of formula I can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The compounds of formula I, or a pharmaceutically acceptable derivative thereof, can be used to treat or prevent UI. Examples of UI treatable or preventable using the compounds of formula I include, but are not limited to, urge incontinence, stress incontinence, overflow incontinence, neurogenic incontinence, and total incontinence.

The compounds of formula I, or a pharmaceutically acceptable derivative thereof, can be used to treat or prevent an ulcer. Examples of ulcers treatable or preventable using the compounds of formula I include, but are not limited to, a duodenal ulcer, a gastric ulcer, a marginal ulcer, an esophageal ulcer, or a stress ulcer.

The compounds of formula I, or a pharmaceutically acceptable derivative thereof, can be used to treat or prevent IBD, including Crohn's disease and ulcerative colitis.

The compounds of formula I, or a pharmaceutically acceptable derivative thereof, can be used to treat or prevent IBS. Examples of IBS treatable or preventable using the compounds of formula I include, but are not limited to, spastic-colon-type IBS and constipation-predominant IBS.

Applicants believe that the compounds of formula I, or a pharmaceutically acceptable derivative thereof, are antagonists for TRPV1. The invention also relates to methods for inhibiting TRPV1 function in a cell comprising contacting a cell capable of expressing TRPV1 with an effective amount of a compound of formula I, or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. The method is also useful for inhibiting TRPV1 function in a cell in vivo, in an animal, a human in one embodiment, by contacting a cell, in an animal, with an effective amount of a compound of formula I, or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

5.8 Therapeutic/Prophylactic Administration and Compositions of the Invention Due to their activity, compounds of formula I, or a pharmaceutically acceptable derivative thereof, are advantageously useful in veterinary and human medicine. As described above, compounds of formula I, or a pharmaceutically acceptable derivative thereof, are useful for treating or preventing a Condition.

When administered to an animal, compounds of formula I, or a pharmaceutically acceptable derivative thereof, are typically administered as a component of a composition that comprises a pharmaceutically acceptable carrier or excipient. The present compositions, which comprise a compound of formula I, or a pharmaceutically acceptable derivative thereof, can be administered orally. Compounds of formula I, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the compound of formula I, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of compounds of formula I, or a pharmaceutically acceptable derivative thereof, into the bloodstream.

In specific embodiments, it can be desirable to administer the compounds of formula I, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the compounds of formula I, or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of formula I can be formulated as a suppository, with traditional binders and excipients such as triglycerides.

In another embodiment, the compounds of formula I, or a pharmaceutically acceptable derivative thereof, can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the compounds of formula I, or a pharmaceutically acceptable derivative thereof, can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Langer and Peppas, *J. Macromol. Sci. Rev. Macromol. Chem.* C23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the compounds of formula I, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the compound of formula I is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or can contain pH buffering agents.

The present compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the compounds of formula I, or a pharmaceutically acceptable derivative thereof, are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

The compounds of formula I, or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a compound of formula I to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the compound of formula I, and can thus reduce the occurrence of adverse side effects.

Controlled- or sustained-release compositions can be designed to immediately release an amount of a compound of formula I, or a pharmaceutically acceptable derivative thereof, that promptly produces the desired therapeutic or prophylactic effect, and gradually and continually release other amounts of the compound of formula I to maintain this level of therapeutic or prophylactic effect over an extended period of time. To maintain a constant level of the compound of formula I in the body, the compound of formula I can be released from the dosage form at a rate that will replace the amount of compound of formula I being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In another embodiment, the compounds of formula I, or a pharmaceutically acceptable derivative thereof, can be formulated for intravenous administration. Typically, compositions for intravenous administration comprise sterile isotonic aqueous buffer. Where necessary, the compositions can also include a solubilizing agent. Compositions for intravenous administration can optionally include a local anaesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of formula I are to be administered by infusion, they can be dispensed, for example, with an infusion bottle containing sterile pharmaceutical grade water or saline. Where the compounds of formula I, or a pharmaceutically acceptable derivative thereof, are administered by injection, an ampoule of sterile water for injection or saline can be provided so that the ingredients can be mixed prior to administration.

The amount of the compound of formula I, or a pharmaceutically acceptable derivative thereof, that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will typically range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a compound of formula I; in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one compound of formula I, or a pharmaceutically acceptable derivative thereof, is administered, the effective dosage amounts correspond to the total amount administered.

Where a cell capable of expressing TRPV1 is contacted with a compound of formula I in vitro, the amount effective for inhibiting the TRPV1 receptor function in a cell will typically range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the compound of formula I, or a pharmaceutically acceptable derivative thereof, is from about 0.01 µL to about 1 mL. In another embodiment, the volume of solution or suspension is about 200 µL.

The compounds of formula I, or a pharmaceutically acceptable derivative thereof, can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering to the animal being administered a compound of formula I, or a pharmaceutically acceptable derivative thereof, another therapeutic agent. In one embodiment, the other therapeutic agent is administered in an effective amount.

The present methods for inhibiting TRPV1 function in a cell capable of expressing TRPV1 can further comprise contacting the cell with an effective amount of another therapeutic agent.

Effective amounts of the other therapeutic agents are known in the art. However, it is within the skilled artisan's purview to determine the other therapeutic agent's optimal effective-amount range. In one embodiment of the invention, where another therapeutic agent is administered to an animal, the effective amount of the compound of formula I is less than its effective amount would be where the other therapeutic agent is not administered. In this case, without being bound by theory, it is believed that the compounds of formula I and the other therapeutic agent act synergistically to treat or prevent a Condition.

The other therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam, isoxicam, and pharmaceutically acceptable derivatives thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9$^{th}$ ed. 1996) and Glen R. Hanson, *Analgesic, Antipyretic and Anti-Inflammatory Drugs* in Remington: *The Science and Practice of Pharmacy Vol II* 1196-1221 (A. R. Gennaro ed., 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can also be an agent useful for reducing any potential side effects of a compound of formula I. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnaciprine, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antogonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT$_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of formula I, or a pharmaceutically acceptable derivative thereof, and the other therapeutic agent can act additively or, in one embodiment, synergistically. In one embodiment, a compound of formula I is administered concurrently with another therapeutic agent; for example, a composition comprising an effective amount of a compound of formula I and an effective amount of another therapeutic agent can be administered. Alternatively, a composition comprising an effective amount of a compound of formula I and a different composition comprising an effective amount of another therapeutic agent can be concurrently administered. In another embodiment, an effective amount of a compound of formula I is administered prior or subsequent to administration of an effective amount of another therapeutic agent. In this embodiment, the compound of formula I is administered while the other therapeutic agent exerts its therapeutic effect, or the other therapeutic agent is administered while the compound of formula I exerts its therapeutic effect for treating or preventing a Condition.

A composition of the invention is prepared by a method comprising admixing a compound of formula I or a pharmaceutically acceptable derivative and a pharmaceutically acceptable carrier or excipient. Admixing can be accomplished using methods known for admixing a compound (or salt) and a pharmaceutically acceptable carrier or excipient. In one embodiment, the compound of formula I is present in the composition in an effective amount.

5.9 Kits

The invention further encompasses kits that can simplify the administration of a compound of formula I, or a pharmaceutically acceptable derivative thereof, to an animal.

A typical kit of the invention comprises a unit dosage form of a compound of formula I. In one embodiment, the unit dosage form is a container, which can be sterile, containing an effective amount of a compound of formula I and a pharmaceutically acceptable carrier or excipient. The kit can further comprise a label or printed instructions instructing the use of the compound of formula I to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a compound of formula I, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experi-

6. EXAMPLES

6.1 Examples 1-9, 10A and 10B: Syntheses of Compounds of Formula I

Example 1: The Syntheses of Compounds Z1, I1, D2, S1, I6, Y1, J6

2,3-Dichloro-5-formylpyridine

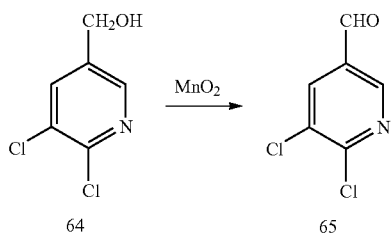

To a 500 mL round-bottom flask, manganese oxide (43.5 g, 0.50 mol) was added to a solution of 2,3-dichloro-5-hydroxylmethylpyridine (64, 8.10 g, 50.0 mmol) in anhydrous CH$_2$Cl$_2$ (150 mL). The reaction mixture was stirred at a temperature of about 25° C. for 48 h, filtered through CELITE, and concentrated under reduced pressure. The mixture was chromatographed by a silica gel chromatography column eluting with a gradient of ethyl acetate (0%-40%)/hexanes to provide 7.2 g of 65 (90% yield). $^1$H NMR (400 MHz, CDCl$_3$) δ 10.08 (1H, s), 8.77 (1H, d, J=1.97 Hz), 8.25 (1H, d, J=1.97 Hz). LC/MS (M+1): 176.

2,3-Dichloro-5-vinylpyridine

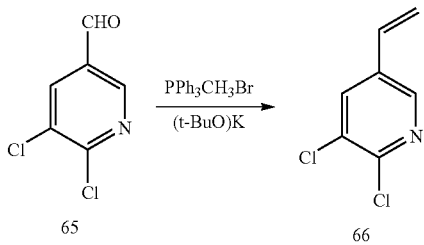

To a stirred slurry of methyltriphenylphosphonium bromide (10.0 g) in toluene (200 mL) at 0° C. was added potassium t-butoxide (3.07 g) portionwise to produce a yellow slurry. After 1 hr, the reaction mixture was cooled to −20° C. and 65 (4.0 grams, 22.72 mmol) dissolved in tetrahydrofuran (6 mL) was added dropwise to produce a purple colored slurry. The reaction mixture was heated to 0° C. and stirred for additional 1 hr. Then the reaction mixture was treated with saturated aqueous brine (150 mL) and diluted with ethyl acetate (200 mL). The resulting organic layer was washed with brine, dried over anhydrous sodium sulfate, and concentrated under reduced pressure. The resulting product was chromatographed by silica gel chromatography column eluting with a gradient of ethyl acetate (0%-10%)/hexanes to provide 2.77 g of 66 (70% yield). $^1$H NMR (400 MHz, CDCl$_3$) δ 8.30 (1H, d, J=2.19 Hz), 7.80 (1H, d, J=2.19 Hz), 6.63 (1H, dd, J=10.96, 17.80 Hz), 5.86 (1H, d, J=17.80 Hz), 5.45 (1H, d, J=10.96 Hz). LC/MS (M+1): 174.

(S)-1-(5,6-dichloropyridin-3-yl)ethane-1,2-diol and (R)-1-(5,6-dichloropyridin-3-yl)ethane-1,2-diol

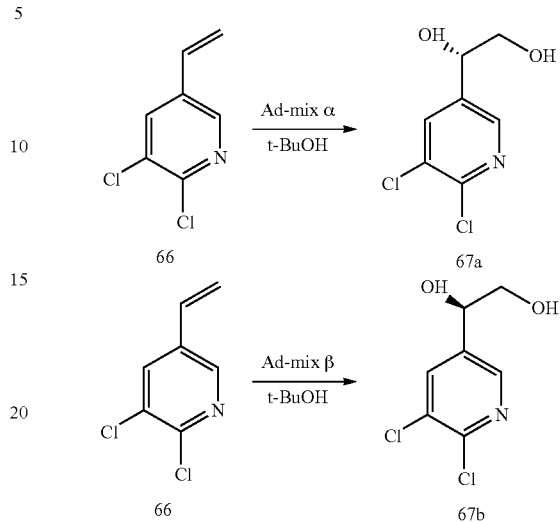

To a stirred slurry of AD-mix α (8.95 g) or AD-mix β (8.95 g) in water (32 mL) and t-butanol (27 mL) at 0° C. was added a solution of 66 (0.909 g, 5.25 mmol) in t-butanol (5 mL). After 24 hrs, solid sodium sulfite (9.57 g) was added and the resulting slurry was allowed to stir at a temperature of about 25° C. for 30 min. The mixture was extracted three times with ethyl acetate (50 mL for each extraction). The organic portions were combined, washed with brine, dried (Na$_2$SO$_4$), and concentrated under reduced pressure. The mixture was chromatographed by a silica gel chromatography column eluting with ethyl acetate (50%-100%)/hexanes to provide 0.75 g of product (67a for AD-mix α or 67b for AD-mix β) as a white solid (70% yield). $^1$H NMR (400 MHz, CDCl$_3$) δ 8.29 (1H, dd, J=0.44, 1.97 Hz), 7.87 (1H, dd, J=0.66, 2.19 Hz), 4.87 (1H, m), 3.84 (1H, m), 3.66 (1H, m), 2.83 (1H, d, J=5.92 Hz), 2.11 (1H, t, J=5.92 Hz). LC/MS (M+1): 208.

(S)-3-Chloro-5-(1,2-dihydroxy-ethyl)-3',6'-dihydro-2'H-[2,4']bipyridinyl-1'-carboxylic acid tert-butyl ester

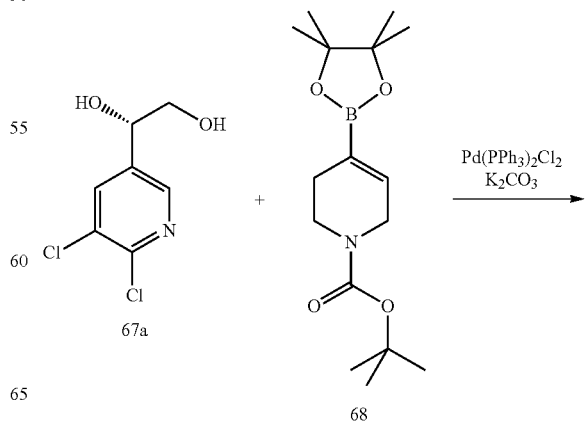

-continued

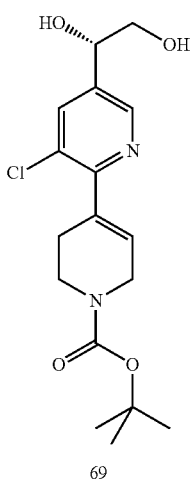

69

A 150 mL vessel was charged with 67a (0.70 g, 3.37 mmol), (N-tert-butoxycarbonyl)-1,2,3,6-tetrahydropyridine-4-boronic acid pinacol ester (68, 1.25 g, 4.04 mmol), Pd(PPh$_3$)$_2$Cl$_2$ (0.189 g, 0.27 mmol), potassium carbonate (0.883 g, 6.40 mmol), and a mixture of DME/EtOH/H$_2$O (8 mL/4 mL/8 mL). The reaction mixture was purged with nitrogen, the vessel sealed, and the reaction mixture heated at 90° C. with vigorous stirring. After 2 hrs, the reaction mixture was cooled to a temperature of about 25° C. and diluted with EtOAc (50 mL). The organic layer was washed with brine, dried (Na$_2$SO$_4$), and concentrated under reduced pressure. The residue was chromatographed by silica gel column chromatography with a gradient of ethyl acetate (50%-100%)/hexanes to provide 0.96 g of 69 (80% yield). $^1$H NMR (400 MHz, CD$_3$OD) δ 8.47 (1H, s), 7.93 (1H, s), 6.06 (1H, m), 4.74 (1H, t, J=5.92 Hz), 4.12 (2H, m), 3.67 (4H, m), 2.54 (2H, m), 1.52 (9H, s). LC/MS (M+1): 355.

(S)-1-(3-Chloro-1',2',3',6'-tetrahydro-[2,4']bipyridinyl-5-yl)-ethane-1,2-diol

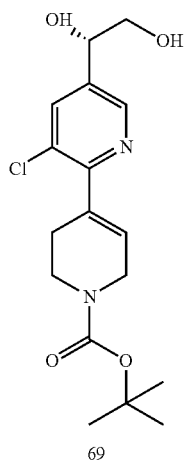

69

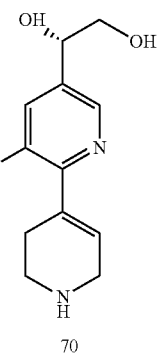

70

A vessel (50 mL) was charged with 69 (0.90 g, mmol) and 2M HCl in Et$_2$O (10 mL) and sealed. The reaction mixture was stirred at 40° C. for 20 hrs. The reaction mixture was cooled to a temperature of about 25° C. and the solid precipitated was filtered, washed with Et$_2$O (20 mL), and dried under reduced pressure to provide 0.65 g of 70 (>99% yield). $^1$H NMR (400 MHz, CD$_3$OD) δ 8.74 (1H, s), 8.52 (1H, s), 6.38 (1H, m), 4.91 (1H, m), 4.00 (2H, m), 3.75 (4H, m), 3.54 (2H, t, J=5.92 Hz), 2.89 (2H, m). LC/MS (M+1): 255.

(S)-3-Chloro-5-(1,2-dihydroxy-ethyl)-3',6'-dihydro-2'H-[2,4']bipyridinyl-1'-carboxylic acid (4-trifluoromethyl-phenyl)amide

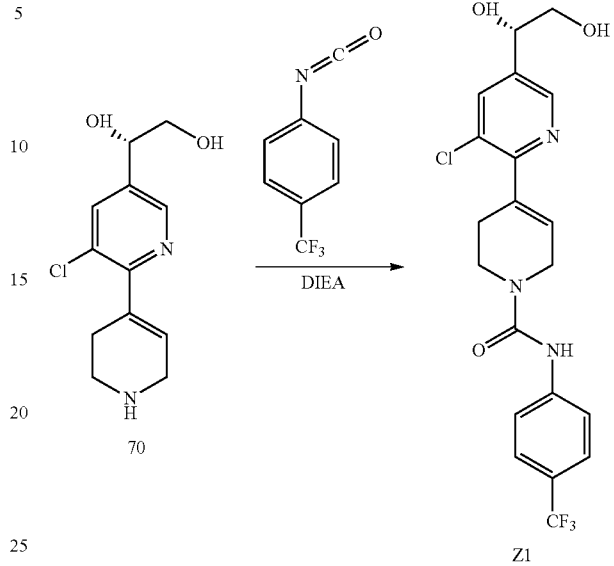

To a suspension of 70 (800 mg, 2.45 mmol) in anhydrous dichloromethane (20 mL), diisopropylethylamine (DIEA, 2 mL) was added dropwise and the reaction mixture was stirred at a temperature of about 25° C. for 10 min. The mixture was cooled to −10° C. and 1-isocyanato-4-(trifluoromethyl)benzene (462 mg, 2.45 mmol) which was diluted with anhydrous dichloromethane (5 mL) was slowly added over 5 min. After stirring at −10° C. for 10 additional minutes, the mixture was chromatographed by a silica gel chromatography column with a gradient of methanol (0%-5%)/ethyl acetate to provide 0.60 g of Z1 (56% yield). $^1$H NMR (400 MHz, CD$_3$OD) δ 8.49 (1H, dd, J=0.44, 1.75 Hz), 7.94 (1H, dd, J=0.44, 1.75 Hz), 7.72 (4H, m), 6.14 (1H, m), 4.78 (1H, t, J=5.70 Hz), 4.27 (2H, m), 3.82 (2H, t, J=5.70 Hz), 3.70 (2H, m), 2.66 (2H, m). MS: m/z=441.

(S)-3-Chloro-5-(1,2-dihydroxy-ethyl)-3',6'-dihydro-2'H-[2,4']bipyridinyl-1'-carboxylic acid (4-tert-butyl-phenyl)amide

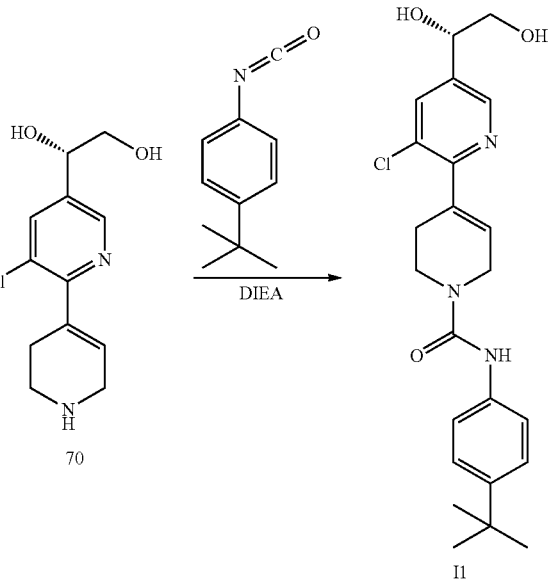

The title compound I1 was obtained using a procedure similar to that described for obtaining Z1 except that 1-tert-butyl-4-isocyanatobenzene was used in place of 1-isocyanato-4-(trifluoromethyl)benzene (59% yield). ¹H NMR (400 MHz, CD₃OD) δ 8.48 (1H, dd, J=0.66, 1.97 Hz), 7.94 (1H, dd, J=0.66, 1.75 Hz), 7.36 (3H, m), 6.14 (1H, m), 4.79 (1H, t, J=5.26 Hz), 4.27 (2H, m), 3.78 (2H, t, J=5.48 Hz), 3.71 (2H, m), 2.64 (2H, m). LC/MS (M+1): 430.

(S)-3-Chloro-5-(1,2-dihydroxy-ethyl)-3',6'-dihydro-2'H-[2,4']bipyridinyl-1'-carboxylic acid (3-chloro-4-trifluoromethyl-phenyl)amide

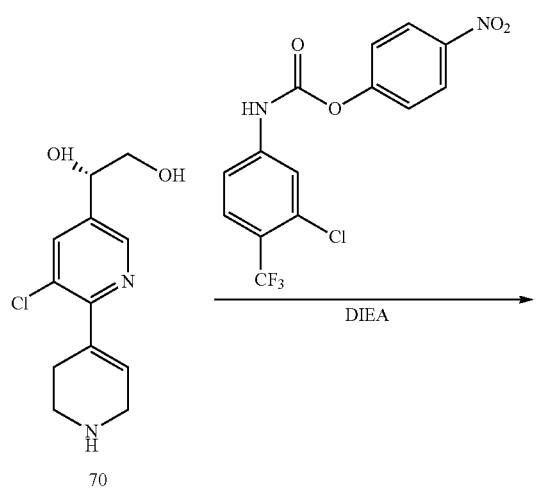

To a suspension of 70 (95 mg, 0.29 mmol) in anhydrous dichloromethane (4 mL), DIEA (0.5 mL) was added dropwise, and the reaction mixture was stirred at a temperature of about 25° C. for 10 min. Then the mixture was cooled to −10° C. and 3-chloro-4-trifluoromethylphenyl)carbamic acid 4-nitrophenyl ester (104 mg, 0.29 mmol, prepared in situ from 2-chloro-4-nitrobenzotrifluoride (Sigma-Aldrich)) in anhydrous dichloromethane (5 mL) was slowly added over 5 min. After stirring at −10° C. for 10 additional minutes, the mixture was chromatographed by a silica gel chromatography column with a gradient of methanol (0%-5%)/ethyl acetate to provide 30 mg of D2 (23% yield). ¹H NMR (400 MHz, CD₃OD) δ 8.50 (1H, m), 7.95 (1H, dd, J=0.44, 1.75 Hz), 7.82 (1H, d, J=1.97 Hz), 7.66 (1H, d, J=8.77 Hz), 7.53 (1H, m), 6.15 (1H, m), 4.78 (1H, t, J=5.48 Hz), 4.27 (2H, m), 3.81 (2H, t, J=5.70 Hz), 3.69 (2H, m), 2.65 (2H, m). MS: m/z=475.

(S)-3-Chloro-5-(1,2-dihydroxy-ethyl)-3',6'-dihydro-2'H-[2,4']bipyridinyl-1'-carboxylic acid (3-fluoro-4-trifluoromethyl-phenyl)amide

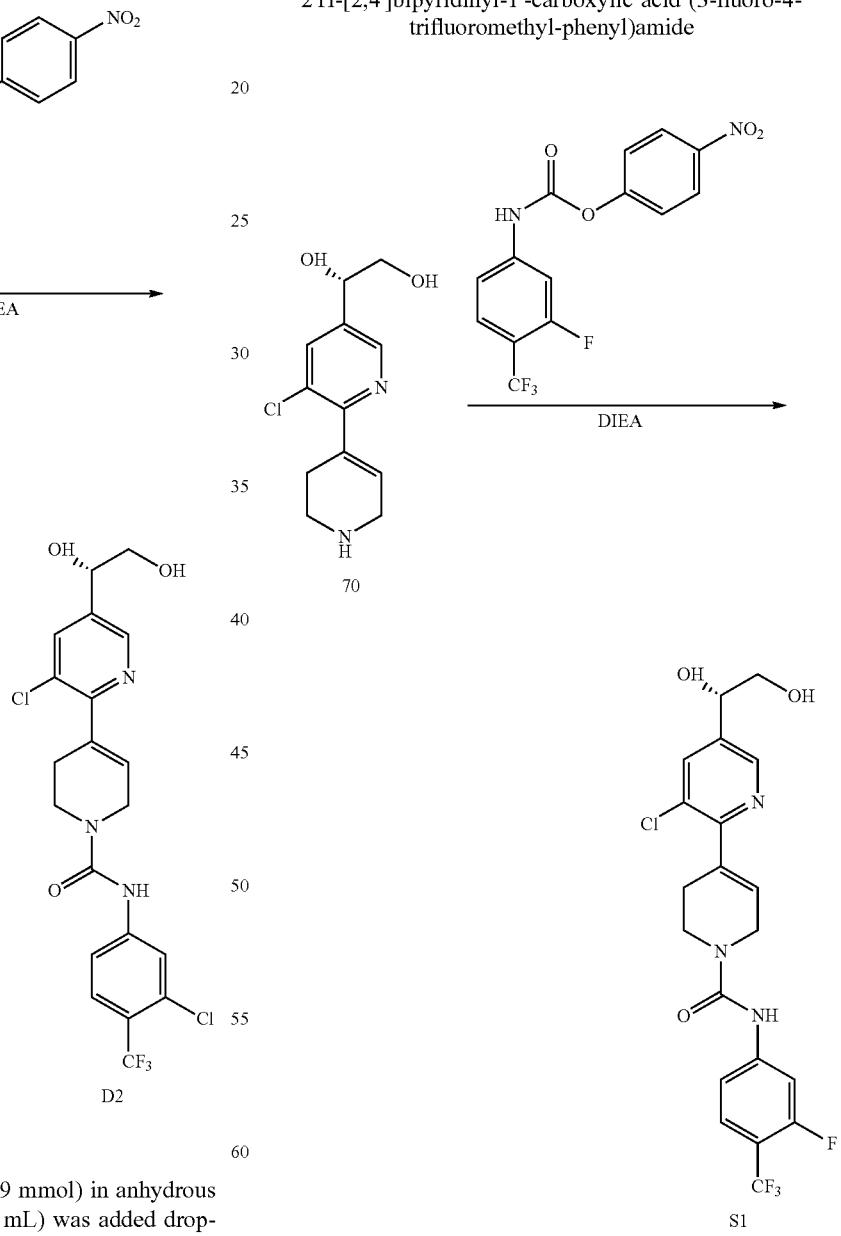

The title compound S1 was obtained using a procedure similar to that described for obtaining D2 except that 4-nitrophenyl 3-fluoro-4-(trifluoromethyl)phenylcarbamate was used in place of 3-chloro-4-trifluoromethylphenyl)carbamic acid 4-nitrophenyl ester (38% yield). ¹H NMR (400 MHz, CD₃OD) δ 8.48 (1H, dd, J=0.44, 1.75 Hz), 7.95 (1H, dd, J=0.66, 1.97 Hz), 7.57 (2H, m), 7.36 (1H, m), 6.14 (1H, m), 4.77 (1H, t, J=5.48 Hz), 4.23 (2H, m), 3.81 (2H, t, J=5.48 Hz), 3.69 (2H, m), 2.65 (2H, m). MS: m/z=459.

(S)-3-Chloro-5-(1,2-dihydroxy-ethyl)-3',6'-dihydro-2'H-[2,4']bipyridinyl-1'-carboxylic acid (3-ethyl-4-trifluoromethyl-phenyl)amide

(S)-3-Chloro-5-(1,2-dihydroxy-ethyl)-3',6'-dihydro-2'H-[2,4']bipyridinyl-1'-carboxylic acid (3-chloro-4-trifluoromethoxy-phenyl)amide

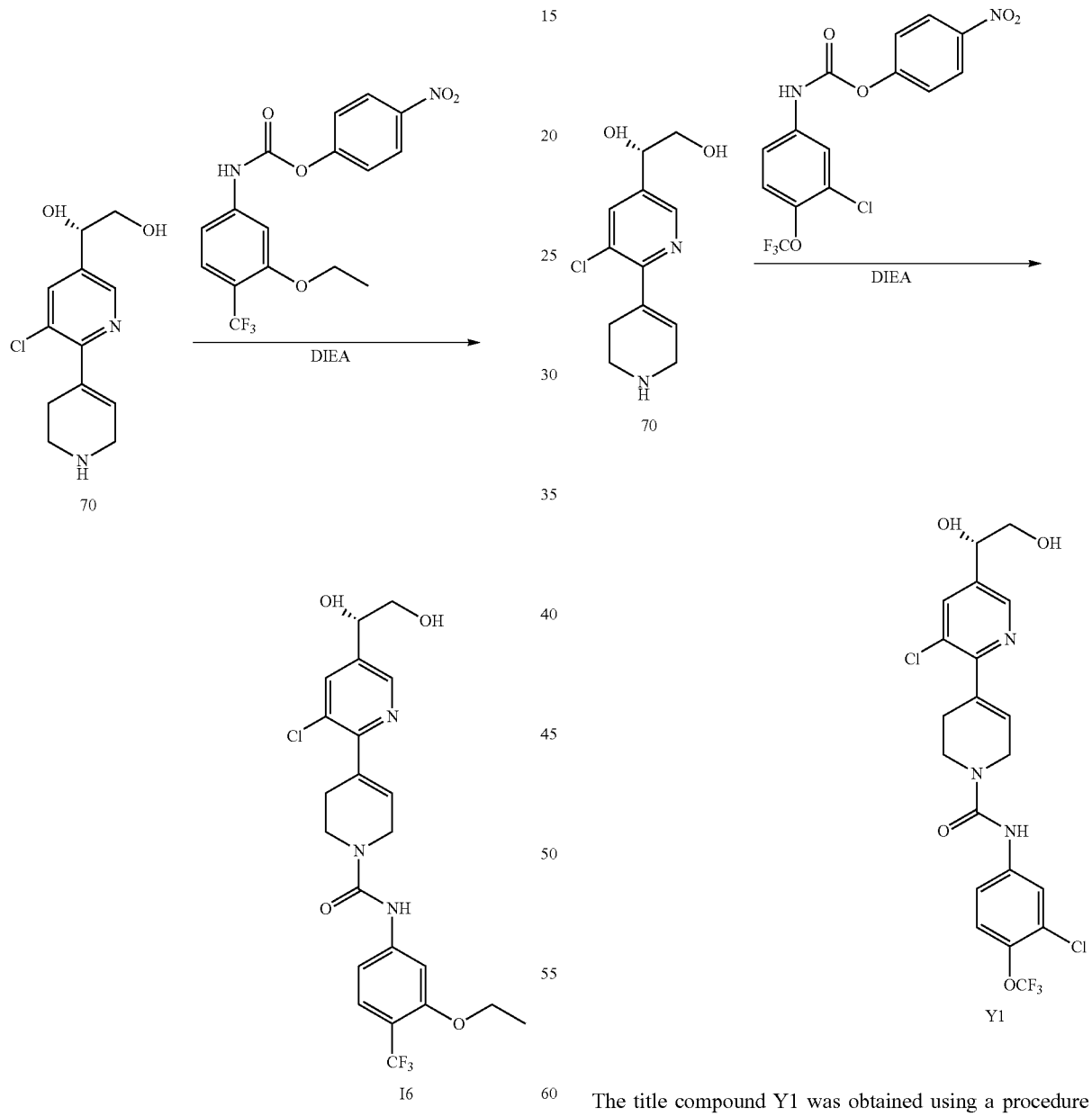

The title compound I6 was obtained using a procedure similar to that described for obtaining D2 except that 4-nitrophenyl 3-ethoxy-4-(trifluoromethyl)phenylcarbamate was used in place of 3-chloro-4-trifluoromethylphenyl)carbamic acid 4-nitrophenyl ester (25% yield). ¹H NMR (400 MHz, CD₃OD) δ 8.27 (1H, dd, J=0.66, 1.97 Hz), 7.72 (1H, dd, J=0.66, 1.97 Hz), 7.25 (2H, m), 6.88 (1H, d, J=8.55 Hz), 5.94 (1H, m), 4.57 (1H, t, J=5.48 Hz), 4.08 (2H, m), 3.96 (2H, q, J=7.02 Hz), 3.64 (2H, m), 3.52 (2H, m), 2.44 (2H, m), 1.23 (3H, t, J=7.02 Hz). LC/MS (M+1): 486.

The title compound Y1 was obtained using a procedure similar to that described for obtaining D2 except that 4-nitrophenyl 3-chloro-4-(trifluoromethoxy)phenylcarbamate was used in place of 3-chloro-4-trifluoromethylphenyl)carbamic acid 4-nitrophenyl ester (20% yield). ¹H NMR (400 MHz, CD₃OD) δ 8.30 (1H, dd, J=0.44, 1.75 Hz), 7.74 (1H, dd, J=0.66, 1.75 Hz), 7.57 (1H, d, J=2.41 Hz), 7.25 (1H, dd, J=2.63, 8.99 Hz), 7.14 (1H, m), 5.94 (1H, m), 4.57 (1H, t, J=5.70 Hz), 4.06 (2H, m), 3.59 (2H, t, J=5.70 Hz), 3.50 (2H, m), 2.46 (2H, m). LC/MS (M+1): 492.

(S)-3-Chloro-5-(1,2-dihydroxy-ethyl)-3',6'-dihydro-2'H-[2,4']bipyridinyl-1'-carboxylic acid (3-ethyl-4-trifluoromethoxy-phenyl)amide

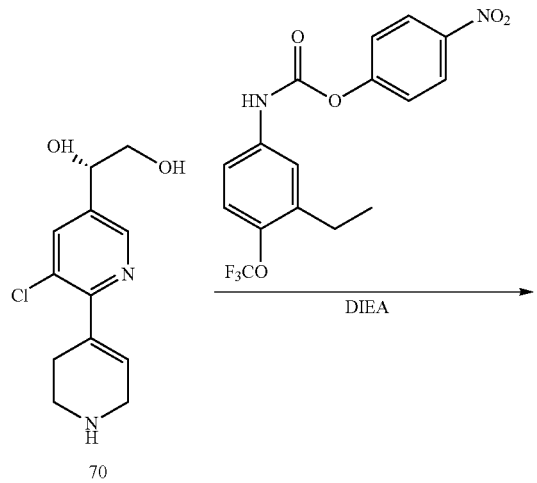

The title compound J6 was obtained using a procedure similar to that described for obtaining D2 except that 4-nitrophenyl 3-ethyl-4-(trifluoromethoxy)phenylcarbamate was used in place of 3-chloro-4-trifluoromethylphenyl)carbamic acid 4-nitrophenyl ester (30% yield). $^1$H NMR (400 MHz, CD$_3$OD) δ 8.49 (1H, d, J=1.97 Hz), 7.94 (1H, d, J=1.75 Hz), 7.42 (1H, d, J=2.63 Hz), 7.33 (1H, dd, J=2.85, 8.99 Hz), 7.17 (1H, m), 6.16 (1H, m), 4.77 (1H, t, J=5.48 Hz), 4.25 (2H, m), 3.80 (2H, t, J=5.48 Hz), 3.70 (2H, m), 2.68 (2H, m), 1.25 (3H, t, J=7.67 Hz). LC/MS (M+1): 486.

Example 2: The Synthesis of Compound N1

2-bromo-3,5-dichloropyridine

A 100 mL round-bottom flask equipped with a condenser was charged with 1.82 g of compound 71 (10.0 mmol) and propiononitrile (20 mL), 3.06 g TMSBr (20.0 mmol) was slowly added to the above solution. The reaction mixture was stirred at 100° C. under nitrogen for 14 hrs, then cooled to a temperature of about 25° C. and diluted with EtOAc (100 mL). The EtOAc layer was isolated, dried, and concentrated under reduced pressure to provide 72 as a yellowish solid (>99% yield).

tert-butyl 4-(3,5-dichloropyridin-2-yl)-4-hydroxypiperidine-1-carboxylate

Under nitrogen atmosphere, to a 200 mL diethyl ether solution of 72 (2.27 g, 10 mmol) at −78° C. was dropwise added an ice-cold 1.7M t-BuLi in pentane solution (6 mL, 10.5 mmol) via a syringe while maintaining the mixture below −75° C. After completion of the addition, the reaction mixture was stirred at −78° C. for 2 hrs. Then 20 mL of an anhydrous diethyl ether solution of 4-BOC-piperridone (1.99 g, 10 mmol) was slowly added via a syringe. The reaction mixture was stirred at −78° C. for 2 hrs and slowly heated to a temperature of about 25° C. Saturated aqueous NH$_4$Cl was added to the mixture and the diethyl ether layer was isolated, dried, and concentrated under reduced pressure with a rotary evaporator. Silica gel column chromatography of the residue with ethyl acetate/hexanes as eluent provided 2.1 g of 74 as a yellowish oil (61% yield over 2 steps).

tert-butyl 4-(3,5-dichloropyridin-2-yl)-4-fluoropiperidine-1-carboxylate (S)-tert-butyl 4-(3-chloro-5-(1,2-dihydroxyethyl)pyridin-2-yl)-4-fluoropiperidine-1-carboxylate

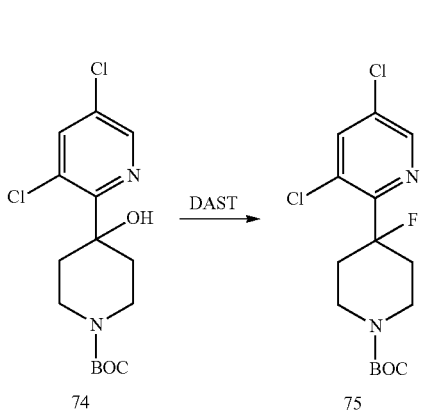

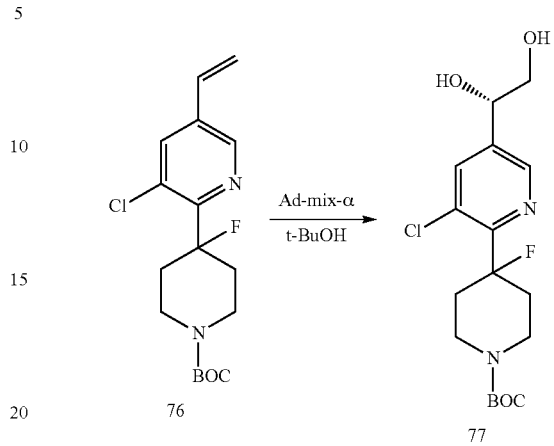

To a 100 mL DCM solution of 74 (6.0 g, 17.3 mmol) at −78° C. was slowly added DAST (2.5 mL, 18.8 mmol) and the resulting mixture was allowed to warm to a temperature of about 25° C. for 16 h, then washed with saturated NaHCO₃, dried (MgSO₄), and concentrated under reduced pressure. Silica gel column chromatography of the residue with EtOAc/hexanes provided 2.5 g of 75 as yellowish solid (42% yield).

In a 100 mL round bottom flask, AD-mix-α (0.5 g) was added to a mixture of t-butanol and water (2 mL/2 mL) and the mixture was stirred at a temperature of about 25° C. for 0.5 hr, then cooled to 0° C. This solution was quickly poured into another ice chilled flask which contained 76 (140 mg, 0.41 mmol). The mixture was stirred vigorously in an ice bath for 96 h and then diluted with ethyl acetate (50 mL) and 2 mL saturated Na₂S₂O₅. The ethyl acetate layer was isolated, dried, and concentrated under reduced pressure with a rotary evaporator to provide 77.

tert-butyl 4-(3-chloro-5-vinylpyridin-2-yl)-4-fluoropiperidine-1-carboxylate (S)-1-(5-chloro-6-(4-fluoropiperidin-4-yl)pyridin-3-yl)ethane-1,2-diol

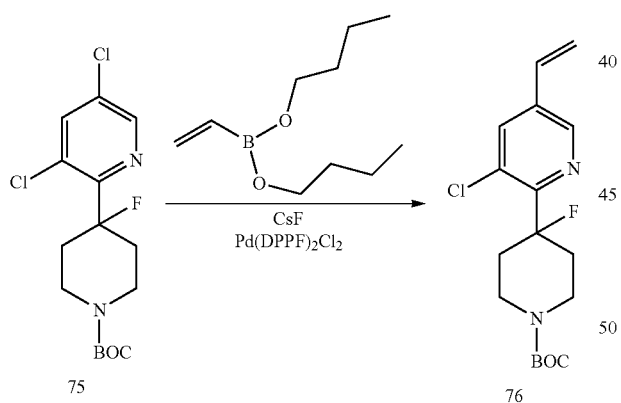

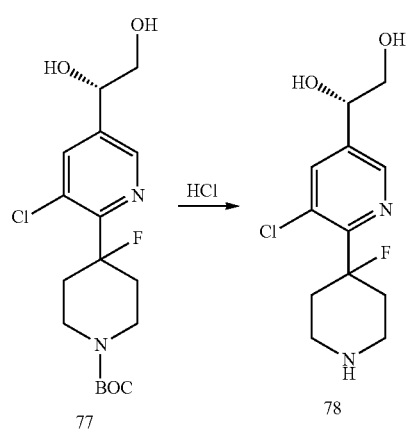 [SMILES: CC(C)(C)OC(=O)N1CCC(F)(c2ncc([C@H](O)CO)cc2Cl)CC1 ; Cl ; OC[C@@H](O)c1cnc(C2(F)CCNCC2)c(Cl)c1]

To a degassed DMF solution of 75 (0.558 g, 1.6 mmol) in a 100 mL round bottom flask, was added CsF (0.486 g, 3.2 mmol), di-n-butyl vinyl boronic ester (0.388 mL, 1.76 mmol) and Pd(DPPF)₂Cl₂ (0.105 g, 0.128 mmol). The reaction mixture was stirred at 100° C. for 14 hr, then cooled to a temperature of about 25° C., diluted with 100 mL ethyl acetate, and washed three times with brine (50 mL for each wash). The organic layer was isolated, dried, and concentrated under reduced pressure. Silica gel column chromatography of the residue provided 0.33 g of 76 as a yellowish oil (60% yield).

A 200 mL round bottom flask was charged with 0.15 g 77 (0.36 mmol) dissolved in about 1 mL dichloromethane. Then 10 mL of 4M HCl in dioxane was slowly added with vigorous stirring. The flask was sealed with a rubber septum and stirred at a temperature of about 25° C. for 16 h. The reaction mixture was filtered and the solid was washed twice with diethyl ether (20 mL for each wash) and dried under reduced pressure to provide 112 mg of 78 as a white solid (>99% yield). MS (M+H): m/z=312.

(S)-4-(3-chloro-5-(1,2-dihydroxyethyl)pyridin-2-yl)-4-fluoro-N-(4-(trifluoromethyl)phenyl)piperidine-1-carboxamide

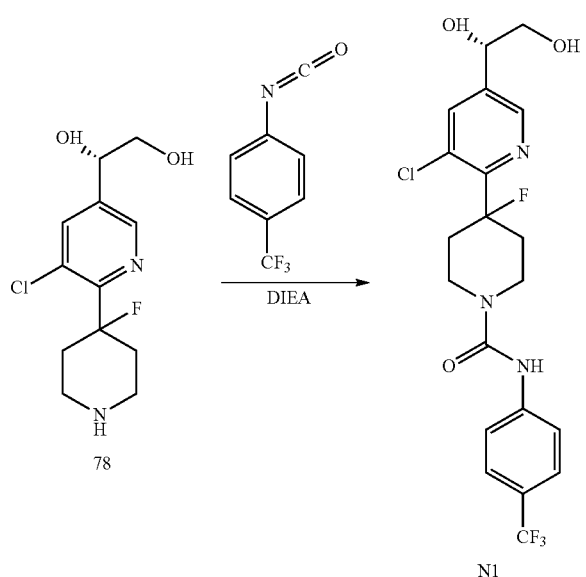

A 100 mL round bottom flask was charged with 90 mg 78 (0.26 mmol) suspended in dichloromethane. DIEA (0.1 mL, 0.72 mmol) and 4-trifluoromethyl phenylisocyanate (48 mg, 0.26 mmol) were added, and the reaction mixture was stirred for 10 minutes. The mixture was chromatographed using a silica flash column with a gradient of 0% to 5% methanol in dichloromethane to provide 50 mg of N1 as a white solid (60% yield). $^1$H NMR (CD$_3$OD) δ 8.49 (d, J=2 Hz, 1H), 7.90 (m, 1H), 7.60 (m, 4H), 4.76 (t, J=6 Hz, 1H), 4.17 (m, 2H), 3.68 (m, 2H), 3.45 (m, 2H), 2.50-2.34 (m, 4H). MS (M+1): m/z=462.1.

Example 3: Syntheses of Piperazine Compounds K6, L6, M6, V6 and W6

2,3-dichloro-5-vinylpyridine

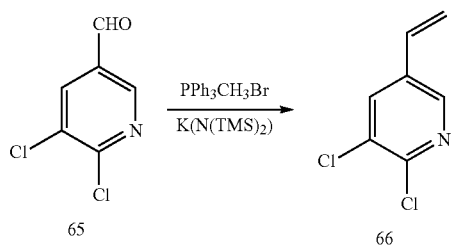

To a suspension of methyltriphenylphosphonium bromide (PPh$_3$CH$_3$Br, 7.08 g, 19.8 mmol, Sigma-Aldrich) in THF (40 mL) at 0° C. was added dropwise a 0.5N solution of potassium bis(trimethylsilyl)amide [K(N(TMS)$_2$)] in toluene (39.6 mL, 19.8 mmol, Sigma-Aldrich). Then the resultant mixture was stirred at 0° C. for 1 hour. To the mixture was added a solution of 65 (3.17 g, 18.0 mmol) in THF (20 mL) at 0° C. The reaction mixture was stirred for 2 h at 0° C. The reaction was quenched with water, and the mixture was extracted three times with EtOAc (150 mL for each extraction). The organic portions were combined, washed with brine, and concentrated to dryness. Compound 66 was obtained as a slight yellowish oil via flash chromatography using ethyl acetate/hexane gradient as an eluent (64% yield). $^1$H NMR: (CDCl$_3$) δ 8.28 (d, J=2.1 Hz, 1H), 7.82 (d, J=2.2 Hz, 1H), 6.65 (dd, J=11.0, 17.5 Hz, 1H), 5.85 (d, J=17.5 Hz, 1H), 5.48 (d, J=11.0 Hz, 1H) ppm.

tert-butyl 4-(3-chloro-5-vinylpyridin-2-yl)piperazine-1-carboxylate

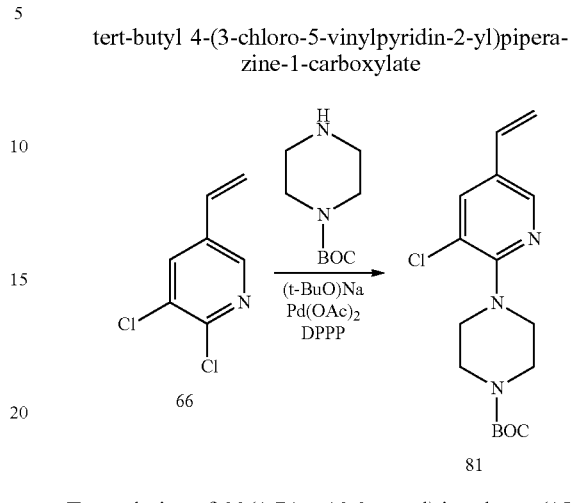

To a solution of 66 (1.74 g, 10.0 mmol) in toluene (15 mL) was added tert-butyl-1-piperazine-carboxylate (1.86 g, 10.0 mmol, Sigma-Aldrich), palladium acetate (0.113 g, 0.5 mmol, Sigma-Aldrich), 1,3-bis(diphenylphosphino)propane (DPPP, 0.220 g, 0.5 mmol, Sigma-Aldrich), and sodium tert-butoxide (1.05 g, 11.0 mmol, Sigma-Aldrich) at a temperature of about 25° C. The reaction mixture was stirred at 75° C. for 16 h. After cooling to a temperature of about 25° C., water was added to quench the reaction. Then the mixture was extracted three times with diethyl ether (150 mL for each extraction). The organic portions were combined, washed with brine, and concentrated to dryness. Compound 81 was obtained as a white solid via silica gel column chromatography using an ethyl acetate/hexane gradient as an eluent (88% yield). $^1$H NMR: (CDCl$_3$) δ 8.14 (m, 1H), 7.69 (d, J=1.5 Hz, 1H), 6.60 (dd, J=11.0, 17.5 Hz, 1H), 5.68 (d, J=17.5 Hz, 1H), 5.28 (d, J=11.0 Hz, 1H), 3.58 (m, 4H), 3.32 (m, 4H), 1.49 (s, 9H) ppm. MS (M+Na): m/z=346.1.

(S)-tert-butyl 4-(3-chloro-5-(1,2-dihydroxyethyl)pyridin-2-yl)piperazine-1-carboxylate

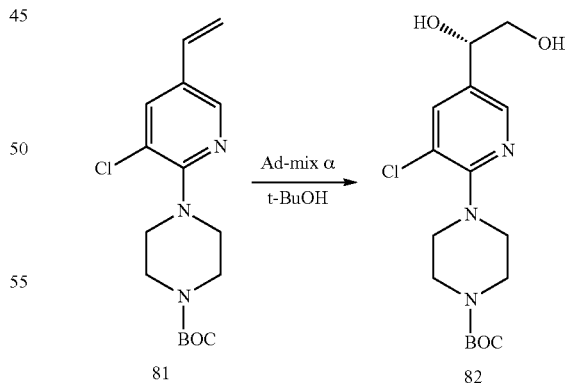

To a suspension of 81 (2.84 g, 8.77 mmol) in tert-butanol (60 mL) and water (60 mL) was added AD-mix-α (11.93 g, 8.77 mmol, Sigma-Aldrich) at 0° C. The reaction mixture was stirred at 0° C. for 8 hours then extracted three times with diethyl ether (150 mL for each extraction). The organic portions were combined, washed with brine, and concentrated to dryness under reduced pressure. Compound 82 was obtained as a white solid via flash chromatography using an ethyl acetate/hexane gradient as an eluent (90% yield). ¹H NMR: (CDCl₃) δ 8.14 (d, J=2.0 Hz, 1H), 7.67 (d, J=2.2 Hz, 1H), 4.79 (m, 1H), 3.77 (m, 1H), 3.64 (m, 1H), 3.56 (m, 4H), 3.28 (m, 4H), 2.87 (d, J=3.2 Hz, 1H), 2.27 (m, 1H), 1.48 (s, 9H) ppm. MS (M+1): m/z=358.1.

(S)-1-(5-chloro-6-(piperazin-1-yl)pyridin-3-yl)ethane-1,2-diol

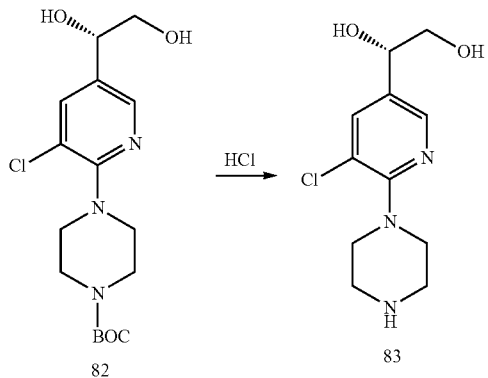 [SMILES: CC(C)(C)OC(=O)N1CCN(c2ncc([C@H](O)CO)cc2Cl)CC1 ; Cl ; OC[C@@H](O)c1cnc(N2CCNCC2)c(Cl)c1]

A suspension of 82 (2.81 g, 7.85 mmol) and 4M HCl in dioxane (60 mL) was stirred at a temperature of about 25° C. for 1 hour. The reaction mixture was concentrated under reduced pressure to provide 83 as a white solid.

(S)—N-(4-tert-butylphenyl)-4-(3-chloro-5-(1,2-dihydroxyethyl)pyridin-2-yl)piperazine-1-carboxamide

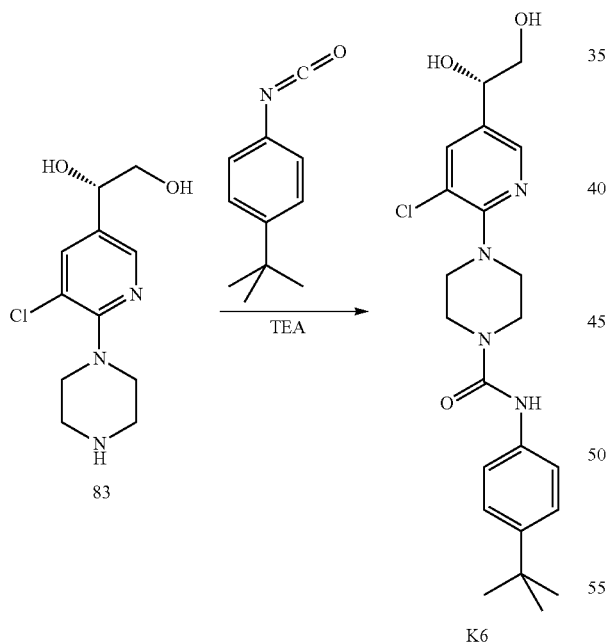

To a mixture of 83 (0.5 mmol) in DCM (2.0 mL) and TEA (0.3 mL) was added dropwise a solution of 4-tert-butylphenyl isocyanate (0.5 mmol, Sigma-Aldrich) in DCM (1.0 mL) at 0° C. The reaction mixture was stirred at a temperature of about 25° C. for 4 hours. Thereafter, silica gel column chromatography using an ethyl acetate/methanol gradient as an eluent provided K6 as a white solid. ¹H NMR: (CD₃OD) δ 8.18 (d, J=2.0 Hz, 1H), 7.78 (d, J=2.0 Hz, 1H), 7.30 (m, 4H), 4.66 (t, J=5.5 Hz, 1H), 3.68 (m, 4H), 3.62 (m, 2H), 3.34 (m, 4H), 1.30 (s, 9H) ppm. MS (M+1): m/z=433.2.

(S)-4-(3-chloro-5-(1,2-dihydroxyethyl)pyridin-2-yl)-N-(4-(trifluoromethoxy)phenyl)piperazine-1-carboxamide

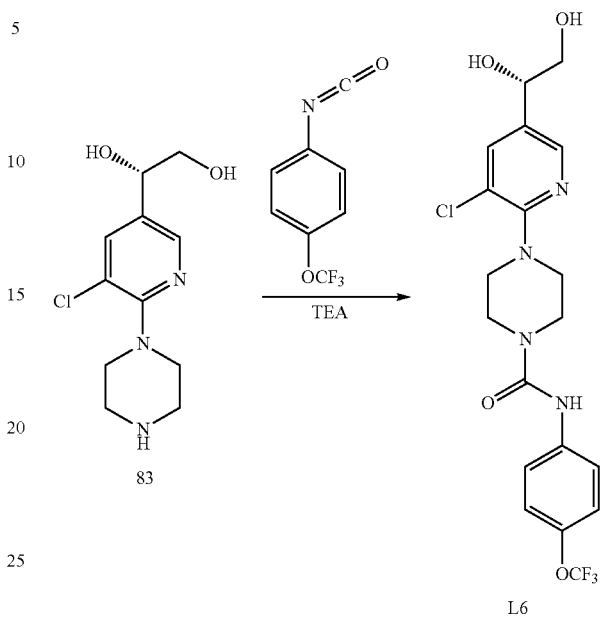

To a mixture of 83 (0.5 mmol) in DCM (2.0 mL) and TEA (0.3 mL), was added dropwise a solution of 4-trifluoromethoxyphenyl isocyanate (0.5 mmol, Sigma-Aldrich) in DCM (1.0 mL) at 0° C. The reaction mixture was stirred at a temperature of about 25° C. for 4 hours. Thereafter, silica gel column chromatography using an ethyl acetate/methanol gradient as an eluent provided L6 as a white solid. ¹H NMR: (CD₃OD) δ 8.18 (d, J=1.6 Hz, 1H), 7.78 (d, J=1.7 Hz, 1H), 7.47 (m, 2H), 7.18 (m, 2H), 4.66 (t, J=5.9 Hz, 1H), 3.69 (m, 4H), 3.63 (m, 2H), 3.35 (m, 4H) ppm. MS (M+1): m/z=461.1.

(S)-4-(3-chloro-5-(1,2-dihydroxyethyl)pyridin-2-yl)-N-(4-(trifluoromethyl)phenyl)piperazine-1-carboxamide

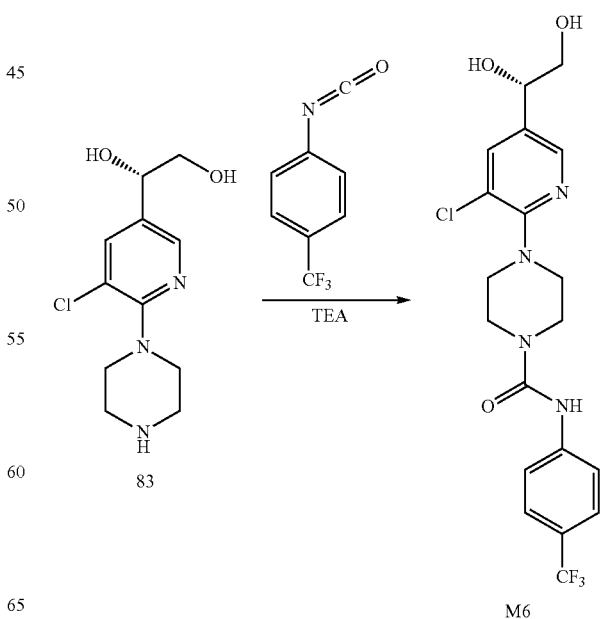

To a mixture of 83 (0.5 mmol) in DCM (2.0 mL) and TEA (0.3 mL) was added dropwise a solution of 4-trifluoromethylphenyl isocyanate (0.5 mmol, Sigma-Aldrich) in DCM (1.0 mL) at 0° C. The mixture reaction was stirred at a temperature of about 25° C. for 4 hours. Thereafter, direct flash chromatography using an ethyl acetate/methanol gradient as an eluent provided M6 as a white solid. $^1$H NMR: (CD$_3$OD) δ 8.18 (m, 1H), 7.78 (m, 1H), 7.58 (m, 4H), 4.66 (t, J=5.5 Hz, 1H), 3.71 (m, 4H), 3.63 (m, 2H), 3.36 (m, 4H) ppm. MS (M+1): m/z=445.0.

N-(6-fluorobenzo[d]thiazol-2-yl)-1H-imidazole-1-carboxamide

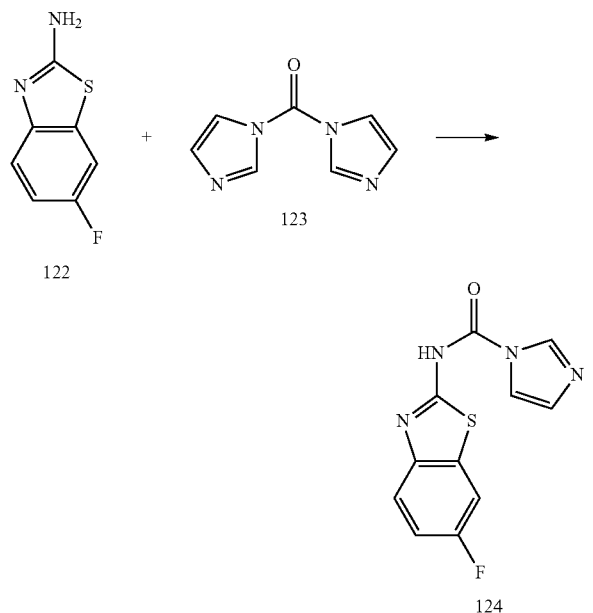

To a solution of 6-fluorobenzo[d]thiazol-2-amine (122, 336 mg, 2 mmol, Sigma-Aldrich) in DMF (5 mL) was added CDI (123, 357 mg, 2.2 mmol, Sigma-Aldrich) at 0° C. Under vigorous stirring, the reaction mixture was slowly allowed to warm to a temperature of about 25° C. over 14 h. A white precipitate formed. The precipitate was collected by vacuum filtration, washed twice with EtOAc (10 mL for each wash), and dried under reduced pressure to provide 124 (yield >99%).

(S)-4-(3-chloro-5-(1,2-dihydroxyethyl)pyridin-2-yl)-N-(6-fluorobenzo[d]thiazol-2-yl)piperazine-1-carboxamide

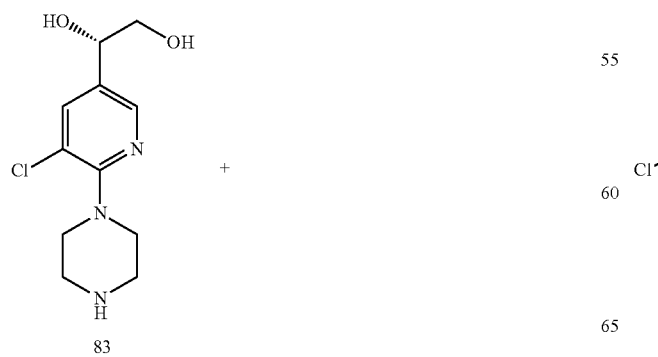

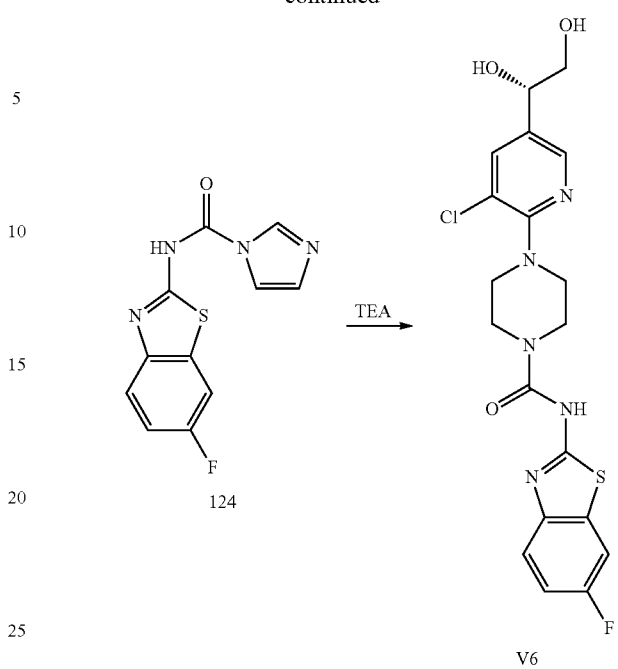

To a mixture of 83 (0.3 mmol) in DCM (2.0 mL) and TEA (0.2 mL) was added dropwise a suspension of 124 (0.3 mmol) in DMF (1.0 mL) at 0° C. The reaction mixture was stirred at a temperature of about 25° C. for 4 hours. Thereafter, direct flash chromatography using an ethyl acetate/methanol gradient as an eluent provided V6 as a slightly yellowish solid. $^1$H NMR: (CD$_3$SOCD$_3$) δ 8.19 (m, 1H), 7.76 (m, 3H), 7.22 (m, 1H), 5.41 (d, J=4.6 Hz, 1H), 4.79 (t, J=6.0 Hz, 1H), 4.53 (m, 1H), 3.71 (m, 4H), 3.50 (m, 2H), 3.26 (m, 4H) ppm. MS (M+1): m/z=452.1.

(S)—N-(4-chloro-3-(trifluoromethyl)phenyl)-4-(3-chloro-5-(1,2-dihydroxyethyl)pyridin-2-yl)piperazine-1-carboxamide

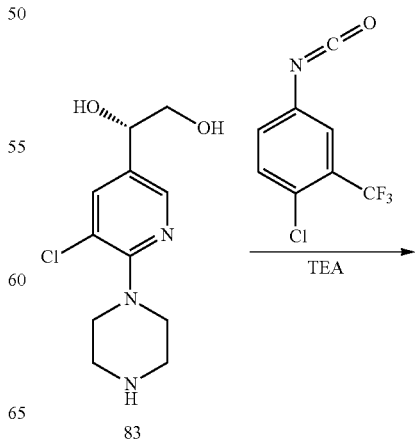

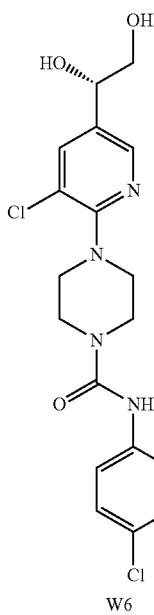

W6

To a mixture of 83 (0.5 mmol) in DCM (2.0 mL) and TEA (0.3 mL) was added dropwise a solution of 1-chloro-4-isocyanato-2-(trifluoromethyl)benzene (0.3 mmol, Sigma-Aldrich) in DCM (1.0 mL) at 0° C. The reaction mixture was stirred at a temperature of about 25° C. for 4 hours. Thereafter, direct flash chromatography using an ethyl acetate/methanol gradient as an eluent provided W6 as a white solid. $^1$H NMR: (CD$_3$OD) δ 8.18 (m, 1H), 7.91 (d, J=2.4 Hz, 1H), 7.78 (d, J=2.6 Hz, 1H), 7.64 (dd, J=2.6, 8.8 Hz, 1H), 7.47 (d, J=9.2 Hz, 1H), 4.66 (m, 1H), 3.70 (m, 4H), 3.63 (m, 2H), 3.35 (m, 4H) ppm. MS (M+1): m/z=479.1.

Example 4: Synthesis of Compound F4

5,6-dichloro-N-methoxy-N-methylnicotinamide

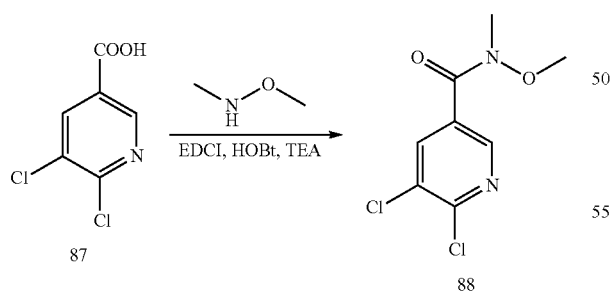

To a stirred solution of 5,6-dichloronicotinic acid (87, 7 g, 36.5 mmol) in dichloromethane (100 mL) at a temperature of about 25° C. was added N,O-dimethylhydroxylamine hydrochloride (3.56 g, 36.5 mmol), 1-(3-dimethylaminopropyl)-3-ethylcarbodiimide hydrochloride (EDCI, 7.69 g, 40.1 mmol), 1-hydroxybenzotriazole (HOBt, 5.42 g, 40.1 mmol), and TEA (7.6 mL, 54.7 mmol). After being stirred for 4.5 h at a temperature of about 25° C., the reaction mixture was diluted with ethyl acetate. The mixture was washed with water, 1N aqueous hydrogen chloride, saturated aqueous sodium hydrogen carbonate and brine, dried (Na$_2$SO$_4$), filtered, and concentrated under reduced pressure to provide 88.

1-(5,6-dichloropyridin-3-yl)ethanone

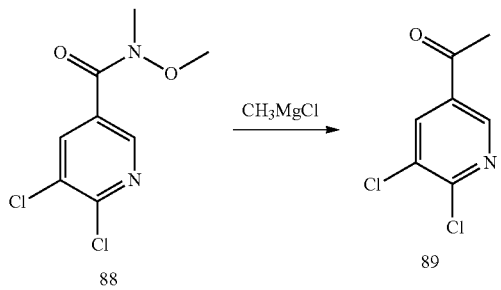

To a stirred solution of 88 in tetrahydrofuran (100 mL) was added dropwise a 3M solution of methylmagnesium chloride in THF (18 mL, 54.7 mmol) at 0° C. under nitrogen. After being stirred for 1 h at 0° C., the reaction mixture was partitioned between ether and saturated aqueous ammonium chloride at 0° C. The aqueous layer was extracted with ethyl acetate. The organic portions were combined, washed with brine, dried (Na$_2$SO$_4$), filtered, and concentrated under reduced pressure. The residue was chromatographed using flash chromatography eluting with a gradient of from 90:10 to 70:30 hexane:ethyl acetate to provide 5.92 g of 89 as a white solid (85% yield for 2 steps).

2-bromo-1-(5,6-dichloropyridin-3-yl)ethanone

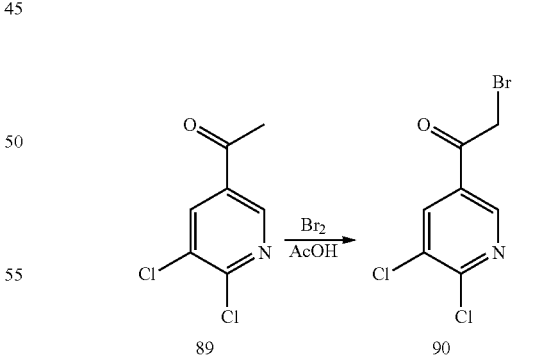

To a stirred solution of 89 (3 g, 15.8 mmol) in glacial acetic acid (25 mL) was added dropwise a solution of bromine (0.81 mL, 15.8 mmol) in glacial acetic acid (5 mL) at a temperature of about 25° C. After being stirred for 24 h at about 25° C., the reaction mixture was precipitated. The precipitate was filtered off and washed with diethyl ether to provide 3.89 g of 90 as a pale yellow solid (92% yield).

2-(5,6-dichloropyridin-3-yl)-2-oxoethyl acetate

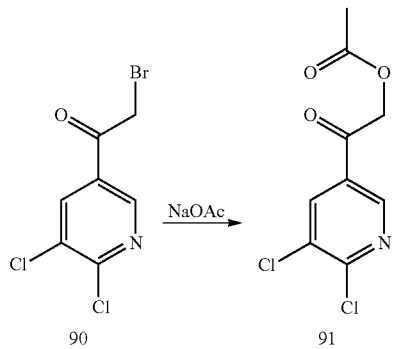

To a stirred solution of 90 (1 g, 3.72 mmol) in DMF (15 mL) at a temperature of about 25° C. was added sodium acetate (457.6 mg, 5.58 mmol). The reaction mixture was heated to 70° C. After being stirred for 1 h at 70° C., the reaction mixture was cooled to a temperature of about 25° C. and diluted with diethyl ether. The mixture was washed with water, washed with brine, dried (Na$_2$SO$_4$), filtered, and concentrated under reduced pressure. The residue was chromatographed using flash chromatography eluting with a gradient of from 90:10 to 65:35 hexane:ethyl acetate to provide 563 mg of 91 as a yellow solid (61% yield).

2-(5,6-dichloropyridin-3-yl)-2,2-difluoroethyl acetate

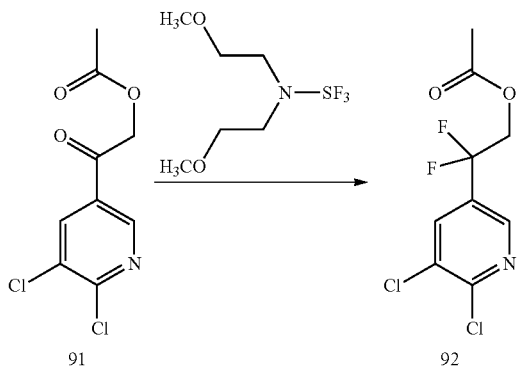

To a stirred solution of 91 (257 mg, 1.04 mmol) in dichloromethane (10 mL) at a temperature of about 25° C. was added bis(2-methoxyethyl)aminosulfur trifluoride (0.57 mL, 3.11 mmol). The reaction mixture was heated to 65° C. and stirred for 18 h. Thereafter, the reaction mixture was cooled to a temperature of about 0° C. and partitioned between ethyl acetate and saturated aqueous sodium hydrogen carbonate. The aqueous layer was extracted with ethyl acetate. The organic portions were combined, washed with brine, dried (Na$_2$SO$_4$), filtered, and concentrated under reduced pressure. The residue was chromatographed using flash chromatography eluting with 90:10 hexane:ethyl acetate to provide 201.3 mg of 92 as a yellow oil (75% yield).

tert-butyl 4-(3-chloro-5-(1,1-difluoro-2-hydroxyethyl)pyridin-2-yl)-5,6-dihydropyridine-1(2H)-carboxylate

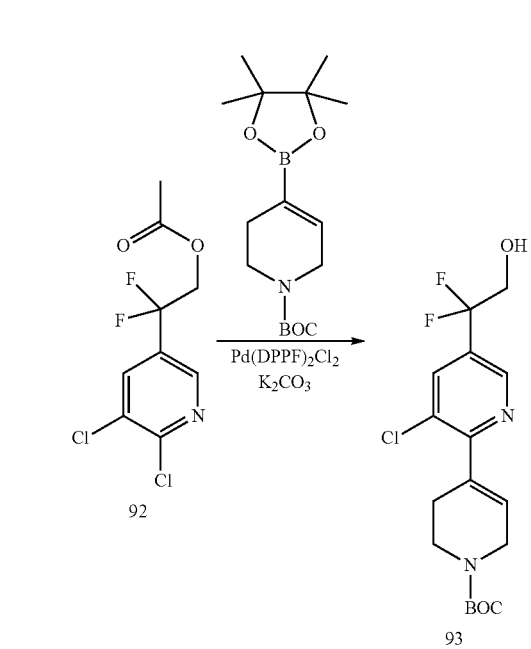

To stirred solution of 92 (326.2 mg, 1.41 mmol) in dimethoxyethane:ethanol (6 mL, 2:1) at a temperature of about 25° C. was added Pd(DPPF)$_2$Cl$_2$ (230.3 mg, 0.282 mmol), boron pinacol ester (436.0 mg, 1.41 mmol), potassium carbonate (389.8 mg, 2.82 mmol), and water (4 mL). The reaction mixture was heated to 70° C. and stirred for 1.5 h. Thereafter, the reaction mixture was cooled to a temperature of about 0° C. and partitioned between ethyl acetate and saturated aqueous ammonium chloride. The aqueous layer was extracted with ethyl acetate. The organic portions were combined, washed with brine, dried (Na$_2$SO$_4$), filtered, and concentrated under reduced pressure. The residue was chromatographed using flash chromatography eluting with a gradient of from 70:30 to 60:40 hexane:ethyl acetate to provide 506.9 mg of 93 as yellow oil (96% yield).

2-(5-chloro-6-(1,2,3,6-tetrahydropyridin-4-yl)pyridin-3-yl)-2,2-difluoroethanol hydrochloride

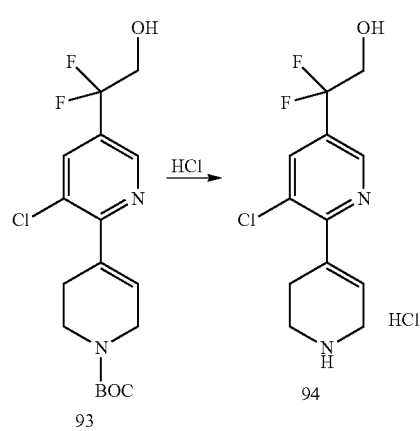 [SMILES: CC(C)(C)OC(=O)N1CC=C(c2ncc(C(F)(F)CO)cc2Cl)CC1 ; Cl ; OCC(F)(F)c1cnc(C2=CCNCC2)c(Cl)c1 ; Cl]

To a stirred solution of 93 (506.9 mg, 1.35 mmol) in dichloromethane (2 mL) at 0° C. was added an excess amount of 4N HCl in dioxane (4 mL). After heating to a temperature of about 25° C. and stirring for 2 h, the reaction mixture was concentrated under reduced pressure. The residue was crystallized from diethyl ether to provide 292.2 mg of the hydrochloride salt of 94 as a pale yellow solid (70% yield).

4-(3-chloro-5-(1,1-difluoro-2-hydroxyethyl)pyridin-2-yl)-N-(4-(trifluoromethyl)phenyl)-5,6-dihydropyridine-1(2H)-carboxamide

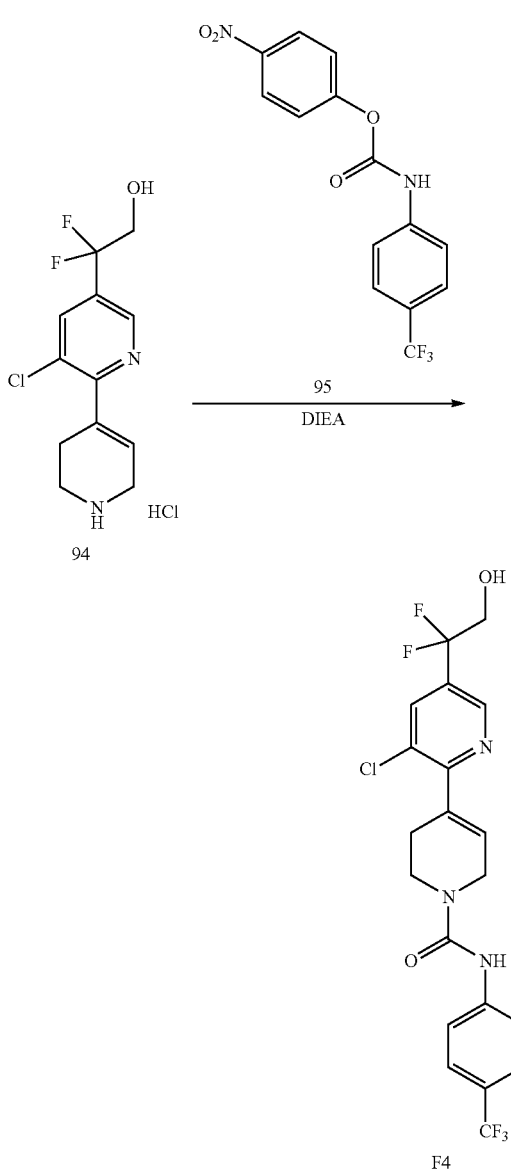

To a stirred solution of 4-trifluoroaniline (26 mL, 0.289 mmol) in dichloromethane (3 mL) at 0° C. was added 4-nitrophenyl chloroformate (58.3 mg, 0.289 mmol) and pyridine (28 mL, 0.347 mmol). After heating to a temperature of about 25° C. and stirring for 2 h, the reaction mixture was cooled to 0° C. and 94 (90 mg, 0.289 mmol) and DIEA (0.13 mL, 0.723 mmol) were added. After 1 h at 0° C., the reaction mixture was concentrated under reduced pressure. The residue was chromatographed using flash chromatography eluting with a gradient of from 70:30 to 65:35 hexane:ethyl acetate. The resulting solid was recrystallized from hexane:ethyl acetate to provide 82.3 mg of F4 as a white solid (62% yield).

Example 5: Synthesis of Compound O4

2-(tert-butyldimethylsilyloxy)-1-(5,6-dichloropyridin-3-yl)ethanone

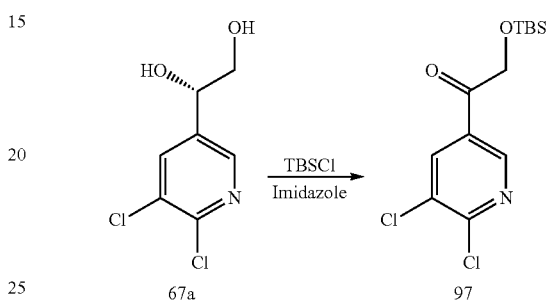

To a stirred solution of 67a (19.2 g, 81.4 mmol) in dichloromethane (250 mL) at 0° C. under nitrogen was added imidazole (11.1 g, 162 mmol) and tert-butyldimethylsilyl chloride (TBSCl, 12.3 g, 81.4 mmol). After heating to a temperature of about 25° C. and stirring for 2.5 h, the reaction mixture was cooled to 0° C. and partitioned between diethyl ether and saturated aqueous ammonium chloride. The aqueous layer was extracted with ethyl acetate. The organic portions were combined, washed with brine, dried (Na$_2$SO$_4$), filtered, and concentrated under reduced pressure. The residue was chromatographed using flash chromatography eluting with a gradient of from 90:10 to 80:20 hexane:ethyl acetate to provide 24.1 g of 97 as pale yellow oil (92% yield).

2-(tert-butyldimethylsilyloxy)-1-(5,6-dichloropyridin-3-yl)ethanone

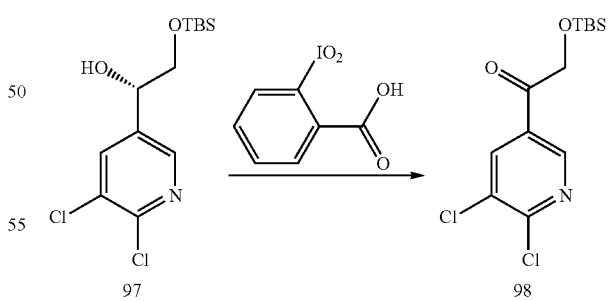

To a stirred solution of silyl ether 97 (8 g, 24.8 mmol) in tetrahydrofuran/methyl sulfoxide (100 mL, 1:1) at a temperature of about 25° C. was added o-iodoxybenzoic acid (20.9 g, 74.5 mmol). The reaction mixture was stirred for 5 h at about 25° C. Thereafter, the reaction mixture was cooled to a temperature of about 0° C. and partitioned between diethyl ether and saturated aqueous sodium hydrogen carbonate. The aqueous layer was extracted with diethyl ether.

The organic portions were combined, washed with saturated aqueous sodium hydrogen carbonate, washed with brine, dried (Na$_2$SO$_4$), filtered, and concentrated under reduced pressure. The residue was chromatographed using flash chromatography eluting with 90:10 hexane:ethyl acetate to provide 8.0 g of 98 as a yellow oil (99% yield).

5-(3-(tert-butyldimethylsilyloxy)prop-1-en-2-yl)-2,3-dichloropyridine

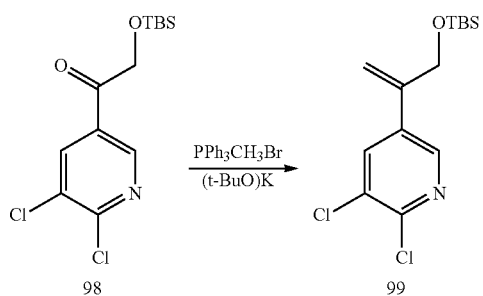 [SMILES: "(t-BuO)K" ; CC(C)(C)[Si](C)(C)OCC(=O)c1cnc(Cl)c(Cl)c1 ; C=C(CO[Si](C)(C)C(C)(C)C)c1cnc(Cl)c(Cl)c1 ; "PPh3CH3Br"]

To a stirred suspension of methyltriphenylphosphonium bromide (11.8 g, 33.0 mmol) in toluene (100 mL) at 0° C. under nitrogen was added potassium tert-butoxide (3.70 g, 33.0 mmol). After being stirred for 1 h at 0° C., a solution of 98 (8.8 g, 27.5 mmol) in toluene (60 mL) was added dropwise to the reaction mixture over 1 h at 0° C. After an additional 2 h at 0° C., the reaction mixture was partitioned between diethyl ether and saturated aqueous ammonium chloride. The aqueous layer was extracted with diethyl ether. The organic portions were combined, washed with water, washed with brine, dried (Na$_2$SO$_4$), filtered, and concentrated under reduced pressure. The residue was chromatographed using flash chromatography eluting with 90:10 hexane:ethyl acetate to provide 7.6 g of 99 as a yellow oil (87% yield).

3-(tert-butyldimethylsilyloxy)-2-(5,6-dichloropyridin-3-yl)propan-1-ol

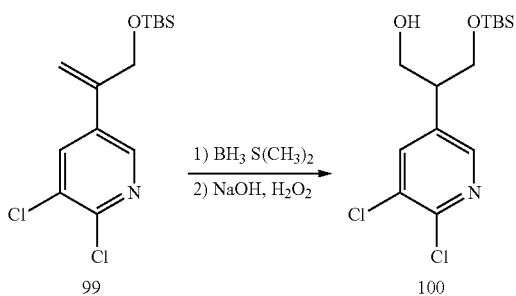 [SMILES: C=C(CO[Si](C)(C)C(C)(C)C)c1cnc(Cl)c(Cl)c1 ; CC(C)(C)[Si](C)(C)OCC(CO)c1cnc(Cl)c(Cl)c1]

To a stirred solution of 99 (7.6 g, 23.9 mmol) in tetrahydrofuran (120 mL) at 0° C. under nitrogen was added borane-methyl sulfide complex (2.3 mL, 23.9 mmol). The reaction mixture was heated to a temperature of about 25° C. and stirred for 5 h. Thereafter, the reaction mixture was cooled to 0° C. and to the reaction mixture was added 1N sodium hydroxide (48 mL) dropwise followed by the addition of hydrogen peroxide (17 mL, 35 wt % solution in water). After 2 h more at 0° C., the reaction mixture was partitioned between ethyl acetate and water. The aqueous layer was extracted with ethyl acetate. The organic portions were combined, washed with water, aqueous sodium sulfite and brine, dried (Na$_2$SO$_4$), filtered, and concentrated under reduced pressure. Compound 100 was isolated by silica gel column chromatography as a yellow oil (42% yield).

tert-butyl 4-(5-(1-(tert-butyldimethylsilyloxy)-3-hydroxypropan-2-yl)-3-chloropyridin-2-yl)-5,6-dihydropyridine-1(2H)-carboxylate

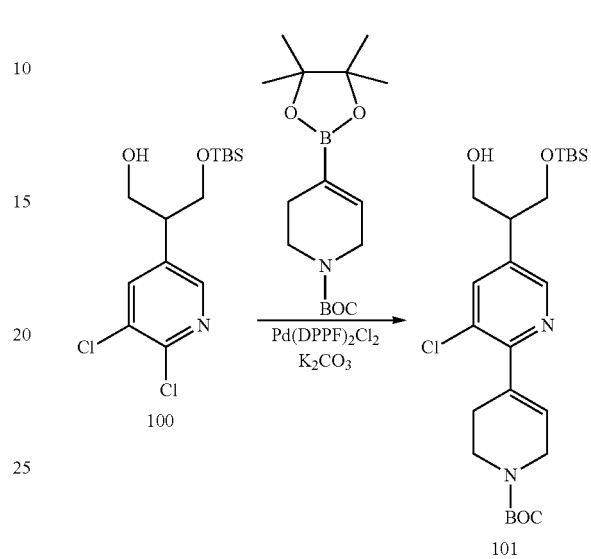

To stirred solution of 100 (1 g, 2.97 mmol) in dimethoxyethane:ethanol (18 mL, 2:1) at a temperature of about 25° C. was added Pd(DPPF)$_2$Cl$_2$ (485.6 mg, 0.595 mmol), pinacol ester (919.4 mg, 2.97 mmol), potassium carbonate (821.9 mg, 5.95 mmol), and water (12 mL). The reaction mixture was heated to 60° C. and stirred for 1.5 h. Thereafter, the reaction mixture was cooled to a temperature of about 0° C. and partitioned between ethyl acetate and saturated aqueous ammonium chloride. The aqueous layer was extracted with ethyl acetate. The organic portions were combined, washed with brine, dried (Na$_2$SO$_4$), filtered, and concentrated under reduced pressure. The residue was chromatographed using flash chromatography eluting with a gradient of from 70:30 to 40:60 hexane:ethyl acetate to provide 1.49 g of 101 as a yellow oil (>99% yield).

2-(5-chloro-6-(1,2,3,6-tetrahydropyridin-4-yl)pyridin-3-yl)propane-1,3-diol hydrochloride

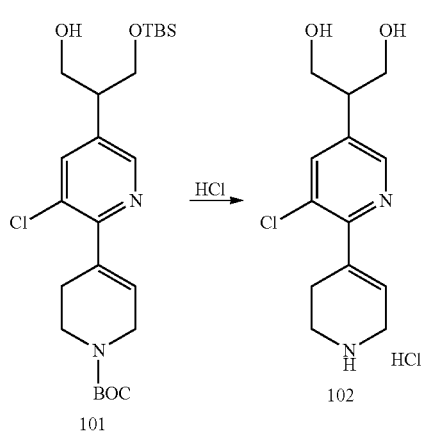 [SMILES: CC(C)(C)OC(=O)N1CC=C(c2ncc(C(CO)CO[Si](C)(C)C(C)(C)C)cc2Cl)CC1 ; Cl ; OCC(CO)c1cnc(C2=CCNCC2)c(Cl)c1 ; Cl]

To a stirred solution of 101 (1.49 g, 2.97 mmol) in dichloromethane (7 mL) and methanol (2 mL) at 25° C. was added excess amount of 4N HCl in dioxane (7.5 mL).

After being stirred for 2 h at a temperature of about 25° C., the reaction mixture was concentrated under reduced pressure. The residue was crystallized from diethyl ether to provide 606.3 mg of the hydrochloride salt of 102 as a pale brown solid (70% yield).

4-(3-chloro-5-(1,3-dihydroxypropan-2-yl)pyridin-2-yl)-N-(4-(trifluoromethyl)phenyl)-5,6-dihydropyridine-1(2H)-carboxamide

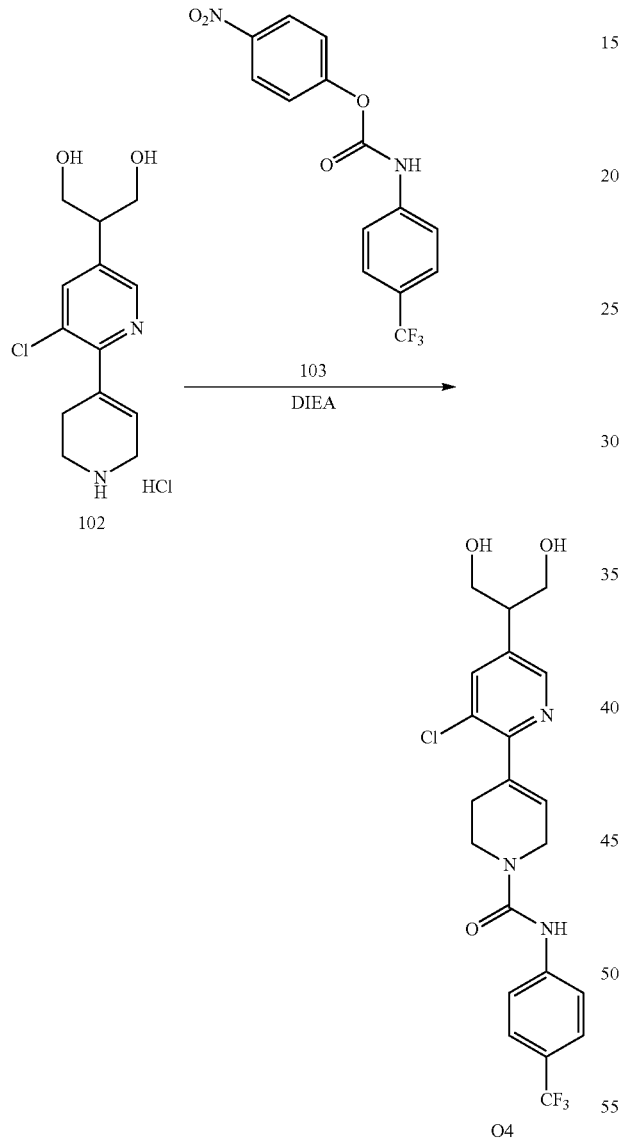

To a stirred solution of 4-trifluoroaniline (29 mL, 0.328 mmol) in dichloromethane (3.5 mL) at 0° C. was added 4-nitrophenyl chloroformate (66.0 mg, 0.328 mmol) and pyridine (32 mL, 0.393 mmol). After heating to a temperature of about 25° C., the reaction mixture was stirred for 2 h. Thereafter, the reaction mixture was cooled to 0° C. and the hydrochloride salt of 102 (100 mg, 0.328 mmol) and DIEA (0.14 mL, 0.819 mmol) were added. After 1 h more at 0° C., the reaction mixture was partitioned between ethyl acetate and water. The aqueous layer was extracted with ethyl acetate. The organic portions were combined, washed with saturated aqueous sodium hydrogen carbonate and brine, dried ($Na_2SO_4$), filtered, and concentrated under reduced pressure. The residue was chromatographed using flash chromatography eluting with a gradient of from 95:5 to 90:10 chloroform:methanol. The resulting solid was recrystallized from isopropyl ether:ethyl acetate to provide 97.2 mg of O4 as a white solid (65% yield).

Example 6: Determination of the Optical Purity for B1 and N1

The % ee was determined for compounds B1 and N1 as shown below:

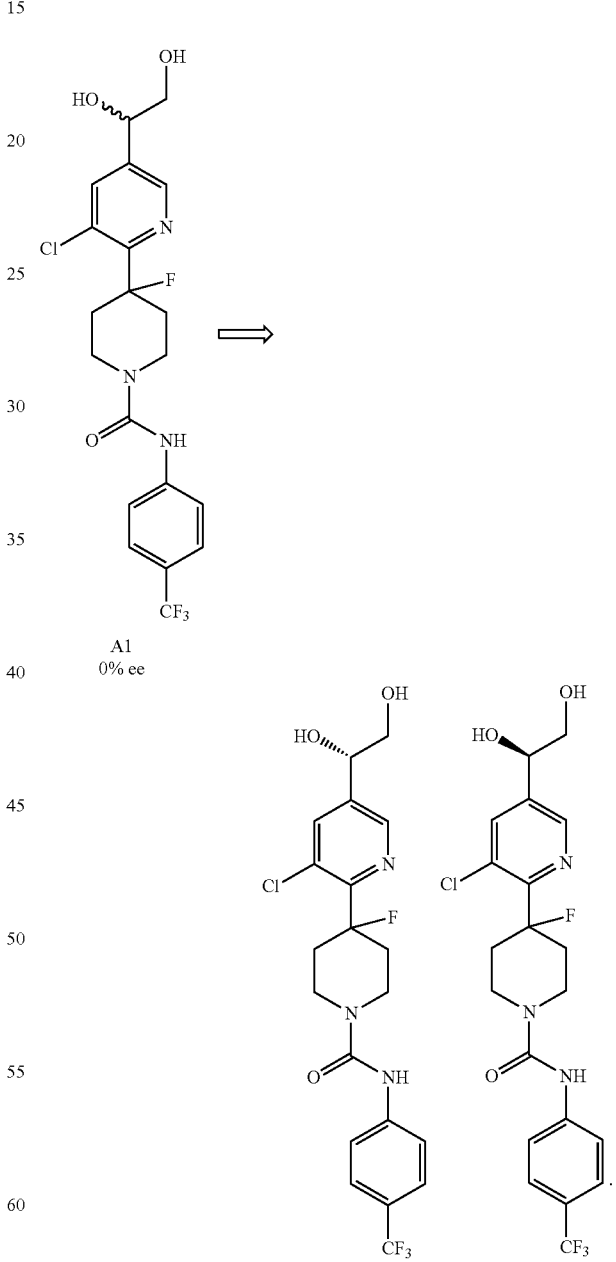

<sup>1</sup>H NMR and chiral HPLC were used to determine the % ee for both N1 and B1. For the HPLC assay, a CHIRALPAK 1A column was used, the peak areas for the major and minor enantiomers were determined, and % ee was calculated from the equation in section 5.3. For $^1$H NMR, bis-Mosher's ester derivatives were synthesized for A1, B1, and N1 by a technique known in the art. The % ee determinations were done by adding an excess of Mosher's acid chloride to A1, B1, or N1 (about 0.6 mg) in pyridine-d$^5$ (0.530 mL) at a temperature of about 25° C. in an NMR tube. A $^1$H NMR was taken 20 h after the addition of Mosher's acid chloride. The peak chosen for the bis-Mosher's ester of N1 is at approximately δ 6.90, and for B1 at δ 6.78. It is important to note the $^{13}$C satellites were observed at δ (7.02 and 6.78) for N1 and δ (6.90 and 6.65) for B1. The $^1$H NMR peaks for the minor and major enantiomer in each case were integrated, the $^{13}$C satellites were subtracted out, and the % ee was calculated.

Example 7: Synthesis of Compound M4

2,3-dichloro-5-methylsulfonamidylmethyl pyridine

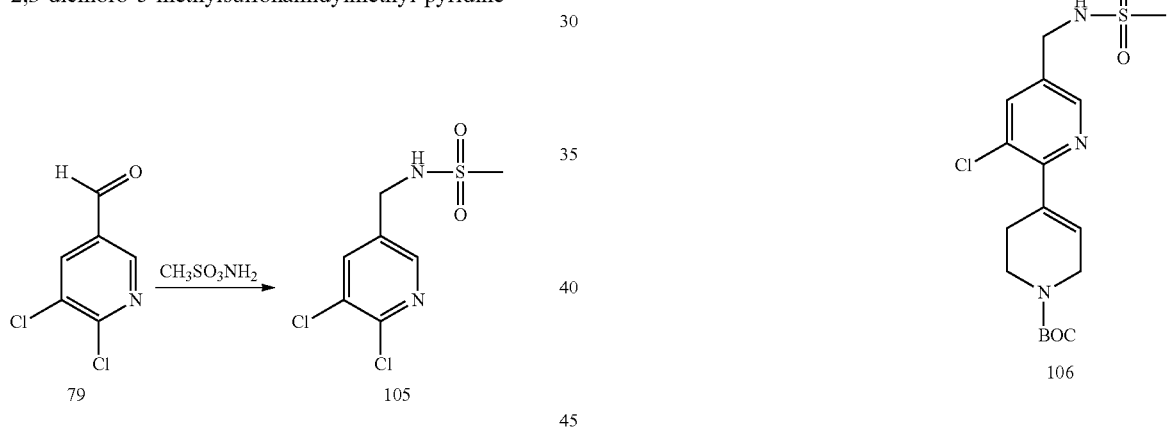

tert-butyl 4-(3-chloro-5-(methylsulfonamidomethyl) pyridin-2-yl)-5,6-dihydropyridine-1(2H)-carboxylate

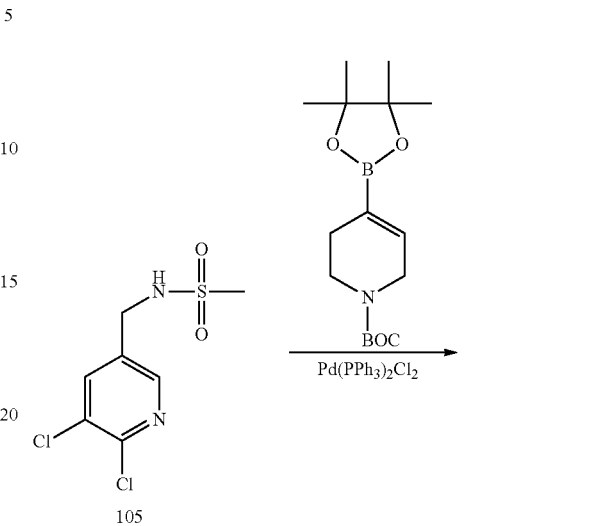

To a suspension of methyl sulfonamide (1.08 g, 11.35 mmol), 2,3-dichloropyridinyl aldehyde, (79, 3.0 g, 17.03 mmol), AcOH (1.35 mL), and NaBH(OAc)$_3$ in dry dichloromethane (70 mL) at 0° C., TEA (3.18 mL, 22.7 mmol) was added. The reaction mixture was heated to a temperature of about 25° C. and stirred for 15 h. Thereafter, saturated NaHCO$_3$ (2 mL) was added. The mixture was extracted twice with ethyl acetate (80 mL for each extraction). The organic portions were combined, washed twice with brine (50 mL for each wash), dried over anhydrous Na$_2$SO$_4$, and concentrated under reduced pressure. The oily residue was chromatographed using a COMBIFLASH apparatus with a 40 g REDISEP column with eluent of 40% ethyl acetate in hexanes to provide 2.8 g of 105 (65% yield) and 20% recovered starting material. $^1$H NMR (CDCl$_3$): δ 8.38 (s, 1H), 8.27 (s, 1H), 5.03 (bs, NH), 4.35 (d, J=17 Hz, 2H), 3.0 (s, 3H).

To a suspension of 105 (3.86 g, 15.1 mmol), boronate (4.78, 15.1 mmol), and Pd(PPh$_3$)$_2$Cl$_2$ in ethylene glycol dimethyl ether (38 mL) and EtOH (19 mL) at a temperature of about 25° C. was added 2M K$_2$CO$_3$ (15 mL). The reaction mixture was heated 40° C. for 9 hr. Thereafter, the reaction mixture was cooled to a temperature of about 25° C., 1N HCl (10 mL) was added. The mixture was extracted twice with ethyl acetate (60 mL for each extraction). The organic portions were combined, washed with water, dried over anhydrous Na$_2$SO$_4$, and concentrated under reduced pressure to provide the oily residue which was then chromatographed using a COMBIFLASH apparatus with a 80 g REDISEP column with 30% EtOAc in hexanes to provide 5.0 g of 106 (83% yield). $^1$H NMR (CDCl$_3$): δ 8.35 (s, 1H), 7.70 (s, 1H), 6.03 (bs, 1H), 5.34 (bs, t, NH), 4.26 (d, J=6.3 Hz, 2H), 4.10 (m, 2H), 3.55 (t, J=5.6 Hz, 2H), 2.89 (s, 3H), 1.42 (s, 9H).

N-((5-chloro-6-(1,2,3,6-tetrahydropyridin-4-yl)pyridin-3-yl)methyl)methane sulfonamide hydrochloride

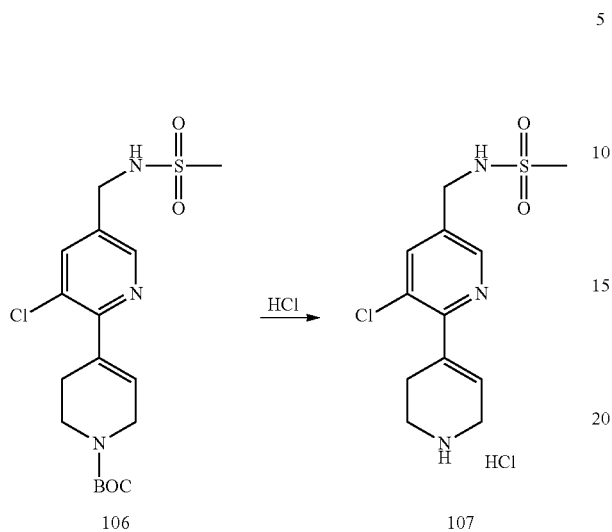

Compound 106 (1.0 g, 2.5 mmol) was dissolved in dry dichloromethane (10 mL) and cooled to 0° C. 4N HCl in dioxane (10 mL, 25 mmol) was added. The reaction mixture was heated a temperature of about 25° C. and stirred for 16 h. The resulting white slurry was filtered and, after drying under reduced pressure, 790 mg of the hydrochloride of 107 was collected as an off-white solid (94% yield).

4-(3-chloro-5-(methylsulfonamidomethyl)pyridin-2-yl)-N-(4-(trifluoromethyl)phenyl)-5,6-dihydropyridine-1(2H)-carboxamide

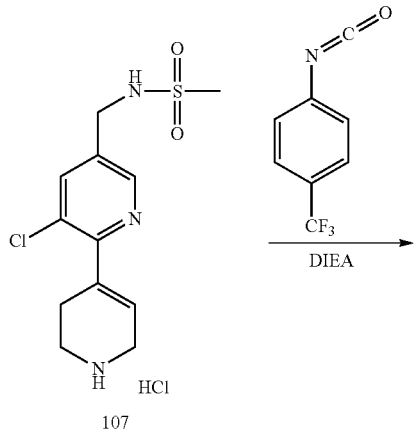

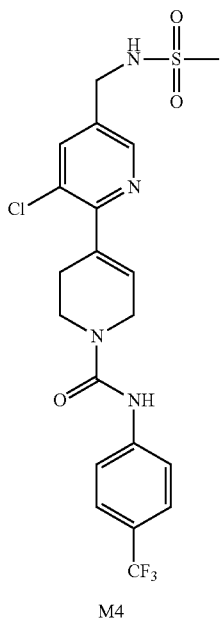

To a suspension of salt (4, 790 mg, 2.34 mmol) in dichloromethane at 0° C. was added DIEA (1.21 mL, 7.03 mmol). The reaction mixture was stirred until it became homogenous. α,α,α-trifluoro-p-tolyl isocyanate (0.3 mL, 2.22 mmol) was added thereto and the reaction mixture stirred for 10 min, until the reaction was complete. The reaction mixture was concentrated under reduced pressure. The oily residue was chromatographed using a COMBI-FLASH apparatus with a 12 g REDISEP column with 50% EtOAc in hexanes to provide 812 mg of M4 as a white solid (71% yield). $^1$H NMR (CDCl$_3$): δ 8.98 (s, 1H), 8.49 (s, 1H), 7.89-7.54 (m, 4H), 6.2 (bs, NH), 4.20-4.24 (m, 4H), 3.70 (t, J=5.5 Hz, 2H), 2.96 (s, 3H), 2.51-2.33 (bs, 2H).

Example 8: Synthesis of Compound N3

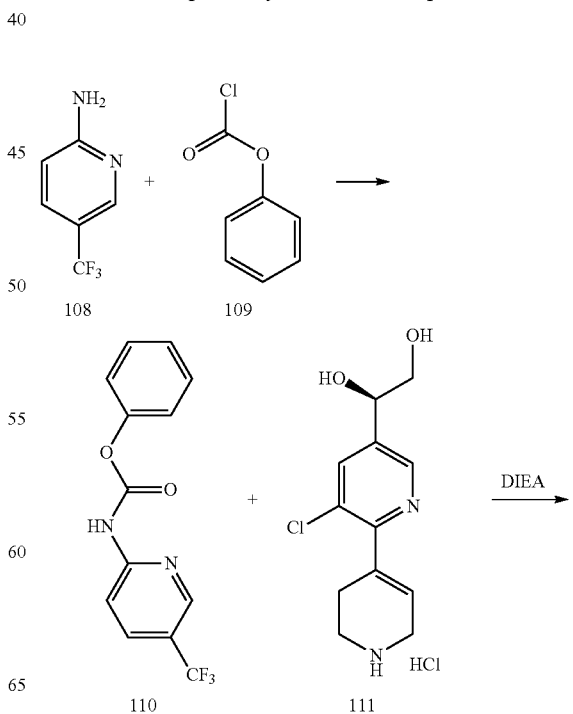

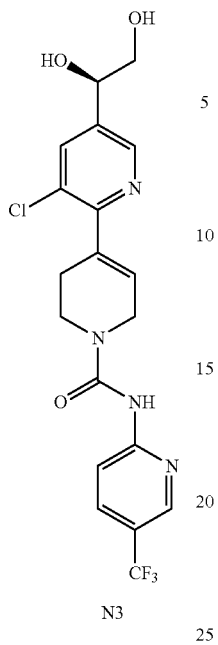

N3 was dissolved in 25 mL hot ethyl acetate and allowed to cool slowly. The precipitate was collected by vacuum filtration and washed twice with a solution of 50% ethyl acetate in hexane (100 mL for each wash) to provide 10.15 g of N3 as a white solid (71% yield). $^1$H NMR (400 MHz, DMSO-d$^6$) δ 9.88 (s, 1H), 8.66-8.60 (m, 1H), 8.49-8.44 (m, 1H), 8.10-8.03 (m, 1H), 8.03-7.96 (m, 1H), 7.85-7.81 (m, 1H), 6.21-6.14 (m, 1H), 5.57-5.51 (m 1H), 4.89-4.82 (m, 1H), 4.64-4.57 (m, 1H), 4.25-4.19 (m, 2H), 3.76-3.67 (m, 2H), 3.60-3.43 (m, 2H), 2.62-2.52 (m, 2H).

Example 9: Synthesis of Compounds of Formula I

Using procedures similar to those described above, the following compounds of formula I were prepared.

Phenyl 5-(trifluoromethyl)pyridin-2-ylcarbamate

To a stirred solution of 5-(trifluoromethyl)pyridin-2-amine 108 (20 g, 123.5 mmol) in dichloromethane (85 mL) at −5° C. was slowly added phenyl carbonochloridate 109 (21.2 g, 136 mmol) over 10 min. At −5° C., pyridine (11.1 mL, 136 mmol) was then added drop wise to the reaction mixture. After heating the reaction mixture to a temperature of about 25° C. and stirring for 1 h, a precipitate gradually formed. The precipitate was filtered and washed with dichloromethane and ethyl acetate to provide 24.1 g of 110 as a white solid (69.2% yield). $^1$H NMR (400 MHz, DMSO-d$^6$) δ 11.3 (br s, 1H), 8.75-8.70 (m, 1H), 8.24-8.17 (m, 1H), 8.05-7.98 (m, 1H), 7.50-7.40 (m, 2H), 7.33-7.22 (m, 2H).

(R)-1-(5-chloro-6-(1,2,3,6-tetrahydropyridin-4-yl)pyridin-3-yl)ethane-1,2-diol

The title compound 111 was obtained using a procedure similar to that described in Example 1 for obtaining 70 except that 67b was used in place of 67a.

(R)-4-(3-chloro-5-(1,2-dihydroxyethyl)pyridin-2-yl)-N-(5-(trifluoromethyl)pyridin-2-yl)-5,6-dihydropyridine-1(2H)-carboxamide To a stirred suspension of the hydrochloride salt of 111 (9.36 g, 32.26 mmol) in dichloromethane (30 mL) at −20° C. was added 110 (8.19 g, 29 mmol) in one portion. Then at −20° C., DIEA (14 mL, 80.65 mmol) was added drop wise to the reaction mixture over 15 min. After being stirred for 2 h at −20° C., the reaction mixture was diluted with 200 mL of dichloromethane, washed twice with 1N aqueous sodium hydroxide (200 mL for each wash), dried (Na$_2$SO$_4$), filtered, and concentrated under reduced pressure. The residue (12 g)

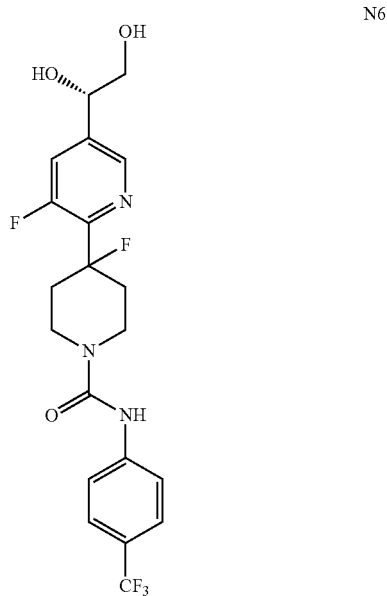 [SMILES: O=C(Nc1ccc(C(F)(F)F)cn1)N1CC=C(c2ncc([C@H](O)CO)cc2F)CC1]

N6

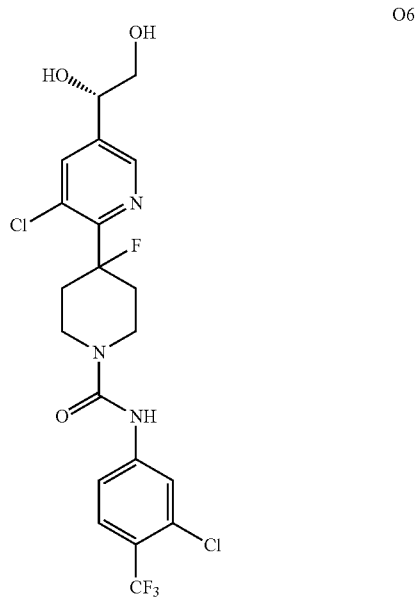

O6

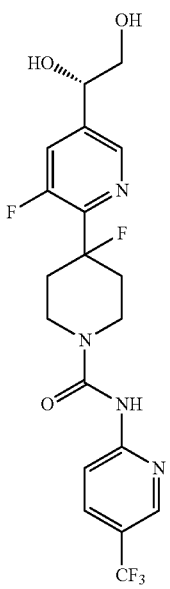
P6
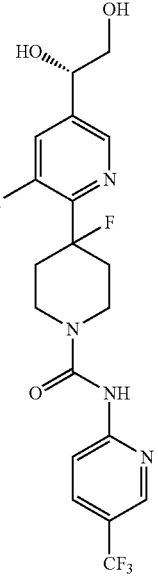
G1
N6: ¹H NMR (CD₃OD) δ 8.41 (s, 1H), 7.59 (m, 5H), 4.80 (t, J=6 Hz, 1H), 4.15 (m, 2H), 3.69 (m, 2H), 3.45 (m, 2H), 2.45-2.26 (m, 4H). MS (M+1): m/z=446.1.
O6: ¹H NMR (CD₃OD) δ 8.38 (m, 1H), 7.79 (m, 1H), 7.68 (m, 1H), 7.52 (d, J=8 Hz, 1H), 7.38 (m, 1H), 4.65 (t, J=6 Hz, 1H), 4.04 (m, 2H), 3.57 (m, 2H), 3.33 (m, 2H), 2.39-2.21 (m, 4H). MS (M+1): m/z=496.0.
P6: ¹H NMR (CD₃OD) δ 8.55 (m, 1H), 8.41 (s, 1H), 7.98 (m, 2H), 7.67 (m, 1H), 4.80 (t, J=6 Hz, 1H), 4.18 (m, 2H), 3.70 (m, 2H), 3.48 (m, 2H), 2.46-2.26 (m, 4H). MS (M+1): m/z=447.1.
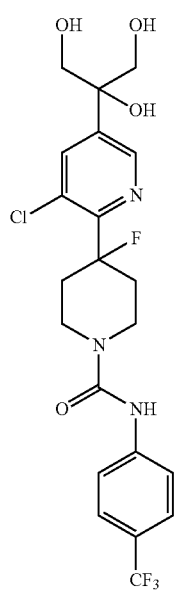
T5
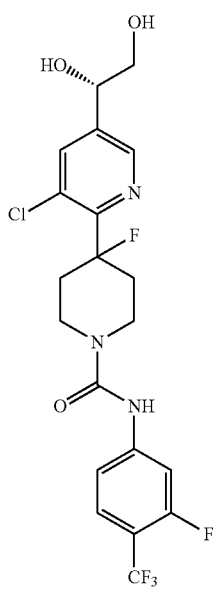
F1
F1: ¹H NMR (CD₃OD) δ 8.38 (m, 1H), 7.79 (m, 1H), 7.44 (m, 2H), 7.21 (m, 1H), 4.65 (t, J=5.6 Hz, 1H), 4.05 (m, 2H), 3.56 (m, 2H), 3.33 (m, 2H), 2.38-2.2.21 (m, 4H). MS (M+1): m/z=480.0.
G1: ¹H NMR (CD₃OD) δ 8.43 (m, 1H), 8.37 (d, J=2 Hz, 1H), 7.87 (m, 2H), 7.79 (m, 1H), 4.65 (t, J=6 Hz, 1H), 4.08 (m, 2H), 3.57 (m, 2H), 3.35 (m, 2H), 2.38-2.22 (m, 4H). MS (M+1): m/z=463.1.
T5: ¹H NMR (CD₃OD) δ 8.64 (dd, J=1.8, 0.6 Hz, 1H), 8.04 (d, J=2.1, 0.3 Hz, 1H), 7.59 (dd, J=14.4, 8.9 Hz, 4H), 4.19-4.15 (br d, J=13.8 Hz, 2H), 3.78 (dd, J=24.8, 11.3 Hz, 4H), 3.49-3.42 (m, 2H), 2.49-2.34 (m, 4H). MS (M+1): m/z=492.

259 | 260
-continued
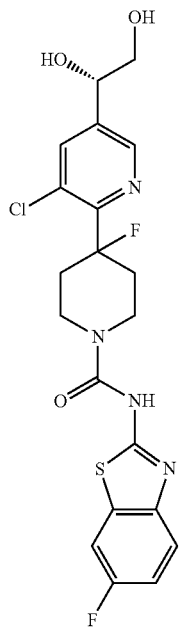
L1
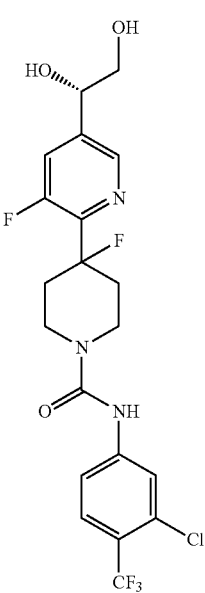
Q3
L1: ¹H NMR (CD₃OD) δ 8.37 (s, 1H), 7.79 (s, 1H), 7.42 (m, 2H), 7.02 (m, 1H), 4.64 (t, J=6 Hz, 1H), 4.21 (m, 2H), 3.56 (m, 2H), 3.35 (m, 2H), 2.35-2.20 (m, 4H). MS (M+1): m/z=469.0.
H1: ¹H NMR (CD₃OD) δ 8.38 (m, 1H), 7.82 (m, 3H), 7.70 (m, 2H), 4.64 (t, J=6 Hz, 1H), 4.06 (m, 2H), 3.57 (m, 2H), 3.36 (m, 2H), 2.40-2.23 (m, 4H). MS (M+1): m/z=526.0.
Q3: ¹H NMR (CD₃OD) δ 8.39 (s, 1H), 7.78 (m, 1H), 7.63 (m, 2H), 7.48 (m, 1H), 4.78 (t, J=6 Hz, 1H), 4.13 (m, 2H), 3.67 (m, 2H), 3.43 (m, 2H), 2.43-2.23 (m, 4H). MS (M+1): m/z=480.5.
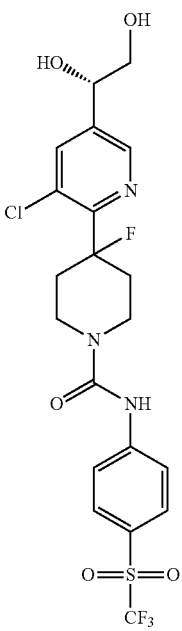
H1
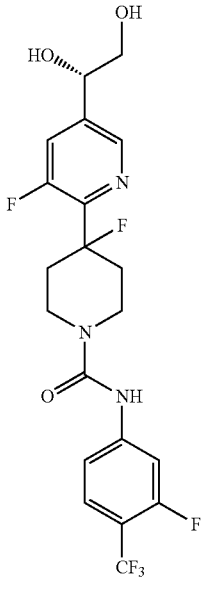
Y3

-continued
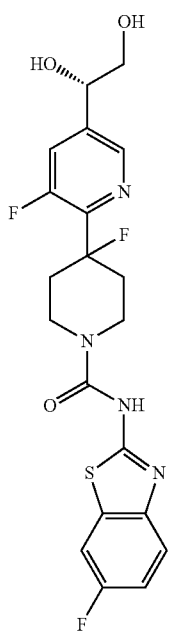
F5
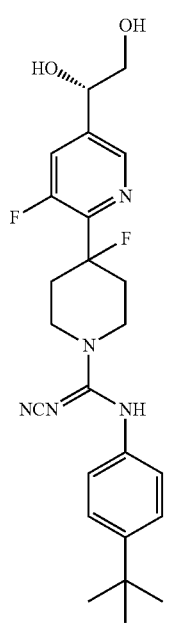
Q6
Y3: ¹H NMR (CD₃OD) δ 8.41 (m, 1H), 7.67 (m, 1H), 7.55 (m, 2H), 7.34 (m, 1H), 4.79 (t, J=6 Hz, 1H), 4.14 (m, 2H), 3.69 (m, 2H), 3.46 (m, 2H), 2.43-2.26 (m, 4H). MS (M+1): m/z=464.1.
F5: ¹H NMR (CD₃OD) δ 8.41 (s, 1H), 7.65 (d, J=12 Hz, 1H), 7.53 (m, 2H), 7.14 (m, 1H), 4.79 (t, J=6 Hz, 1H), 4.28 (m, 2H), 3.69 (m, 2H), 3.48 (m, 2H), 2.45-2.26 (m, 4H). MS (M+1): m/z=453.1.
Q6: ¹H NMR (CD₃OD) δ 8.41 (s, 1H), 7.66 (m, 1H), 7.41 (m, 2H), 7.10 (m, 2H), 4.80 (t, J=6 Hz, 1H), 4.08 (m, 2H), 3.69 (m, 2H), 3.50 (m, 2H), 2.49-2.23 (m, 4H), 1.33 (s, 9H). MS (M+1): m/z=458.5.
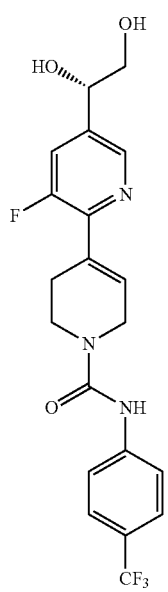
U1
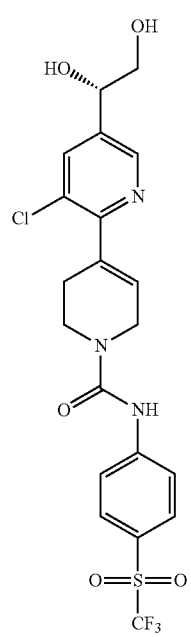
Q1

263
-continued
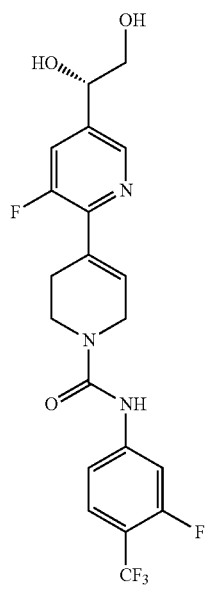
J1
264
-continued
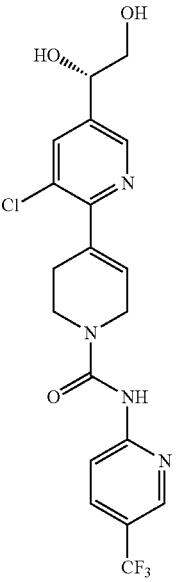
K1
U1: ¹H NMR (MeOD) δ 8.44-8.38 (1H, m), 7.68-7.54 (5H, m), 6.60-6.53 (1H, m), 4.82-4.74 (1H, m), 4.34-4.25 (2H, m), 3.84-3.75 (2H, m), 3.74-3.66 (2H, m), 2.82-2.72 (2H, m). MS: m/z=425.
Q1: ¹H NMR (MeOD) δ 8.51-8.46 (1H, m), 7.99-7.92 (3H, m), 7.89-7.82 (2H, m), 6.17-6.12 (1H, m), 4.80-4.73 (1H, m), 4.33-4.25 (2H, m), 3.87-3.76 (2H, m), 3.75-3.64 (2H, m), 2.70-2.61 (2H, m). MS: m/z=505.
J1: ¹H NMR (MeOD) δ 8.44-8.37 (1H, m), 7.96-7.89 (1H, m), 7.69-7.51 (3H, m), 7.41-7.34 (1H, m), 6.60-6.53 (1H, m), 4.83-4.75 (1H, m), 4.34-4.26 (2H, m), 3.83-3.75 (2H, m), 3.74-3.65 (2H, m), 2.82-2.73 (2H, m). MS: m/z=443.
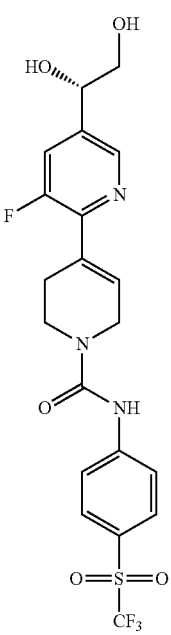
P1
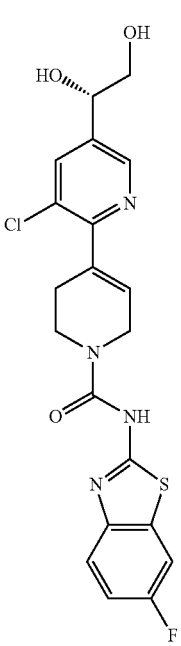
R1
P1: ¹H NMR (MeOD) δ 8.47-8.37 (1H, m), 8.05-7.83 (5H, m), 7.71-7.59 (1H, m), 6.66-6.53 (1H, m), 4.85-4.74 (1H, m), 4.42-4.28 (2H, m), 3.91-3.64 (4H, m), 2.89-2.74 (2H, m). MS: m/z=489.
K1: ¹H NMR (CDCl₃) δ 8.51-8.43 (2H, m), 8.25-8.18 (1H, m), 7.92-7.85 (1H, m), 7.83-7.78 (1H, m), 7.53 (1H, br s), 6.22-6.15 (1H, m), 4.95-4.84 (1H, m), 4.31-4.19 (2H, m), 3.93-3.64 (4H, m), 3.08-2.97 (1H, m), 2.77-2.63 (2H, m), 2.24-2.14 (1H, m). MS: m/z=442.

R1: ¹H NMR (DMSO) δ 8.50-8.44 (1H, m), 7.87-7.82 (1H, m), 7.82-7.75 (1H, m), 7.70 (1H, br s), 7.26-7.17 (1H, m), 6.23-6.17 (1H, m), 5.58-5.51 (1H, m), 4.89-4.82 (1H, m), 4.64-4.57 (1H, m), 4.31-4.21 (2H, m), 3.85-3.73 (2H, m), 3.60-3.42 (2H, m), 2.61-2.51 (2H, m). MS: m/z=448.

U3

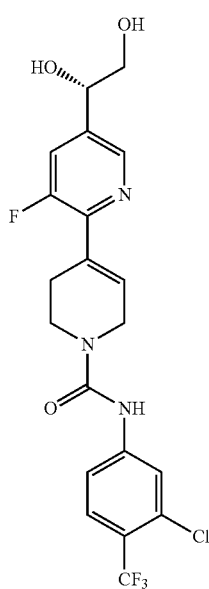

K4

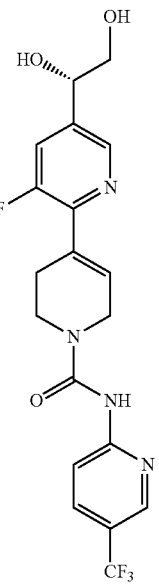

U3: ¹H NMR (MeOD) δ 8.42-8.36 (1H, m), 7.92 (1H, s), 7.83-7.77 (1H, m), 7.67-7.58 (2H, m), 7.55-7.48 (1H, m), 6.58-6.52 (1H, m), 4.80-4.72 (1H, m), 4.31-4.24 (2H, m), 3.81-3.74 (2H, m), 3.72-3.63 (2H, m), 2.80-2.71 (2H, m). MS: m/z=459.

L4: ¹H NMR (DMSO) δ 8.45-8.33 (1H, m), 7.85-7.73 (1H, m), 7.69-7.51 (2H, m), 7.29-7.51 (1H, m), 6.63-6.49 (1H, m), 5.62-5.49 (1H, m), 4.91-4.79 (1H, m), 4.70-4.56 (1H, m), 4.37-4.23 (2H, m), 3.87-3.71 (2H, m), 3.59-3.41 (2H, m), 2.73-2.59 (2H, m). MS: m/z=432.

K4: ¹H NMR (MeOD) δ 8.61-8.49 (1H, m), 8.46-8.34 (1H, m), 8.09-7.87 (2H, m), 7.70-7.56 (1H, m), 6.63-6.51 (1H, m), 4.82-4.72 (1H, m), 4.38-4.26 (2H, m), 3.89-3.75 (2H, m), 3.74-3.62 (2H, m), 2.84-2.70 (2H, m). MS: m/z=426.

Example 10: Alternate Synthesis of Compound 67a 5,6-dichloronicotinoyl chloride

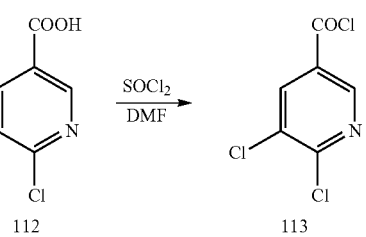

L4

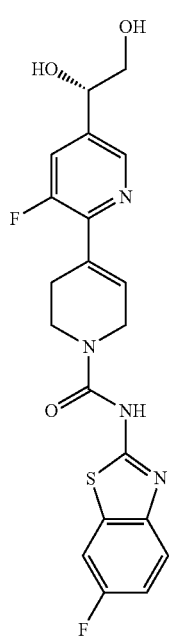

To a well stirred suspension of 5,6-dichloronicotinic acid 112 (600 g. 3.125 mol) and N,N-dimethylformamide (20.0 mL) in dichloroethane (1.2 L) a temperature of about 25° C. was added drop wise with stirring thionyl chloride (743.56 g, 6.25 mol). In a reflux apparatus fitted with a gas trap filled with saturated aqueous sodium bicarbonate, the reaction mixture was heated and refluxed, at about to 75° C., until the reaction mixture became a clear solution, after about 3 h. LC/MS analysis of a sample quenched in methanol showed only the presence of the methyl ester. The reaction mixture was cooled to a temperature of about 25° C. and concentrated under reduced pressure to provide 113 as a thick slurry.

1-(5,6-dichloropyridin-3-yl)ethanone

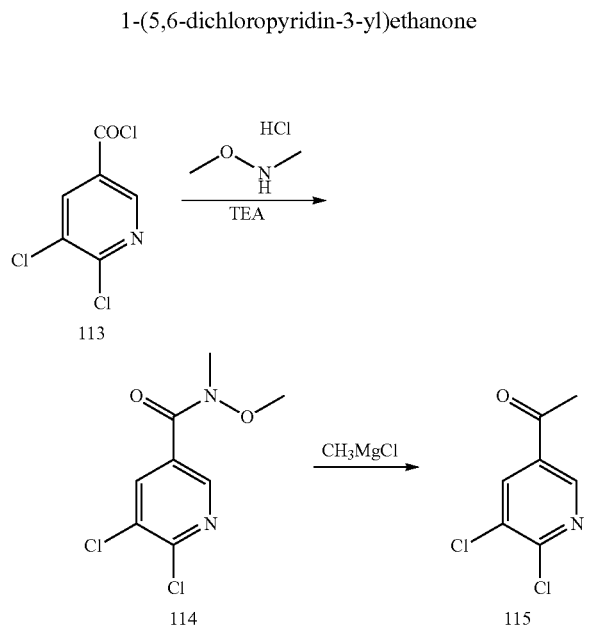

In a dry ice/acetone bath, a suspension of N,O-dimethylhydroxylamine hydrochloride (350.53 g, 3.59 mol) in methylene chloride was cooled to 0° C. and TEA (711.5 g, 7.03 mol) was added. Compound 113 was dissolved in methylene chloride (2.4 L) and added to the mixture at a rate such that the reaction mixture temperature did not exceed 15° C. After the addition of 113 was complete, the reaction mixture was allowed to warm slowly to a temperature of about 25° C. over 16 h. Then the reaction mixture was poured into 2 L of water, the layers were separated, and the aqueous portion was extracted twice with methylene chloride (500 mL for each extraction). The organic portions were combined, dried (MgSO$_4$), and concentrated under reduced pressure to yield a brown solid. The solid was treated with 1 L of boiling hexanes and heated at reflux for about 10 minutes. The resulting pale orange solution was decanted from the dark yellow-brown tar and allowed to cool. This boiling hexanes treatment was repeated twice on the tar (500 mL for each treatment). The hexane mixtures were combined, allowed to cool to a temperature of about 25° C., then cooled in an ice/water bath. The resulting yellow needles were collected by vacuum filtration and dried in air to provide 730 g of 5,6-dichloro-N-methoxy-N-methylnicotinamide 114 (99% yield). $^1$H NMR (400 MHz, CDCl$_3$) δ 8.68 (m, 1H), 8.18 (m, 1H), 3.59 (OCH$_3$, 3H), 3.40, (NCH$_3$, 3H).

431 g of 115 was obtained using a procedure similar to that described in Example 4 for obtaining 89 except that 114 was used in place of 88 (97% yield). $^1$H NMR (400 MHz, CDCl$_3$) δ 8.82 (m, 1H), 8.29 (m, 1H), 2.62 (COCH$_3$, 3H).

1-(5,6-dichloropyridin-3-yl)ethanol

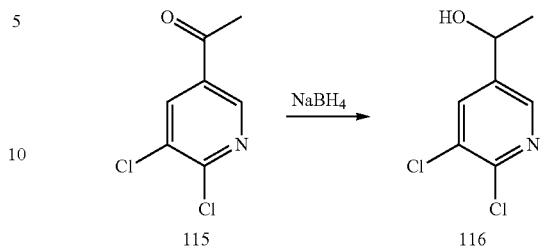

To a well-stirred suspension of 115 (665 g, 3.5 mol) in methanol (3.5 L) at 0° C. was added sodium borohydride (66.21 g, 1.75 mol) portionwise at a rate such that the reaction mixture temperature did not exceed 5° C. After the addition was complete, the reaction mixture was warmed to a temperature of about 25° C. and stirred an additional 1 h. LC/MS analysis of an aliquot showed that the reaction was essentially complete. The reaction mixture was concentrated under reduced pressure. The residue was mixed with 2 L diethyl ether and 2 L 1N HCl. The layers were separated and the aqueous layer was extracted twice with diethyl ether (250 mL for each extraction). The organic portions were combined, dried (MgSO$_4$), and concentrated under reduced pressure to provide 670 g of 116 as a pale yellow oil (99% yield). $^1$H NMR (400 MHz, CDCl$_3$) δ 8.20 (m, 1H), 4.96 (m, 1H), 3.57 (s, 1H), 1.51 (d, J=6.5 Hz, 3H).

2,3-dichloro-5-vinylpyridine

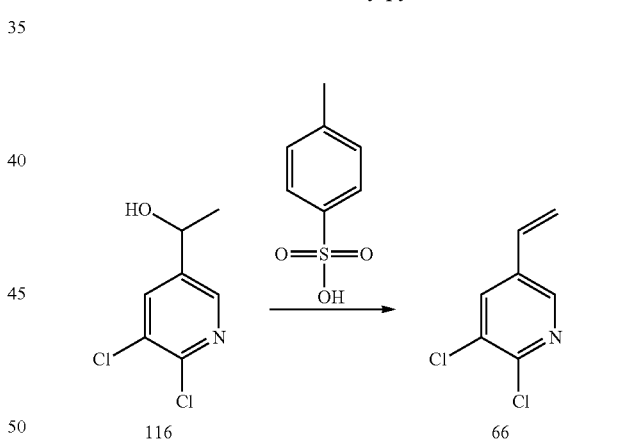

To a solution of 116 (311 g, 1.62 mol) in chlorobenzene (3 L) was added p-toluene sulfonic acid (431 g, 2.5 mol). The reaction mixture was heated to reflux, about 140° C., and water was removed concurrently. At the completion of the reaction, the mixture was concentrated under reduced pressure to about 500 mL, diluted with 2 L of water, and extracted three times with ethyl acetate (1 L for each extraction). The organic portions were combined, dried (Na$_2$SO$_4$), and concentrated under reduced pressure under mild heating to provide a residue. The residue was added to 500 mL of methylene chloride and applied to the top of column packed with 2 kg silica eluted with a 0% to 10% gradient of ethyl acetate in hexane to provide 178.55 g of >99% pure 2,3-dichloro-5-vinylpyridine 66 as a clear oil, which solidified upon cooling to 4° C. (63% yield). $^1$H NMR (400 MHz, CDCl₃) δ 8.32 (m, 1H), 7.85 (m, 1H), 5.72 (m, 1H), 4.88 (m, 1H), 4.37 (m, 1H).

(S)-1-(5,6-dichloropyridin-3-yl)ethane-1,2-diol

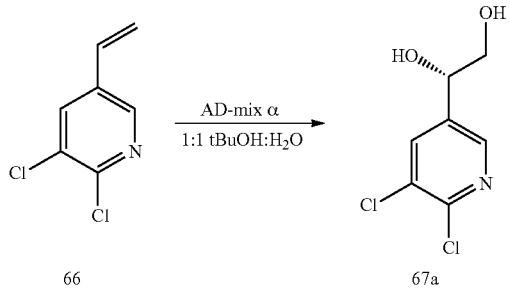

In a 5 L three neck round bottom flask fitted with an overhead mechanical stirrer and a thermocouple, a stirred mixture of 66 (150 g, 0.861 mol), t-butanol (2.15 L), and water (2.15 L) was cooled with an ice/water bath until the temperature of the mixture was below 10° C. AD-mix α (729 g, 1.15 eq.) was added all at once; an endothermic heat of solution lowered the temperature of the reaction mixture to 7° C. The bath was packed with ice and the reaction mixture was allowed to stir for 16 h while its temperature gradually increased to about 25° C. Thereafter, an aliquot of the reaction mixture was removed, diluted with methanol, filtered, and analyzed by LC/MS; the LC/MS results showed that the reaction was essentially complete.

To promote clumping of the solids and aid filtration, the reaction mixture was diluted with 2 L ethyl acetate and filtered under reduced pressure to remove the solids. The resulting clear mixture was phase separated. The aqueous portion was extracted twice with ethyl acetate (250 mL for each extraction). The organic portions were combined, dried (MgSO₄) and concentrated under reduced pressure to provide a dark gray solid. The solid was added to 500 mL of methanol, treated with decolorizing carbon, boiled, filtered warm through a pad of CELITE, and concentrated under reduced pressure to provide a gray solid. The solid was recrystallized from chloroform to provide 115 g of 67a as a white solid. A second crop of 67a, 12.3 g, was obtained by concentrating the supernatant (71% total yield). ¹H NMR (400 MHz, CD₃OD) δ 8.32 (m, 1H), 8.0 (m, 1H), 4.75 (t, J=6 Hz, 1H), 3.65 (m, 2H).

Example 10a: Synthesis of Compound E6

(5,6-dichloropyridin-3-yl)methyl methanesulfonate

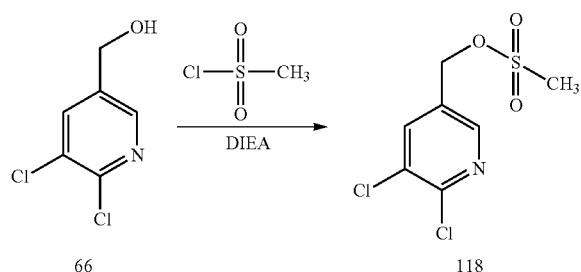

To a solution of (5,6-dichloropyridin-3-yl)methanol (117, 5000 mg, 28.1 mmol, Tokyo Chemical Industry Co., Tokyo, Japan) in CH₂Cl₂ (150 mL) at a temperature of about 25° C. was added DIEA (30.9 mmol). The mixture was cooled to 0° C. and methansulfonyl chloride (MsCl, 30.9 mmol) was added dropwise over 15 min. Thereafter, the reaction mixture was stirred at 0° C. for 1 h. After quenching with water, the mixture was extracted three times with CHCl₃/H₂O (100 mL for each extraction), dried (MgSO₄), and concentrated under reduced pressure to provide a yellow oil. The oil was chromatographed by silica gel column chromatography (Yamazen) with a gradient of ethyl acetate (20%-50%)/n-hexane to provide 6360 mg of 118 as a yellow oil (88% yield). ¹H NMR (400 MHz, DMSO) δ: 8.51 (1H, s), 8.26 (1H, s), 5.35 (2H, s), 3.32 (3H, s).

2-(5,6-dichloropyridin-3-yl)acetonitrile

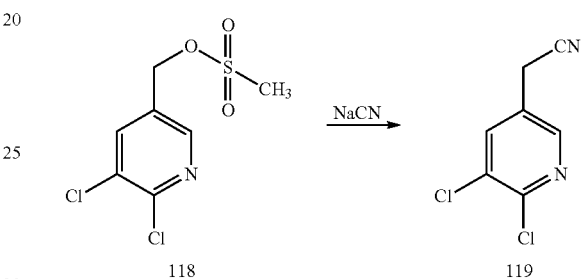

To a solution of 118 (6360 mg, 24.8 mmol) in ethanol (75 mL) at a temperature of about 25° C. was added a solution of NaCN (32.3 mmol) in water (25 mL). The reaction mixture was heated to 80° C. and stirred for 1 h. After concentration under reduced pressure, the mixture was extracted three times with EtOAc/H₂O (100 mL for each extraction), dried (Na₂SO₄), and concentrated under reduced pressure to provide an orange oil. The oil was chromatographed by silica gel column chromatography (Yamazen) with a gradient of ethyl acetate (30%-50%)/n-hexane to provide 2648 mg of 119 as a colorless solid (57% yield). ¹H NMR (400 MHz, DMSO) δ: 8.42 (1H, s), 8.18 (1H, s), 4.15 (2H, s).

tert-butyl 4-(3-chloro-5-(cyanomethyl)pyridin-2-yl)-5,6-dihydropyridine-1(2H)-carboxylate

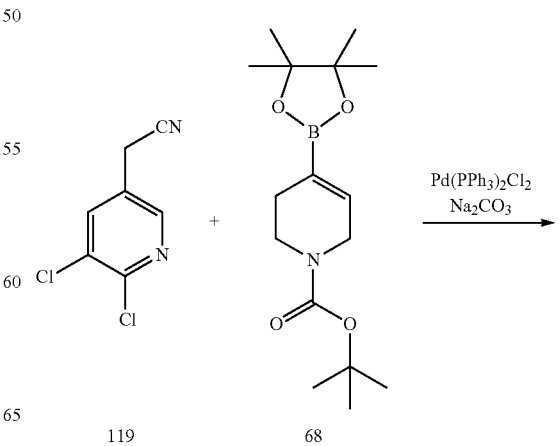

271
-continued

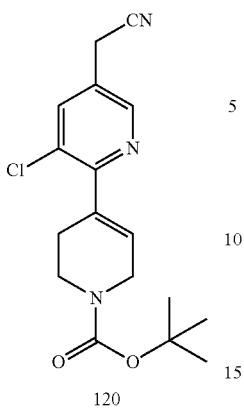
120

To a mixture of 119 (187 mg, 1 mmol), 68 (1 mmol), and Na$_2$CO$_3$ (1.5 mmol) in 2/1/2 DME/EtOH/H$_2$O (10 mL) at a temperature of about 25° C. was added Pd(PPh$_3$)$_2$Cl$_2$ (0.1 mmol). The reaction mixture was heated to 120° C. and stirred for 30 min. After cooling to a temperature of about 25° C., the mixture was diluted with water, extracted three times with CHCl$_3$/H$_2$O (30 mL for each extraction), dried (Na$_2$SO$_4$), and concentrated under reduced pressure to provide a yellow oil. The oil was chromatographed by silica gel column chromatography (Yamazen) with a gradient of ethyl acetate (20%-50%)/n-hexane to provide 287 mg of 120 as a pale yellow oil (86% yield). $^1$H NMR (400 MHz, DMSO) δ: 8.50 (1H, s), 7.95 (1H, s), 6.17 (1H, s), 4.11 (2H, s), 4.02 (2H, s), 3.54 (2H, m), 2.47 (2H, m), 1.43 (9H, s).

2-(5-chloro-6-(1,2,3,6-tetrahydropyridin-4-yl)pyridin-3-yl)acetonitrile

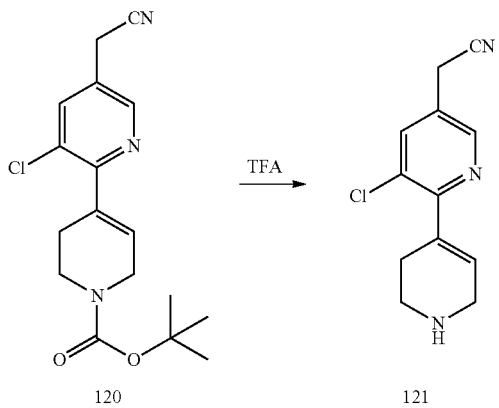 [SMILES: CC(C)(C)OC(=O)N1CC=C(c2ncc(CC#N)cc2Cl)CC1 ; N#CCc1cnc(C2=CCNCC2)c(Cl)c1]

To a solution of 120 (287 mg, 0.86 mmol) in CH$_2$Cl$_2$ (3 mL) at 0° C. was added trifluoroacetic acid (TFA, 8.6 mmol). The reaction mixture was heated to a temperature of about 25° C. and stirred for 45 min. After concentration under reduced pressure, the mixture was neutralized with 28% aqueous ammonia, extracted three times with CHCl$_3$/H$_2$O (50 mL for each extraction), dried (Na$_2$SO$_4$), and concentrated under reduced pressure to provide 200 mg of 121 as a yellow oil (>99% yield). $^1$H NMR (400 MHz, DMSO) δ: 8.53 (1H, s), 7.98 (1H, s), 6.12 (1H, s), 4.11 (2H, s), 3.40 (2H, s), 3.19 (1H, br), 2.90 (2H, s), 2.24 (2H, s).

272
4-(3-chloro-5-(cyanomethyl)pyridin-2-yl)-N-(4-(trifluoromethyl)phenyl)-5,6-dihydropyridine-1 (2H)-carboxamide

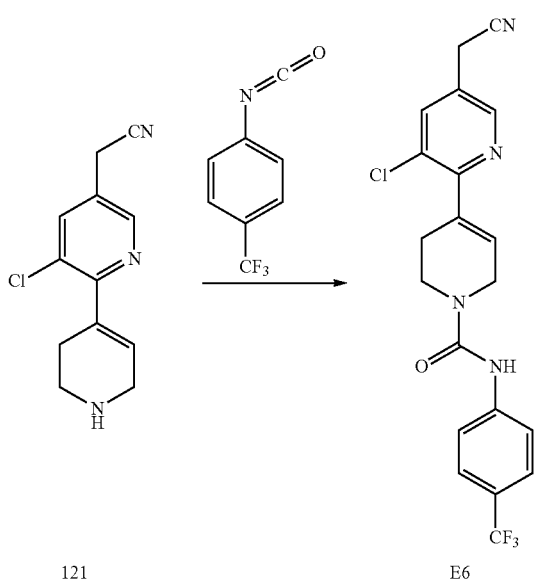

To a solution of 121 (200 mg, 0.86 mmol) in CH$_2$Cl$_2$ (7 mL) at a temperature of about 25° C. was added 1-isocyanato-4-(trifluoromethyl)benzene (0.86 mmol, Acros Organics, Geel, Belgium). The reaction mixture was stirred at a temperature of about 25° C. for 1.5 h. After concentration under reduced pressure, the mixture was chromatographed by silica gel column chromatography (Yamazen) with a gradient of CHCl$_3$ (99%-20%)/MeOH to provide 64 mg of E6 as a colorless solid (18% yield). $^1$H NMR (400 MHz, DMSO) δ: 8.96 (1H, s), 8.52 (1H, s), 7.97 (1H, s), 7.73 (1H, d, J=8 Hz), 7.60 (1H, d, J=8 Hz), 6.25 (1H, s), 4.21 (2H, s), 4.12 (2H, s), 3.70 (2H, t, J=8 Hz), 2.58 (1H, s), 2.50 (1H, s). LC/MS (100%, tr=6.72 min) [M+H]$^+$, m/z=420.8 (Calc: 420.1).

Example 10B: Synthesis of Compound L1

(S)-4-(3-chloro-5-(1,2-dihydroxyethyl)pyridin-2-yl)-4-fluoro-N-(6-fluorobenzo[d]thiazol-2-yl)piperidine-1-carboxamide

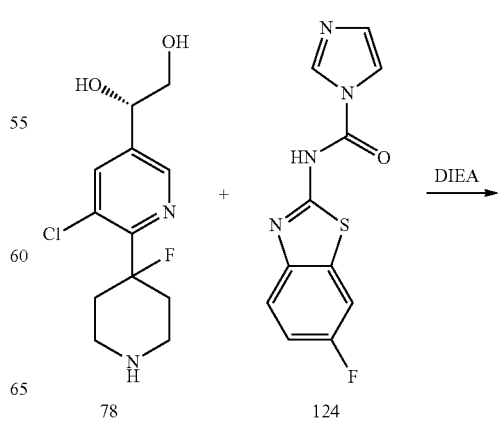

273
-continued

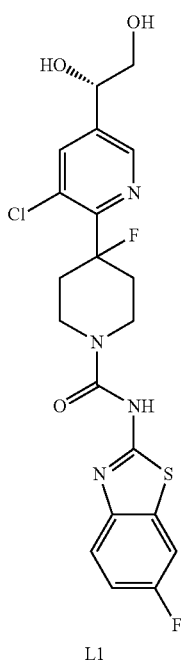

L1

A 100 mL round bottom flask was charged with 78 (800 mg, 2.56 mmol) suspended in DMF (2 mL). DIEA (0.87 mL, 5.12 mmol) and 124 (672 mg, 2.56 mmol) were added. The resulting reaction mixture was stirred at a temperature of about 25° C. until all the solids dissolved, about 2 h. The reaction mixture diluted with water; an off-white precipitate formed. The precipitate was collected by vacuum filtration. The precipitate was washed with water, washed twice with DCM (10 mL for each wash), and dried under reduced pressure to provide 1.0 g of L1 (yield 90%) which was then recrystallized from EtOAc/MeOH. $^1$H NMR: δ 8.35 (s, 1H), 7.80 (s, 1H), 7.35 (m, 2H), 6.98 (m, 1H), 4.70 (t, 1H), 4.2 (m, 2H), 3.6 (m, 2H), 3.3 (m, 2H), 2.25 (m, 4H) ppm. MS (M+1): m/z=468.

6.2 Example 11

In Vivo Assays for Prevention or Treatment of Pain

Test Animals:

Each experiment uses rats weighing between 200-260 g at the start of the experiment. The rats are group-housed and have free access to food and water at all times, except prior to oral administration of a compound of formula I when food is removed for 16 hours before dosing. A control group acts as a comparison to rats treated with a compound of formula I. The control group is administered the carrier for the compound of formula I. The volume of carrier administered to the control group is the same as the volume of carrier and compound of formula I administered to the test group.

Acute Pain:

To assess the actions of the compounds of formula I on the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are as defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of formula I. Data are expressed as tail flick latency(s) and the percentage of the maximal possible effect (% MPE), i.e., 20 seconds, is calculated as follows:

$$\% \ MPE = \frac{\left[\begin{array}{c}(\text{post administration latency}) - \\ (\text{pre-administration latency})\end{array}\right]}{(20 \ s \ \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain:

To assess the actions of the compounds of formula I on the treatment or prevention of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the PWT, or to noxious thermal stimuli by determining the PWL, as described below. Rats are then administered a single injection of 1, 3, 10 or 30 mg/Kg of either a compound of formula I; 30 mg/Kg of a control selected from Celebrex, indomethacin or naproxen; or carrier. Responses to noxious mechanical or thermal stimuli are then determined 1, 3, 5 and 24 hours post administration. Percentage reversal of hyperalgesia for each animal is defined as:

$$\% \ \text{Reversal} = \frac{\left[\begin{array}{c}(\text{post administration } PWT \text{ or } PWL) - \\ (\text{pre-administration } PWT \text{ or } PWL)\end{array}\right]}{\left[\begin{array}{c}(\text{baseline } PWT \text{ or } PWL) - \\ (\text{pre-administration } PWT \text{ or } PWL)\end{array}\right]} \times 100$$

Assessments of the actions of the compounds of formula III that were tested revealed these compounds were surprisingly efficacious, e.g., compounds of formula III significantly reduced FCA-induced thermal hyperalgesia, with $ED_{50}$ values of from about 0.1 mg/kg to about 10 mg/kg and maximum % reversal values of from about 50% to about 100%. For example, for compound D2 the $ED_{50}$ value for reversal of thermal hyperalgesia was 0.95 mg/kg at 3 hours after administration and 1.63 mg/kg at 5 hours after administration of D2. Additionally, the maximum % reversal of thermal hyperalgesia was 78.7% at 5 hours after administration of D2.

Neuropathic Pain:

To assess the actions of the compounds of formula I for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," Pain 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ Reversal} = \frac{\left[\begin{array}{c}(\text{post administration} PWT) - \\ (\text{pre-administration} PWT)\end{array}\right]}{[(\text{baseline } PWT) - (\text{pre-administration} PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anaesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after being administered a compound of formula I for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," Pain 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," Pharmacol. Biochem. and Behavior 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia:

The plantar test can be used to assess thermal hyperalgesia. For this test, hind paw withdrawal latencies (PWL) to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia:

To assess tactile allodynia, rats are placed in clear, Plexiglas compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test:

To assess the effect of compounds of formula I on TRPV1 receptor-mediated pain, the capsaicin-induced eye wipe test is used (N. R. Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", J. Pharmacol. Exp. Ther. 313: 474-484 (2005)). The eye wipe test is a reliable high-throughput test of the effect of TRPV1 antagonists. Rats are given a single injection of 1, 3, 10 or 30 mg/kg of either a compound of formula I; 30 mg/kg of a control selected from Celebrex, indomethacin or naproxen; or carrier. At 1, 3 or 5 hours after drug administration, 3 μL of a 100 μM capsaicin solution (in 10% EtOH/PBS) is instilled in one eye of each animal with a pipette. The number of forelimb movements (touching or wiping of the capsaicin-treated eye) are counted during a 2 minute period following instillation of capsaicin into the eye.

Assessments of the actions of the compounds of formula III revealed these compounds were surprisingly efficacious, e.g., compounds of formula III dose-dependently reduced the number of capsaicin-induced eye wipes by from about 25% to about 100% after their administration relative to the pre-administration eye wipe value. For example, for compound N1 the number of eye wipes decreased to 1 to 3 after the administration of N1 relative to the pre-administration eye wipe value of 24. Specifically, the eye wipe value was 3 at 1 hour after the administration of N1 (87.5% decrease), 1 at 3 hours after the administration (96% decrease), and 2 at 5 hours after the administration of N1 (92% decrease).

6.3 Example 12

Binding of Compounds of Formula I to TRPV1

Methods for assaying compounds capable of inhibiting TRPV1 are known in the art, for example, those methods disclosed in U.S. Pat. No. 6,239,267 to Duckworth et al.; U.S. Pat. No. 6,406,908 to Mc Intyre et al.; or U.S. Pat. No. 6,335,180 to Julius et al. The results of these assays will demonstrate that compounds of formula I bind to and modulate the activity of TRPV1.

Protocol 1

Human TRPV1 Cloning:

Human spinal cord RNA (commercially available from Clontech, Palo Alto, Calif.) is used. Reverse transcription is conducted on 1.0 µg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer, GAAGATCTTCGCTGGTTGCACACTGGGCCACA (SEQ ID No: 1); and reverse primer, GAAGATCTTCGGGGACAGTGACGGTTGGATGT (SEQ ID No: 2).

Using these primers, PCR of TRPV1 is performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 µg/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 µg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 µM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-Based Assay:

Two days prior to performing this assay, cells are seeded on poly-D-lysine-coated 96-well clear-bottom black plates (commercially available from Becton-Dickinson) at 75,000 cells/well in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells are washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is diluted in assay buffer, and 50 µL of the resultant solution is added to the cell plates and the solution is monitored for two minutes. The final concentration of the test compound is adjusted to range from about 50 picoM to about 3 µM. Agonist buffer (wash buffer titrated with 1N HCl to provide a solution having a pH of 5.5 when mixed 1:1 with assay buffer) (0.1 mL) is then added to each well, and the plates are incubated for 1 additional minute. Data are collected over the entire time course and analyzed using Excel and Graph Pad Prism to determine the $IC_{50}$.

Capsaicin-Based Assay:

Two days prior to performing this assay, cells are seeded in poly-D-lysine-coated 96-well clear-bottom black plates (50,000 cells/well) in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1 mM CaCl$_2$ and 20 mM HEPES, pH 7.4, and cells are loaded using 0.1 mL of wash buffer containing Fluo-4 (3 µM final). After one hour, the cells are washed twice with 0.2 mL of wash buffer and resuspended in 0.1 mL of wash buffer. The plates are transferred to a FLIPR for assay. 50 µL of test compound diluted with assay buffer (1× Hank's Balanced Salt Solution containing 1 mM CaCl$_2$ and 20 mM HEPES, pH 7.4) are added to the cell plates and incubated for 2 min. The final concentration of the compound is adjusted to range from about 50 picoM to about 3 µM. Human TRPV1 is activated by the addition of 50 µL of capsaicin (400 nM), and the plates are incubated for an additional 3 min. Data is collected over the entire time course and analyzed using Excel and GraphPad Prism to determine the IC$_{50}$.

Protocol 2

For Protocol 2, a Chinese Hamster Ovary cell line (CHO) that has been engineered to constitutively express human recombinant TRPV1 was used (TRPV1/CHO cells). The TRPV1/CHO cell line was generated as described below.

Human TRPV1 Cloning:

A cDNA for the human TRPV1 receptor (hTRPV1) was amplified by PCR (KOD-Plus DNA polymerase, ToYoBo, Japan) from a human brain cDNA library (BioChain) using primers designed surrounding the complete hTRPV1 open reading frame (forward 5'-GGATCCAGCAAGGAT-GAAGAAATGG (SEQ ID NO:3), and reverse 5'-TGTCT-GCGTGACGTCCTCACTTCT (SEQ ID NO:4)). The resulting PCR products were purified from agarose gels using Gel Band Purification Kit (GE Healthcare Bioscience) and were subcloned into pCR-Blunt vector (Invitrogen). The cloned cDNA was fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA was subjected to restriction digestion with EcoR1. The restriction fragment was subcloned into expression vector pcDNA3.1(−) (Invitrogen) and named pcDNA3.1(−)-hVR1 plasmid. The sequence of the cDNA encoding TRPV1 is available at GenBank accession number AJ277028.

Generation of the TRPV1/CHO Cell Line:

CHO—K1 cells were maintained in growth medium consisting of α-MEM, 10% FBS (Hyclone), and 100 IU/mL of penicillin—100 µg/mL of streptomycin mixed solution (Nacalai Tesque, Japan) at 37° C. in an environment of humidified 95% air and 5% CO$_2$. The cells were transfected with the pcDNA3.1(−)-hVR1 plasmid using FuGENE6 (Roche) according to the manufacturer's protocol. 24 hr after transfection, neomycin-resistant cells were selected using 1 mg/mL G418 (Nacalai Tesque). After 2 weeks, individual colonies were picked, expanded, and screened for the expression of hTRPV1 in the capsaicin-induced Ca$^{2+}$ influx assay (see below) with a FLIPR (Molecular Devices). A clone with the largest Ca$^{2+}$ response to capsaicin was selected and re-cloned by the same procedure. The cells expressing hTRPV1 were cultured in the growth medium supplemented with 1 mg/mL G418. Approximately 1 month later, stable expression of functional TRPV1 receptors in the selected cell line was confirmed by validating Ca$^{2+}$ responses with or without capsazepine (Sigma, at 1 nM-1 µM) in capsaicin assay.

Capsaicin-Induced Ca$^{2+}$ Influx Assay for Cell Selection:

The following assay was performed to identify cells with hTRPV1 expression. CHO—K1 cells transfected with pcDNA3.1(−)-hVR1 plasmid were seeded in 384-well black-wall clear-bottom plates (Corning) and cultivated in growth medium (see above) for 1 day. On the day of experiment, culture medium was exchanged to assay buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, pH 7.4) containing 4 µM Fluo-3-AM (Dojin, Japan). After the incubation at 37° C. for 1 hr, each well was washed 3 times with assay buffer using an EMBLA 384 plate washer (Molecular Devices) and refilled with assay buffer. The plates were incubated at a temperature of about 25° C. for 10 min. Subsequently, the plates were inserted into a FLIPR, and 1. µM capsaicin (Sigma) solution prepared in assay buffer was added to each well (final concentration was 500 nM). Cellular responses were monitored for 5 min.

Cell Culture:

1. Cell Culture Media
1. Alpha-MEM (Gibco, CAT: 12561-056, LOT: 1285752): 450 mL.
2. Fetal Bovine Serum (FBS), heat inactivated (Gibco, CAT: 16140-071, LOT: 1276457): 50 mL.
3. HEPES Buffer Solution, 1M stock (Gibco, CAT: 15630-080): 10 mL (final 20 mM).
4. Geneticin, 50 mg/mL stock (Gibco, CAT: 10135-035): 10 mL (final 1 mg/mL).
5. Antimicotic Antibiotic Mixed Solution, 100× stock (Nacalai Tesque, Japan, CAT: 02892-54): 5 mL.

Components 1-5 above were combined at the indicated amounts and stored at 4° C. The cell culture media were brought to about 37° C. before use. Optionally, component 5 can be replaced by penicillin-streptomycin solution (for example, Gibco 15140-122 or Sigma P-0781).

2. Thawing the Cells

TRPV1/CHO cells were frozen in Cellbanker™ (Juji-Field INC, Japan, CAT: BLC-1) and stored at −80° C. Optimized cryopreservation solution containing dimethyl sulphoxide and FBS was used.

Vials containing the TRPV1/CHO cells were stored at −80° C. After removal from −80° C., the vial was immediately transferred to a 37° C. water bath to thaw for ca. 1-2 minutes. Once completely thawed, the contents of the vial (1 mL/vial) was transferred to a sterile 15 mL test tube and 9 mL warm culture media were slowly added. The test tube was subsequently centrifuged at 1000 rpm for 4 min at a temperature of about 25° C. The supernatant was removed and the pellet resuspended in 10 mL of culture media. The cell suspension was transferred to a sterile 75 cm$^2$ plastic flask and incubated at humidified 5% CO$_2$/95% air at 37° C. To monitor viability, the cells were visually inspected and/or counted, beginning at approximately 1 hr after incubation.

3. Passaging the Cells

The cells in a flask were close to confluence at the time of passaging. Cell culture media were removed from the culture flask and 10 mL of sterile PBS(−) added and the flask gently shaken. The PBS was removed from the flask and 2 mL of trypsin/EDTA solution (0.05% trypsin with EDTA-4Na; Gibco, CAT: 25300-054) was added and the flask gently shaken. The flask was incubated at 37° C. for about 2 min. 8 mL cell culture media were subsequently added to the flask and the flask shaken to ensure that all cells were in solution. The cell suspension was then transferred to a sterile 15 mL or 50 mL plastic tube, centrifuged at 1,000 rpm for 4 min at a temperature of about 25° C. The supernatant was removed and the pellet resuspended in ca. 5 mL of culture media. The cell count was measured using the Burker-Turk hemocytometer.

The cells were seeded into a sterile 75 cm² plastic flask in ca. $0.8 \times 10^5$ cells/mL for 72 hr and incubated in humidified 5% $CO_2$/95% air at 37° C.

4. Freezing the Cells

The procedure up to the measurement of the cell count was the same as in the section Passaging the Cells above. Subsequently, the cell suspension was centrifuged at 1,000 rpm for 4 min at a temperature of about 25° C. The supernatant was removed and the pellet resuspended in Cellbanker™ solution to get a final concentration of from $5 \times 10^5$ to $5 \times 10^6$ cells/mL. The cell suspension was transferred into appropriately labeled 1 mL cryovials and then placed into the −80° C. freezer.

pH-Based Assay:

The following assay was conducted to determine the concentration of sulfuric acid that would give rise to a pH that induces a $Ca^{2+}$ response optimal to test compounds for their effect on TRPV1.

1. Cells

TRPV1/CHO cells were seeded in the 96-well clear-bottom black-wall plate (Nunc) at densities of $1-2 \times 10^4$ cells/well and grown in 100 μL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Different agonist solutions with sulfuric acid concentrations of from 15 mM to 18 mM (see FIG. 1) were prepared by diluting 1M sulfuric acid with measuring buffer. The different sulfuric acid concentrations in the agonist solutions were selected such that a 1:4 dilution would result in a final sulfuric acid concentration of between 3.0 mM to 3.6 mM, respectively, as indicated in FIG. 1.

2.2. Assay pH dependent $Ca^{2+}$ responses in TRPV1/CHO cells cultured in a 96-well plate are shown in FIG. 2. In particular, $Ca^{2+}$ influx into TRPV1/CHO cells in response to low pH as measured by Fura-2 AM fluorescence is indicated in FIG. 2. The cells were stimulated using 3.0 mM (well number B1-6), 3.1 mM (C1-6), 3.2 mM (D1-6), 3.3 mM (E1-6), 3.4 mM (F1-6), 3.5 mM (G1-6), or 3.6 mM (H1-6) $H_2SO_4$ or pH 7.2 measuring buffer without $H_2SO_4$ (A1-6) (FIG. 2).

(1) Culture medium was removed using an 8-channel-pipette (Rainin, USA) from the 96-well plate and the wells were refilled with 100 μL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 μM Fura-2 AM (Dojin, Japan).

(2) The 96-well plate was incubated at 37° C. for 45 min.

(3) The loading buffer was removed from each well. The cells were subsequently washed twice with 150 μL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells were then refilled with 80 μL of measuring buffer.

(4) After an incubation at 4° C. for 15 min, the 96-well plate was transferred to FDSS-3000 (Hamamatsu Photonics, Japan).

(5) The Fura-2 fluorescent intensity was monitored at a wavelength of 340 nm and at 380 nm, respectively, at a rate of 0.5 Hz for a total of 240 seconds. After 16 time points (32 sec) of baseline detection, 20 μL of agonist solution was added to each well. The final volume was 100 μL/well.

(6) Fluorescence intensity ratio refers to the fluorescence intensity at 340 nm over the fluorescence intensity at 380 nm at a particular time point. The baseline was set as the average of the fluorescent intensity ratios for the first 16 time points before the addition of agonist solution. The maximum response was the highest fluorescent intensity ratio during the 60 time points following addition of agonist solution.

(7) Maximal signal ratios from each well were calculated as output data using the FDSS-3000 analysis program. Data were analyzed using Excel (Microsoft) and XLfit (idbs) software.

2.3. pH Determination

After the observation of $Ca^{2+}$ responses, the buffer of each lane (50 μL/well, 8-20 wells/plate) was collected well by well and the pH values were measured using a portable pH meter (Shindengen, Japan).

As shown in FIG. 2, the $Ca^{2+}$ responses in lanes D and E were intermediate and therefore optimal for testing the effects of compounds on the TRPV1 calcium channel. The final sulfuric acid concentrations in the wells of these lanes were 3.2 mM and 3.3 mM, respectively. These final sulfuric acid concentrations were obtained using agonist solutions with 16.0 mM and 16.5 mM sulfuric acid concentrations, respectively (lanes D and E in FIG. 1). The pH obtained using these sulfuric acid concentrations was ca. 5.0-5.1.

Thus, agonist solutions with 16.0 mM and 16.5 mM sulfuric acid concentrations, respectively, (lanes D and E in FIG. 1) were selected for the experiments described below in section 3.

3. pH Assay 3.1. Agonist

Two different agonist solutions with different $H_2SO_4$ concentrations were used for the pH assay (FIG. 3A). For one half of a 96-well plate one agonist solution was used, for the other half the other agonist solution. The agonist solutions were obtained by diluting sulfuric acid ($H_2SO_4$, 1M) with measuring buffer. The concentrations for the two agonist solutions were determined as described above in Section 2 of Protocol 2.

The sulfuric acid concentrations between the two agonist solutions differed by 0.5 mM. In the experiment described in Section 2 of Protocol 2, the sulfuric acid concentrations in the agonist solutions were determined to be 16 mM and 16.5 mM, respectively. After 1:4 dilution of the agonist solutions, the final sulfuric acid concentration was 3.2 mM and 3.3 mM, respectively. The resulting pH value for the pH assay was 5.0 to 5.1.

3.2. Test Compounds

Test compounds were dissolved in DMSO to yield 1 mM stock solutions. The stock solutions were further diluted using DMSO in 1:3 serial dilution steps with 6 points (1000 μM, 250 μM, 62.5 μM, 15.625 μM, 3.9062 μM and 0.977 μM). The thereby-obtained solutions were further diluted in measuring buffer (1:100) as 10× stock serial dilutions with a DMSO concentration of 1%. 10 μL of a 10× stock was added into each well at step 3.3.(4) of Protocol 2. Thus, the final concentrations of antagonists ranged from 1000-0.977 nM containing 0.1% DMSO (FIG. 3B).

3.3. Assay

Steps (1) and (2) of this Assay were the same as steps 2.2.(1) and 2.2.(2) of Protocol 2, respectively.

(3) The cells were washed twice with 150 μL of measuring buffer (mentioned in 2.2.(3) of Protocol 2, no probenecid). The wells were subsequently refilled with 70 μL of measuring buffer.

(4) Either 10 μL of measuring buffer or 10 μL of 10× stock serial dilution of test compound (described in 3.2. above) were applied to each well. Usually, only one test compound was tested per 96-well plate. The number of replicates per 96-well plate for a particular antagonist at a particular concentration was 7×2 since two different sulfuric acid concentrations were used per 96-well plate (N=7×2) (FIG. 3).

Step (5) was the same as 2.2.(4) above.

(6) Fura-2 fluorescent intensity was monitored as described in 2.2.(5) above. After 16 time points of baseline detection, 20 μL of agonist solution (measuring buffer titrated with $H_2SO_4$ to yield pH 5.0-5.1 when mixed 1:4 with the measuring buffer containing test compound) was added to each well (final volume 100 μL/well).

Steps (7) and (8) were as described in 2.2.(6) and 2.2.(7) above, respectively.

3.4. pH Check (1) The pH values of the buffer in the wells of A1→H1 and A7→H7 (longitudinally; FIG. 3) were measured one by one using a portable pH meter.

(2) When a well was confirmed as pH 5.0 or 5.1, the next five wells to its right were checked one after another.

(3) For $IC_{50}$ calculation, only the data from wells with pH values of 5.0-5.1 were used.

The number of wells tested for their pH varied among plates (about 16-60 wells/plate). The number depended on the results of 3.4.(1) above and the $Ca^{2+}$ responses.

Capsaicin-Based Assay:

One day prior to assay, TRPV1/CHO cells were seeded in 96-well clear-bottom black plates (20,000 cells/well) in growth media. On the day of the experiment, the cells were washed with 0.2 mL 1× Hank's Balanced Salt Solution (Life Technologies) containing 1.6 mM $CaCl_2$ and 20 mM HEPES, pH 7.4 ("wash buffer"). Subsequently, the cells were loaded by incubation in 0.1 mL of wash buffer containing Fluo-4 at 3 μM final concentration. After 1 hour, the cells were washed twice with 0.2 mL wash buffer and resuspended in 0.1 mL wash buffer. The plates were then transferred to a Fluorescence Imaging Plate Reader (Molecular Devices). Fluorescence intensity was monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO were added to the cell plate and fluorescence was monitored for 2 minutes. The final concentration of the compound was adjusted to range from 100 μM to 1.5625 μM. If the test compound was an especially potent antagonist, the final concentration of the compound was adjusted to range from 10 μM to 1.5625 nM. Human TRPV1 was then activated by the addition of 50 μL capsaicin (100 nM final concentration) and plates incubated for an additional 3 min. Data were collected over the entire time course and analyzed using Excel and the curve-fitting formula GraphPad Prism.

The results of the assays of Protocol 2 are shown in Table I, which demonstrates that many compounds of formula I have superior potency. The $IC_{50}$ data provided in Table I are shown as mean±standard error of the mean; the number of trials conducted for each assay is shown in parentheses except for only a single trial where no number of trials is shown in parentheses. No standard error of the mean is determined when the number of trials is less than 3.

TABLE I

| | TRPV1 $IC_{50}$ Potency | | |
|---|---|---|---|
| Compound | Human Capsaicin CHO (hCAP-CHO) (nM) | Human pH CHO (hpH-CHO) (nM) | Structure |
| A1 | 7.0 ± 1.8 (4) | | 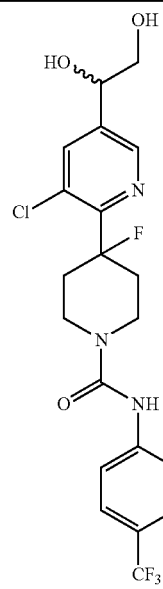 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| B1 | 7.81 ± 1.2 (4) | 7.40 ± 0.3 (3) | 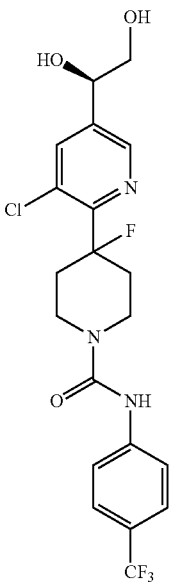 [SMILES: O=C(Nc1ccc(C(F)(F)F)cc1)N1CCC(F)(c2ncc([C@@H](O)CO)cc2Cl)CC1] |
| C1 | 15.3 ± 6.9 (3) | 11.3 ± 0.8 (3) | 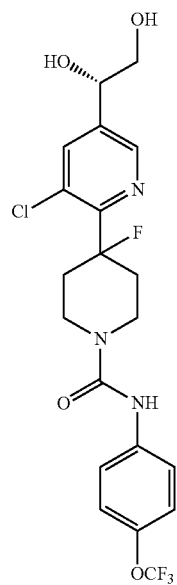 [SMILES: O=C(Nc1ccc(OC(F)(F)F)cc1)N1CCC(F)(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| D1 | 16.5 ± 4.1 (3) | 0.9 (2) | 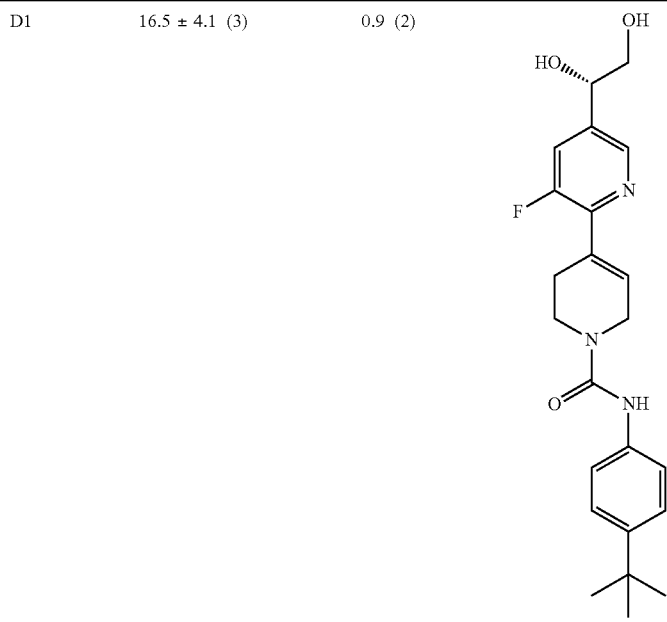 |
| E1 | 18.5 ± 4.9 (3) | | 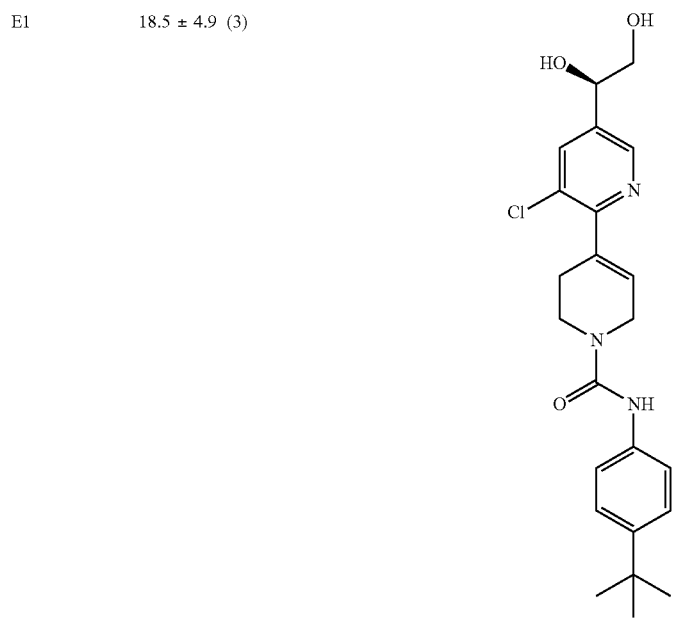 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| F1 | 18.6 ± 6.8 (3) | 9.0 ± 2.3 (3) | 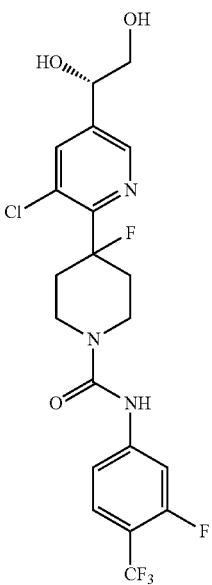 [SMILES: O=C(Nc1ccc(C(F)(F)F)c(F)c1)N1CCC(F)(c2ncc([C@H](O)CO)cc2Cl)CC1] |
| G1 | 31.3 ± 8.8 (3) | 16.4 (2) | 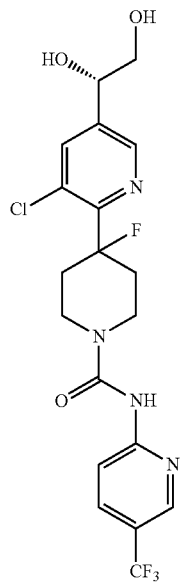 [SMILES: O=C(Nc1ccc(C(F)(F)F)cn1)N1CCC(F)(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| H1 | 31.7 ± 8.9 (3) | | 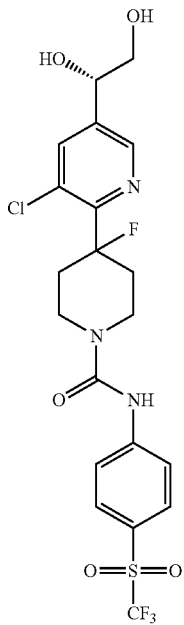 [SMILES: O=C(Nc1ccc(S(=O)(=O)C(F)(F)F)cc1)N1CCC(F)(c2ncc([C@H](O)CO)cc2Cl)CC1] |
| I1 | 33.8 ± 9.1 (3) | 1.1 ± 0.2 (3) | 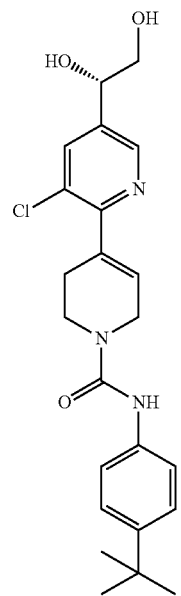 [SMILES: CC(C)(C)c1ccc(NC(=O)N2CC=C(c3ncc([C@H](O)CO)cc3Cl)CC2)cc1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| J1 | 34.5 ± 17.5 (3) | 18.0 (2) | |
| K1 | 35.1 ± 8.8 (3) | 39.5 (2) | |
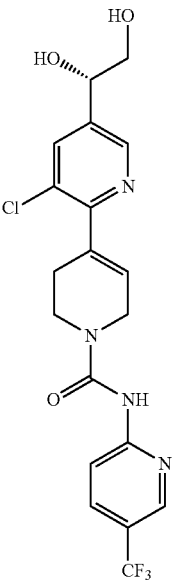 [SMILES: O=C(Nc1ccc(C(F)(F)F)cn1)N1CC=C(c2ncc([C@H](O)CO)cc2Cl)CC1]

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| L1 | 35.3 ± 12.0 (3) | 27.5 ± 3.4 (4) | 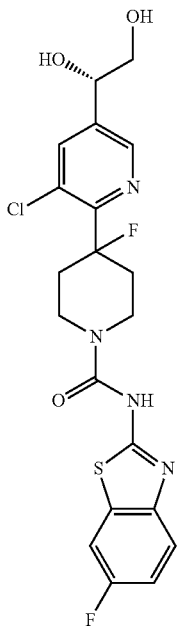 [SMILES: O=C(Nc1nc2ccc(F)cc2s1)N1CCC(F)(c2ncc([C@H](O)CO)cc2Cl)CC1] |
| M1 | 37.5 ± 9.0 (3) | 5.7 ± 0.3 (5) | 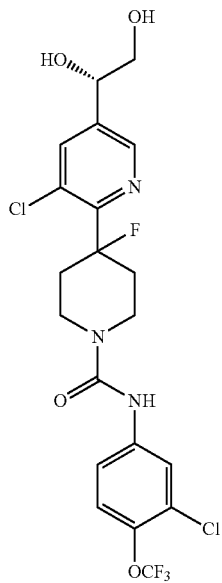 [SMILES: O=C(Nc1ccc(OC(F)(F)F)c(Cl)c1)N1CCC(F)(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| N1 | 38.7 ± 5.3 (3) | 6.3 ± 0.8 (5) | 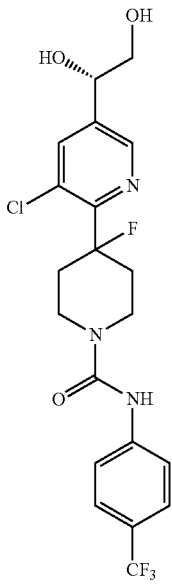 [SMILES: O=C(Nc1ccc(C(F)(F)F)cc1)N1CCC(F)(c2ncc([C@H](O)CO)cc2Cl)CC1] |
| O1 | 41.1 ± 17.8 (3) | | 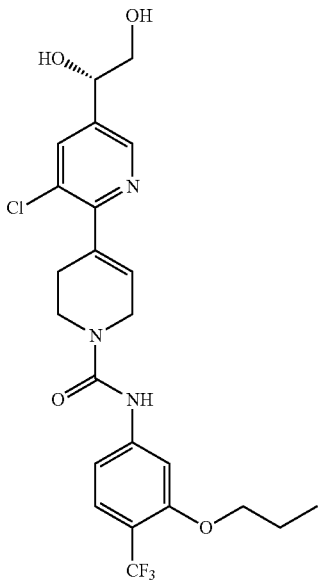 [SMILES: CCCOc1cc(NC(=O)N2CC=C(c3ncc([C@H](O)CO)cc3Cl)CC2)ccc1C(F)(F)F] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| P1 | 50.5 ± 9.5 (3) | | 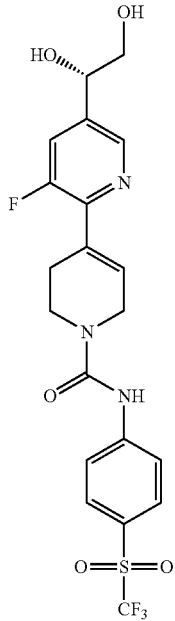 [SMILES: O=C(Nc1ccc(S(=O)(=O)C(F)(F)F)cc1)N1CC=C(c2ncc([C@H](O)CO)cc2F)CC1] |
| Q1 | 51.0 ± 16.4 (3) | 8.1 ± 0.7 (3) | 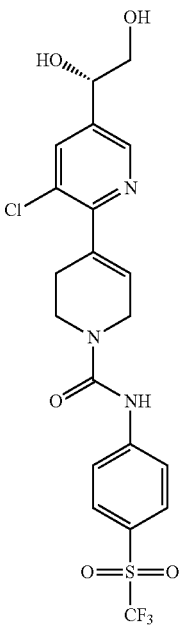 [SMILES: O=C(Nc1ccc(S(=O)(=O)C(F)(F)F)cc1)N1CC=C(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| R1 | 51.0 ± 18.8 (3) | | 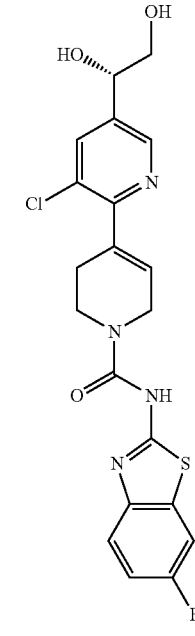 |
| S1 | 53.5 ± 16.3 (3) | 16.3 ± 2.0 (3) | 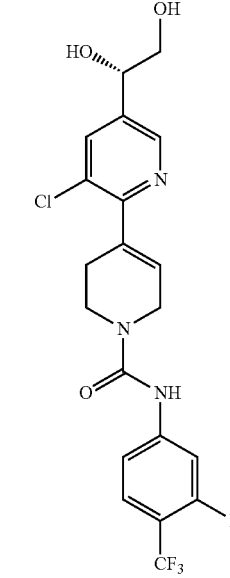 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| T1 | 60.3 ± 19.0 (3) | 29.7 ± 2.3 (3) | 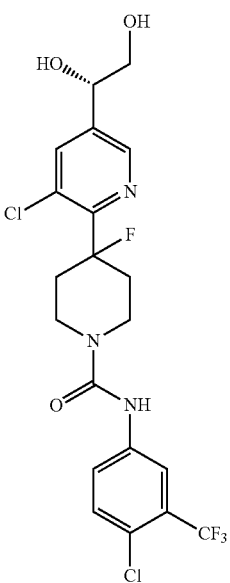 [SMILES: O=C(Nc1ccc(Cl)c(C(F)(F)F)c1)N1CCC(F)(c2ncc([C@H](O)CO)cc2Cl)CC1] |
| U1 | 61.3 ± 22.5 (3) | 14.7 ± 3.3 (3) | 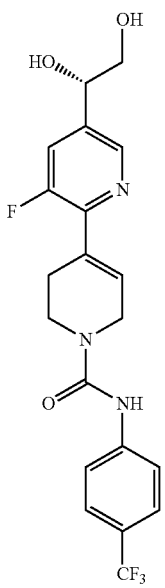 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| V1 | 66.3 ± 5.7 (3) | 22.4 ± 1.1 (3) | 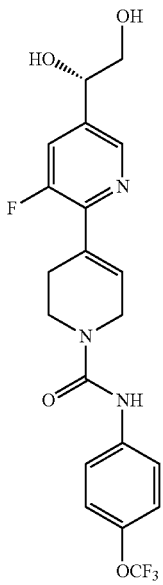 [SMILES: O=C(Nc1ccc(OC(F)(F)F)cc1)N1CC=C(c2ncc([C@H](O)CO)cc2F)CC1] |
| W1 | 68.9 ± 18.4 (3) | 9.3 ± 1.9 (3) | 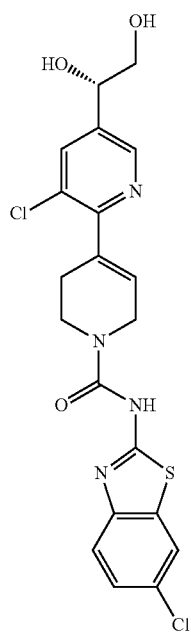 [SMILES: O=C(Nc1nc2ccc(Cl)cc2s1)N1CC=C(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| X1 | 74.4 ± 11.5 (3) | 18.8 ± 1.6 (6) | 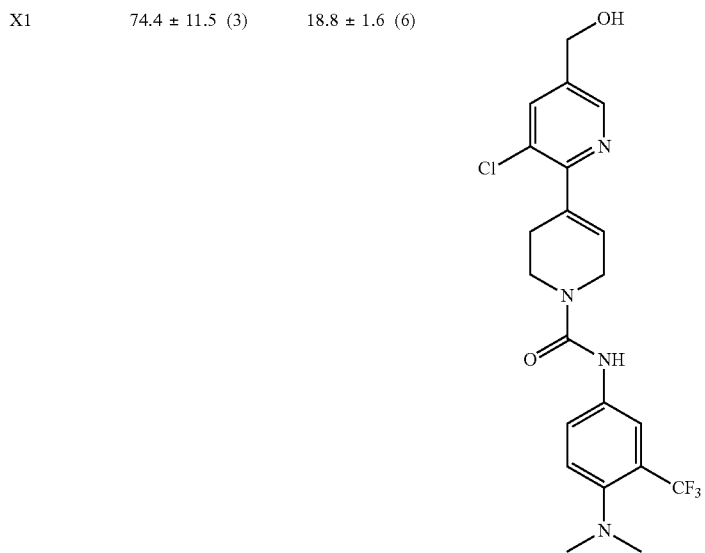 |
| Y1 | 74.7 ± 18.4 (4) | 13.5 ± 1.2 (3) | 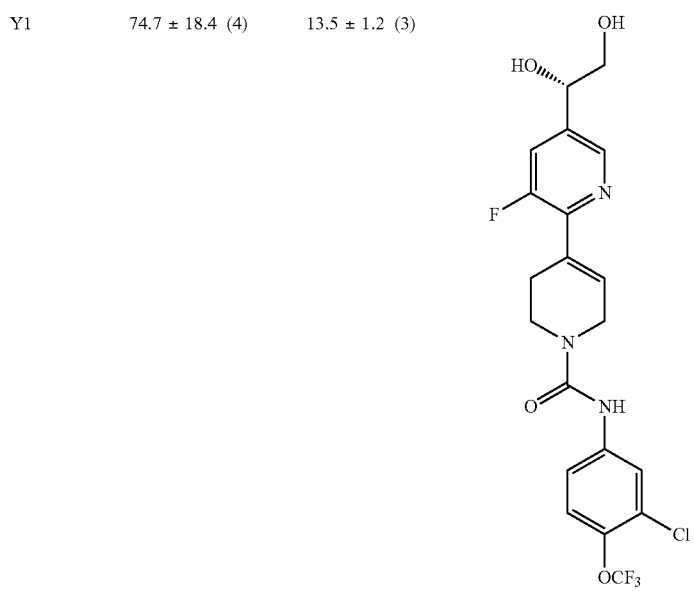 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Z1 | 75.8 ± 12.4 (4) | 11.6 ± 0.7 (3) | 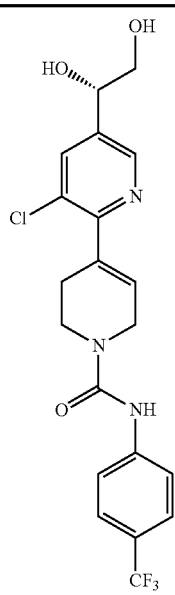 |
| A2 | 84.1 ± 11.2 (3) | | 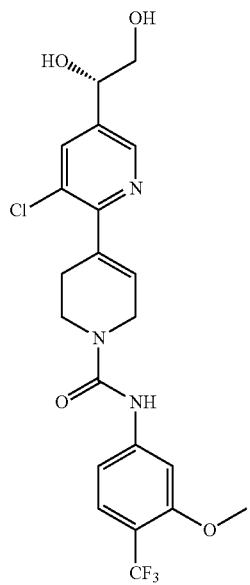 [SMILES: COc1cc(NC(=O)N2CC=C(c3ncc([C@H](O)CO)cc3Cl)CC2)ccc1C(F)(F)F] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| B2 | 77.6 ± 12.0 (4) | 40.5 (2) | 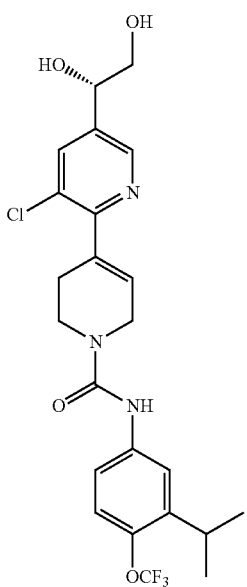 [SMILES: CC(C)c1cc(NC(=O)N2CC=C(c3ncc([C@H](O)CO)cc3Cl)CC2)ccc1OC(F)(F)F] |
| C2 | 98.7 ± 33.9 (5) | 41.8 ± 3.8 (3) | 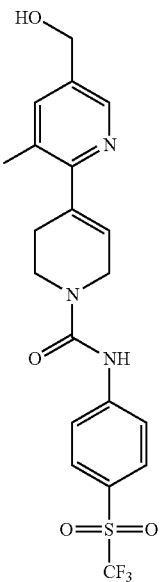 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| D2 | 85.3 ± 20.7 (6) | 10.8 ± 0.9 (3) | 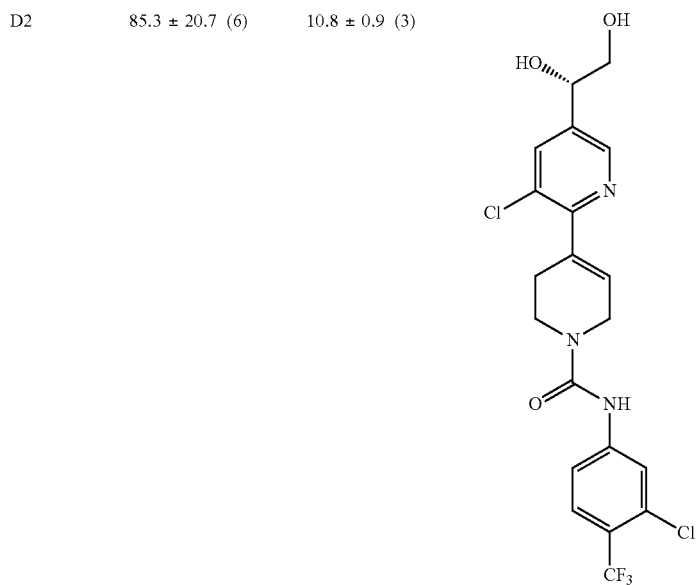 |
| E2 | 107.4 ± 18.8 (5) | 20.3 ± 1.7 (4) | 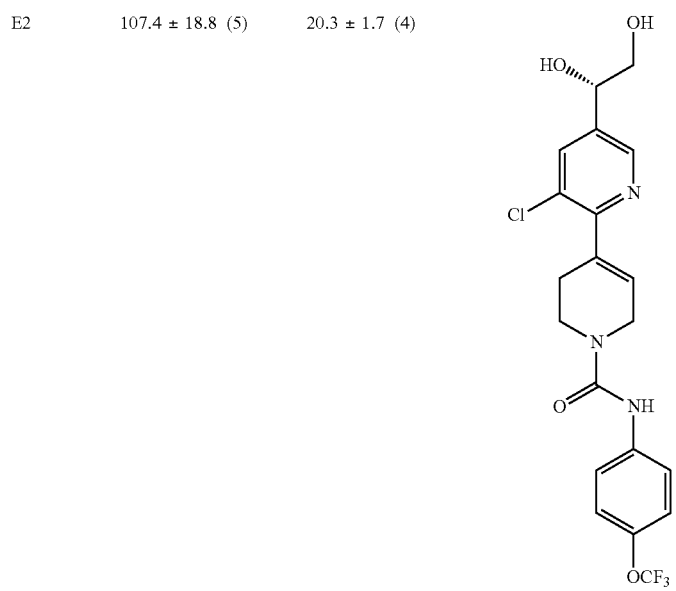 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| F2 | 108.0 ± 24.3 (3) | 62.9 ± 8.8 (4) | 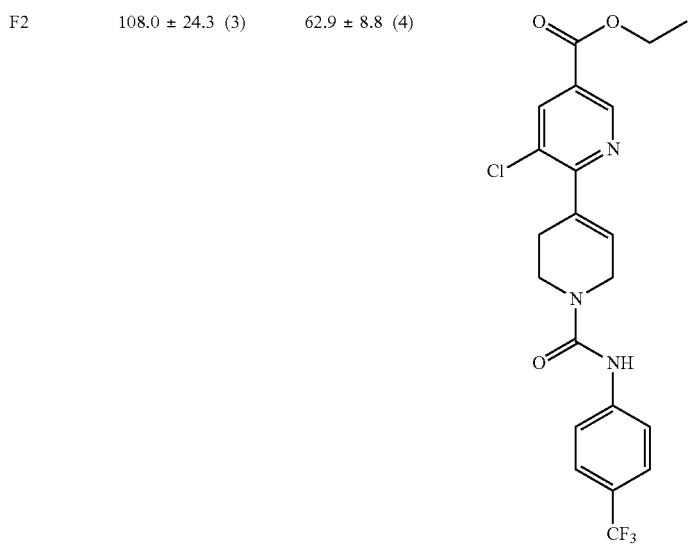 |
| G2 | 112.4 ± 22.3 (3) | 84.8 ± 8.8 (3) | 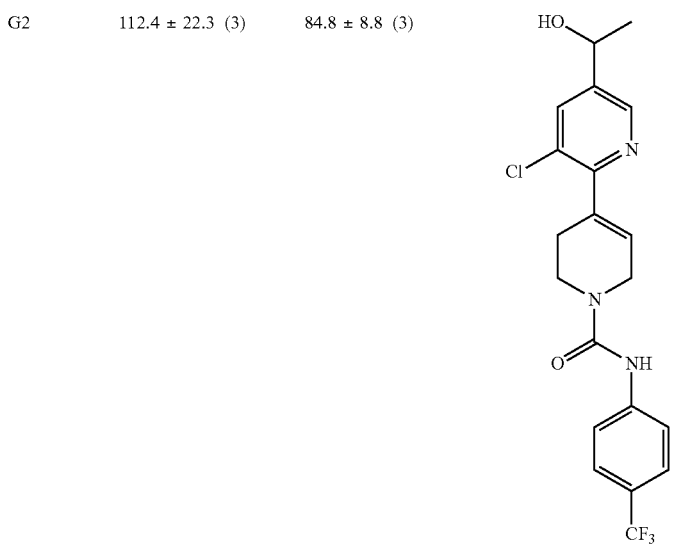 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| H2 | 118.1 ± 22.1 (3) | 13.1 ± 2.1 (3) | 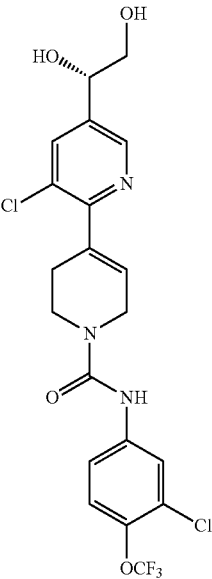 [SMILES: O=C(Nc1ccc(OC(F)(F)F)c(Cl)c1)N1CC=C(c2ncc([C@H](O)CO)cc2Cl)CC1] |
| I2 | 122.0 ± 7.1 (3) | 18.0 ± 1.0 (5) | 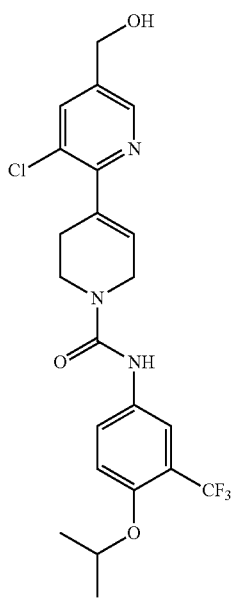 [SMILES: CC(C)Oc1ccc(NC(=O)N2CC=C(c3ncc(CO)cc3Cl)CC2)cc1C(F)(F)F] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| J2 | 128.6 ± 26.0 (3) | 41.7 ± 4.4 (3) | 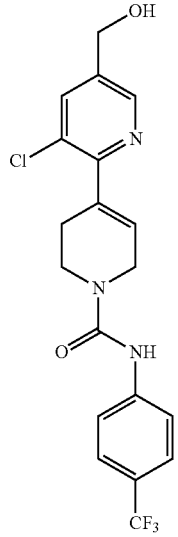 [SMILES: O=C(Nc1ccc(C(F)(F)F)cc1)N1CC=C(c2ncc(CO)cc2Cl)CC1] |
| K2 | 140.8 ± 41.9 (3) | 47.2 ± 6.7 (3) | 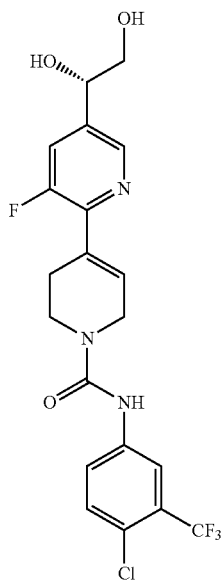 [SMILES: O=C(Nc1ccc(Cl)c(C(F)(F)F)c1)N1CC=C(c2ncc([C@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| L2 | 153.0 ± 24.4 (3) | 57.4 ± 9.1 (5) | 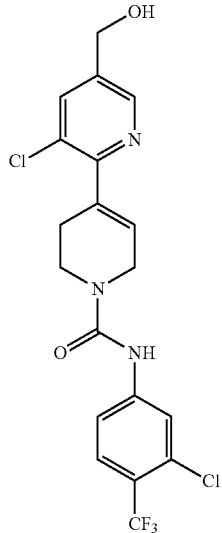 [SMILES: O=C(Nc1ccc(C(F)(F)F)c(Cl)c1)N1CC=C(c2ncc(CO)cc2Cl)CC1] |
| M2 | 156.3 ± 5.6 (3) | 42.0 ± 9.1 (3) | 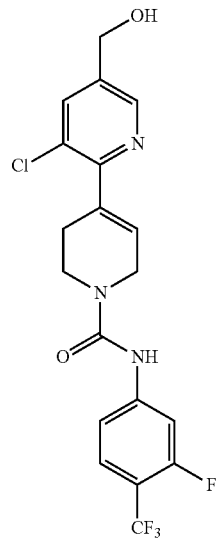 [SMILES: O=C(Nc1ccc(C(F)(F)F)c(F)c1)N1CC=C(c2ncc(CO)cc2Cl)CC1] |

TABLE I-continued

| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| N2 | 161.4 ± 16.6 (3) | 27.3 ± 2.6 (6) | |
| O2 | 161.8 ± 29.5 (3) | 18.8 ± 4.0 (4) | |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| P2 | 172.9 ± 40.3 (4) | 44.4 (2) | 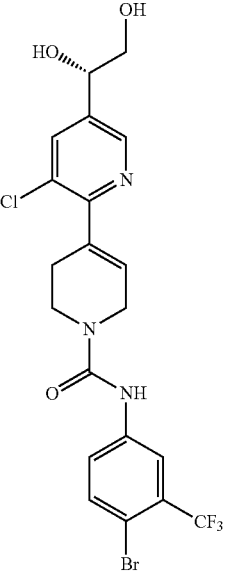 [SMILES: O=C(Nc1ccc(Br)c(C(F)(F)F)c1)N1CC=C(c2ncc([C@H](O)CO)cc2Cl)CC1] |
| Q2 | 194.4 ± 27.1 (3) | 85.9 ± 21.8 (4) | 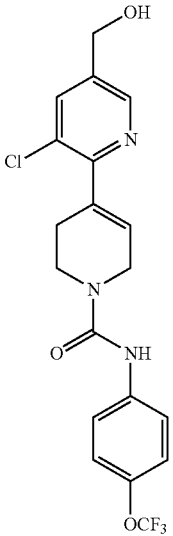 [SMILES: O=C(Nc1ccc(OC(F)(F)F)cc1)N1CC=C(c2ncc(CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| R2 | 199.9 ± 26.8 (3) | 49.6 ± 3.4 (5) | 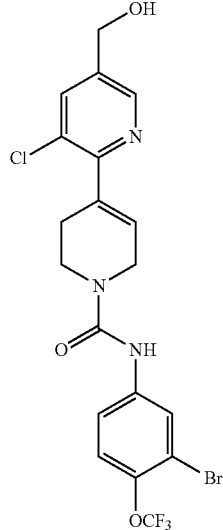 |
| S2 | 205.3 ± 35.4 (3) | 31.9 ± 2.5 (3) | 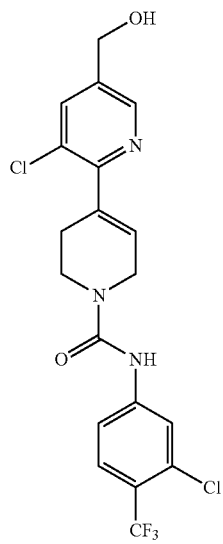 [SMILES: O=C(Nc1ccc(C(F)(F)F)c(Cl)c1)N1CC=C(c2ncc(CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| T2 | 225.8 ± 69.3 (5) | | 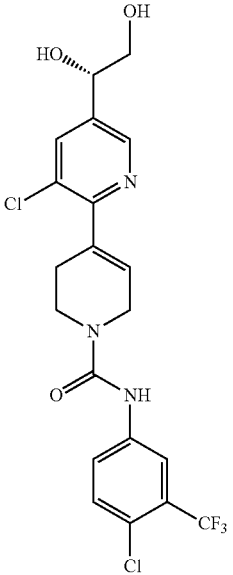 [SMILES: O=C(Nc1ccc(Cl)c(C(F)(F)F)c1)N1CC=C(c2ncc([C@H](O)CO)cc2Cl)CC1] |
| U2 | 230.5 ± 45.3 (4) | 53.4 ± 5.9 (3) | 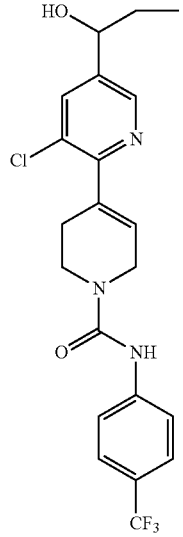 [SMILES: CCC(O)c1cnc(C2=CCN(C(=O)Nc3ccc(C(F)(F)F)cc3)CC2)c(Cl)c1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| V2 | 234.2 ± 44.6 (3) | 83.2 ± 7.6 (3) | 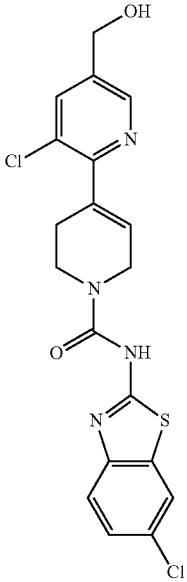 [SMILES: O=C(Nc1nc2ccc(Cl)cc2s1)N1CC=C(c2ncc(CO)cc2Cl)CC1] |
| W2 | 244.8 ± 34.4 (3) | 241.3 ± 34.9 (5) | 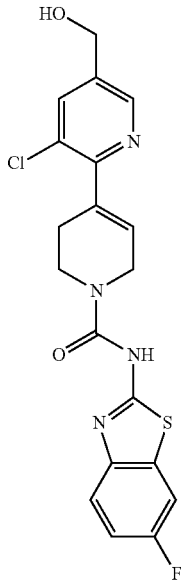 [SMILES: O=C(Nc1nc2ccc(F)cc2s1)N1CC=C(c2ncc(CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| X2 | 248.4 ± 25.1 (3) | 81.1 ± 10.5 (3) | 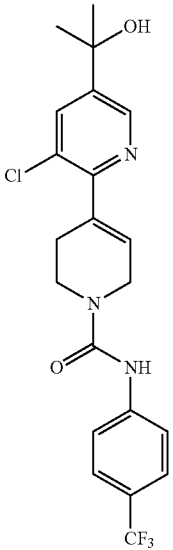 [SMILES: CC(C)(O)c1cnc(C2=CCN(C(=O)Nc3ccc(C(F)(F)F)cc3)CC2)c(Cl)c1] |
| Y2 | 350.9 ± 69.8 (3) | 59.9 ± 11.8 (3) | 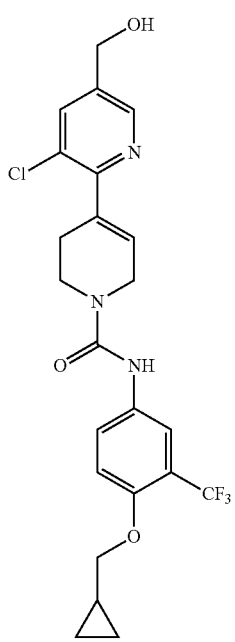 [SMILES: O=C(Nc1ccc(OCC2CC2)c(C(F)(F)F)c1)N1CC=C(c2ncc(CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Z2 | 401.0 ± 122.4 (3) | 247.6 ± 45.3 (3) | 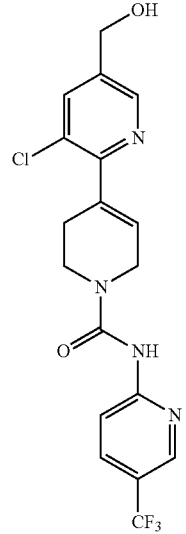 [SMILES: O=C(Nc1ccc(C(F)(F)F)cn1)N1CC=C(c2ncc(CO)cc2Cl)CC1] |
| A3 | 414.1 ± 99.6 (3) | 309.5 ± 38.9 (3) | 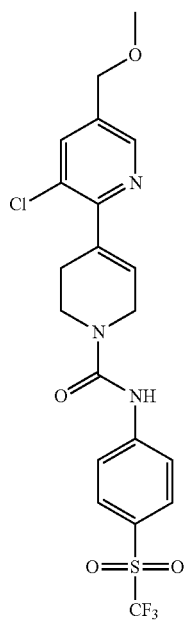 [SMILES: COCc1cnc(C2=CCN(C(=O)Nc3ccc(S(=O)(=O)C(F)(F)F)cc3)CC2)c(Cl)c1] |

TABLE I-continued
TRPV1 IC$_{50}$ Potency
| Compound | Human Capsaicin CHO (hCAP-CHO) (nM) | Human pH CHO (hpH-CHO) (nM) | Structure |
|---|---|---|---|
| B3 | 537.2 ± 62.0 (3) | 106.0 ± 11.4 (5) | 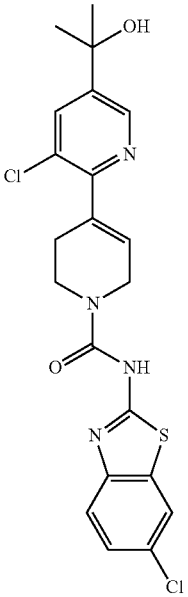 [SMILES: CC(C)(O)c1cnc(C2=CCN(C(=O)Nc3nc4ccc(Cl)cc4s3)CC2)c(Cl)c1] |
| C3 | 541.4 ± 215.8 (3) | | 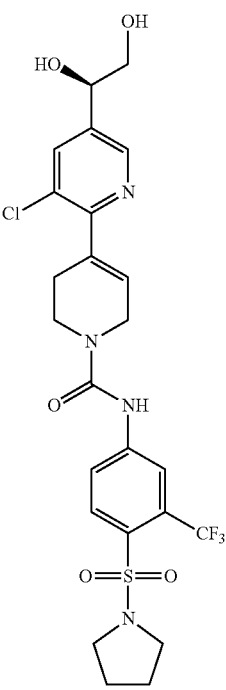 [SMILES: O=C(Nc1ccc(S(=O)(=O)N2CCCC2)c(C(F)(F)F)c1)N1CC=C(c2ncc([C@@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| D3 | 564.8 ± 58.6 (3) | 39.8 ± 2.2 (3) | 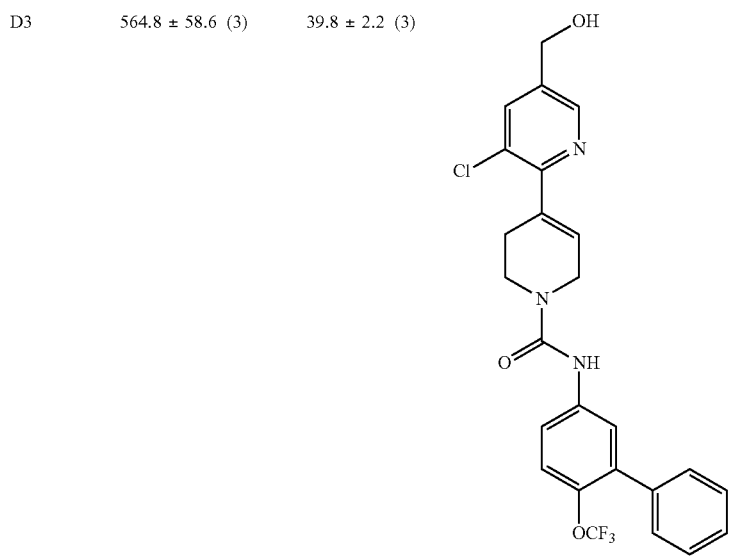 |
| E3 | 670.7 ± 133.1 (3) | 141.0 ± 23.1 (3) | 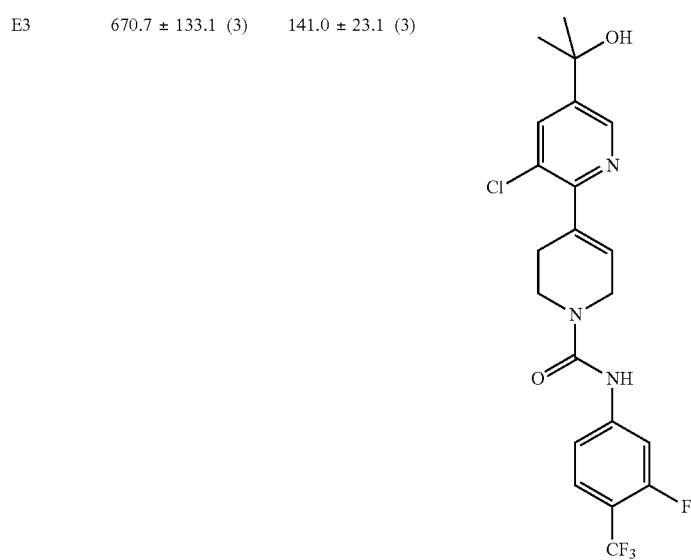 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| F3 | 915.7 ± 305.6 (4) | 584.8 (2) | 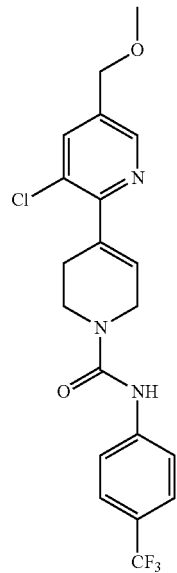 [SMILES: COCc1cnc(C2=CCN(C(=O)Nc3ccc(C(F)(F)F)cc3)CC2)c(Cl)c1] |
| G3 | 1075.9 ± 201.8 (3) | | 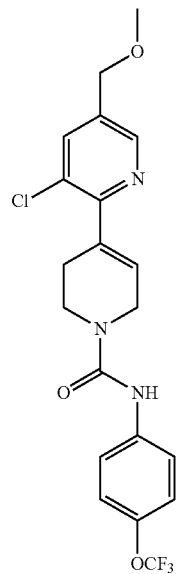 [SMILES: COCc1cnc(C2=CCN(C(=O)Nc3ccc(OC(F)(F)F)cc3)CC2)c(Cl)c1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| H3 | 1114.9 ± 134.0 (3) | | 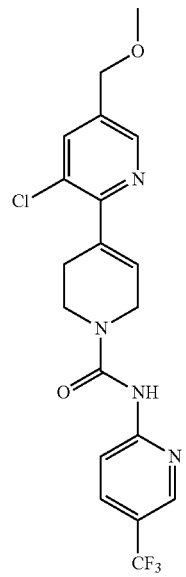 [SMILES: COCc1cnc(C2=CCN(C(=O)Nc3ccc(C(F)(F)F)cn3)CC2)c(Cl)c1] |
| I3 | 1363.7 ± 337.4 (3) | | 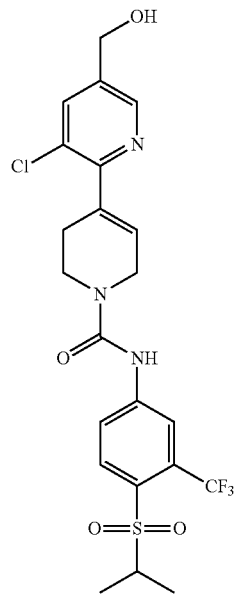 [SMILES: CC(C)S(=O)(=O)c1ccc(NC(=O)N2CC=C(c3ncc(CO)cc3Cl)CC2)cc1C(F)(F)F] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| J3 | 2940.7 ± 318.9 (3) | | 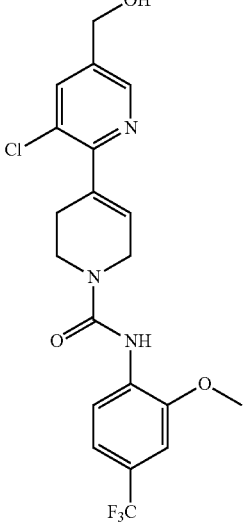 |
| K3 | >10,000 (3) | | 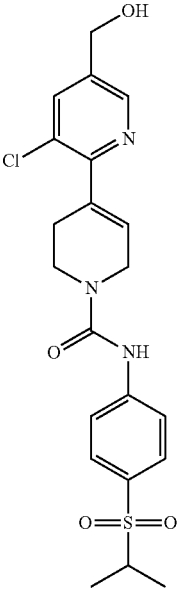 [SMILES: CC(C)S(=O)(=O)c1ccc(NC(=O)N2CC=C(c3ncc(CO)cc3Cl)CC2)cc1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| L3 | 37.1 ± 14.8 (3) | 38.3 ± 4.0 (3) | 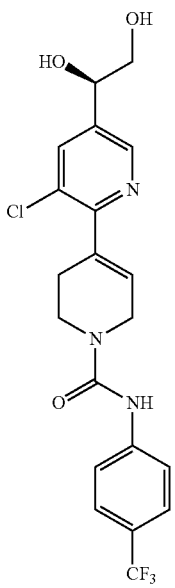 [SMILES: O=C(Nc1ccc(C(F)(F)F)cc1)N1CC=C(c2ncc([C@@H](O)CO)cc2Cl)CC1] |
| M3 | 186.9 ± 43.7 (3) | 30.0 ± 2.1 (3) | 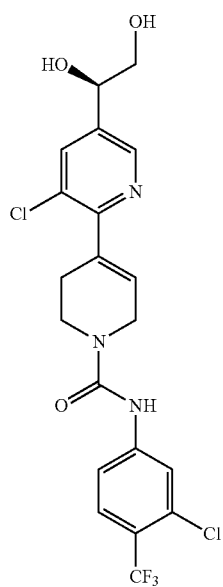 [SMILES: O=C(Nc1ccc(C(F)(F)F)c(Cl)c1)N1CC=C(c2ncc([C@@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| N3 | 161.1 ± 41.7 (3) | 223.3 ± 14.0 (3) | 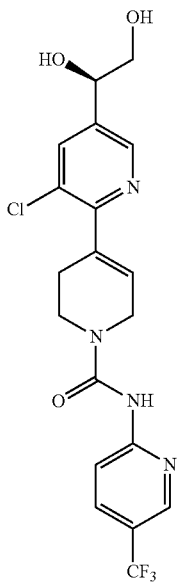 [SMILES: O=C(Nc1ccc(C(F)(F)F)cn1)N1CC=C(c2ncc([C@@H](O)CO)cc2Cl)CC1] |
| O3 | 46.0 ± 11.3 (3) | | 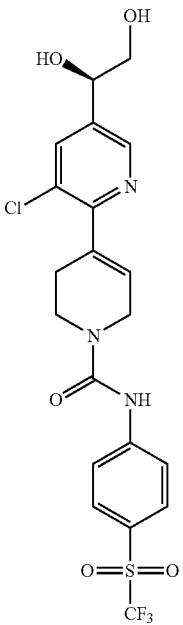 [SMILES: O=C(Nc1ccc(S(=O)(=O)C(F)(F)F)cc1)N1CC=C(c2ncc([C@@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| P3 | 183.4 ± 38.1 (3) | 28.5 (2) | 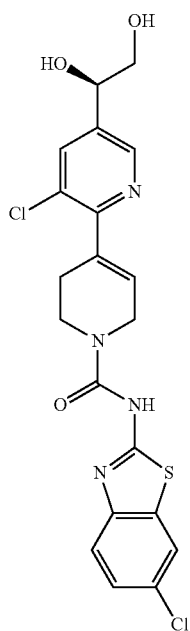 [SMILES: O=C(Nc1nc2ccc(Cl)cc2s1)N1CC=C(c2ncc([C@@H](O)CO)cc2Cl)CC1] |
| Q3 | 14.3 ± 1.3 (3) | 5.3 ± 1.0 (4) | 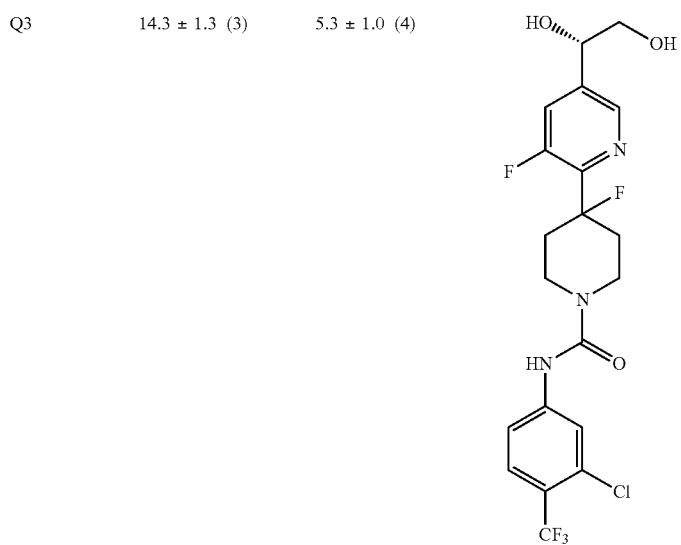 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| R3 | 15.5 ± 3.5 (3) | | 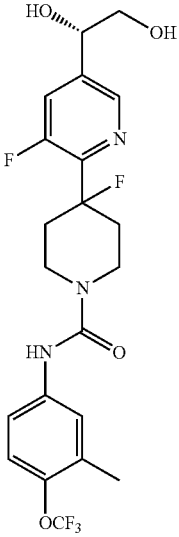 |
| S3 | 17.7 ± 2.0 (3) | 9.2 (3) | 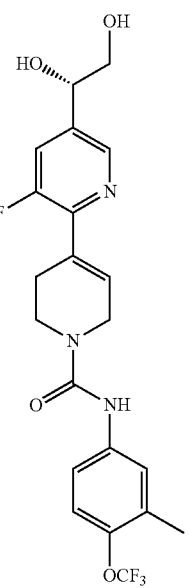 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| T3 | 23.8 ± 6.8 (3) | 12.9 (3) | 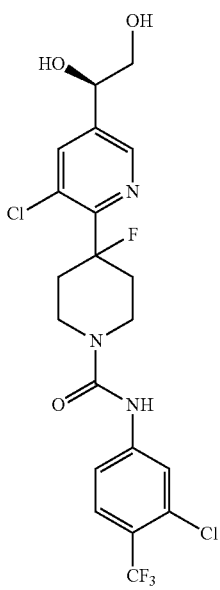 [SMILES: O=C(Nc1ccc(C(F)(F)F)c(Cl)c1)N1CCC(F)(c2ncc([C@@H](O)CO)cc2Cl)CC1] |
| U3 | 27.9 ± 9.9 (3) | 13.5 (2) | 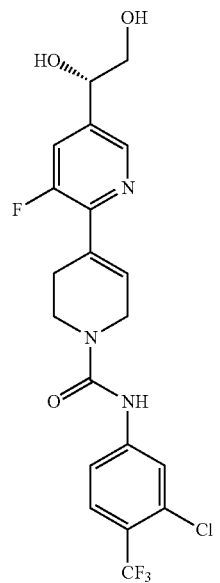 [SMILES: O=C(Nc1ccc(C(F)(F)F)c(Cl)c1)N1CC=C(c2ncc([C@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| V3 | 34.0 ± 9.2 (3) | | 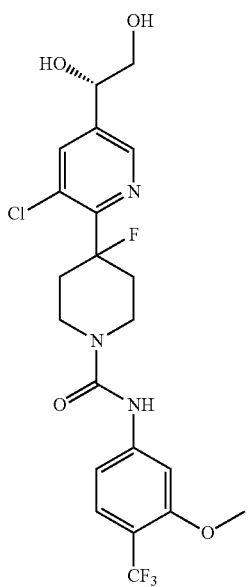 [SMILES: COc1cc(NC(=O)N2CCC(F)(c3ncc([C@H](O)CO)cc3Cl)CC2)ccc1C(F)(F)F] |
| W3 | 35.6 ± 8.9 (3) | 22.4 (2) | 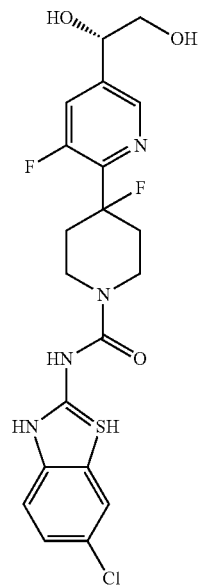 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Y3 | 43.9 ± 10.0 (3) | | 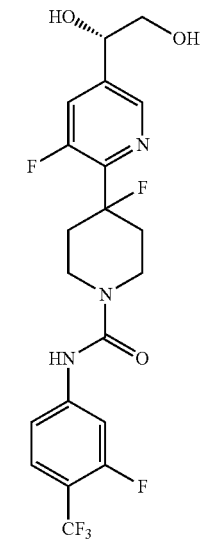 [SMILES: O=C(Nc1ccc(C(F)(F)F)c(F)c1)N1CCC(F)(c2ncc([C@H](O)CO)cc2F)CC1] |
| A4 | 55.1 ± 8.6 (4) | | 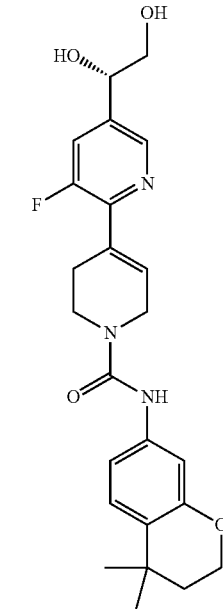 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| B4 | 57.2 ± 11.6 (3) | 5.8 ± 1.3 (4) | 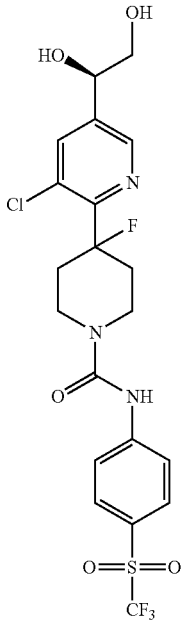 [SMILES: O=C(Nc1ccc(S(=O)(=O)C(F)(F)F)cc1)N1CCC(F)(c2ncc([C@@H](O)CO)cc2Cl)CC1] |
| C4 | 66.2 ± 7.5 (3) | 18.6 ± 2.8 (3) | 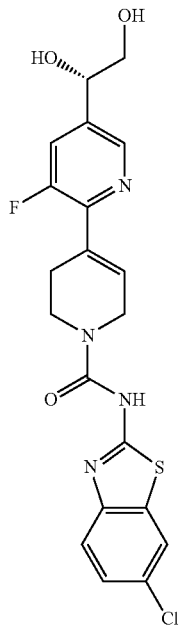 [SMILES: O=C(Nc1nc2ccc(Cl)cc2s1)N1CC=C(c2ncc([C@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| D4 | 69.6 ± 6.9 (3) | 54.8 (2) | 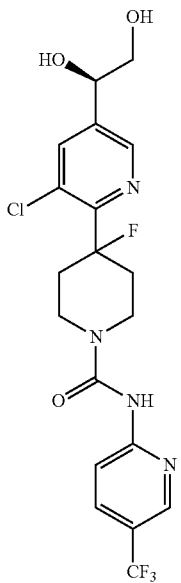 [SMILES: O=C(Nc1ccc(C(F)(F)F)cn1)N1CCC(F)(c2ncc([C@@H](O)CO)cc2Cl)CC1] |
| E4 | 75.7 ± 12.8 (3) | | 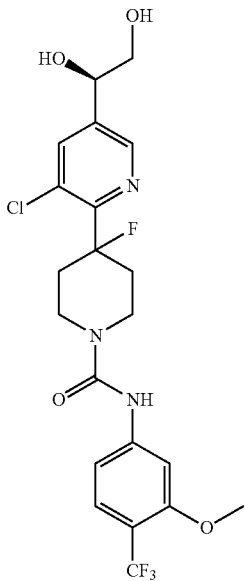 [SMILES: COc1cc(NC(=O)N2CCC(F)(c3ncc([C@@H](O)CO)cc3Cl)CC2)ccc1C(F)(F)F] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| F4 | 86.7 ± 18.9 (3) | 32.5 ± 2.4 (3) | 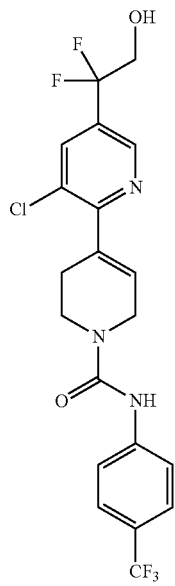 [SMILES: O=C(Nc1ccc(C(F)(F)F)cc1)N1CC=C(c2ncc(C(F)(F)CO)cc2Cl)CC1] |
| H4 | 175.8 ± 28.4 (3) | 97.0 ± 9.9 (3) | 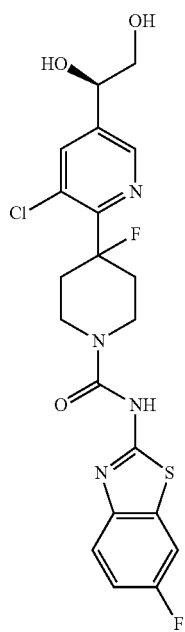 [SMILES: O=C(Nc1nc2ccc(F)cc2s1)N1CCC(F)(c2ncc([C@@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| K4 | 210.2 ± 19.5 (3) | | 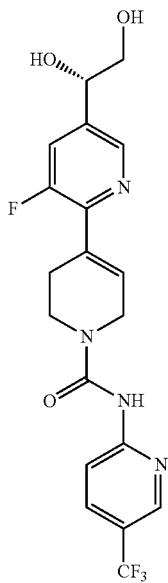 |
| L4 | 439.4 ± 139.8 (3) | | 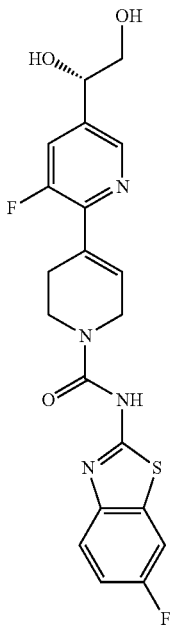 [SMILES: O=C(Nc1nc2ccc(F)cc2s1)N1CC=C(c2ncc([C@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| M4 | 471.3 ± 127.3 (3) | | 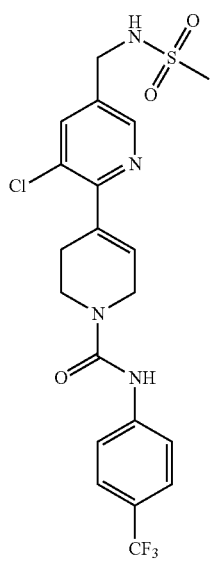 [SMILES: CS(=O)(=O)NCc1cnc(C2=CCN(C(=O)Nc3ccc(C(F)(F)F)cc3)CC2)c(Cl)c1] |
| N4 | 1312.9 ± 220.5 (3) | | 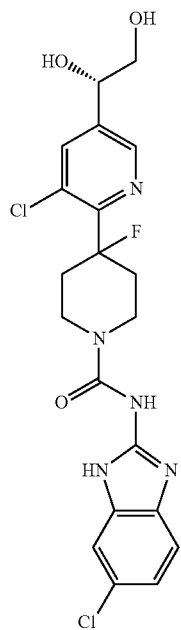 [SMILES: O=C(Nc1nc2ccc(Cl)cc2[nH]1)N1CCC(F)(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| O4 | 1517.2 ± 338.6 (3) | | 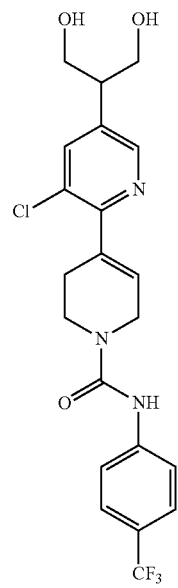 [SMILES: O=C(Nc1ccc(C(F)(F)F)cc1)N1CC=C(c2ncc(C(CO)CO)cc2Cl)CC1] |
| P4 | 1809.9 ± 302.1 (4) | | 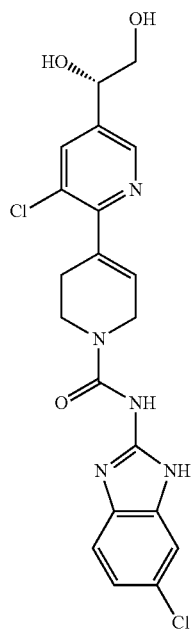 [SMILES: O=C(Nc1nc2ccc(Cl)cc2[nH]1)N1CC=C(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Q4 | 2897.7 ± 302.1 (3) | | 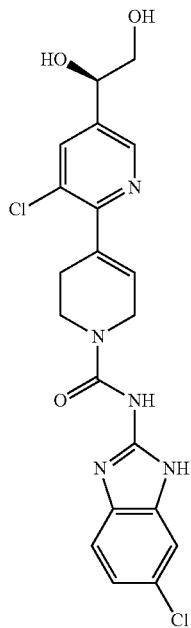 [SMILES: O=C(Nc1nc2ccc(Cl)cc2[nH]1)N1CC=C(c2ncc([C@@H](O)CO)cc2Cl)CC1] |
| R4 | 3278.6 ± 760.6 (3) | | 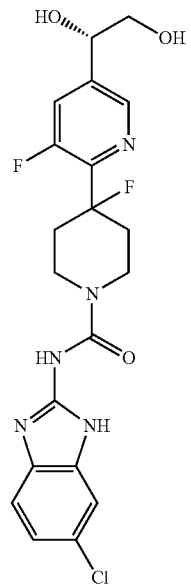 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| S4 | 7028.4 ± 2059.0 (3) | | 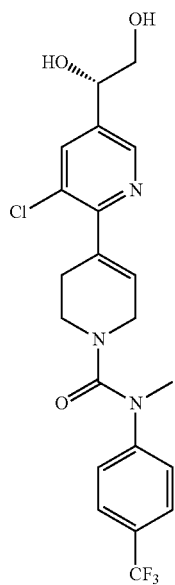 [SMILES: CN(C(=O)N1CC=C(c2ncc([C@H](O)CO)cc2Cl)CC1)c1ccc(C(F)(F)F)cc1] |
| X4 | 38.4 ± 8.0 (3) | | 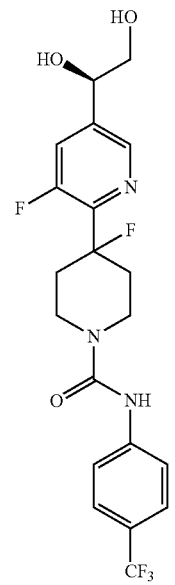 [SMILES: O=C(Nc1ccc(C(F)(F)F)cc1)N1CCC(F)(c2ncc([C@@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Z4 | 62.8 ± 11.4 (3) | 16.5 ± 3.3 (3) | 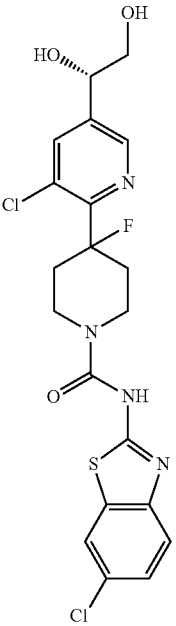 [SMILES: O=C(Nc1nc2ccc(Cl)cc2s1)N1CCC(F)(c2ncc([C@H](O)CO)cc2Cl)CC1] |
| B5 | 106.5 ± 21.0 (3) | 15.0 ± 3.0 (3) | 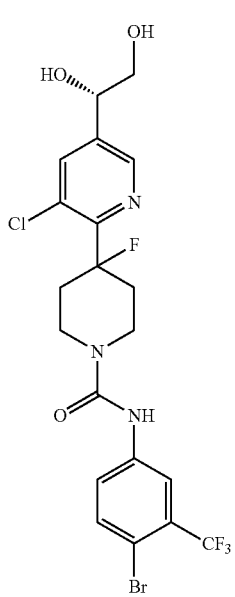 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| C5 | 107.7 ± 38.4 (3) | 39.9 ± 7.9 (3) | 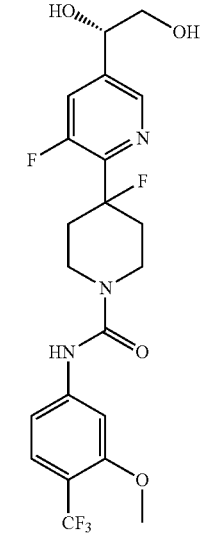 |
| D5 | 132.7 ± 29.1 (3) | | 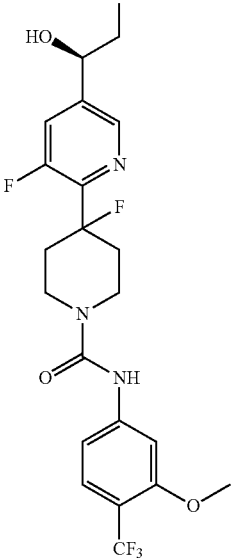 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| E5 | 132.8 ± 28.5 (3) | 33.8 (2) | 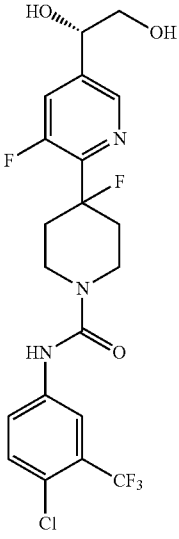 [SMILES: O=C(Nc1ccc(Cl)c(C(F)(F)F)c1)N1CCC(F)(c2ncc([C@H](O)CO)cc2F)CC1] |
| F5 | 166.1 ± 24.7 (3) | | 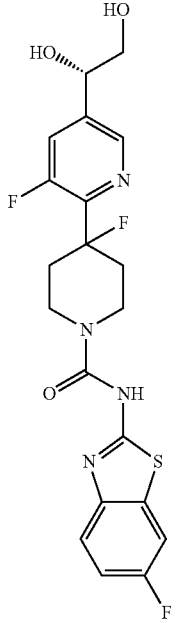 [SMILES: O=C(Nc1nc2ccc(F)cc2s1)N1CCC(F)(c2ncc([C@H](O)CO)cc2F)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| G5 | 400.0 ± 10.6 (3) | 108.5 (2) | 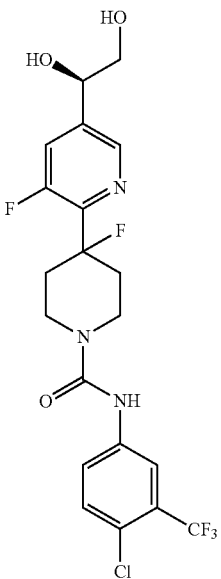 [SMILES: O=C(Nc1ccc(Cl)c(C(F)(F)F)c1)N1CCC(F)(c2ncc([C@@H](O)CO)cc2F)CC1] |
| H5 | 520.0 ± 88.6 (3) | 515.6 ± 99.2 (3) | 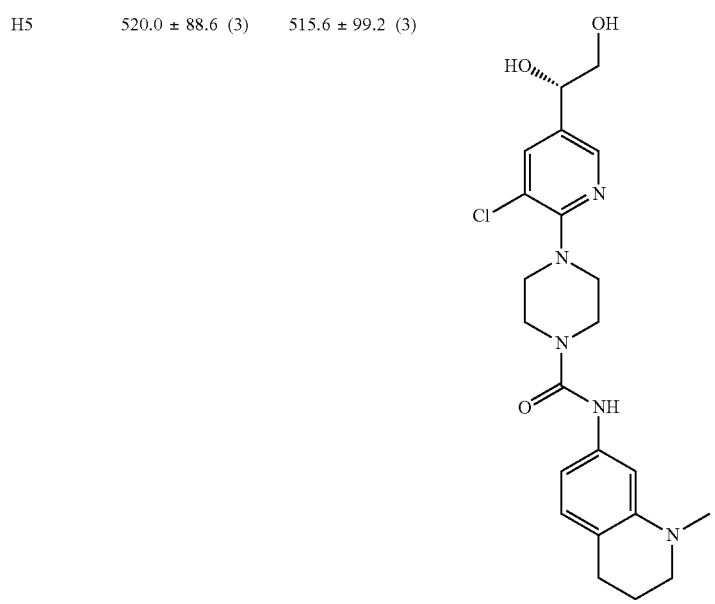 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| I5 | 709.1 ± 94.1 (3) | 117.6 ± 27.5 (3) | 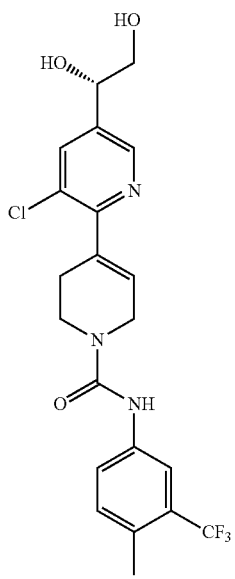 [SMILES: Cc1ccc(NC(=O)N2CC=C(c3ncc([C@H](O)CO)cc3Cl)CC2)cc1C(F)(F)F] |
| T4 | 1330.7 ± 334.3 (3) | 1175.1 ± 147.2 (3) | 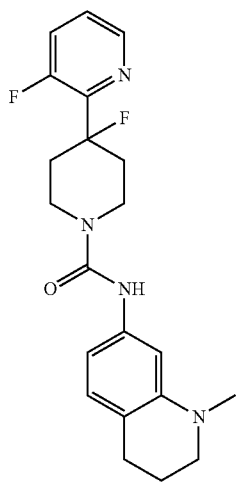 [SMILES: CN1CCCc2ccc(NC(=O)N3CCC(F)(c4ncccc4F)CC3)cc21] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| J5 | 1879.8 ± 633.8 (3) | | 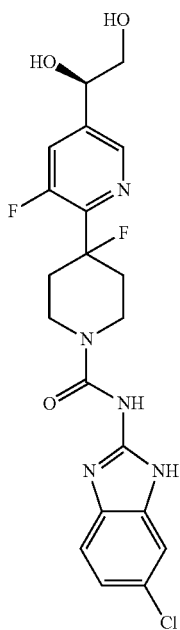 |
| K5 | 2753.2 ± 541.9 (3) | | 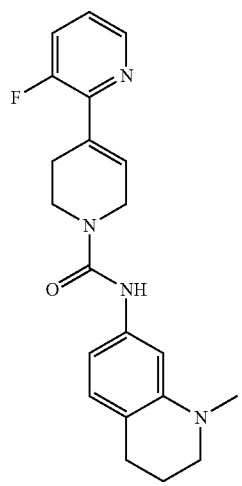 [SMILES: CN1CCCc2ccc(NC(=O)N3CC=C(c4ncccc4F)CC3)cc21] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| L5 | >10,000 (3) | | 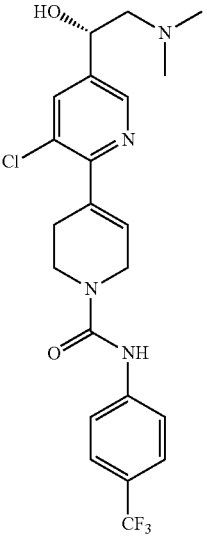 [SMILES: CN(C)C[C@@H](O)c1cnc(C2=CCN(C(=O)Nc3ccc(C(F)(F)F)cc3)CC2)c(Cl)c1] |
| M5 | >25,000 (2) | | 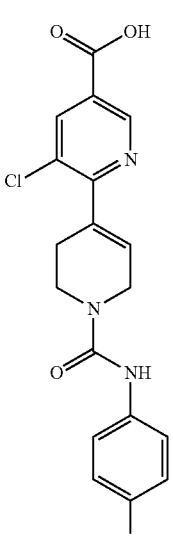 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| N5 | 140.25 (2) | | 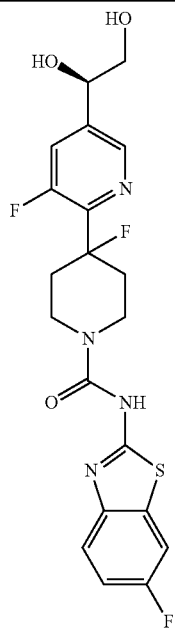 |
| O5 | 243.62 (2) | | 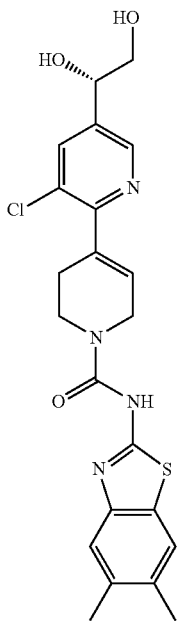 [SMILES: Cc1cc2nc(NC(=O)N3CC=C(c4ncc([C@H](O)CO)cc4Cl)CC3)sc2cc1C] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| P5 | 49.51 (2) | | 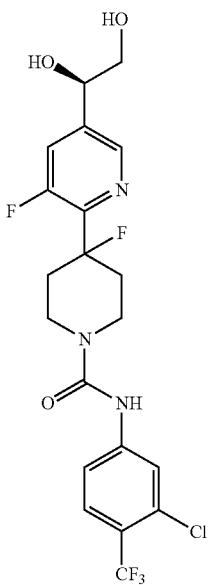 [SMILES: O=C(Nc1ccc(C(F)(F)F)c(Cl)c1)N1CCC(F)(c2ncc([C@@H](O)CO)cc2F)CC1] |
| R5 | 346.05 (2) | | 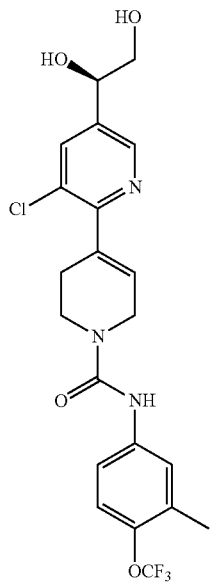 |

TABLE I-continued

| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| T5 | 451.5 ± 92.4 (3) | | |
| U5 | 19.9 ± 6.9 (3) | | |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| V5 | 45.5 ± 2.1 (3) | 10.1 ± 1.4 (6) | 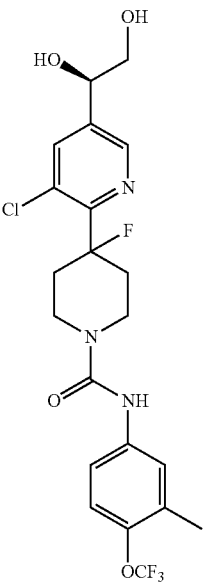 [SMILES: Cc1cc(NC(=O)N2CCC(F)(c3ncc([C@@H](O)CO)cc3Cl)CC2)ccc1OC(F)(F)F] |
| W5 | 423.2 ± 122.5 (3) | 71.2 ± 10.5 (5) | 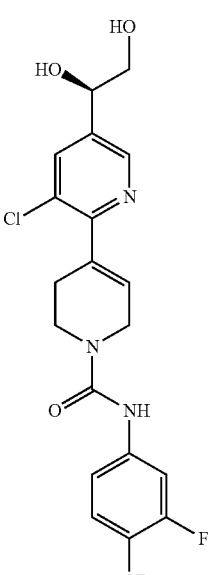 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| X5 | 229.8 ± 65.5 (3) | | 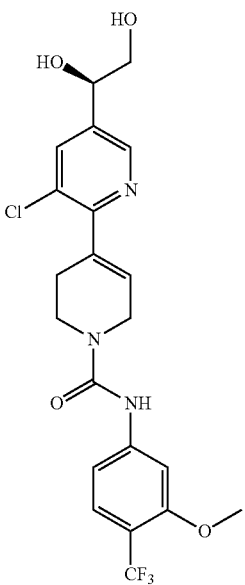 [SMILES: COc1cc(NC(=O)N2CC=C(c3ncc([C@@H](O)CO)cc3Cl)CC2)ccc1C(F)(F)F] |
| Y5 | 196.4 ± 37.7 (3) | 108.5 ± 7.7 (3) | 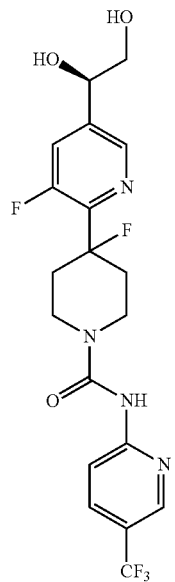 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| Z5 | 35.5 ± 3.9 (3) | 16.4 ± 1.9 (5) | 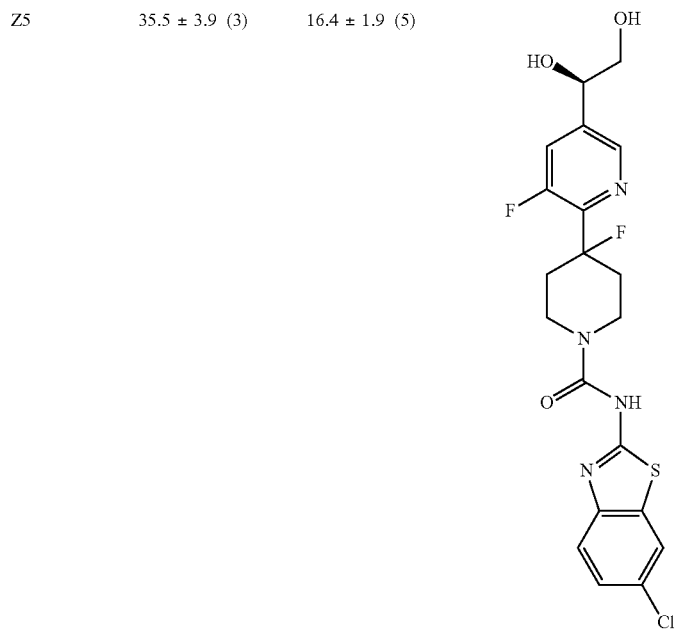 |
| A6 | 49.8 ± 12.1 (3) | 9.0 ± 0.8 (4) | 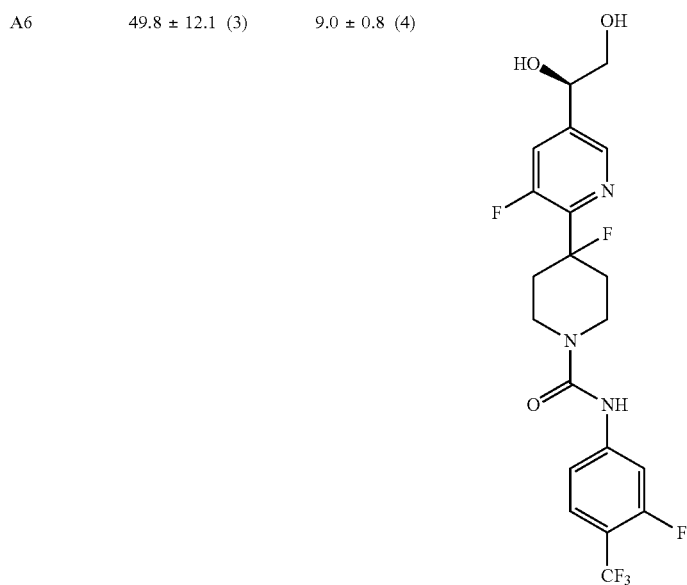 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| B6 | 922.2 ± 204.6 (3) | 361.6 ± 69.1 (3) | 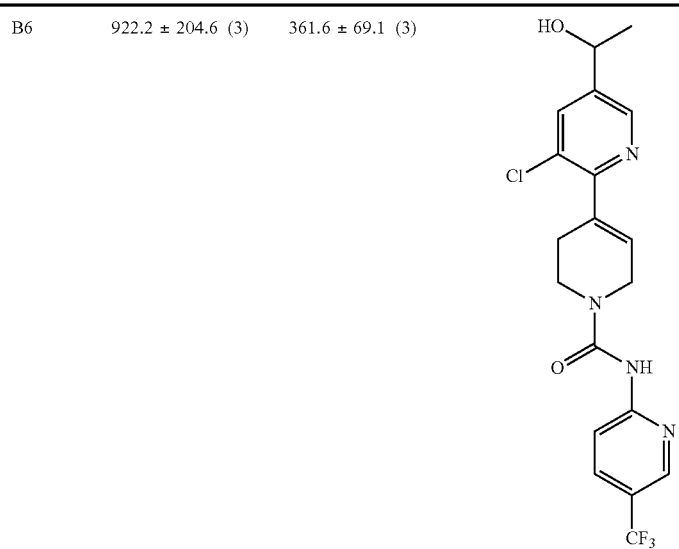 |
| C6 | >25,000 (2) | | 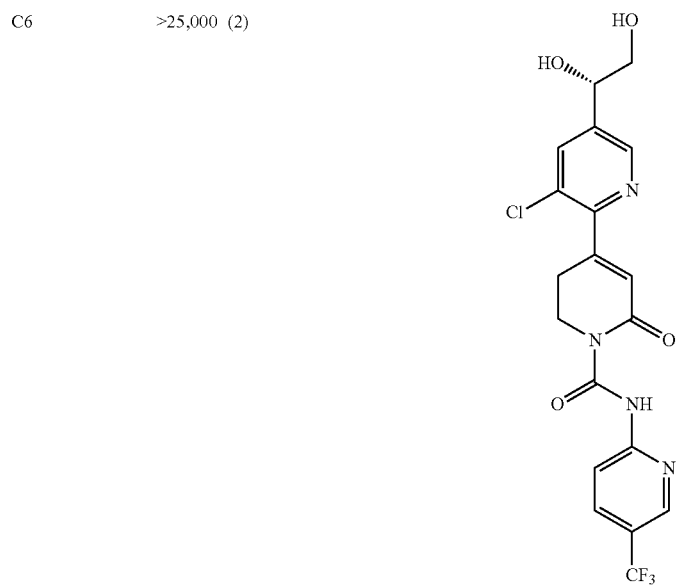 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| D6 | 620.5 ± 116.5 (3) | | 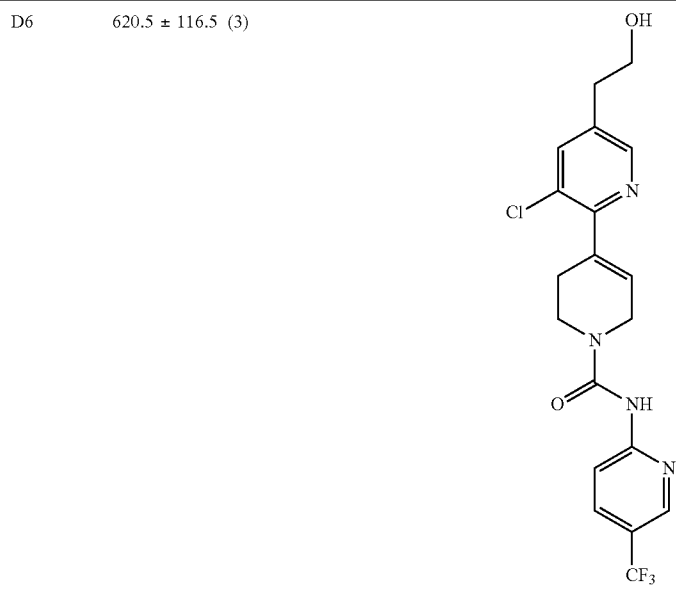 |
| E6 | 265 | 165 | 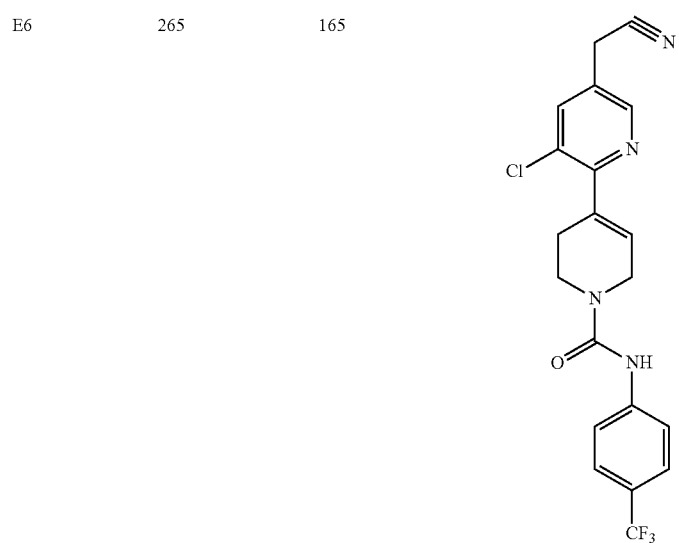 |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| F6 | 864 | 467 | 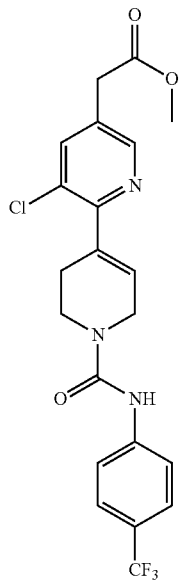 [SMILES: COC(=O)Cc1cnc(C2=CCN(C(=O)Nc3ccc(C(F)(F)F)cc3)CC2)c(Cl)c1] |
| G6 | >25,000 | | 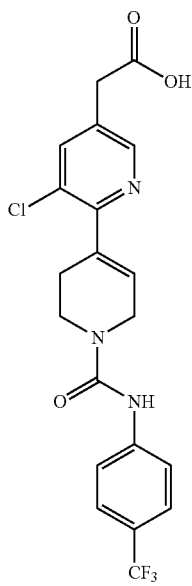 [SMILES: O=C(O)Cc1cnc(C2=CCN(C(=O)Nc3ccc(C(F)(F)F)cc3)CC2)c(Cl)c1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| H6 | 924 | | 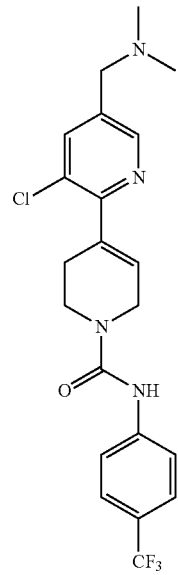 [SMILES: CN(C)Cc1cnc(C2=CCN(C(=O)Nc3ccc(C(F)(F)F)cc3)CC2)c(Cl)c1] |
| K6 | 9.8 ± 2.3 (4) | 0.8 ± 0.1 (3) | 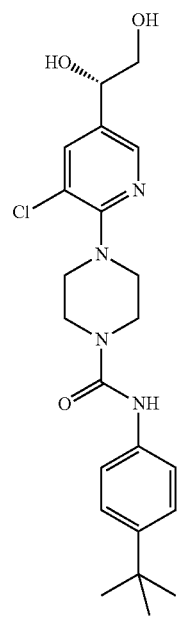 [SMILES: CC(C)(C)c1ccc(NC(=O)N2CCN(c3ncc([C@H](O)CO)cc3Cl)CC2)cc1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| L6 | 14.2 ± 1.4 (3) | 5.8 (2) | 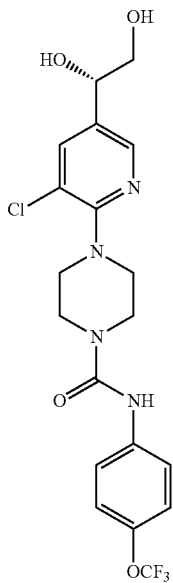 [SMILES: O=C(Nc1ccc(OC(F)(F)F)cc1)N1CCN(c2ncc([C@H](O)CO)cc2Cl)CC1] |
| M6 | 7.0 ± 1.0 (5) | 3.5 ± 1.0 (3) | 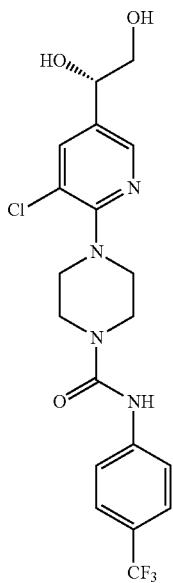 [SMILES: O=C(Nc1ccc(C(F)(F)F)cc1)N1CCN(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| V6 | 16.0 ± 1.6 (3) | 6.2 (2) | 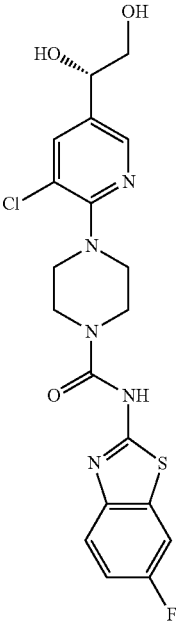 [SMILES: O=C(Nc1nc2ccc(F)cc2s1)N1CCN(c2ncc([C@H](O)CO)cc2Cl)CC1] |
| W6 | 32.9 ± 11.8 (3) | 14.9 ± 2.2 (4) | 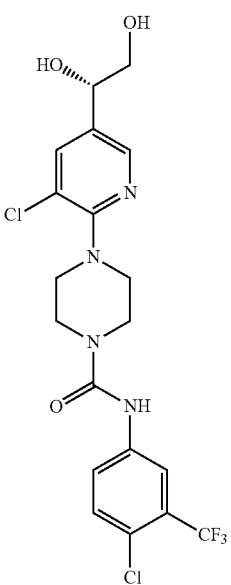 [SMILES: O=C(Nc1ccc(Cl)c(C(F)(F)F)c1)N1CCN(c2ncc([C@H](O)CO)cc2Cl)CC1] |

TABLE I-continued
| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| 200 | 136 | 31.8 | 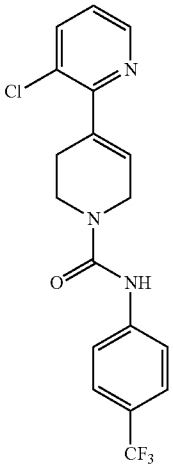 [SMILES: O=C(Nc1ccc(C(F)(F)F)cc1)N1CC=C(c2ncccc2Cl)CC1] |
| 201 | 131 | 185 | 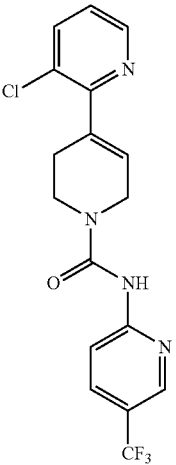 [SMILES: O=C(Nc1ccc(C(F)(F)F)cn1)N1CC=C(c2ncccc2Cl)CC1] |
| 202 | 182 | 590 | 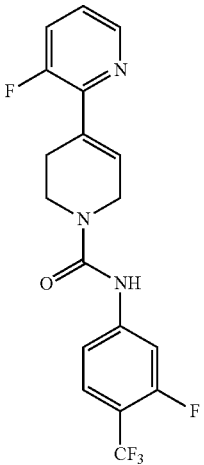 [SMILES: O=C(Nc1ccc(C(F)(F)F)c(F)c1)N1CC=C(c2ncccc2F)CC1] |

TABLE I-continued

| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| 203 | 90.2 | 51.2 | |
| 204 | 167 | 154 | |
| 205 | >25,000 | | |

TABLE I-continued

| | TRPV1 IC$_{50}$ Potency | | |
|---|---|---|---|
| Compound | Human Capsaicin CHO (hCAP-CHO) (nM) | Human pH CHO (hpH-CHO) (nM) | Structure |
| 206 | 508 | 1463 | 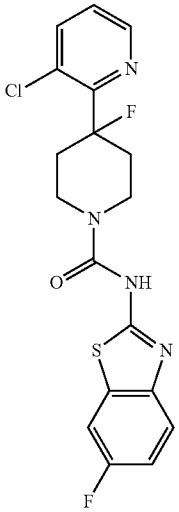 [SMILES: O=C(Nc1nc2ccc(F)cc2s1)N1CCC(F)(c2ncccc2Cl)CC1] |

The invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed:

1. A compound of formula IA:

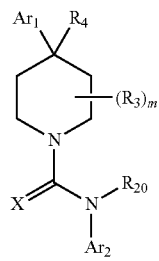

(IA)

or a pharmaceutically acceptable salt, solvate, stereoisomer, geometric isomer or tautomer thereof, wherein X is O, S, N—CN, N—OH, or N—OR$_{10}$;

R$_4$ is —H, —OH, —OCF$_3$, -halo, —(C$_1$-C$_6$)alkyl, —CH$_2$OH, —CH$_2$Cl, —CH$_2$Br, —CH$_2$I, —CH$_2$F, —CH(halo)$_2$, —CF$_3$, —OR$_{10}$, —SR$_{10}$, —C(O)OH, —C(O)OR$_{10}$, —C(O)R$_{10}$, —C(O)H, —OC(O)R$_{10}$, —OC(O)NHR$_{10}$, —NHC(O)R$_{13}$, —C(O)N(R$_{13}$)$_2$, —S(O)$_2$R$_{10}$, or —NO$_2$;

R$_{10}$ is —(C$_1$-C$_4$)alkyl;

each R$_{13}$ is independently —H, —(C$_1$-C$_4$)alkyl, —(C$_1$-C$_4$)alkenyl, —(C$_1$-C$_4$)alkynyl, or -phenyl;

Ar$_1$ is

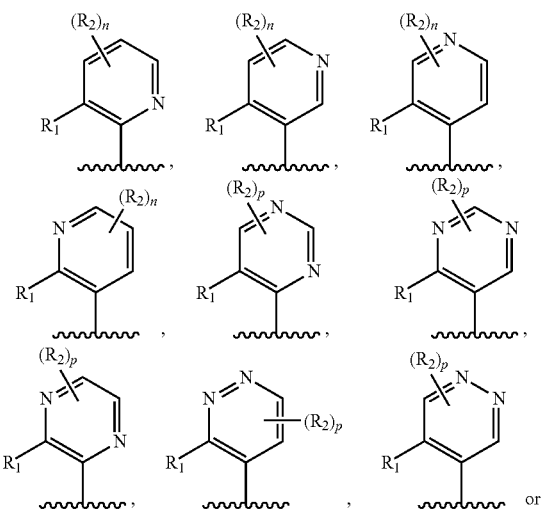

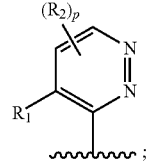

Ar$_2$ is

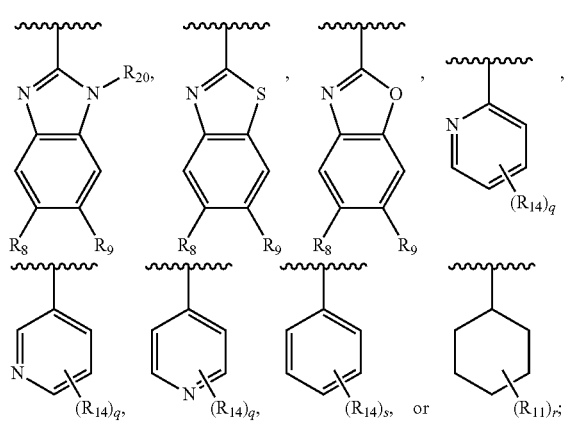

R$_1$ is —H, -halo, —(C$_1$-C$_4$)alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each R$_2$ is independently:
(a) -halo, —OH, —O(C$_1$-C$_4$)alkyl, —CN, —NO$_2$, —NH$_2$, —(C$_1$-C$_{10}$)alkyl, —(C$_2$-C$_{10}$)alkenyl, —(C$_2$-C$_{10}$)alkynyl, or -phenyl, or
(b) a group of formula Q;

wherein Q is

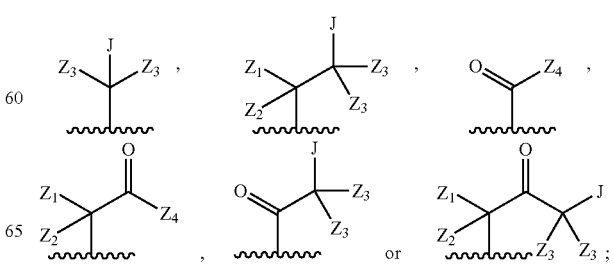

$Z_1$ is —H, —OR$_7$, —SR$_7$, —CH$_2$—OR$_7$, —CH$_2$—SR$_7$, —CH$_2$—N(R$_{20}$)$_2$, or -halo;

$Z_2$ is —H, —(C$_1$-C$_6$)alkyl, —(C$_2$-C$_6$)alkenyl, —(C$_2$-C$_6$)alkynyl, —CH$_2$—OR$_7$, -phenyl, or -halo;

each $Z_3$ is independently —H, —(C$_1$-C$_6$)alkyl, —(C$_2$-C$_6$)alkenyl, —(C$_2$-C$_6$)alkynyl, or -phenyl;

$Z_4$ is —H, —OH, —OR$_{20}$, —(C$_1$-C$_6$)alkyl, or —N(R$_{20}$)$_2$;

J is —OR$_{20}$, —SR$_2$O, —N(R$_{20}$)$_2$, or —CN;

provided that at least one R$_2$ group is a group of formula Q, and provided that when Z$_1$ is —OR$_7$ or —SR$_7$, then Z$_2$ is not -halo;

each R$_3$ is independently:
—H, or —(C$_1$-C$_6$)alkyl;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$)alkyl-N(R$_{20}$)$_2$, or —C(O)N(R$_{20}$)$_2$;

each R$_8$ and R$_9$ is independently:
(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, or -phenyl, each of which is unsubstituted or substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each R$_{11}$ is independently —CN, —OH, —(C$_1$-C$_6$)alkyl, —(C$_2$-C$_6$)alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, or —OC(O)OR$_7$;

each R$_{14}$ is independently —H, —(C$_1$-C$_6$)alkyl, —(C$_2$-C$_6$)alkenyl, —(C$_2$-C$_6$)alkynyl, —(C$_3$-C)cycloalkyl, —(C$_5$-C$_8$)cycloalkenyl, —(C$_1$-C$_6$)alkoxy-(C$_2$-C$_6$)alkyl, -phenyl, —C(halo)$_3$, —CH(halo)$_2$, —CH$_2$(halo), -(3- to 7-membered)heterocycle, —(C$_1$-C$_6$)haloalkyl, —(C$_2$-C$_6$)haloalkenyl, —(C$_2$-C$_6$)haloalkynyl, —(C$_2$-C$_6$)hydroxyalkenyl, —(C$_2$-C$_6$)hydroxyalkynyl, —(C$_1$-C$_6$)alkoxy(C$_2$-C$_6$)alkyl, —(C$_1$-C$_6$)alkoxy(C$_2$-C$_6$)alkenyl, —(C$_1$-C$_6$)alkoxy(C$_2$-C$_6$)alkynyl, —(C$_1$-C$_6$)alkoxy(C$_3$-C$_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —C(O)N(R$_7$)$_2$, —(C$_1$-C$_5$)alkyl-C=NOR$_7$, —(C$_1$-C$_5$)alkyl-C(O)—N(R$_7$)$_2$, —(C$_1$-C$_6$)alkyl-NHS(O)$_2$N(R$_7$)$_2$, or —(C$_1$-C$_6$)alkyl-C(=NH)—N(R$_7$)$_2$;

each R$_{20}$ is independently —H, —(C$_1$-C$_6$)alkyl, or —(C$_3$-C$_8$)cycloalkyl;

each halo is independently —F, —Cl, —Br, or —I;

n is the integer 1, 2, or 3;

p is the integer 1 or 2;

each b is independently 1 or 2;

q is the integer 0, 1, 2, 3, or 4;

r is the integer 0, 1, 2, 3, 4, 5, or 6;

s is the integer 0, 1, 2, 3, 4, or 5; and m is the integer 0, 1, or 2.

2. The compound of claim 1 or a pharmaceutically acceptable salt, solvate, stereoisomer, geometric isomer or tautomer thereof, wherein X is O.

3. A compound of formula II:

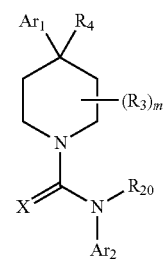

(II)

or a pharmaceutically acceptable salt, solvate, stereoisomer, geometric isomer or tautomer thereof, wherein X is O;

R$_4$ is —H, —OH, —OCF$_3$, -halo, —(C$_1$-C$_6$)alkyl, —CH$_2$OH, —CH$_2$Cl, —CH$_2$Br, —CH$_2$I, —CH$_2$F, —CH(halo)$_2$, —CF$_3$, —OR$_{10}$, —SR$_{10}$, —C(O)OH, —C(O)OR$_{10}$, —C(O)R$_{10}$, —C(O)H, —OC(O)R$_{10}$, —OC(O)NHR$_{10}$, —NHC(O)R$_{13}$, —C(O)N(R$_{13}$)$_2$, —S(O)$_2$R$_{10}$, or —NO$_2$;

R$_{10}$ is —(C$_1$-C$_4$)alkyl;

each R$_{13}$ is independently —H, —(C$_1$-C$_4$)alkyl, —(C$_1$-C$_4$)alkenyl, —(C$_1$-C$_4$)alkynyl, or -phenyl;

Ar$_1$ is

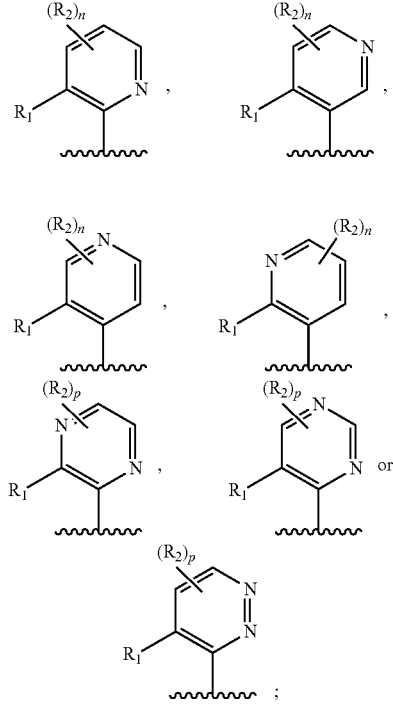

Ar$_2$ is

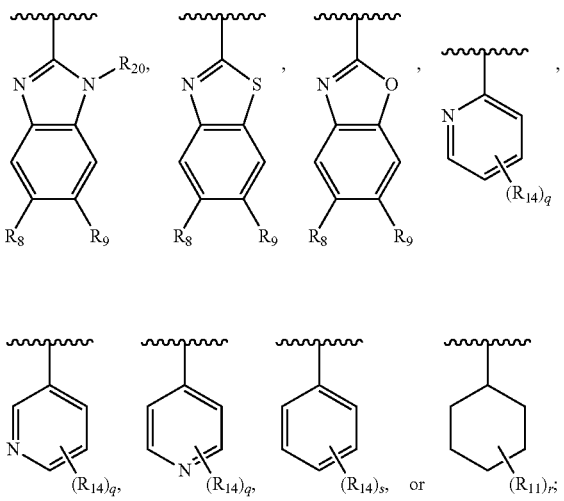

R$_1$ is —H, -halo, —(C$_1$-C$_4$)alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each R$_2$ is independently:
(a) -halo, —OH, —O(C$_1$-C$_4$)alkyl, —CN, —NO$_2$, —NH$_2$, —(C$_1$-C$_{10}$)alkyl, —(C$_2$-C$_{10}$)alkenyl, —(C$_2$-C$_{10}$)alkynyl, or -phenyl, or
(b) a group of formula Q;

wherein Q is

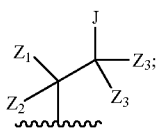

Z$_1$ is —OH, —SH, —N(R$_{20}$)$_2$, —CH$_2$—OH, —CH$_2$—SH, or —CH$_2$—N(R$_{20}$)$_2$;
Z$_2$ is —H, —CH$_3$, or —CH$_2$OR$_7$ and
each Z$_3$ is independently —H or —CH$_3$;
J is —OH, —SH, or —N(R$_{20}$)$_2$;
provided that at least one R$_2$ group is a group of formula Q;

each R$_3$ is independently:
—H or —(C$_1$-C$_6$)alkyl;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$)alkyl-N(R$_{20}$)$_2$, or —C(O)N(R$_{20}$)$_2$;

each R$_8$ and R$_9$ is independently:
(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, or -phenyl, each of which is unsubstituted or substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each R$_{11}$ is independently —CN, —OH, —(C$_1$-C$_6$)alkyl, —(C$_2$-C$_6$)alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, or —OC(O)OR$_7$;

each R$_{14}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, —(C$_1$-C$_6$)alkoxy-(C$_1$-C$_6$)alkyl, -phenyl, —C(halo)$_3$, —CH(halo)$_2$, —CH$_2$(halo), -(3- to 7-membered)heterocycle, —(C$_1$-C$_6$)haloalkyl, —(C$_2$-C$_6$)haloalkenyl, —(C$_2$-C$_6$)haloalkynyl, —(C$_2$-C$_6$)hydroxyalkenyl, —(C$_2$-C$_6$)hydroxyalkynyl, —(C$_1$-C$_6$)alkoxy(C$_2$-C$_6$)alkyl, —(C$_1$-C$_6$)alkoxy(C$_2$-C$_6$)alkenyl, —(C$_1$-C$_6$)alkoxy(C$_2$-C$_6$)alkynyl, —(C$_1$-C$_6$)alkoxy(C$_3$-C$_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —C(O)N(R$_7$)$_2$, —(C$_1$-C$_5$)alkyl-C=NOR$_7$, —(C$_1$-C$_5$)alkyl-C(O)—N(R$_7$)$_2$, —(C$_1$-C$_6$)alkyl-NHS(O)$_2$N(R$_7$)$_2$, or —(C$_1$-C$_6$)alkyl-C(=NH)—N(R$_7$)$_2$;

each R$_{20}$ is independently —H, —(C$_1$-C$_6$)alkyl, or —(C$_3$-C$_8$)cycloalkyl;

each halo is independently —F, —Cl, —Br, or —I;

n is the integer 1, 2, or 3;

p is the integer 1 or 2;

each b is independently 1 or 2;

q is the integer 0, 1, 2, 3, or 4;

r is the integer 0, 1, 2, 3, 4, 5, or 6;

s is the integer 0, 1, 2, 3, 4, or 5; and m is the integer 0, 1, or 2.

4. A compound of formula III:

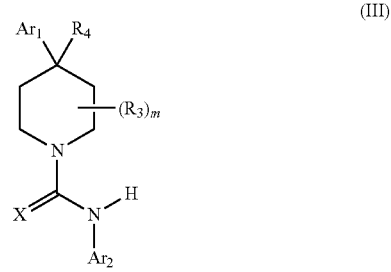

or a pharmaceutically acceptable salt thereof, wherein
X is O;
R$_4$ is -halo;

each R₃ is independently:
—H or —(C₁-C₆)alkyl;
m is the integer 0, 1, or 2;
Ar₁ is:

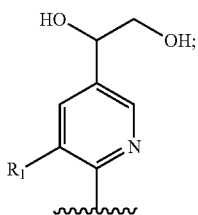

R₁ is —Cl, —F, or —CF₃;
Ar₂ is:

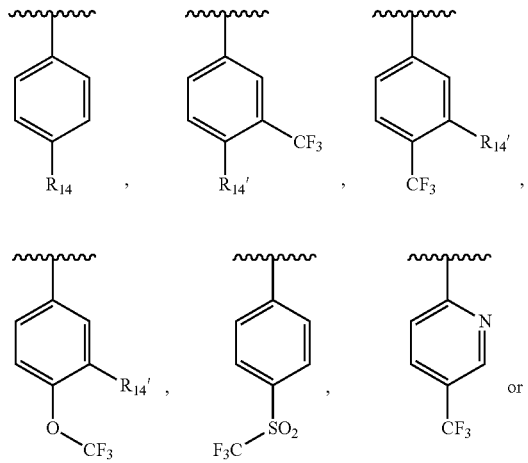

R₁₄ is —H, —Cl, —F, —Br, —CF₃, —OCF₃, —(C₁-C₆)alkyl, —S(O)₂CF₃, —S(O)₂(C₁-C₆)alkyl, —OCH₃, —OCH₂CH₃, or —OCH(CH₃)₂;
R₁₄' is —H, —Cl, —F, —Br, —CF₃, —OCF₃, —(C₁-C₆)alkyl, —S(O)₂CF₃, —S(O)₂(C₁-C₆)alkyl, —OCH₃, —OCH₂CH₃, or —OCH(CH₃)₂; and
R₈ and R₉ are independently —H, —Cl, —Br, —F, —CH₃, —OCH₃, —OCH₂CH₃, —CF₃, —OCF₃, isopropyl, or tert-butyl.

5. The compound of claim 1, wherein the pharmaceutically acceptable salt, solvate, stereoisomer, geometric isomer or tautomer is a pharmaceutically acceptable salt.

6. The compound of claim 3, wherein the pharmaceutically acceptable salt, solvate, stereoisomer, geometric isomer or tautomer is a pharmaceutically acceptable salt.

7. A composition comprising the compound of claim 1 or a pharmaceutically acceptable salt, solvate, stereoisomer, geometric isomer or tautomer thereof and a pharmaceutically acceptable carrier or excipient.

8. A composition comprising the compound of claim 3 or a pharmaceutically acceptable salt, solvate, stereoisomer, geometric isomer or tautomer thereof and a pharmaceutically acceptable carrier or excipient.

9. A composition comprising the compound of claim 4 or a pharmaceutically acceptable salt thereof and a pharmaceutically acceptable carrier or excipient.

10. The compound of claim 1, which is:

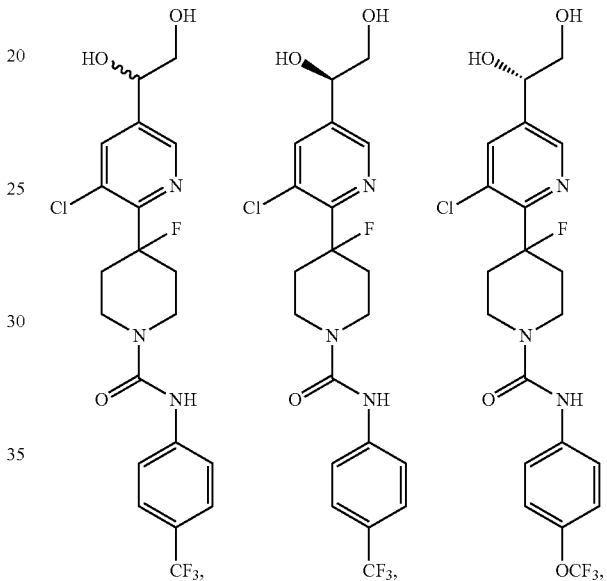

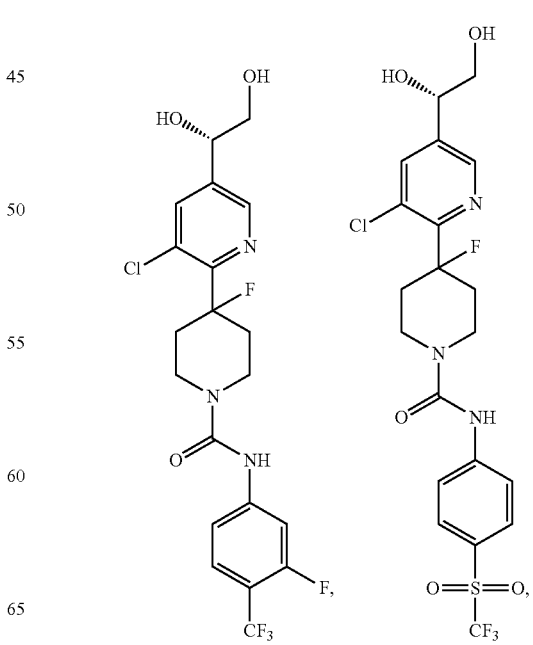

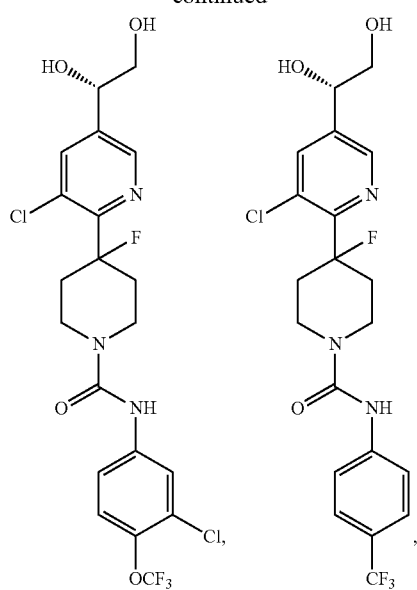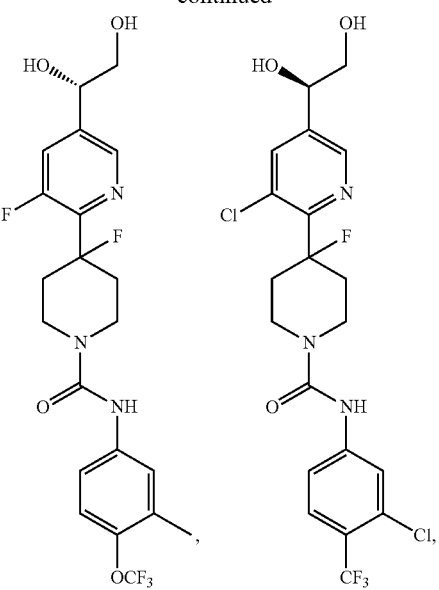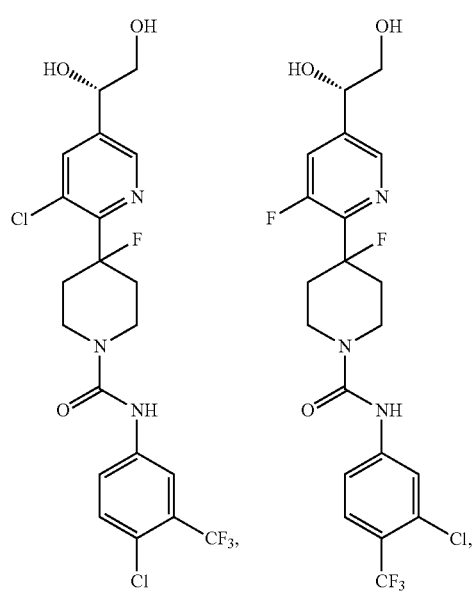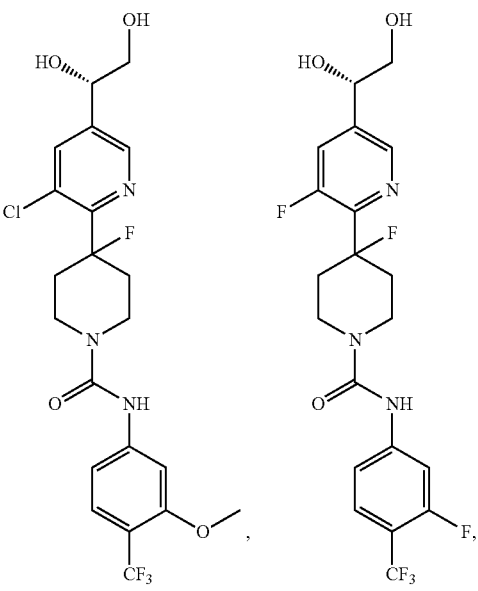

431
-continued
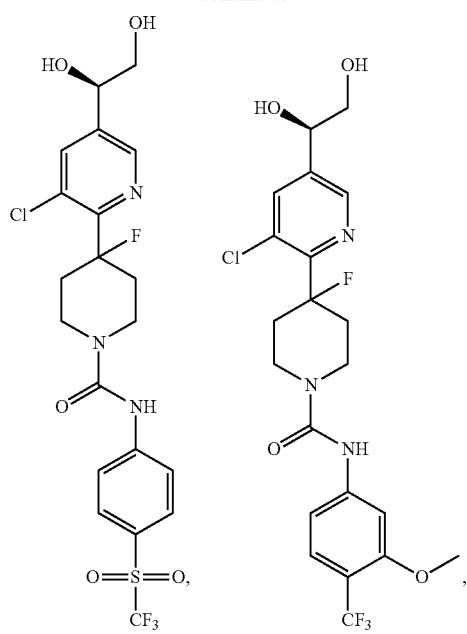
432
-continued
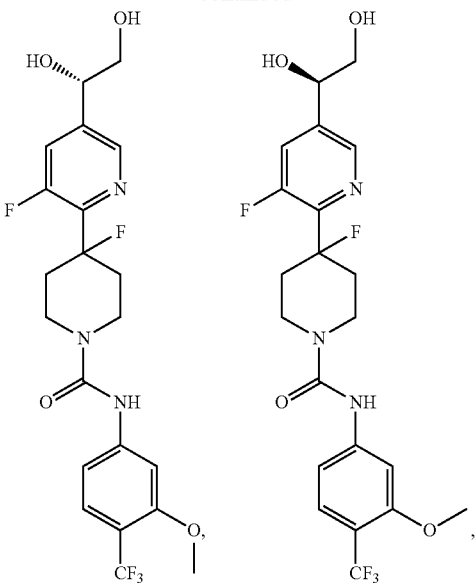
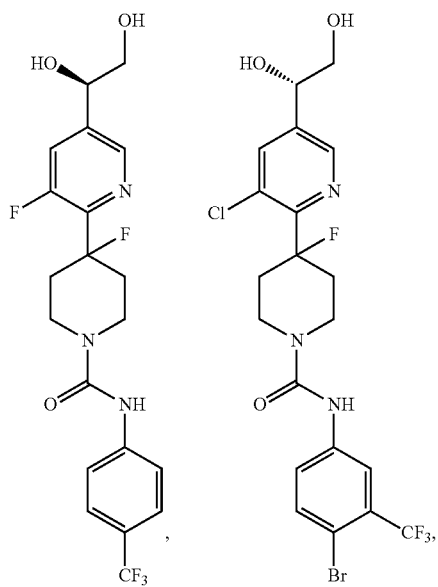
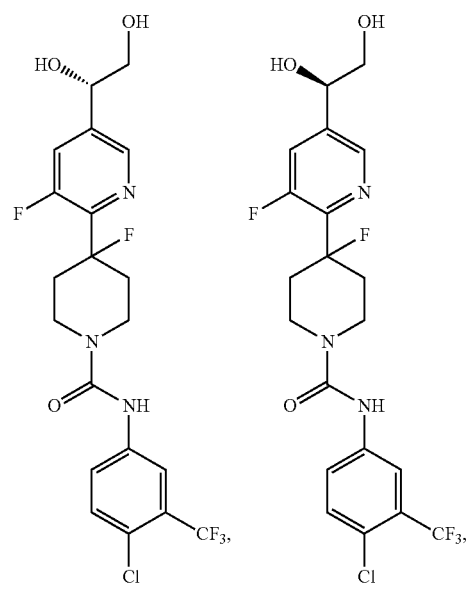

-continued or a pharmaceutically acceptable salt thereof.

11. The compound of claim 4, which is:

or a pharmaceutically acceptable salt thereof.

12. The compound of claim 4, which is:
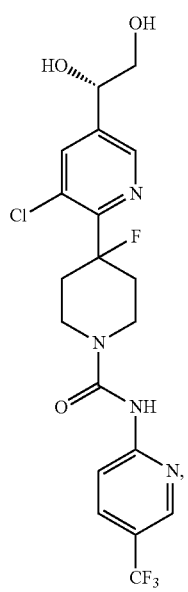 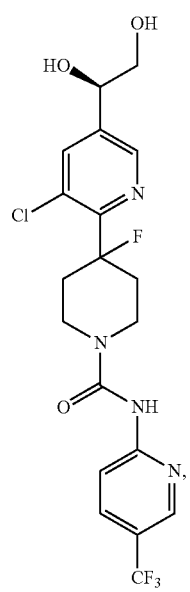
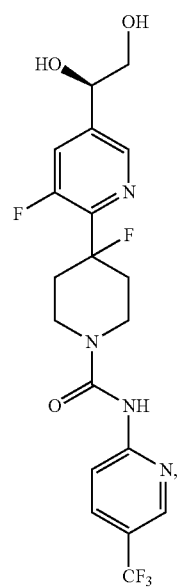 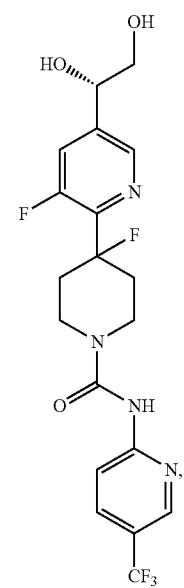
or a pharmaceutically acceptable salt thereof.
13. The compound of claim 4, which is:
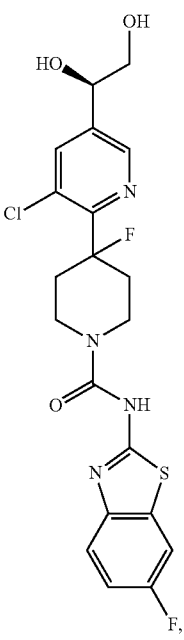 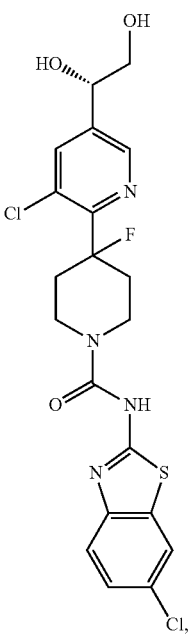
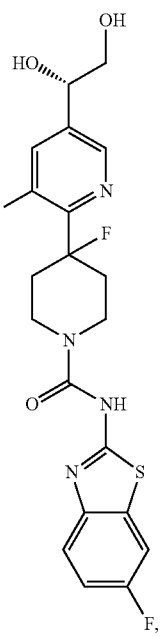 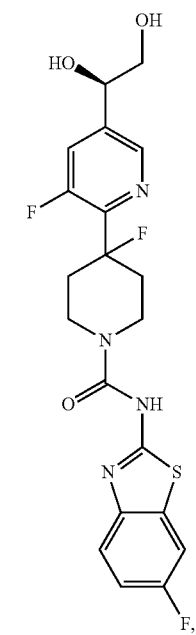

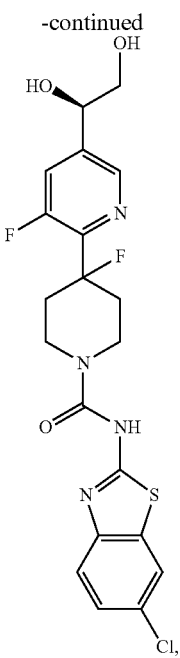

or a pharmaceutically acceptable salt thereof.

14. The compound of claim 3, which is:

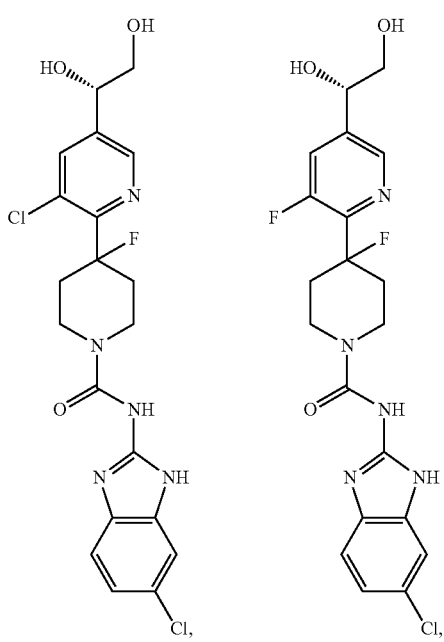

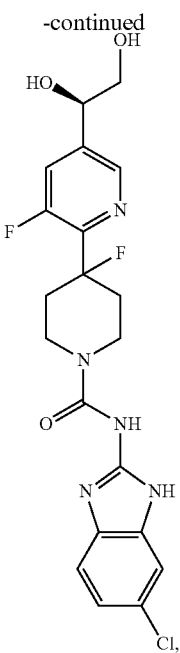

or a pharmaceutically acceptable salt thereof.

15. A method for treating pain, urinary incontinence, an ulcer, inflammatory-bowel disease, or irritable-bowel syndrome in an animal, comprising administering to an animal in need thereof, an effective amount of the compound of claim 10 or a pharmaceutically acceptable salt thereof.

16. A method for treating pain, urinary incontinence, an ulcer, inflammatory-bowel disease, or irritable-bowel syndrome in an animal, comprising administering to an animal in need thereof, an effective amount of the compound of claim 12 or a pharmaceutically acceptable salt thereof.

17. A method for treating pain, urinary incontinence, an ulcer, inflammatory-bowel disease, or irritable-bowel syndrome in an animal, comprising administering to an animal in need thereof, an effective amount of the compound of claim 13 or a pharmaceutically acceptable salt thereof.

18. A method for treating pain, urinary incontinence, an ulcer, inflammatory-bowel disease, or irritable-bowel syndrome in an animal, comprising administering to an animal in need thereof, an effective amount of the compound of claim 14 or a pharmaceutically acceptable salt thereof.

19. A method of inhibiting TRPV1 function in a cell comprising contacting a cell capable of expressing TRPV1 with an effective amount of the compound of claim 10 or a pharmaceutically acceptable salt thereof.

20. A method of inhibiting TRPV1 function in a cell comprising contacting a cell capable of expressing TRPV1 with an effective amount of the compound of claim 12 or a pharmaceutically acceptable salt thereof.

21. A method of inhibiting TRPV1 function in a cell comprising contacting a cell capable of expressing TRPV1 with an effective amount of the compound of claim 13 or a pharmaceutically acceptable salt thereof.

22. A method of inhibiting TRPV1 function in a cell comprising contacting a cell capable of expressing TRPV1 with an effective amount of the compound of claim 14 or a pharmaceutically acceptable salt thereof.

* * * * *